United States Patent
Beigelman et al.

(10) Patent No.: US 10,364,226 B2
(45) Date of Patent: Jul. 30, 2019

(54) PYRIDAZINONE COMPOUNDS AND USES THEREOF

(71) Applicant: Alios BioPharma, Inc., South San Francisco, CA (US)

(72) Inventors: Leonid Beigelman, San Mateo, CA (US); Robert Than Hendricks, San Carlos, CA (US); Antitsa Dimitrova Stoycheva, Half Moon Bay, CA (US); Jerome Deval, Pacifica, CA (US); Sarah Katherine Stevens, San Francisco, CA (US)

(73) Assignee: ALIOS BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 15/021,073

(22) PCT Filed: Sep. 10, 2014

(86) PCT No.: PCT/US2014/055018
§ 371 (c)(1),
(2) Date: Mar. 10, 2016

(87) PCT Pub. No.: WO2015/038660
PCT Pub. Date: Mar. 19, 2015

(65) Prior Publication Data
US 2016/0221963 A1 Aug. 4, 2016

Related U.S. Application Data

(60) Provisional application No. 61/877,171, filed on Sep. 12, 2013.

(51) Int. Cl.
| | | |
|---|---|---|
| C07D 237/20 | (2006.01) | |
| C07D 237/24 | (2006.01) | |
| C07D 403/12 | (2006.01) | |
| C07D 401/04 | (2006.01) | |
| C07D 401/08 | (2006.01) | |
| C07D 401/10 | (2006.01) | |
| C07D 401/12 | (2006.01) | |
| C07D 403/04 | (2006.01) | |
| C07D 403/06 | (2006.01) | |
| C07D 403/08 | (2006.01) | |
| C07D 403/10 | (2006.01) | |
| C07D 405/04 | (2006.01) | |
| C07D 405/06 | (2006.01) | |
| C07D 405/10 | (2006.01) | |
| C07D 405/12 | (2006.01) | |
| C07D 409/10 | (2006.01) | |
| C07D 409/12 | (2006.01) | |
| C07D 413/06 | (2006.01) | |
| C07D 471/04 | (2006.01) | |
| C07D 498/22 | (2006.01) | |

(Continued)

(52) U.S. Cl.
CPC .......... *C07D 237/24* (2013.01); *A61K 31/245* (2013.01); *A61K 31/50* (2013.01); *A61K 31/501* (2013.01); *A61K 31/504* (2013.01); *A61K 31/506* (2013.01); *A61K 31/529* (2013.01); *A61K 31/5377* (2013.01); *A61K 31/55* (2013.01); *A61K 31/553* (2013.01); *A61K 45/06* (2013.01); *C07D 401/04* (2013.01); *C07D 401/08* (2013.01); *C07D 401/10* (2013.01); *C07D 401/12* (2013.01); *C07D 403/04* (2013.01); *C07D 403/06* (2013.01); *C07D 403/08* (2013.01); *C07D 403/10* (2013.01); *C07D 403/12* (2013.01); *C07D 405/04* (2013.01); *C07D 405/06* (2013.01); *C07D 405/10* (2013.01); *C07D 405/12* (2013.01); *C07D 409/10* (2013.01); *C07D 409/12* (2013.01); *C07D 413/06* (2013.01); *C07D 471/04* (2013.01); *C07D 471/22* (2013.01); *C07D 487/18* (2013.01); *C07D 487/22* (2013.01); *C07D 498/08* (2013.01); *C07D 498/10* (2013.01); *C07D 498/18* (2013.01); *C07D 498/22* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 4,345,934 | A | 8/1982 | Fujimoto |
| 5,202,323 | A | 4/1993 | Tanikawa et al. |

(Continued)

FOREIGN PATENT DOCUMENTS

| | | |
|---|---|---|
| CN | 101541802 A | 9/2007 |
| CN | 102365020 A | 2/2012 |

(Continued)

OTHER PUBLICATIONS

STN Accession No. 2012:199179.*
Office Action dated Nov. 7, 2016 for EA Application No. 201690371, filed Sep. 10, 2014.
Carey, Francis, Organic Chemistry, 2nd ed., McGraw Hill, Inc., New York (1992), pp. 328-331.
Clark et al., "Novel inhibitors of bacterial protein synthesis: structure-activity relationships for 1,8-naphthyridine derivatives incorporating position 3 and 4 variants" Bioorg.Med.Chem.Lett., (2004) 14(12): 3299-3302.

(Continued)

*Primary Examiner* — Craig D Ricci
(74) *Attorney, Agent, or Firm* — Morrison & Foerster LLP

(57) ABSTRACT

Disclosed herein are pyridazinone compounds, pharmaceutical compositions that include one or more pyridazinone compounds, and methods of synthesizing the same. Also disclosed herein are methods of ameliorating and/or treating a disease and/or a condition, including an orthomyxovirus infection, with a pyridazinone compounds. Examples of an orthomyxovirus viral infection includes an influenza infection.

36 Claims, 5 Drawing Sheets
Specification includes a Sequence Listing.

(51) Int. Cl.
C07D 471/22 (2006.01)
C07D 498/10 (2006.01)
C07D 519/00 (2006.01)
A61K 31/245 (2006.01)
A61K 31/50 (2006.01)
A61K 31/501 (2006.01)
A61K 31/504 (2006.01)
A61K 31/506 (2006.01)
A61K 31/529 (2006.01)
A61K 31/5377 (2006.01)
A61K 31/55 (2006.01)
A61K 31/553 (2006.01)
A61K 45/06 (2006.01)
C07D 487/18 (2006.01)
C07D 487/22 (2006.01)
C07D 498/08 (2006.01)
C07D 498/18 (2006.01)

(56) References Cited

U.S. PATENT DOCUMENTS

| | | | |
|---|---|---|---|
| 7,390,787 | B2 | 6/2008 | Fraser et al. |
| 9,328,119 | B2 | 5/2016 | Hendricks et al. |
| 2009/0281107 | A1 | 11/2009 | Congy et al. |
| 2010/0197651 | A1 | 8/2010 | Taniguchi et al. |
| 2012/0022251 | A1 | 1/2012 | Sumino et al. |
| 2012/0184734 | A1 | 7/2012 | Akiyama et al. |
| 2013/0197219 | A1 | 8/2013 | Takahashi et al. |
| 2015/0072982 | A1 | 3/2015 | Hendricks et al. |
| 2016/0228438 | A1 | 8/2016 | Hendricks et al. |
| 2016/0264581 | A1 | 9/2016 | Hendricks et al. |
| 2017/0260189 | A1 | 9/2017 | Welch et al. |

FOREIGN PATENT DOCUMENTS

| | | | | |
|---|---|---|---|---|
| CN | 102482219 | A | 5/2012 | |
| JP | 2001-500477 | A | 1/2001 | |
| WO | WO 95/20583 | | 8/1995 | |
| WO | WO 98/041511 | | 9/1998 | |
| WO | WO 02/076939 | | 10/2002 | |
| WO | WO 03/059891 | | 7/2003 | |
| WO | WO 2009/004146 | | 1/2009 | |
| WO | WO 2010/090737 | | 8/2010 | |
| WO | WO 2011/120153 | | 10/2011 | |
| WO | WO 2012/039414 | | 3/2012 | |
| WO | WO 2012/018058 | * | 9/2012 | ........... C07D 403/14 |
| WO | WO 2015/038655 | | 3/2015 | |
| WO | WO 2017/223231 | | 12/2017 | |

OTHER PUBLICATIONS

Gilchrist et al., "Formation of Pyridazino[6,1-c][1,4]oxazin-8(7H)ones by Intramolecular Cycloaddition of Azoalkenes" J. Chem. Soc. Perkin Trans. 1 (1987) 11:2517-2522.
Greene, et al., Protective Groups in Organic Synthesis, 3. Ed., John Wiley & Sons, (1999) Cover & Contents pages.
Hassall et al., "Amino-acids and Peptides. Part XII. The Molecular Structures of the Monamycins, Cyclodepsipeptides Antibiotics" J. Chem. Soc. C: Organic (1971) 3:526-532.
Imada et al., "Design, Synthesis, and Structure-Activity Relationships of Thieno[2,3-b]pyridine-4-one Derivatives as a Novel Class of Potent, Orally Active, Non-Peptide Luteinizing Hormone-Releasing Hormone Receptor Antagonists" J. Med. Chem., 2006, 49(13): 3809-3825.
"IUPAC-IUB Commission on Biochemical Nomenclature Abbreviated Nomenclature of Synthetic Polypeptides (Polymerized Amino Acids)* Revised Recommendations (1971)" Biochemistry. (1972) 11(5) :942-944.
Kurosawa et al., "Total synthesis of (-)-stevastelin B" Chemical Communications (2002), (12):1280-1281.
McMurry, Organic Chemistry, 5th ed., Brooks/Cole, Pacific Grove, CA (2000), Chapter 11.5, pp. 398 and 408.
McOmie, J. F. W., Protective Groups in Organic Chemistry, Plenum Press, 1973. Cover & Contents pages only.
Miyamoto et al., "A New Cinnoline Ring Construction by the Reaction of 2-Diazo-3-(2-fluorophenyl)-3-oxopropionates with Tri-n-butylphosphine" Chem. Pharm. Bull., (1988) 36:1321-1327.
Miyamoto et al., "Fluorocinnoline Deriviates II. Synthesis and Antibacterial Activity of Fluorinated 1-Alkyl-1,4-dihydro-4-oxocinnoline-3-carboxylic Acids" Chem. Pharm. Bull., (1989) 37:93-99.
Nantermet et al., "Potent thrombin inhibitors via a 20-membered ring olefin metathesis macrocyclization" Tetrahedron Letters (2003), 44(11):2401-2404.
Streitwieser et al., Introduction to Organic Chemistry, 2nd ed., Macmillan Publishing Co. Inc., New York, NY 1981, pp. 169-171.
International Search Report and Written Opinion mailed Nov. 3, 2014 for PCT Application No. PCT/US2014/055018, filed Sep. 10, 2014.
International Preliminary Report on Patentability issued Mar. 15, 2016 for PCT Application No. PCT/US2014/055018, filed Sep. 10, 2014.
Extended European Search Report dated Feb. 13, 2017 for EP Application No. 14843298.2, filed Sep. 10, 2014.
Zou et al., "Synthesis of the thiosemicarbazides of 1-aryl-1,4,-dihydro-3-carboxy-6-methyl-4-pyridazinone and their antiviral activity against TMV" Chemical Journal of Chinese Universities (2002) 23(3):403-406.
Search Report and Written Opinion completed Mar. 16, 2017 for Singapore Application No. 11201601576S, filed Sep. 10, 2014.
Communication dated Oct. 4, 2017 for EP Application No. 14843298.2, filed Sep. 10, 2014.
Office Action dated Jan. 22, 2018 for CN Application No. 201480061772.4, filed May 11, 2016.
Office Action dated May 2, 2017 for CN Application No. 20140061772.4, filed Sep. 10, 2014.
Eurasian Office Action dated Dec. 26, 2018 for EA Application No. 201690371, filed Sep. 10, 2014.
Philippines Substantive Examination Report dated Nov. 8, 2018 for PH Application No. 1/2016/500492 filed Sep. 10, 2014.
European Decision to Grant dated Jan. 24, 2019 for EP Application No. 14843298.2, filed Sep. 10, 2014.
Israeli Office Action dated Dec. 18, 2018 for IL Application No. 244434 filed Sep. 10, 2014.
Philippines Office Action dated Jan. 29, 2019 for PH Application No. 1/2016/500492 filed Sep. 10, 2014.
Chinese Office Action dated Sep. 20, 2018 for CN Application No. 20140061772.4, filed Sep. 10, 2014.
European Intention to Grant dated Aug. 27, 2018 for EP Application No. 14843298.2, filed Sep. 10, 2014.
Australian Examination Report No. 1 dated May 14, 2018 for AU Application No. 2014318837, filed Sep. 10, 2014.
European Intention to Grant dated Mar. 21, 2018 for EP Application No. 14843298.2, filed Sep. 10, 2014.
Japanese Notice of Allowance dated May 22, 2018 for Japanese Patent Application No. 2016-542074 filed Sep. 10, 2014.
Mexican Office Action dated Apr. 4, 2019 for MX Application No. MX/a/2016/003135 filed Sep. 10, 2014.
Australian Examination Report No. 2 dated May 10, 2019 for AU Application No. 2014318837, filed Sep. 10, 2014.
Australian Notice of Acceptance dated May 17, 2019 for AU Application No. 2014318837, filed Sep. 10, 2014.
Chinese Notice of Allowance dated May 5, 2019 for CN Application No. 20140061772.4, filed Sep. 10, 2014.

* cited by examiner

| Name or CAS No. | IUPAC Name | Structure |
|---|---|---|
| amantadine | adamantan-1-amine | 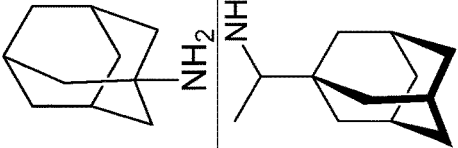 |
| rimantadine | (RS)-1-(1-adamantyl)ethanamine | 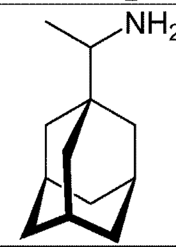 |
| zanamivir | (2R,3R,4S)-4-guanidino-3-(prop-1-en-2-ylamino)-2-((1R,2R)-1,2,3-trihydroxypropyl)-3,4-dihydro-2H-pyran-6-carboxylic acid | 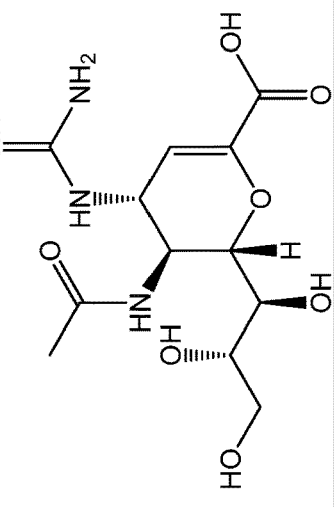 |

| Name or CAS No. | IUPAC Name | Structure |
|---|---|---|
| (cont.) | | |
| oseltamivir | ethyl (3R,4R,5S)-5-amino-4-acetamido-3-(pentan-3-yloxy)-cyclohex-1-ene-1-carboxylate | 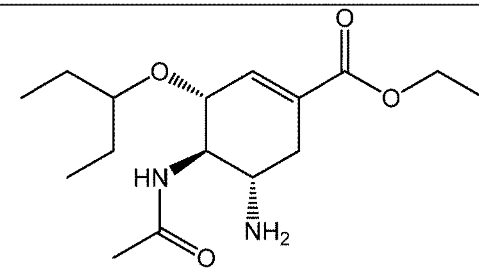 |
| peramivir | (1S,2S,3S,4R)-3-[(1S)-1-acetamido-2-ethylbutyl]-4-(diaminomethylideneamino)-2-hydroxycyclopentane-1-carboxylic acid | 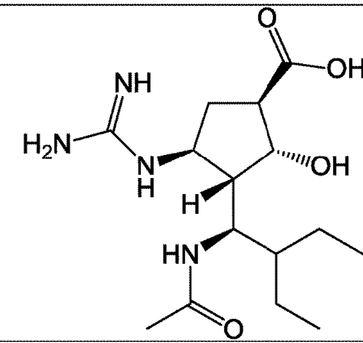 |
| laninamivir | (4S,5R,6R)-5-acetamido-4-carbamimidamido-6-[(1R,2R)-3-hydroxy-2-methoxypropyl]-5,6-dihydro-4H-pyran-2-carboxylic acid | 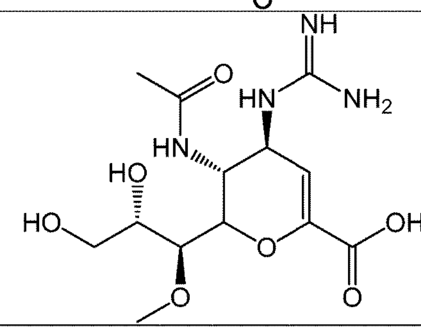 |

| Name or CAS No. | IUPAC Name | Structure |
|---|---|---|
| laninamivir octanoate | (3R,4S)-3-acetamido-4-guanidino-2-((1S,2S)-2-hydroxy-1-methoxy-3-(octanoyloxy)propyl)-3,4-dihydro-2H-pyran-6-carboxylic acid | 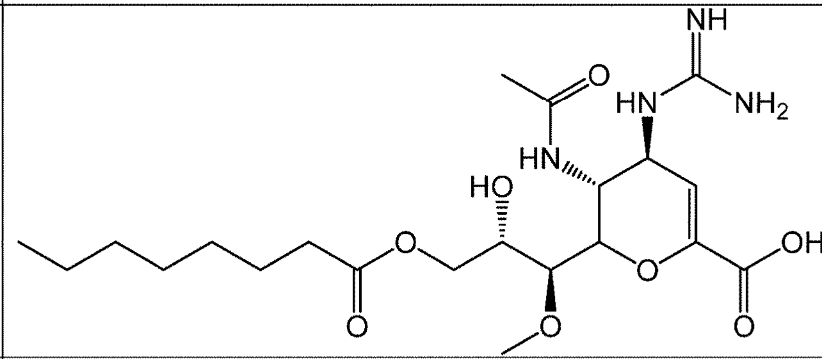 |
| favipiravir | 6-fluoro-3-hydroxy-2-pyrazinecarboxamide | 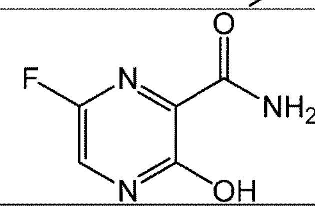 |

(cont.)

(cont.)
| Name or CAS No. | IUPAC Name | Structure |
|---|---|---|
| beraprost | 4-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid | 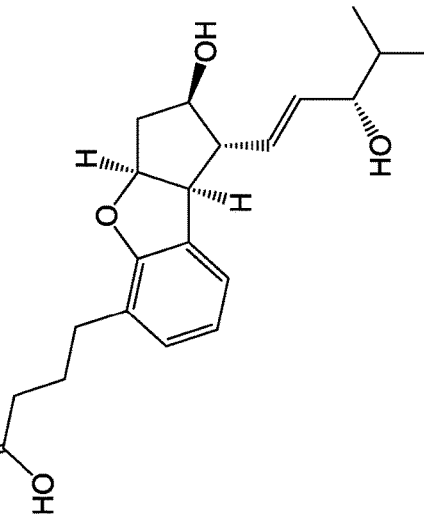 |
| ribavirin | 1-[(2R,3R,4S,5R)-3,4-dihydroxy-5-(hydroxymethyl)oxolan-2-yl]-1H-1,2,4-triazole-3-carboxamide | 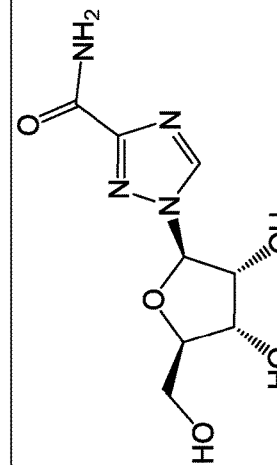 |

(cont.)

| Name or CAS No. | IUPAC Name | Structure |
|---|---|---|
| 1422050-75-6 | (R)-3-((5-fluoro-2-(5-fluoro-1H-pyrrolo[2,3-b]pyridin-3-yl)pyrimidin-4-yl)amino)-4,4-dimethylpentanoic acid | 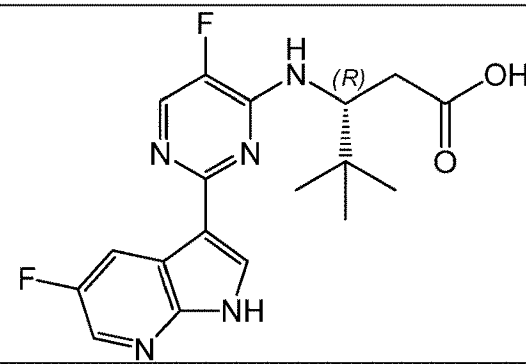 |
| VX-787 | (2S,3S)-3-((5-fluoro-2-(5-fluoro-1H-pyrrolo[2,3-b]pyridin-3-yl)pyrimidin-4-yl)amino)bicyclo[2.2.2]octane-2-carboxylic acid | 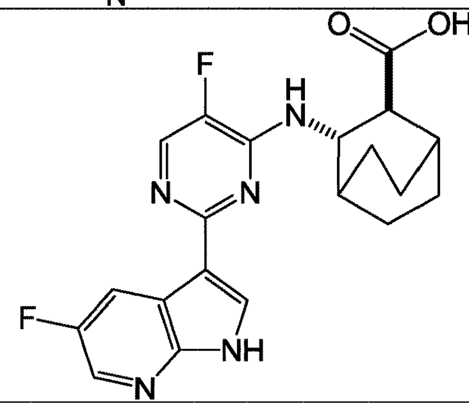 |

SEQUENCE LISTING

<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
<223> OTHER INFORMATION: synthetic oligoribonucleotide

<400> SEQUENCE: 1
auuuuguuuu uaauauuuc                                            19

PYRIDAZINONE COMPOUNDS AND USES THEREOF

CROSS REFERENCE TO RELATED APPLICATIONS

This application is the national stage application under 35 U.S.C. § 371 of International Application No. PCT/US2014/055018, filed internationally on Sep. 10, 2014, which claims the benefit of U.S. Provisional Application No. 61/877,171, filed Sept. 12, 2013.

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6.

SEQUENCE LISTING

The present application is being filed along with a Sequence Listing in electronic format. The Sequence Listing is provided as a file entitled ALIOS081, created Sep. 9, 2014, which is 4 kb bytes in size. The information in the electronic format of the Sequence Listing is incorporated herein by reference in its entirety.

BACKGROUND

Field

The present application relates to the fields of chemistry, biochemistry and medicine. More particularly, disclosed herein are pyridazinone compounds, pharmaceutical compositions that include one or more pyridazinone compounds, and methods of synthesizing the same. Also disclosed herein are methods of ameliorating and/or treating an orthomyxovirus viral infection with one or more pyridazinone compounds.

Description

The viruses of the Orthomyxoviridae family are negative-sense, single-stranded RNA viruses. The Orthomyxoviridae family contains several genera including Influenzavirus A, Influenzavirus B, Influenzavirus C, Isavirus and Thogotovirus. Influenzaviruses can cause respiratory viral infections, including upper and lower respiratory tract viral infections. Respiratory viral infections are a leading cause of death of millions of people each year. Upper respiratory tract viral infections involve the nose, sinuses, pharynx and/or larynx. Lower respiratory tract viral infections involve the respiratory system below the vocal cords, including the trachea, primary bronchi and lungs.

SUMMARY

Some embodiments disclosed herein relate to a compound of Formula (I), or a pharmaceutically acceptable salt thereof. Other embodiments disclosed herein relate to a compound of Formula (II), or a pharmaceutically acceptable salt thereof.

Some embodiments disclosed herein relate to methods of ameliorating and/or treating an orthomyxovirus viral infection that can include administering to a subject suffering from the orthomyxovirus viral infection an effective amount of one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing. Other embodiments described herein relate to using one or more compounds of Formulae (I) and/or (II), or a pharmaceutically acceptable salt of the foregoing, in the manufacture of a medicament for ameliorating and/or treating an orthomyxovirus viral infection. Still other embodiments described herein relate to compounds of Formulae (I) and/or (II), or a pharmaceutically acceptable salt of the foregoing, that can be used for ameliorating and/or treating an orthomyxovirus viral infection. Yet still other embodiments disclosed herein relate to methods of ameliorating and/or treating an orthomyxovirus viral infection that can include contacting a cell infected with the orthomyxovirus with an effective amount of one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing. Some embodiments disclosed herein relate to methods of preventing an orthomyxovirus infection that can include administering to a subject an effective amount of one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing. For example, the orthomyxovirus viral infection can be an influenza viral infection (such as influenza A, B and/or C).

Some embodiments disclosed herein relate to methods of inhibiting the replication of an orthomyxovirus that can include contacting a cell infected with the orthomyxovirus with an effective amount of one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing. For example, the orthomyxovirus viral infection can be an influenza viral infection (such as influenza A, B and/or C). Other embodiments disclosed herein relate to a method for inhibiting endonuclease activity of an influenza endonuclease that can include contacting the active site of the endonuclease with an effective amount of one or more compounds of Formulae (I) and/or (II), or a pharmaceutically acceptable salt of the foregoing, or a pharmaceutical composition that includes one or more compounds of Formulae (I) and/or (II), or a pharmaceutically acceptable salt of the foregoing. These and other embodiments are described in greater detail below.

BRIEF DESCRIPTION OF THE DRAWINGS

FIG. 1 shows example anti-influenza agents.

DETAILED DESCRIPTION

Influenza is a negative sense, single stranded RNA virus and a member of the Orthomyxoviridae family. There are currently three species of influenza; influenza A, influenza B and influenza C. Influenza A has a lipid membrane derived from the host cell, which contains the hemagglutinin, neuramidiadase and M2 proteins that project from the surface of the virus. Influenza A has been further classified based the hemagglutinin (H or HA) and the neuramididase (N). There are approximately 16 H antigens (H1 to H16) and 9 N antigens (N1 to N9). Influenza A includes several subtypes, including H1N1, H1N2, H2N2, H3N1, H3N2, H3N8, H5N1, H5N2, H5N3, H5N8, H5N9, H7N1, H7N2, H7N3, H7N4, H7N7, H7N9, H9N2 and H10N7. The influenza virus polymerase is a heterotrimer composed of three subunits, polymerase acid (PA), polymerase basic 1 (PB1) and polymerase basic 2 (PB2). This polymerase is responsible for replication and transcription of the viral RNA in the nuclei of infected cells. The PA subunit contains the endonuclease active site. The endonuclease activity of the PA cleaves the cellular mRNA, which is then used by the PB1 subunit as a primer for the viral mRNA synthesis.

Influenza viruses can be transmitted from person to person via direct contact with infected secretions and/or contaminated surfaces or objections. Complications from an influenza viral infection include pneumonia, bronchitis, dehydration, and sinus and ear infections. Medications currently approved by the FDA against an influenza infection include a limited number of neuraminidase inhibitors and M2 protein inhibitors. Examples of approved neuraminidase inhibitors and M2 protein inhibitors include amantadine, rimantadine, Relenza® (zanamivir, GlaxoSmithKline) and Tamiflu® (oseltamivir, Genentech).

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail sinless stated otherwise.

As used herein, any "R" group(s) such as, without limitation, $R^1$, $R^2$, $R^3$, $R^4$, $R^5$ and $R^6$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together." it means that they are covalently bonded to one another to form a ring:

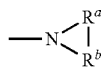

In addition, if two "R" groups are described as being "taken together" with the atom(s) to which they are attached to form a ring as an alternative, the R groups may not be limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroyclyl group. That is, the alkyl, alkenyl, alkynyl, ring(s) of the cycloalkyl, ring(s) of the cycloalkenyl, ring(s) of the aryl, ring(s) of the heteroaryl or ring(s) of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl (straight and branched) and hexyl (straight and branched). The alkyl group may be substituted or unsubstituted.

As used herein, "alkenyl" refers to an alkyl group that contains in the straight or branched hydrocarbon chain one or more double bonds. Examples of alkenyl groups include Amyl, vinylmethyl and ethenyl. An alkenyl group may be unsubstituted or substituted.

As used herein, "alkynyl" refers to an alkyl group that contains in the straight or branched hydrocarbon chain one or more triple bonds. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "aryl" refers to a carbocyclic (all carbon) mono-cyclic or multi-cyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a mono-cyclic or multi-cyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-eight-, nine-ten-, up to 18-membered mono-cyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl or a heteroalicyclyl may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrroidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline and 3,4-methylenedioxyphenyl).

As used herein, the term "alkylene" refers to a straight or a branched tethering fully saturated (no double or triple bonds) hydrocarbon group that connect molecular fragments via its terminal carbon atoms. Examples include but are not limited to methylene (—$CH_2$—), ethylene (—$CH_2CH_2$—), propylene (—$CH_2CH_2CH_2$—), and butylene (—$(CH_2)_4$—) groups. A "lower alkylene group" refers to an alkylene group containing 1 to 6 carbons. A lower alkylene and alkylene group can be substituted by replacing one or more hydrogen of the lower alkylene group or alkylene group with a substituent(s) listed under the definition of "substituted."

As used herein, the term "alkenylene" refers to a straight or a branched tethering hydrocarbon group containing one or more double bonds that connect molecular fragments via its terminal carbon atoms. Examples include but are not limited to ethenylene (—CH=CH—), propenylene (—CH=CHCH$_2$— or —CH$_2$CH=CH—), and butenylene (—CH=CHCH$_2$CH$_2$—, —CH$_2$CH=CHCH$_2$— or —CH$_2$CH$_2$CH=CH—) groups. An alkenylene group may be substituted or unsubstituted.

As used herein, the term "heteroalkylene" refers to an alkylene containing one or more heteroatom groups or heteroatom containing groups in the carbon back bone (i.e., an alkylene group in which one or more carbon atoms is replaced with a heteroatom group or heteroatom containing group). In some embodiments, heteroalkyls may be substituted or unsubstituted. Heteroalkyls include, but are not limited to ether, thioether, amino-alkylene, and alkylene-amino-alkylene moieties. Examples of heteroalkyls include, but are not limited to, —CH$_2$O—, —CH$_2$CH$_2$CH$_2$CH$_2$O—, —CH$_2$OCH$_2$—, —CH$_2$OCH$_2$CH$_2$—, —CH$_2$CH$_2$OCH$_2$CH$_2$—, —CH$_2$OCH$_2$CH$_2$CH$_2$—, —CH$_2$OCH$_2$CH$_2$—, —(CH$_2$)$_2$O(CH$_2$)$_2$—, —CH$_2$S—, —CH$_2$CH$_2$CH$_2$CH$_2$S—, —CH$_2$SCH$_2$—, —CH$_2$SCH$_2$CH$_2$—, —CH$_2$CH$_2$SCH$_2$CH$_2$—, —CH$_2$SCH$_2$CH$_2$CH$_2$—, —CH$_2$SCH$_2$CH$_2$—, —(CH$_2$)$_2$S(CH$_2$)$_2$—, —CH$_2$CH$_2$CH$_2$CH$_2$NH—, —CH$_2$NHCH$_2$—, —CH$_2$NHCH$_2$CH$_2$—, —CH$_2$CH$_2$NHCH$_2$CH$_2$—, —CH$_2$NHCH$_2$CH$_2$CH$_2$—, —CH$_2$NHCH$_2$CH$_2$—, —(CH$_2$)$_2$ NH(CH$_2$)$_2$—, and the like.

As used herein, the term "heteroalkenylenes" refers to an alkenylene containing one or more heteroatoms in the carbon back bone (i.e., an alkenylene group in which one or more fully saturated carbon atoms (i.e. CH$_2$) is replaced with a heteroatom group or a heteroatom containing group). In some embodiments, heteroalkenyls may be substituted or unsubstituted. Examples of heteroalkenyls include, but are not limited to, —CH=CHCH$_2$OCH$_2$CH$_2$—, —CH=CHCH$_2$OCH$_2$CH$_2$CH$_2$—, —CH=CHCH$_2$OCH$_2$CH$_2$—, —CH$_2$CH=CHCH$_2$O—, —CH$_2$CH$_2$CH=CHCH$_2$O—, —CH$_2$CH$_2$CH$_2$CH=CHCH$_2$O—, —(CH$_2$)$_2$CH=CH (CH$_2$)$_2$O—, —CH=CHCH$_2$S—, —CH=CHCH$_2$SCH$_2$—, —CH=CHCH$_2$SCH$_2$CH$_2$—, —CH=CHCH$_2$CH$_2$SCH$_2$CH$_2$—, —CH=CHCH$_2$SCH$_2$CH$_2$CH$_2$—, —CH=CHCH$_2$SCH$_2$CH$_2$—, —CH$_2$CH=CFICH$_2$S—, —CH$_2$CH$_2$CH=CHCH$_2$S—, —CH$_2$CH$_2$CH$_2$CH=CHCH$_2$S—, —(CH$_2$)$_2$CH=CH (CH$_2$)$_2$ S—, —CH=CHCH$_2$NH—, —CH=CHCH$_2$NHCH$_2$—, —CH=CHCH$_2$NHCH$_2$CH$_2$—, —CH=CHCH$_2$CH$_2$NHCH$_2$CH$_2$—, —CH=CHCH$_2$NHCH$_2$CH$_2$CH$_2$—, —CH=CHCH$_2$NHCH$_2$CH$_2$—, —CH$_2$CH=CHCH$_2$NH—,
—CH$_2$CH$_2$CH=CHCH$_2$NH—,
—CH$_2$CH$_2$CH$_2$CH=CHCH$_2$NH—, —(CH$_2$)$_2$CH=CH(CH$_2$)$_2$NH—, and the like.

As used herein, "aralkyl" and "aryl(alkyl)" refer to an aryl group connected, as a substituent, via a lower alkylene group. The lower alkylene and/or aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group connected, as a substituent, via a lower alkylene group. The lower alkylene and/or heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl, and their benzo-fused analogs.

A "(heteroalicyleakyl" and "(heterocyclyl)alkyl" refer to a heterocyclic or a heteroalicylylic group connected, as a substituent, via a lower alkylene group. The lower alkylene and/or heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl.

As used herein. "alkoxy" refers to the formula —OR wherein R is alkyl, alkenyl, alkynyl, cycloalkyl, cycloalkenyl, aryl, heteroaryl, heterocyclyl, aralkyl, (heteroaryl)alkyl or (heterocyclyl)alkyl is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group of the formula —O-alkyl in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl.

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An O-carbamyl may be substituted or unsubstituted.

An "N-cathamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-thiocarbamyl may be substituted or unsubstituted.

A "C-amido" group refers to a "—C(=O)N($R_A R_B$)" group in which $R_A$ and $R_B$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aralkyl, (heteroaryl)alkyl or (heterocyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl and isobutyryl); arylalkylcarbonyls and arylalkoxycarbonyls (e.g., benzyloxycarbonyl); substituted methyl ether (e.g. methoxymethyl ether and tetrahydropyranyl ether); substituted ethyl ether; a substituted benzyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl and t-butyldiphenylsilyl); esters (e.g. benzoate ester); carbonates (e.g. methoxymethylcarbonate); sulfonates (e.g. tosylate and mesylate); acyclic ketal (e.g. dimethyl acetal and diisopropyl acetal); cyclic ketals (e.g., 1,3-dioxane and 1,3-dioxolane); acyclic acetal; cyclic acetal; acyclic hemiacetal; cyclic hemiacetal; dithioacetals (both cyclic and acyclic); dithioketals (both cyclic and acyclic) (e.g., S,S'-dimethyl, S,S'-diethyl, S,S'-diisopropyl, 1,3-dithiane and 1,3-dithiolane); orthoesters (including cyclic orthoesters, such as cyclic orthoformates); carbamates (e.g., N-phenylcarbamate) and triarylmethyl groups (e.g., trityl, monomethoxytrityl (MMTr), 4,4'-dimethoxytrityl (DMTr), and 4,4',4"-trimethoxytrityl (TMTr); and those described herein).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments. "leaving groups" are any atoms or moieties that are conjugate bases of strong acids. Examples of suitable leaving groups include, but are not limited to, tosylates, mesylates and halogens (e.g., I, Br, and Cl). Non-limiting characteristics and examples of leaving groups can be found, for example in *Organic Chemistry,* 2d ed., Francis Carey (1992), pages 328-331; *Introduction to Organic Chemistry,* 2d ed., Andrew Streitwieser and Clayton Heathcock (1981), pages 169-171; and *Organic Chemistry,* $5^{th}$ ed., John McMuny (2000), pages 398 and 408; all of which are incorporated herein by reference for the limited purpose of disclosing characteristics and examples of leaving groups.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof,

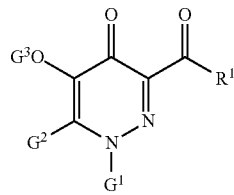

(I)

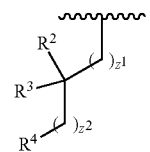

wherein: $G^1$ can be selected from and $R^5$; $G^2$ can be hydrogen, halogen, —CN, an optionally substituted $C_{1-6}$ alkyl, an optionally substituted aryl, an optionally substituted heteroaryl, —CH$_2$OH, —CH(Y$^1$)(OH) or —C(O)Y$^1$; $G^3$ can be selected from hydrogen, —C(O)Y$^2$, —C(O)O—Y$^2$, —(CH$_2$)—O(CO)Y$^2$, —(CH$_2$)—O(CO)OY$^2$, —(CHCH$_3$)—O(CO)Y$^2$, and —(CHCH$_3$)—O(CO)OY$^2$; Y$^1$ and Y$^2$ can be independently an optionally substituted $C_{1-6}$ alkyl or an optionally substituted aryl; $R^1$ can be selected from OR$^6$, NH$_2$, an optionally substituted mono-substituted amine, an optionally substituted di-substituted amine, an optionally substituted heterocyclyl, an optionally substituted N-sulfonamido and an optionally substituted alkoxyamine, or $R^{10}$; $R^2$ can be hydrogen, $C_{1-6}$ alkyl, an optionally substituted $C_{3-6}$ cycloalkyl, an optionally substituted aryl, an optionally substituted aryl($C_{1-6}$ alkyl) or an optionally substituted C-amido: $R^3$ can be hydrogen or $C_{1-6}$ alkyl; or $R^2$ and $R^3$ can be taken together to form an optionally substituted $C_{3-6}$ cycloalkyl, an optionally substituted 5 to 6 membered heterocyclyl or =O; $R^4$ can be selected from an optionally substituted aryl, an optionally substituted cycloalkyl, an optionally substituted cycloalkenyl, an optionally substituted heteroaryl and an optionally substituted heterocyclyl; or $R^4$ can be A$^1$R$^{A4}$R$^{B4}$, wherein A$^1$ can be CH or N; and R$^{A4}$ and R$^{B4}$ can be each independently an optionally substituted phenyl; $R^5$ can be selected from an optionally substituted aryl, an optionally substituted cycloalkyl, an optionally substituted cycloalkenyl, an optionally substituted heteroaryl and an optionally substituted heterocyclyl; $R^6$ can be selected from hydrogen, $C_{1-6}$ alkyl, —C(O)R$^7$ and —C(O)NR$^8$R$^9$; $R^7$ can be selected from hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl); R$^8$ and R$^9$ can be independently selected from hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl); or R$^8$ and R$^9$ can be taken together to form an optionally substituted heterocyclyl; wherein when R$^1$ is R$^{10}$, then R$^{10}$ and R$^4$ can be taken together and include L$^1$, where L$^1$ connects R$^{10}$ and R$^4$ to form an 11- to 20-membered ring, or wherein when R$^1$ is R$^{10}$ then R$^{10}$ and R$^5$ can be taken together and include L$^1$, where L$^1$ connects R$^1$ and R$^5$ to form an 11- to 20-membered ring; wherein R$^{10}$ is optionally substituted —CH$_2$—, optionally substituted —CH═CH—, O (oxygen), S (sulfur), or NR$^{11}$; wherein R$^{11}$ can be hydrogen or C$_{1-6}$ alkyl; and Z$^1$ and Z$^2$ can be independently 0, 1, 2, 3 or 4.

In some embodiments, G$^3$ can be hydrogen. In other embodiments, the compound of Formula (I), or a pharmaceutically acceptable salt thereof, is a prodrug in which G$^3$ can be selected from —C(O)Y$^2$, —C(O)O—Y$^2$, —(CH$_2$)—O(CO)Y$^2$, —(CH$_2$)—O(CO)OY$^2$, —(CHCH$_3$)—O(CO)Y$^2$, and —(CHCH$_3$)—O(CO)OY$^2$.

A variety of substituents can be present on the 6-membered ring of Formula (I). For example, in some embodiments, G$^2$ can be hydrogen. In other embodiments, G$^2$ can be halogen. In still other embodiments, G$^2$ can be —CN. In yet still other embodiments, G$^2$ can be an optionally substituted aryl. In some embodiments, G$^2$ can be an optionally substituted heteroaryl. In other embodiments, G$^2$ can be —CH$_2$OH. In still other embodiments, G$^2$ can be —CH(Y$^1$)(OH). In yet still other embodiments, G$^2$ can be —C(O)Y$^1$. In some embodiments, G$^2$ can be an optionally substituted C$_{1-6}$ alkyl. In some embodiments, G$^2$ can be an unsubstituted C$_{1-6}$ alkyl, such as methyl. When Y$^1$ and Y$^2$ are present in G$^2$ and/or G$^3$, respectively, Y$^1$ and Y$^2$ can be independently an optionally substituted C$_{1-6}$ alkyl or an optionally substituted aryl (such as an optionally substituted phenyl).

Various groups can be present at R$^1$. In some embodiments, R$^1$ can be OR$^6$. For example, in some embodiments, R$^1$ can be hydroxy. In other embodiments, when R$^1$ is OR$^6$, R$^6$ can be C$_{1-6}$ alkyl. In still other embodiments, when R$^1$ is OR$^6$, R$^6$ can be —C(O)R$^7$. Example of suitable R$^7$ groups include, but are not limited to, hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl). In yet still other embodiments, when R$^1$ is OR$^6$, R$^6$ can be —C(O)NR$^8$R$^9$. R$^8$ and R$^9$ can be independently various substituents, such as hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl (C$_{1-6}$ alkyl) or heterocyclyl(C$_{1-6}$ alkyl). In some embodiments, R$^8$ and R$^9$ can be taken together to form an optionally substituted heterocyclyl Examples of suitable optionally substituted heterocyclyls that can be formed from R$^8$ and R$^9$ include 5 to 6 membered heterocyclyls. In some embodiments, R$^6$ can be hydrogen, C$_{1-6}$ alkyl, an acyl or C-amido. In some embodiments, R$^6$ can be hydrogen. —C(O)R$^7$ and —C(O)NR$^8$R$^9$. In other embodiments. R$^6$ can be —C(O)R$^7$ and —C(O)NR$^8$R$^9$.

In some embodiments, R$^1$ can be NH$_2$. In other embodiments. R$^1$ can be an optionally substituted mono-substituted amine. An example of a suitable mono-substituted amine is a group having the formula of —NHR$^{1AA}$, wherein R$^{1AA}$ can be selected from alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl). In some embodiments, R$^{1AA}$ can be selected from alkyl, alkenyl, cycloalkyl, aryl, heteroaryl, heterocyclyl, aryl(C$_{1-6}$ alkyl), heteroaryl(C$_{1-6}$ alkyl) and heterocyclyl(C$_{1-6}$ alkyl). In other embodiments, R$^{1AA}$ can be selected from alkyl, aryl, and aryl(C$_{1-6}$ alkyl). When R$^1$ is a mono-substituted amine having the formula —NHR$^{1AA}$, R$^{1AA}$ can be a substituted or unsubstituted group.

In other embodiments, R$^1$ can be an optionally substituted di-substituted amine. For example, R$^1$ can be a group having the formula of —NR$^{1BB}$R$^{1CC}$, wherein R$^{1BB}$ and R$^{1CC}$ can be independently selected from alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl). In some embodiments, R$^{1BB}$ and R$^{1CC}$ can be independently selected from alkyl, alkenyl, cycloalkyl, aryl, heteroaryl, heterocyclyl, aryl(C$_{1-6}$ alkyl), heteroaryl(C$_{1-6}$ alkyl) and heterocyclyl(C$_{1-6}$ alkyl). In other embodiments, R$^{1BB}$ and R$^{1CC}$ can be independently selected from alkyl, aryl, and aryl(C$_{1-6}$ alkyl). In some embodiments, R$^{1BB}$ and R$^{1CC}$ can be the same. In other embodiments, R$^{1BB}$ and R$^{1CC}$ can be different. When R$^1$ is a di-substituted amine having the formula —NR$^{1BB}$R$^{1CC}$. R$^{1BB}$ and R$^{1CC}$ can be substituted or unsubstituted groups.

In still other embodiments, R$^1$ can be an optionally substituted heterocyclyl. Various heterocyclyls can be used and can be connected either through a ring carbon or a ring heteroatom. In some embodiments, the heterocyclyl can be a 5 to 6 membered heterocyclyl. In some embodiments, the heterocyclyl can include 1 heteroatom. In other embodiments, the heterocyclyl can include 2 heteroatoms, wherein the heteroatoms can be the same or different. In some embodiments, R$^1$ can be an optionally substituted heterocyclyl that contains at least one nitrogen in the ring and is an N-linked heterocyclyl. In some embodiments. R$^1$ can be an unsubstituted heterocyclyl. In some embodiments, R$^1$ can be a substituted heterocyclyl.

In still other embodiments, R$^1$ can be an optionally substituted N-sulfonamido. In some embodiments, when R$^1$ is an optionally substituted N-sulfonamido, the groups attached to the sulfur can be independently selected from hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl). An example of suitable structure for the optionally substituted N-sulfonamido is —NHS(O)$_2$R$^{1DD}$, wherein R$^{1DD}$ can be selected from hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl). In some embodiments, R$^{1DD}$ can be selected from alkyl, alkenyl, cycloalkyl, aryl, heteroaryl, heterocyclyl, aryl(C$_{1-6}$ alkyl), heteroaryl(C$_{1-6}$ alkyl) and heterocyclyl(C$_{1-6}$ alkyl). In other embodiments, R$^{1DD}$ can be selected from alkyl, aryl, and aryl(C$_{1-6}$ alkyl). When R$^1$ is a N-sulfonamido having the formula —NHS(O)$_2$R$^{1DD}$, R$^{1DD}$ can be a substituted or unsubstituted group.

In yet still other embodiments, R$^1$ can be an optionally substituted alkoxyamine. Examples of an optionally substituted alkoxyamine include, but are not limited to, the following: —NH(C$_{1-6}$ alkoxy) and —N(C$_{1-6}$ alkyl)(C$_{1-6}$ alkoxy), —NH(OCH$_3$) and —NCH$_3$(OCH$_3$).

In some embodiments, G$^1$ can be

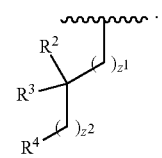

In some embodiments, $R^2$ can be hydrogen. In other embodiments, $R^2$ can be a $C_{1-6}$ alkyl. Examples of suitable $C_{1-6}$ alkyl include methyl, ethyl, n-propyl, isopropyl, n-butyl, isobutyl, tert-butyl, straight or branched pentyl and straight or branched hexyl. In still other embodimens, $R^2$ can be an optionally substituted $C_{3-6}$ cycloalkyl. In some embodiments, $R^2$ can be an optionally substituted $C_{5-6}$ cycloalkyl, such as an optionally substituted monocyclic $C_{5-6}$ cycloalkyl or an optionally substituted fused, bicyclic $C_{5-6}$ cycloalkyl. In yet still other embodimens, $R^2$ can be an optionally substituted aryl, such as an optionally substituted phenyl. In some embodimens, $R^2$ can be an optionally substituted aryl($C_{1-6}$ alkyl), for example, an optionally substituted benzyl. In other embodimens, $R^2$ can be an optionally substituted C-amido. For example, $R^2$ can be $C(=O)NH-(C_{1-6}$ alkyl). In some embodiments, $R^3$ can be hydrogen. In other embodiments, $R^3$ can be a $C_{1-6}$ alkyl.

In some embodiments, $R^2$ and $R^3$ can be the same. In other embodiments. $R^2$ and $R^3$ can be different. In some embodiments, $R^2$ and $R^3$ can both be hydrogen. In other embodiments, $R^2$ and $R^3$ can both be a $C_{1-6}$ alkyl. For example, $R^2$ and $R^3$ can both be methyl. In some embodimens, $R^2$ can be $C_{1-6}$ alkyl, an optionally substituted $C_{3-6}$ cycloalkyl, an optionally substituted aryl, an optionally substituted aryl($C_{1-6}$ alkyl) or an optionally substituted C-amido, and $R^3$ can be hydrogen.

Alternatively, in some embodiments, $R^2$ and $R^3$ can be taken together to form an optionally substituted $C_{3-6}$ cycloalkyl. Suitable cycloalkyls include cyclopropyl, cyclobutyl, cyclopentyl and cyclohexyl. When $R^2$ and $R^3$ are taken together, the cycloalkyl group can be unsubstituted. In the alternative, the cycloalkyl group can be substituted with one or more substituents. In some embodiments, $R^2$ and $R^3$ can be taken together to form an optionally substituted $C_5$ cycloalkyl. In some embodiments. $R^2$ and $R^3$ can be taken together to form an unsubstituted $C_5$ cycloalkyl. In other embodiments, $R^2$ and $R^3$ can be taken together to form a mono-substituted or di-substituted $C_5$ cycloalkyl. In some embodiments, $R^2$ and $R^3$ can be taken together to form an optionally substituted 5 to 6 membered heterocyclyl. Examples of heterocyclyls that can be formed include, but are not limited to, optionally substituted nitrogen containing 5 to 6 membered heterocyclyls. In some embodiments, $R^2$ and $R^3$ can be taken together to form an optionally substituted 5 to 6 membered N-linked heterocyclyl, for example, an optionally substituted piperdino or an optionally substituted pyrrolidino. In some embodiments, $R^2$ and $R^3$ can be taken together to form =O, such that the carbon to which $R^2$ and $R^3$ are attached together with $R^2$ and $R^3$ form a carbonyl group.

Various groups can be $R^4$. In some embodiments, $R^4$ can be an optionally substituted aryl. In some embodiments, $R^4$ can be an optionally substituted naphthyl. In other embodiments, $R^4$ can be an optionally substituted phenyl. In some embodiments, $R^4$ can be an unsubstituted phenyl. In other embodiments, $R^4$ can be a substituted phenyl. One or more groups can be present on a substituted phenyl. For example, the substituted phenyl can be a mono-substituted phenyl, such as an ortho-substituted phenyl, a meta-substituted phenyl or a para-substituted phenyl. As another example, the substituted phenyl can be a di-substituted phenyl, such as a 2,5-di-substituted phenyl, 2,4-di-substituted phenyl and 2,3-di-substituted phenyl. In some embodiments, the substituted phenyl can be substituted with 3 or more substituent.

In other embodiments, $R^4$ can be an optionally substituted cycloalkyl or an optionally substituted cycloalkenyl. For example, $R^4$ can be an optionally substituted $C_{4-6}$ cycloalkyl.

In some embodiments, $R^4$ can be an unsubstituted cycloalkyl. In other embodiments, $R^4$ can be a substituted cycloalkyl.

In still other embodiments, $R^4$ can be an optionally substituted heteroaryl. In some embodiments, $R^4$ can be an unsubstituted heteroaryl. In other embodiments, $R^4$ can be a substituted heteroaryl. Examples of suitable heteroaryls are described herein. In some embodiments, $R^4$ can be an optionally substituted monocyclic heteroaryl. In other embodiments, $R^4$ can be an optionally substituted bicyclic heteroaryl, for example, an optionally substituted 1H-pyrrolo[2,3-b]pyridine.

In yet still other embodiments, $R^4$ can be an optionally substituted heterocyclyl. In some embodiments, $R^4$ can be an unsubstituted heterocyclyl. In other embodiments, $R^4$ can be a substituted heterocyclyl. In some embodiments, $R^4$ can be an optionally substituted monocyclic heterocyclyl. In other embodiments, $R^4$ can be an optionally substituted bicyclic heterocyclyl.

When $R^4$ is substituted, one or more groups can be present. When two or more of the substituents are present, two or more of the substituents can be the same. In some embodiments, when multiple substituents are present on $R^4$, at least one of the substituents is different from the remaining substituents. In some embodiments, all of the substituents present on $R^4$ are different. In some embodiments, $R^4$ can be substituted with one or more substituents selected from halogen. $C_{1-6}$ alkyl, alkoxy, aryloxy, haloalkyl, haloalkoxy, hydroxyalkyl, N-sulfonamido, S-sulfonamido, sulfonyl, an optionally substituted aryl, an optionally substituted cycloalkyl, an optionally substituted heterocyclyl, carbonyl. C-carboxy, —$CH_2$-(mono-substituted amine) and $CH_2$-(di-substituted amine). In some embodiments, when $R^4$ is a substituted aryl, the aryl can be substituted with one or more groups selected from $C_{1-6}$ alkyl, alkoxy, aryl (for example, phenyl), cyano, halogen, haloalkyl and haloalkoxy. In some embodiments, when $R^4$ is a substituted cycloalkyl, the cycloalkyl can be substituted with $C_{1-6}$ alkyl, alkoxy, halogen and haloalkyl. In some embodiments, when $R^4$ is a substituted heterocyclyl, the heterocyclyl can be substituted with $C_{1-6}$ alkyl, alkoxy, halogen, haloalkyl, aryl($C_{1-6}$ alkyl) and C-carboxy. In some embodiments, the substituted heterocyclyl of $R^4$ can be substituted with a substituted or an unsubstituted benzyl.

The pyridazinone ring can be connected to $R^4$ via a substituted or unsubstituted alkylene. In some embodiments, $Z^1$ can be 0. In other embodiments, $Z^1$ can be 1. In still other embodiments, $Z^1$ can be 2. In yet still other embodiments, $Z^1$ can be 3. In some embodiments, $Z^1$ can be 4. In some embodiments, $Z^2$ can be 0. In other embodiments, $Z^2$ can be 1. In still other embodiments, $Z^2$ can be 2. In yet still other embodiments, $Z^2$ can be 3. In some embodiments, $Z^2$ can be 4. In some embodiments, $Z^1$ can be 1, and $Z^2$ can be 0. In other embodiments, $Z^1$ and $Z^2$ can be both 1. In still other embodiments, $Z^1$ and $Z^2$ can be both >1. In yet still other embodiments, at least one of $Z^1$ and $Z^2$ can be 1. In some embodiments, at least one of $Z^1$ and $Z^2$ can be 1, and the other of $Z^1$ and $Z^2$ can be >1.

In some embodiments, $R^4$ can be $A^1R^{A4}R^{B4}$, wherein $A^1$ can be CH or N; and $R^{A4}$ and $R^{B4}$ can be each independently an optionally substituted phenyl. For example, $R^4$ can be $CHR^{A4}R^{B4}$ or $NR^{A4}R^{B4}$. As described herein, the phenyl groups can be the same or different, and can be substituted or unsubstituted.

In other embodiments, $G^1$ can be $R^5$. As with $R^4$, $R^5$ can be a variety of groups. In some embodiments, $R^5$ can be an optionally substituted aryl. In some embodiments, $R^5$ can be an optionally substituted naphthyl. In other embodiments, $R^5$ can be an optionally substituted phenyl. In some embodiments, $R^5$ can be an unsubstituted phenyl. In other embodiments, $R^5$ can be a substituted phenyl. One or more groups can be present on a substituted phenyl. For example, the substituted phenyl can be a mono-substituted phenyl, such as an ortho-substituted phenyl, a meta-substituted phenyl or a para-substituted phenyl. As another example, the substituted phenyl can be a di-substituted phenyl, such as a 2,5-di-substituted phenyl, 2,4-di-substituted phenyl and 2,3-di-substituted phenyl. In some embodiments, the substituted phenyl can be substituted with 3 or more substituents.

In other embodiments, $R^5$ can be an optionally substituted cycloalkyl or an optionally substituted cycloalkenyl. For example, $R^5$ can be a substituted or an unsubstituted $C_{4-6}$ cycloalkyl. In some embodiments, $R^5$ can be an unsubstituted cycloalkyl. In other embodiments, $R^5$ can be a substituted cycloalkyl.

In still other embodiments, $R^5$ can be an optionally substituted heteroaryl. In some embodiments, $R^5$ can be an unsubstituted heteroaryl. In other embodiments, $R^5$ can be a substituted heteroaryl. In some embodiments, $R^5$ can be an optionally substituted monocyclic heteroaryl. In other embodiments, $R^5$ can be an optionally substituted bicyclic heteroaryl.

In yet still other embodiments, $R^5$ can be an optionally substituted heterocyclyl. In some embodiments, $R^5$ can be an unsubstituted heterocyclyl. In other embodiments, $R^5$ can be a substituted heterocyclyl. In some embodiments, $R^5$ can be an optionally substituted monocyclic heterocyclyl. In other embodiments, $R^5$ can be an optionally substituted bicyclic heterocyclyl.

When $R^5$ is substituted, one or more groups can be present. When two or more of the substituents are present, two or more of the substituents can be the same. In some embodiments, when multiple substituents are present on $R^5$, at least one of the substituents is different from the remaining substituents. In some embodiments, all of the substituents present on $R^5$ are different. In some embodiments, $R^5$ can be substituted with one or more substituents selected from halogen, $C_{1-6}$ alkyl, alkoxy, aryloxy, haloalkoxy, hydroxyalkyl, N-sulfonamido, S-sulfonamido, sulfonyl, an optionally substituted aryl, an optionally substituted cycloalkyl, an optionally substituted heterocyclyl, carbonyl, C-carboxy, —CH$_2$-(mono-substituted amine) and CH$_2$-(di-substituted amine). In some embodiments, when $R^5$ is a substituted aryl, the aryl can be substituted with one or more groups selected from $C_{1-6}$ alkyl, alkoxy, halogen and haloalkyl. In other embodiments, when $R^5$ is a substituted aryl, the aryl can be substituted with one or more groups selected from $C_{1-6}$ alkyl, alkoxy, aryl (for example, phenyl), cyano, halogen, haloalkyl and haloalkoxy. In some embodiments, when $R^5$ is a substituted cycloalkyl, the cycloalkyl can be substituted with $C_{1-6}$ alkyl, alkoxy, halogen and haloalkyl. In some embodiments, when $R^5$ is a substituted heterocyclyl, the heterocyclyl can be substituted with $C_{1-6}$ alkyl, alkoxy, halogen, haloalkyl, aryl($C_{1-6}$ alkyl) and C-carboxy. In some embodiments, the substituted heterocyclyl of $R^5$ can be substituted with a substituted or an unsubstituted benzyl.

In some embodiments, $R^1$ is not mono-substituted amine, such as —NH— alkyl. In other embodiments, $R^1$ is not di-substituted amine. For example, in some embodiments, $R^1$ is not —N(alkyl)$_2$, including —N(CH$_3$)$_2$. In some embodiments, $R^6$ is not $C_{1-6}$ alkyl. In still other embodiments, $R^1$ is not an optionally substituted heterocyclyl. In other embodiments, $R^1$ is not an optionally substituted N-linked heterocyclyl.

In some embodiments, the pyridazinone ring can be connected to $R^4$ to form a cyclic compound, for example, a compound of Formula (Ih) In other embodiments, the pyridazinone ring can be connected to $R^5$ to form a cyclic compound, such as a compound of Formula (Ij). In some embodiments, when $R^1$ is $R^{10}$, then $R^{10}$ and $R^4$ can be taken together and include $L^1$, where $L^1$ connects $R^{10}$ and $R^4$ to form an 11- to 20-membered ring, or wherein when $R^1$ is $R^{10}$, then $R^{10}$ and $R^5$ can be taken together and include $L^1$, where $L^1$ connects $R^1$ and $R^5$ to form an 11- to 20-membered ring; wherein $R^{10}$ can be an optionally substituted —CH$_2$—, an optionally substituted —CH=CH—, O (oxygen), S (sulfur), or NR$^{11}$; and wherein $R^{11}$ can be hydrogen or $C_{1-6}$ alkyl. In some embodiments, $R^{10}$ can be NR$^{11}$. For example, $R^{10}$ can be NH. In other embodiments, $R^{10}$ can be an optionally substituted —CH$_2$—. In still other embodiments, $R^{10}$ can be O (oxygen). In yet still other embodiments, $R^{10}$ can be S (sulfur).

With respect to $L^1$, in some embodiments, $L^1$ can be -$L^2$-. In some embodiments, when $L^1$ is -$L^2$-, $L^2$ can be selected from an optionally substituted alkylene, an optionally substituted alkenylene, an optionally substituted heteroalkylene and an optionally substituted heteroalkenylene. In some embodiments, $L^2$ can be an optionally substituted alkylene, for example, an optionally substituted $C_{4-7}$ alkylene. In other embodiments, $L^2$ can be an optionally substituted alkenylene, such as an optionally substituted $C_{4-7}$ alkenylene. In still other embodiments, $L^2$ can be an optionally substituted heteroalkylene. Examples of suitable optionally substituted heteroalkylenes include the following: an optionally substituted —(CH$_2$)$_3$—O—, an optionally substituted —(CH$_2$)$_4$—O—, an optionally substituted —(CH$_2$)$_5$—O—, an optionally substituted —(CH$_2$)$_3$—S—, an optionally substituted —(CH$_2$)$_4$—S—, an optionally substituted —(CH$_2$)$_5$—S—, an optionally substituted —(CH$_2$)$_3$—NH—, an optionally substituted —(CH$_2$)$_4$—NH—, and an optionally substituted —(CH$_2$)$_5$—NH—. In yet still other embodiments, $L^2$ can be an optionally substituted heteroalkenylene, such as an optionally substituted —(CH$_2$)(CH=CH)(CH$_2$)—O—, an optionally substituted —(CH$_2$)$_2$(CH=CH)(CH$_2$)—O—, an optionally substituted —(CH$_2$)(CH=CH)(CH$_2$)$_2$—O—, an optionally substituted —(CH$_2$)$_2$(CH=CH)(CH$_2$)$_2$—O—, an optionally substituted —(CH$_2$)$_2$(CH=CH)(CH$_2$)—S—, an optionally substituted —(CH$_2$)(CH=CH)(CH$_2$)$_2$—S—, an optionally substituted —(CH$_2$)$_2$(CH=CH)(CH$_2$)$_2$—S an optionally substituted —(CH$_2$)$_2$(CH=CH)(CH$_2$)—NH—, an optionally substituted —(CH$_2$)(CH=CH)(CH$_2$)$_2$—NH— and an optionally substituted —(CH$_2$)$_2$(CH=CH)(CH$_2$)$_2$—NH—. In some embodiments, $L^2$ can be an optionally substituted —(CH$_2$)$_3$O—, an optionally substituted —(CH$_2$)$_4$—O—, or an optionally substituted —(CH$_2$)$_5$—O—. In other embodiments, $L^2$ can be an optionally substituted $C_3$ oxygen-containing heteroalkenylene, an optionally substituted $C_4$ oxygen-containing heteroalkenylene, or an optionally substituted $C_5$ oxygen-containing heteroalkenylene.

In other embodiments, $L^1$ can be -$L^3$-$L^4$-$L^5$-, wherein $L^3$ can be an optionally substituted $C_{1-4}$ alkylene; $L^4$ can be an optionally substituted cycloalkyl, an optionally substituted aryl, an optionally substituted heteroaryl, an optionally substituted heterocyclyl, O (oxygen), S (sulfur), or NR$^{11}$; and $L^5$ can be an optionally substituted $C_{1-6}$ alkylene or an optionally substituted heteroalkylene. In some embodiments, $L^3$ can be an optionally substituted $C_{1-4}$ alkylene; $L^4$ can be optionally substituted cycloalkyl, optionally substituted aryl, or optionally substituted heteroaryl; and $L^5$ can be an optionally substituted $C_{1-4}$ alkylene. In other embodiments, $L^3$ can be an optionally substituted $C_{1-4}$ alkylene; $L^4$ can be O (oxygen), S (sulfur), or $NR^{11}$; and $L^5$ can be an optionally substituted $C_{1-4}$ alkylene. In still other embodiments, $L^3$ can be optionally substituted $C_{2-4}$ alkylene; $L^4$ can be optionally substituted cycloalkyl, optionally substituted aryl, optionally substituted heteroaryl, optionally substituted heterocyclyl, O (oxygen), S (sulfur), or $NR^{11}$; and $L^5$ can be optionally substituted $C_{2-4}$ alkylene.

In some embodiments, a compound of Formula (I) can be a compound selected from Formula (Ia), Formula (Ib), Formula (Ic), Formula (Id), Formula (Ie), Formula (If) and Formula (Ig).

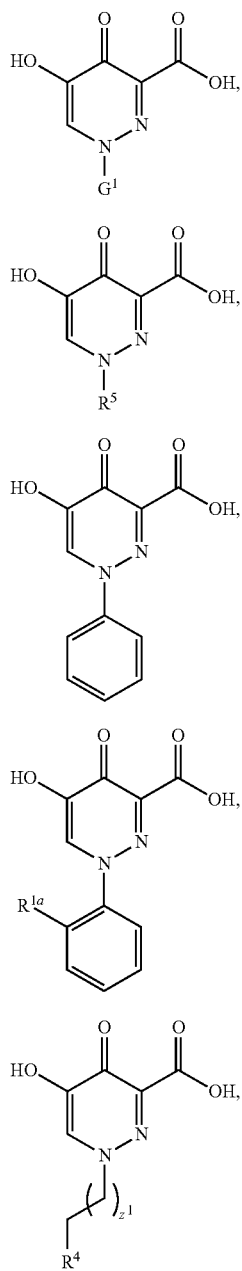

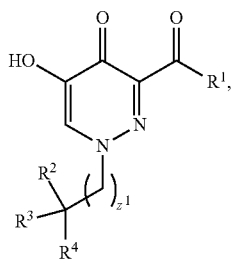

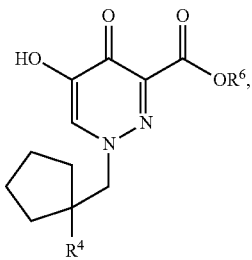

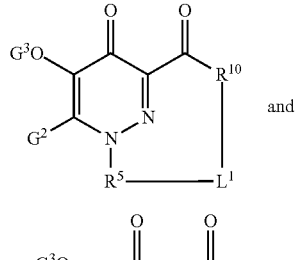

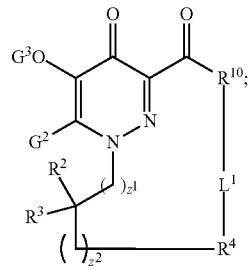

wherein $G^1$, $R^1$, $R^2$, $R^3$, $R^4$, $R^5$ and $z^1$ are as defined above with respect to Formula (I). In various embodiments, for Formula (Ic), the phenyl ring can be substituted or unsubstituted; for Formula (Id), $R^{1a}$ can be an optionally substituted N-linked heterocyclyl; for Formula (If), $R^6$ is not hydrogen; and for Formula (If), $R^1$ is not $OR^6$. In some embodiments, $R^6$ is not hydrogen and/or not a $C_{1-6}$ alkyl for Formulae (If) and/or (Ig).

Examples of compounds of Formula (I) include the following:

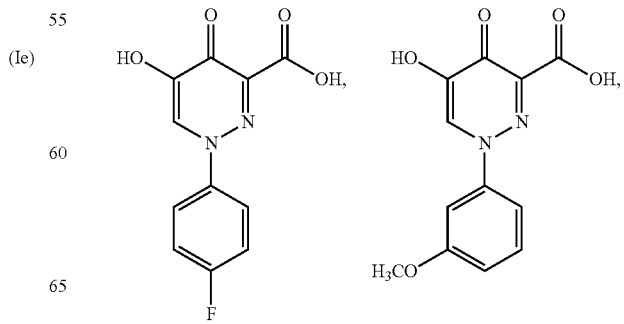

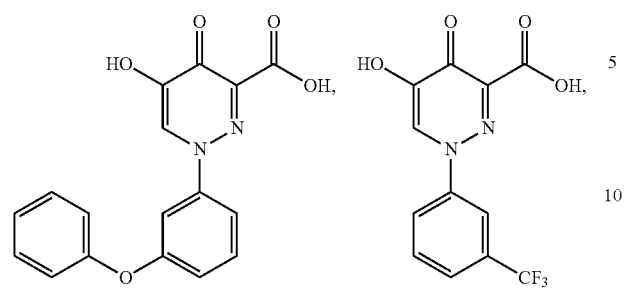
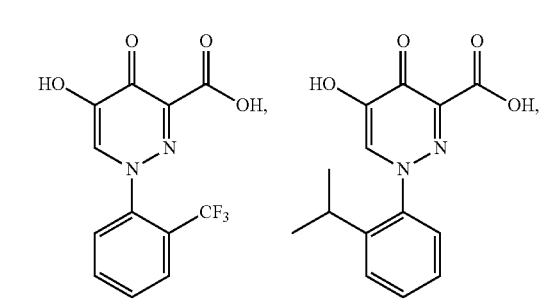
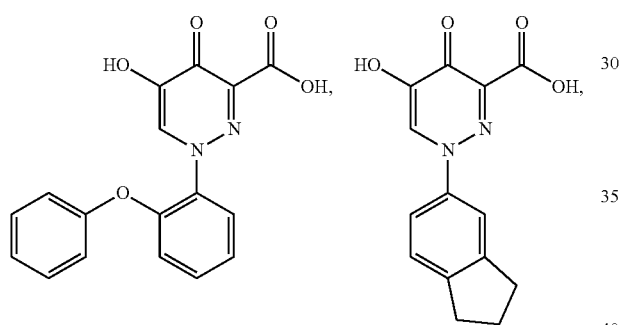
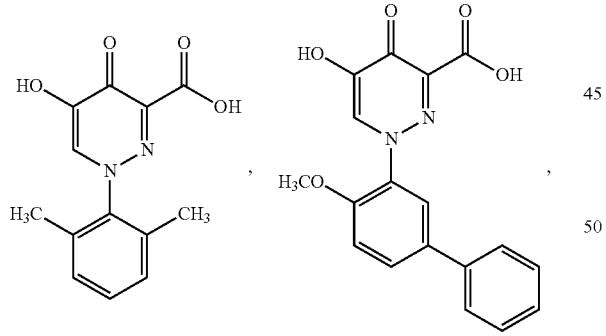
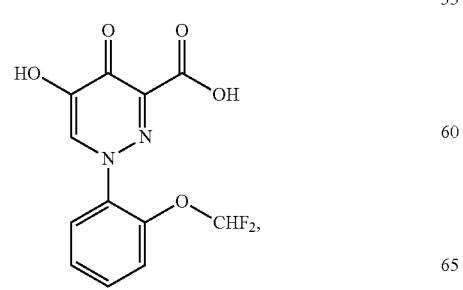
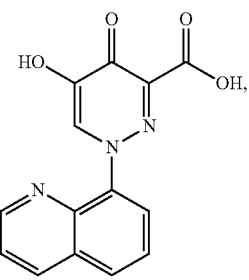
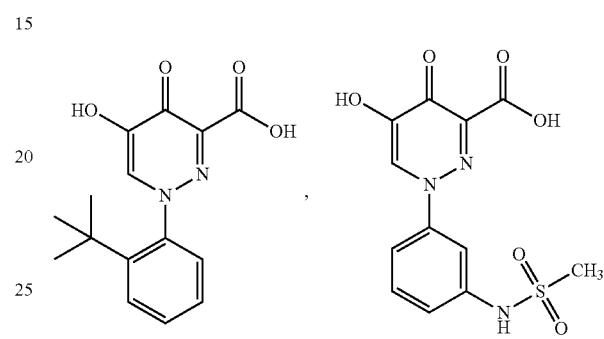
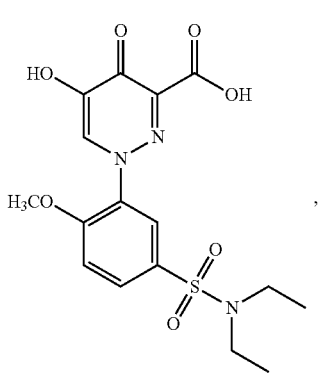
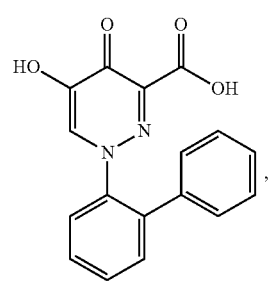
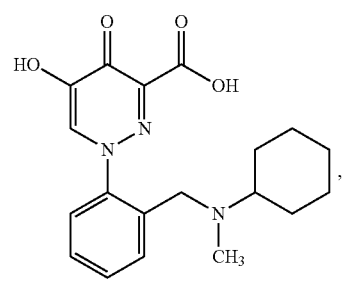

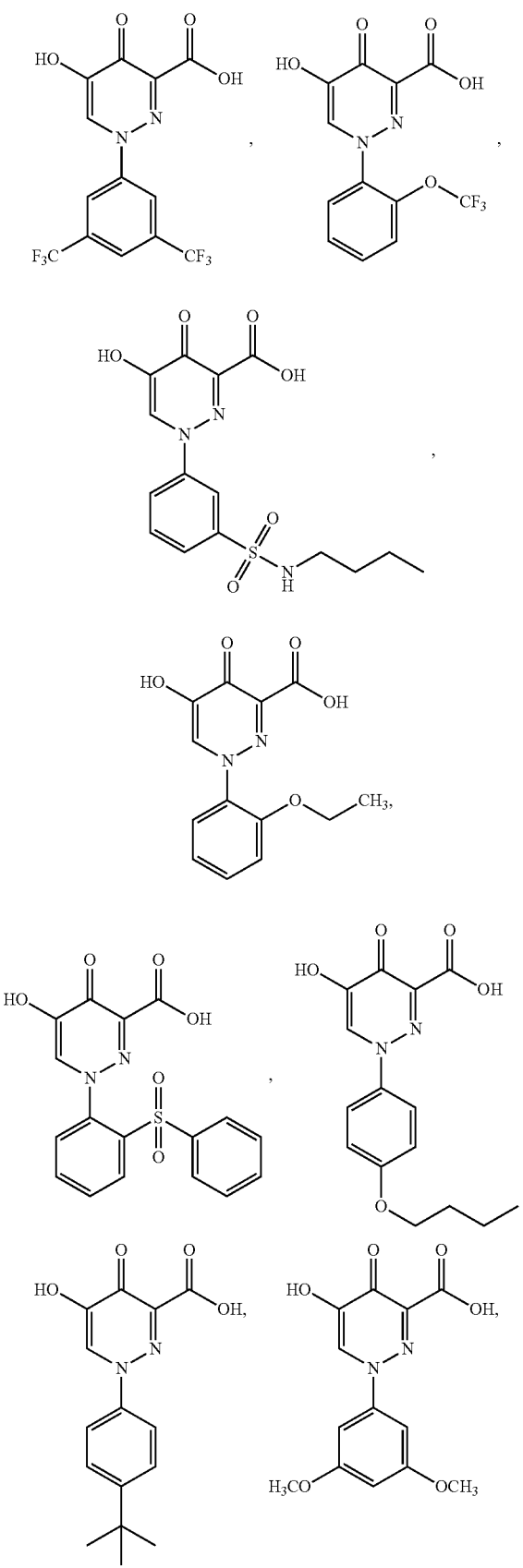
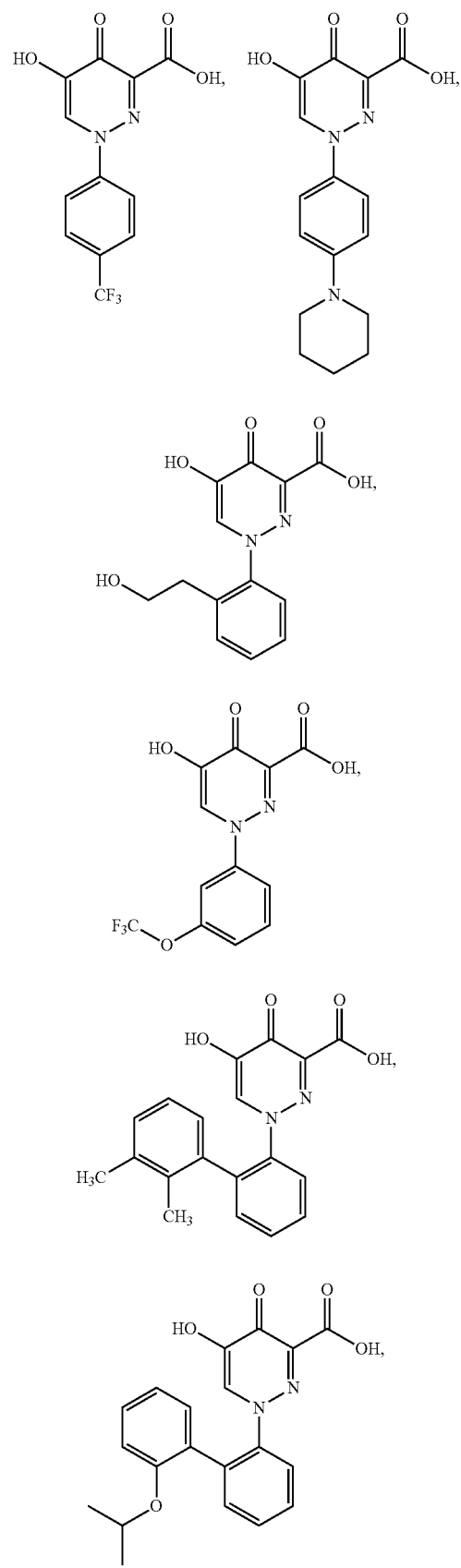

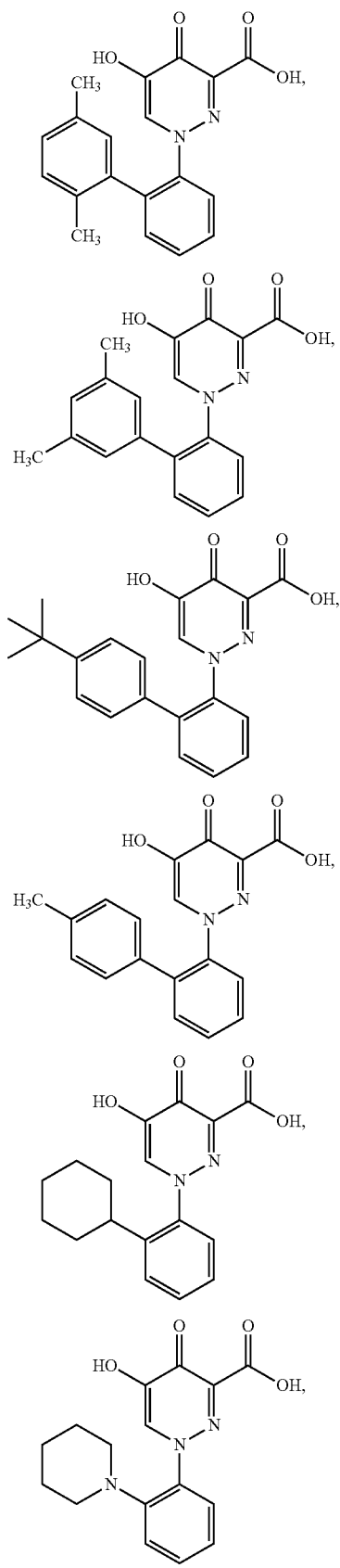
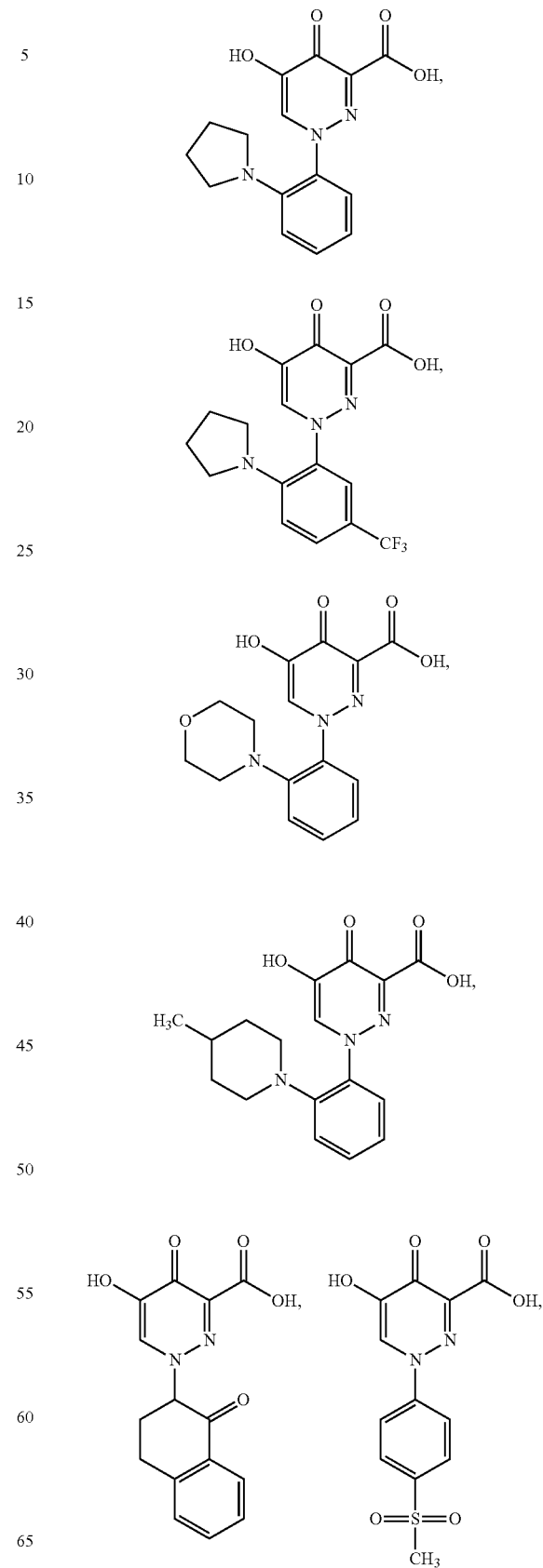

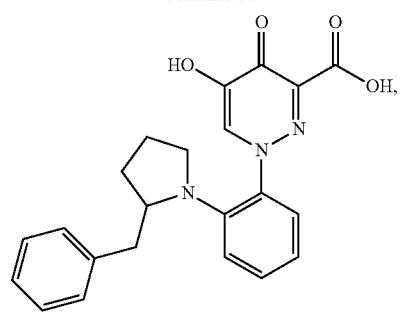
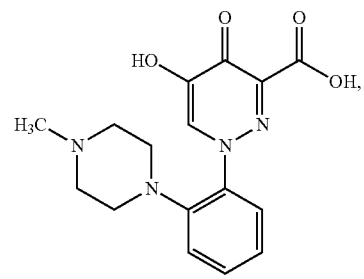
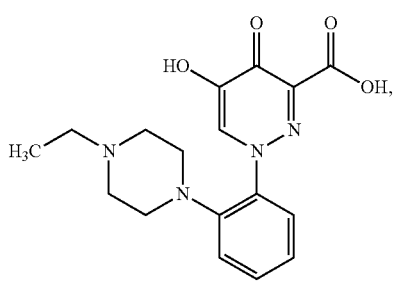
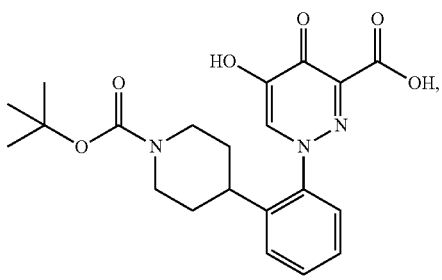
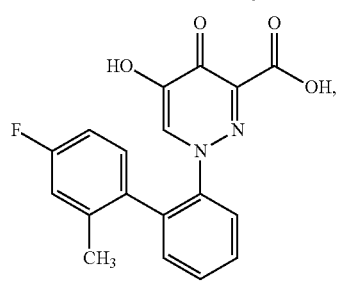
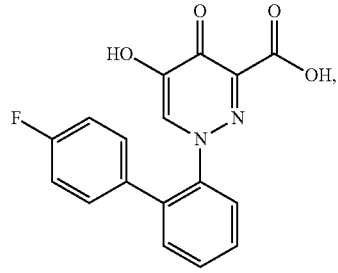
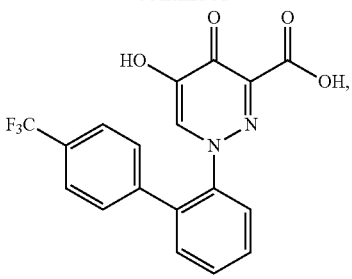
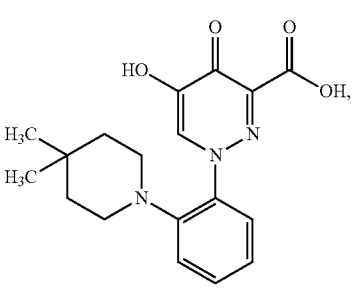
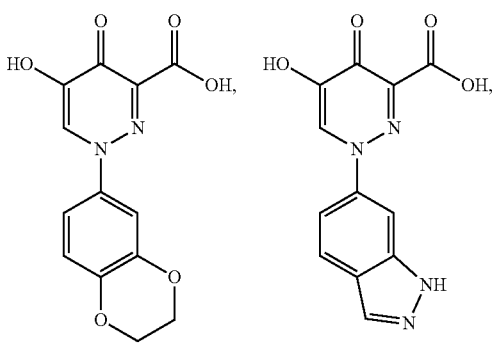
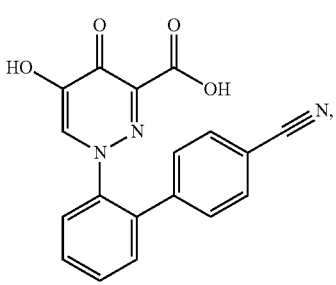

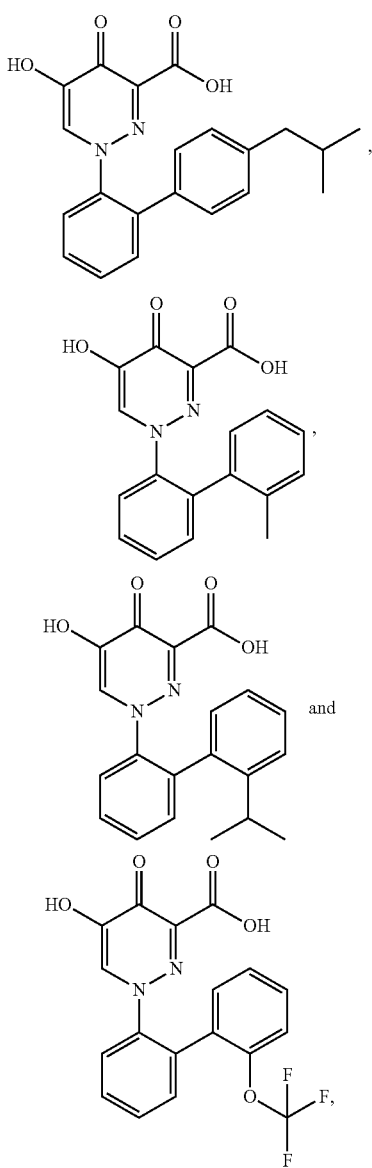
or a pharmaceutically acceptable salt of any of the foregoing.
Additional examples of compounds of Formula (I) include the following:
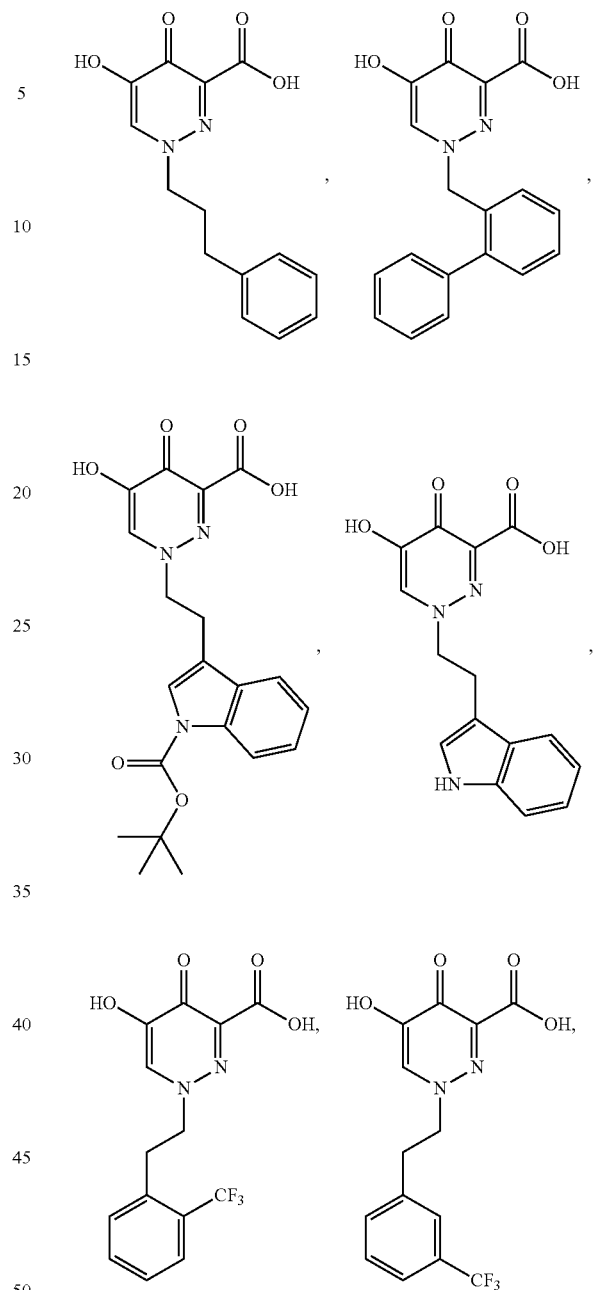
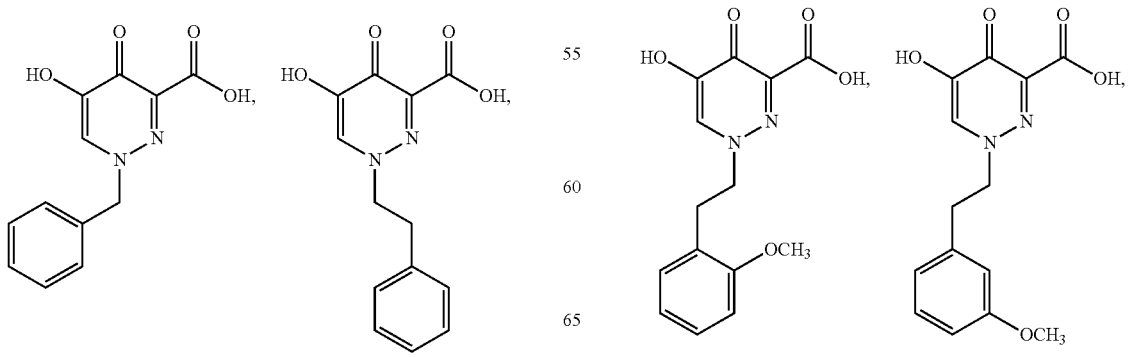

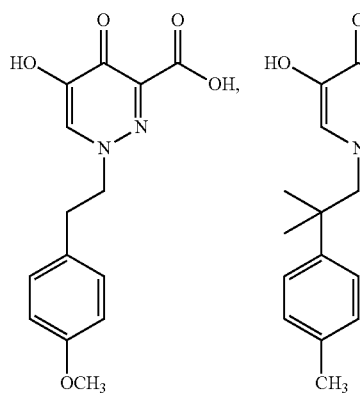
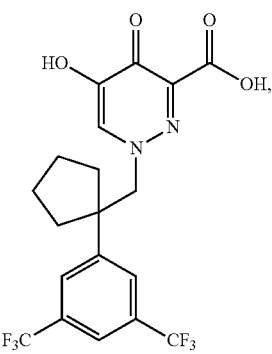
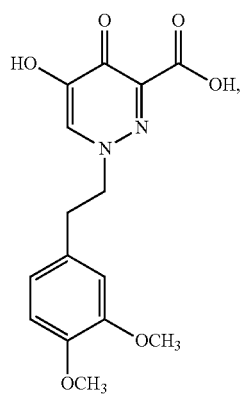
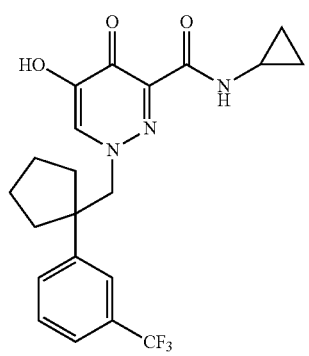
or a pharmaceutically acceptable salt of any of the foregoing.
Further examples of compounds of Formula (I) include the following:
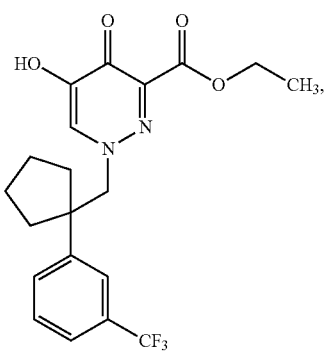
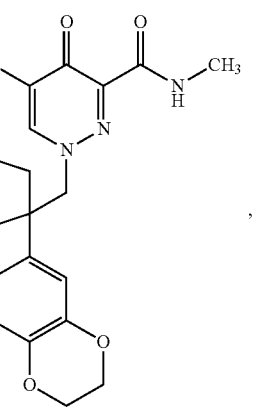
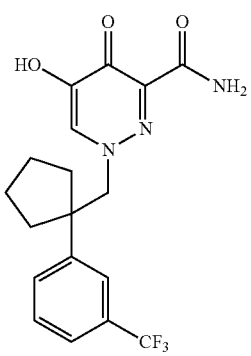
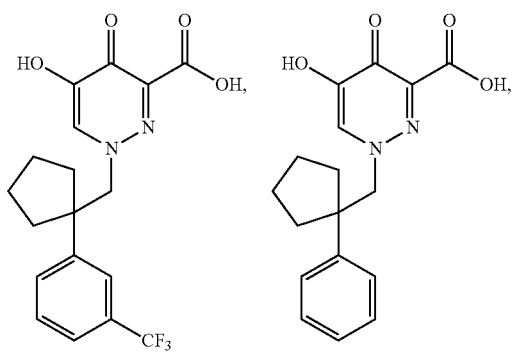
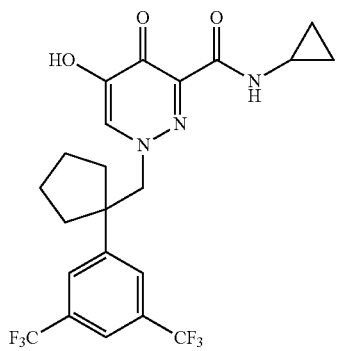

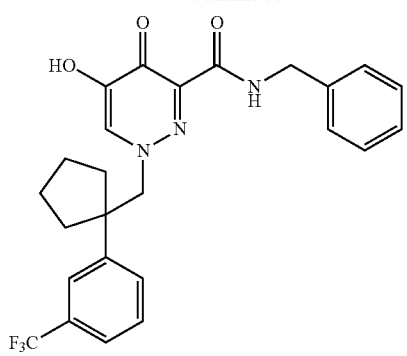
and
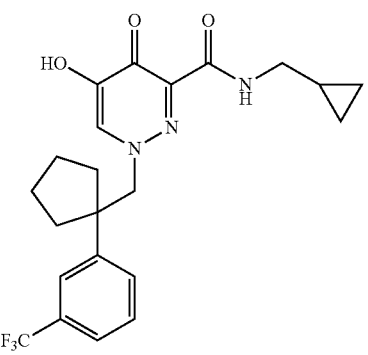
or a pharmaceutically acceptable salt of any of the foregoing.
Examples of compounds of Formula (I) include the following:
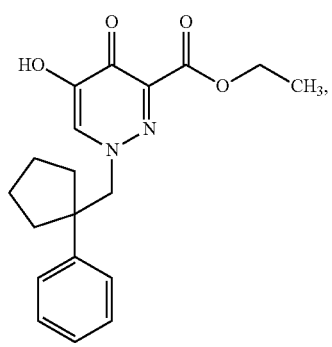
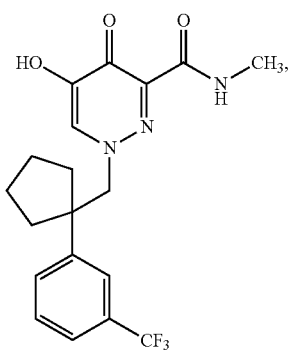
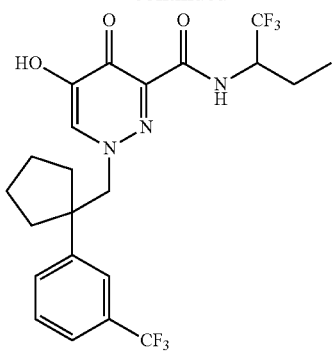
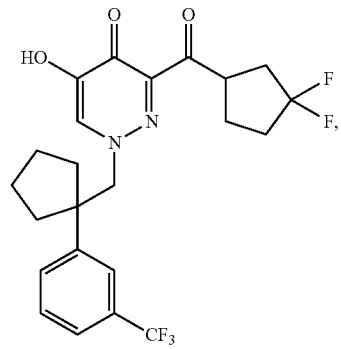
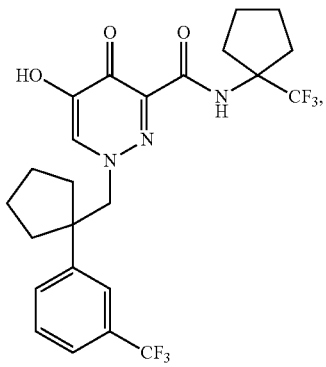
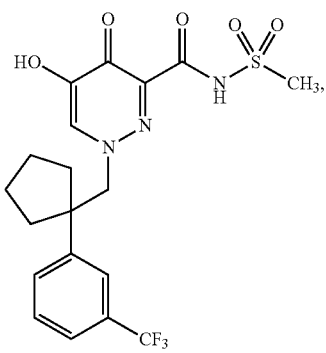

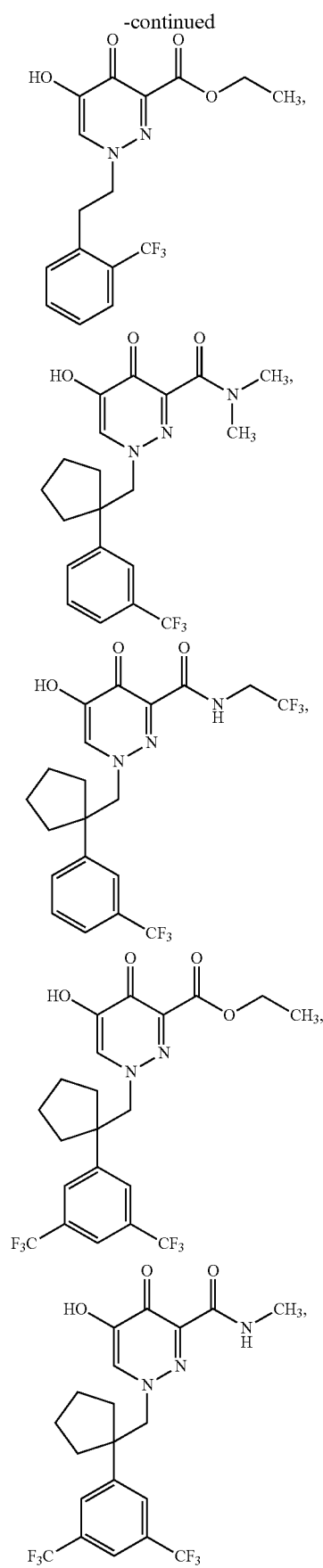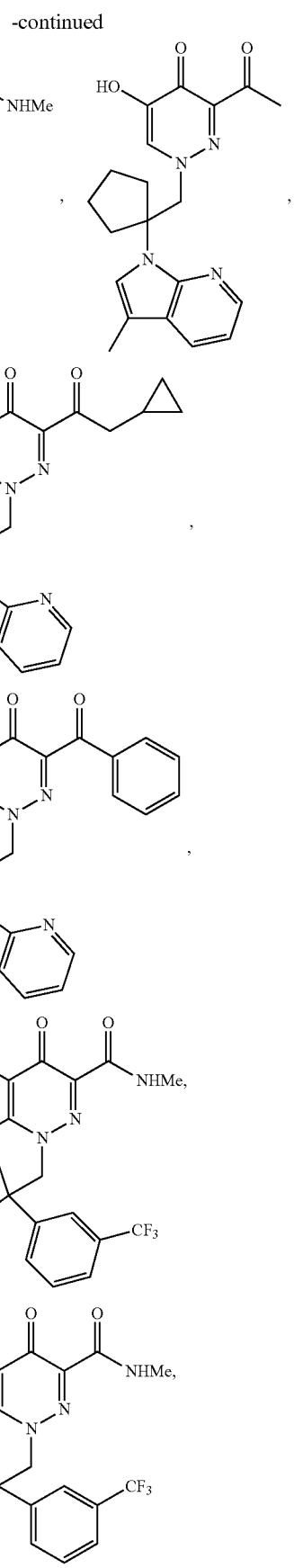

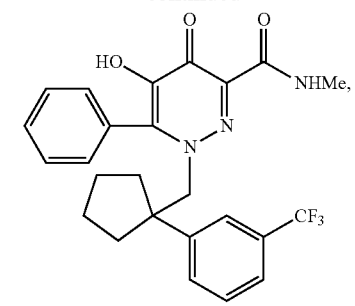
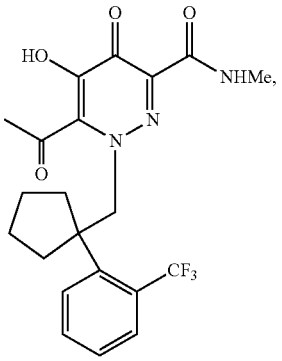
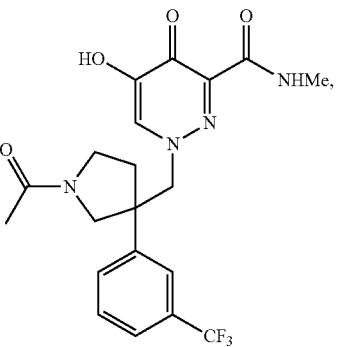
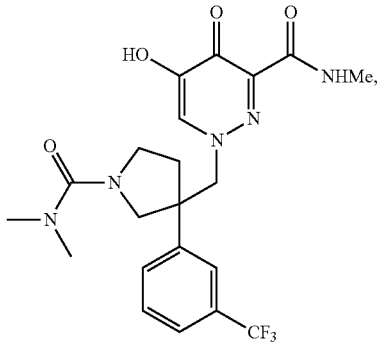
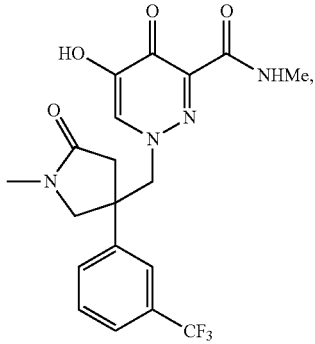
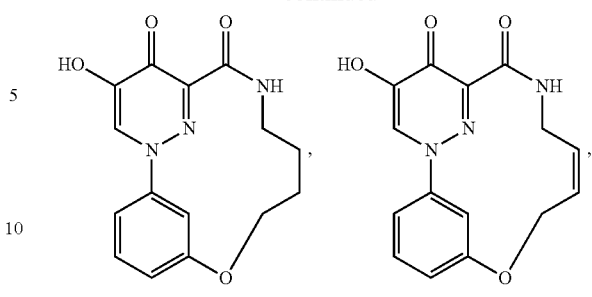
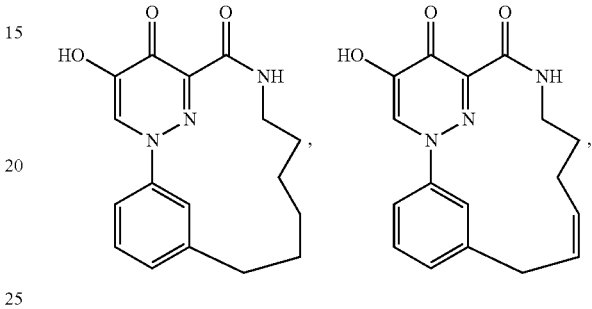
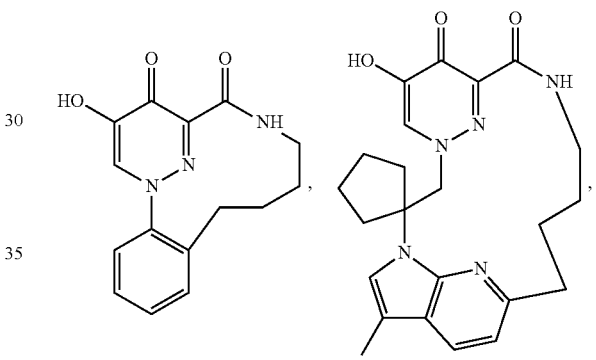
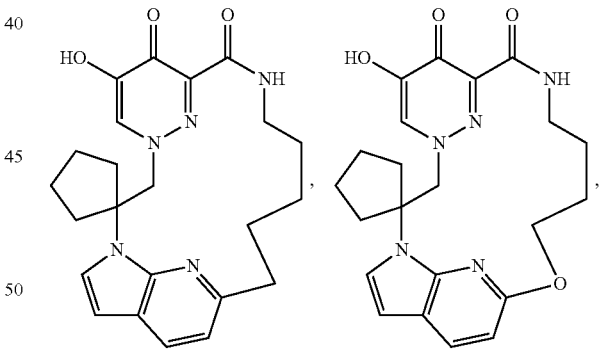
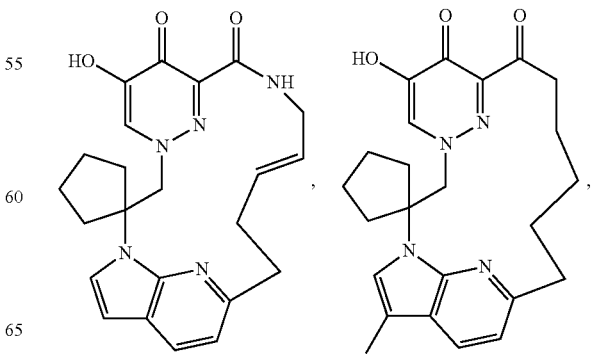

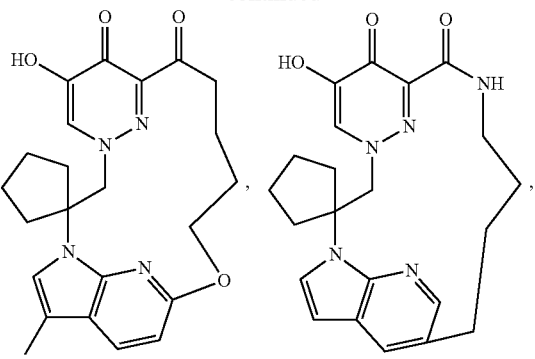
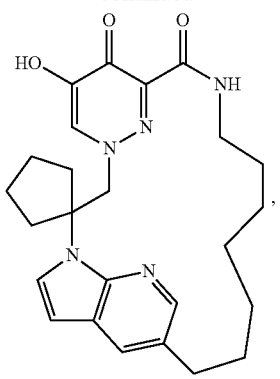
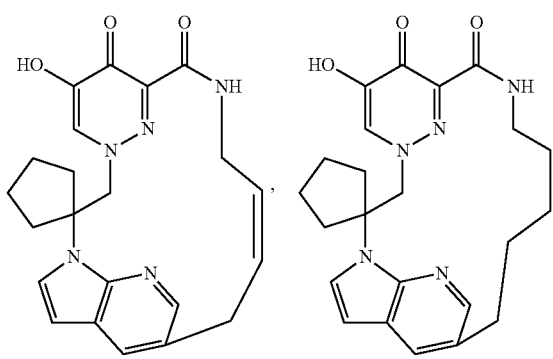
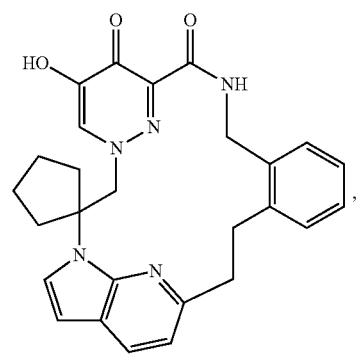
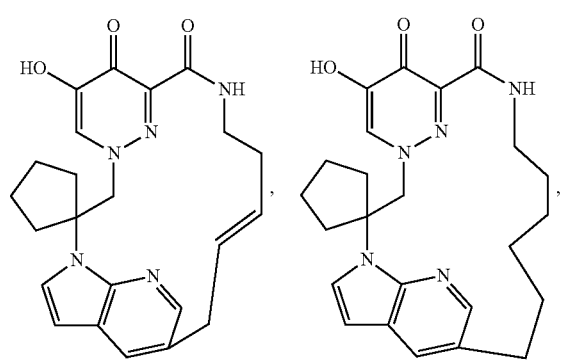
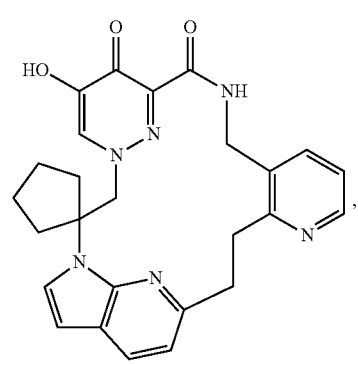
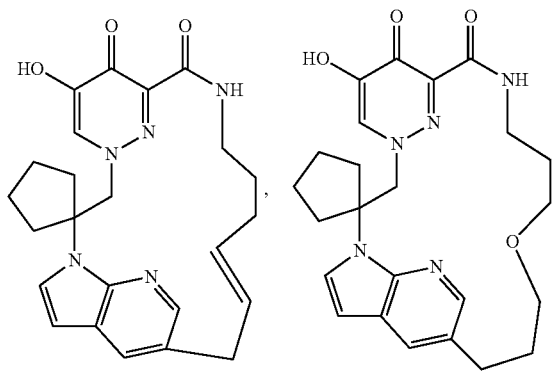
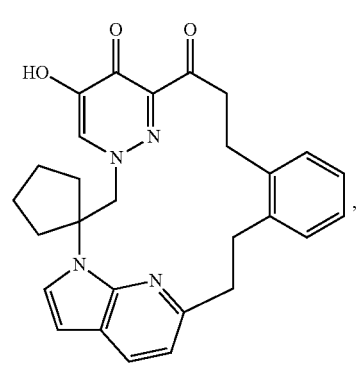

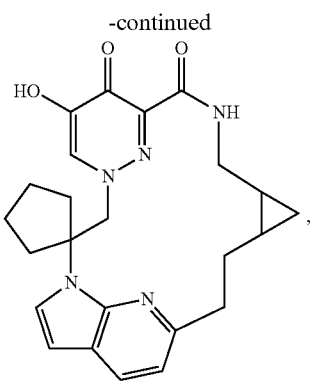

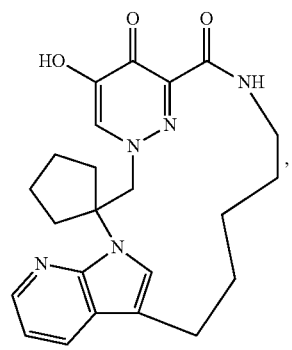

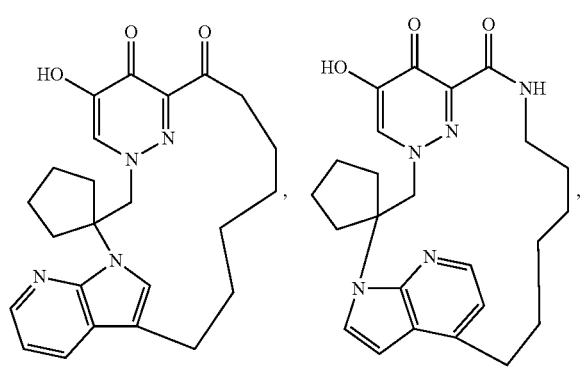

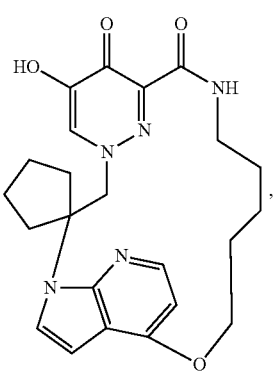

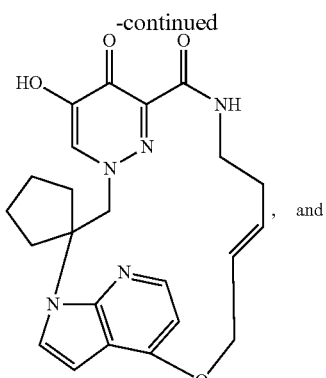

, and

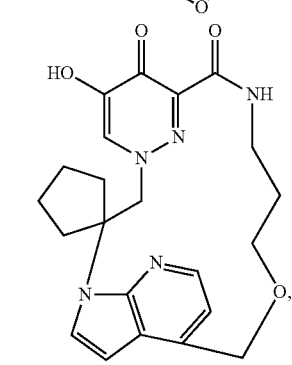

pharmaceutically acceptable salt of any of the foregoing.

Some embodiments disclosed herein relate to a compound of Formula (II), or a pharmaceutically acceptable salt thereof,

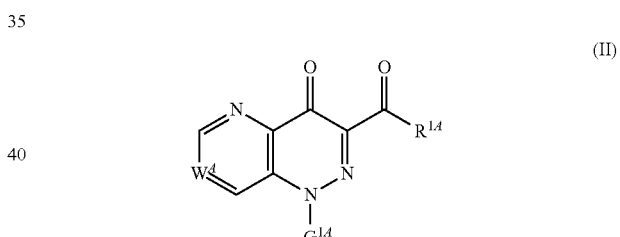

(II)

wherein: $G^{1A}$ can be selected from

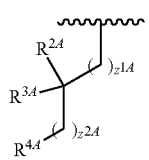

and $R^{5A}$; $R^{1A}$ can be selected from $OR^{6A}$, $NH_2$, an optionally substituted alkyl, an optionally substituted aryl, an optionally substituted mono-substituted amine, an optionally substituted di-substituted amine, an optionally substituted heterocyclyl and an optionally substituted N-sulfonamido, or $R^{10A}$; $W^A$ can be —CH— or —N—; $R^{2A}$ can be hydrogen or $C_{1-6}$ alkyl; $R^{3A}$ can be hydrogen or $C_{1-6}$ alkyl; or $R^{2A}$ and $R^{3A}$ can be taken together to form an optionally substituted $C_{3-6}$ cycloalkyl or an optionally substituted 5 to 6 membered heterocyclyl; $R^{4A}$ can be selected from an optionally substituted aryl, an optionally substituted cycloalkyl, an optionally substituted cycloalkenyl, an optionally substituted heteroaryl and an optionally substituted heterocyclyl; $R^{5A}$ can be selected from an optionally substituted aryl, an optionally substituted cycloalkyl, an optionally substituted cycloalkenyl, an optionally substituted heteroaryl and an optionally substituted heterocyclyl; $R^{6A}$ can be selected from hydrogen, $C_{1-6}$ alkyl, —C(O)$R^{7A}$ and —C(O)NR$^{8A}$R$^{9A}$; $R^{7A}$ can be selected from hydrogen, alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) and heterocyclyl($C_{1-6}$ alkyl); $R^{8A}$ and $R^{9A}$ can be independently selected from hydrogen, alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) and heterocyclyl($C_{1-6}$ alkyl); or $R^{8A}$ and $R^{9A}$ can be taken together to form an optionally substituted heterocyclyl; wherein when $R^{1A}$ is $R^{10A}$, then $R^{10A}$ and $R^{4A}$ can be taken together and include $L^{1A}$, where $L^{1A}$ connects $R^{10A}$ and $R^{4A}$ to form an 11- to 20-membered ring, or wherein when $R^{1A}$ is $R^{10A}$, then $R^{10A}$ and $R^{5A}$ can be taken together and include $L^{1A}$, where $L^{1A}$ connects $R^{1A}$ and $R^{5A}$ to form an 11- to 20-membered ring; wherein $R^{10A}$ is optionally substituted —CH$_2$—, optionally substituted —CH═CH—, O (oxygen), S (sulfur), or NR$^{11A}$; wherein $R^{11A}$ can be hydrogen or $C_{1-6}$ alkyl; and $Z^{1A}$ and $Z^{2A}$ can be independently 0, 1, 2, 3 or 4.

Various groups can be present at $R^{1A}$. In some embodiments, $R^{1A}$ can be OR$^{6A}$. For example, in some embodiments, $R^{1A}$ can be hydroxy. In other embodiments, when $R^{1A}$ is OR$^{6A}$, $R^{6A}$ can be $C_{1-6}$ alkyl. In still other embodiments, when $R^{1A}$ is OR$^{6A}$, $R^{6A}$ can be —C(O)$R^{7A}$. Example of suitable $R^{7A}$ groups include, but are not limited to, hydrogen, alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) and heterocyclyl($C_{1-6}$ alkyl). In yet still other embodiments, when $R^{1A}$ is OR$^{6A}$, $R^{6A}$ can be —C(O)NR$^{8A}$R$^{9A}$. $R^{8A}$ and $R^{9A}$ can be independently various substituents, such as hydrogen, alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) or heterocyclyl($C_{1-6}$ alkyl). In some embodiments. $R^{8A}$ and $R^{9A}$ can be taken together to form an optionally substituted heterocyclyl. Examples of suitable optionally substituted heterocyclyls that can be formed from $R^{8A}$ and $R^{9A}$ include 5 to 6 membered heterocyclyls. In some embodiments, $R^{6A}$ can be hydrogen, $C_{1-6}$ alkyl, an acyl or C-amido. In some embodiments, $R^{6A}$ can be hydrogen, —C(O)$R^{7A}$ and —C(O)NR$^{8A}$R$^{9A}$. In other embodiments, $R^{6A}$ can be —C(O)$R^{7A}$ and —C(O)NR$^{8A}$R$^{9A}$.

In some embodiments, $R^{1A}$ can be NH$_2$. In other embodiments, $R^{1A}$ can be an optionally substituted mono-substituted amine. An example of a suitable mono-substituted amine is a group having the formula of —NHR$^{1Aa}$, wherein $R^{1Aa}$ can be selected from alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) and heterocyclyl($C_{1-6}$ alkyl). In some embodiments, $R^{1Aa}$ can be selected from alkyl, alkenyl, cycloalkyl, aryl, heteroaryl, heterocyclyl, aryl($C_{1-6}$ alkyl), heteroaryl($C_{1-6}$ alkyl) and heterocyclyl($C_{1-6}$ alkyl). In other embodiments, $R^{1Aa}$ can be selected from alkyl, aryl, and aryl($C_{1-6}$ alkyl). When $R^{1A}$ is a mono-substituted amine having the formula —NHR$^{1Aa}$. $R^{1Aa}$ can be a substituted or unsubstituted group.

In other embodiments, $R^{1A}$ can be an optionally substituted di-substituted amine. For example, $R^{1A}$ can be a group having the formula of —NR$^{1Bb}$R$^{1Cc}$, wherein $R^{1Bb}$ and $R^{1Cc}$ can be independently selected from alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) and heterocyclyl($C_{1-6}$ alkyl). In some embodiments, $R^{1Bb}$ and $R^{1Cc}$ can be independently selected from alkyl, alkenyl, cycloalkyl, aryl, heteroaryl, heterocyclyl, aryl($C_{1-6}$ alkyl), heteroaryl($C_{1-6}$ alkyl) and heterocyclyl($C_{1-6}$ alkyl). In other embodiments, $R^{1Bb}$ and $R^{1Cc}$ can be independently selected from alkyl, aryl, and aryl($C_{1-6}$ alkyl). In some embodiments, $R^{1Bb}$ and $R^{1Cc}$ can be the same. In other embodiments, $R^{1Bb}$ and $R^{1Cc}$ can be different. When $R^{1A}$ is a di-substituted amine having the formula —NR$^{1Bb}$R$^{1Cc}$. $R^{1Bb}$ and $R^{1Cc}$ can be substituted or unsubstituted groups.

In still other embodiments, $R^{1A}$ can be an optionally substituted heterocyclyl. Various heterocyclyls can be used and can be connected either through a ring carbon or a ring heteroatom. In some embodiments, the heterocyclyl can be a 5 to 6 membered heterocyclyl. In some embodiments, the heterocyclyl can include 1 heteroatom. In other embodiments, the heterocyclyl can include 2 heteroatoms, wherein the heteroatoms can be the same or different. In some embodiments, $R^{1A}$ can be an optionally substituted heterocyclyl that contains at least one nitrogen in the ring and is an N-linked heterocyclyl. In some embodiments, $R^{1A}$ can be an unsubstituted heterocyclyl. In some embodiments, $R^{1A}$ can be a substituted heterocyclyl.

In still other embodiments, $R^{1A}$ can be an optionally substituted N-sulfonamido. In some embodiments, when $R^{1A}$ is an optionally substituted N-sulfonamido, the groups attached to the sulfur can be independently selected from hydrogen, alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) and heterocyclyl($C_{1-6}$ alkyl). An example of suitable structure for the optionally substituted N-sulfonamido is —NHS(O)$_2$R$^{1Dd}$, wherein $R^{1Dd}$ can be selected from alkyl, alkenyl, alkynyl, cycloalkyl, cycloalkenyl, cycloalkynyl, aryl, heteroaryl, heterocyclyl, aryl($C_{1-6}$ alkyl), heteroaryl($C_{1-6}$ alkyl) and heterocyclyl($C_{1-6}$ alkyl). In some embodiments, $R^{1Dd}$ can be selected from alkyl, alkenyl, cycloalkyl, aryl, heteroaryl, heterocyclyl, aryl($C_{1-6}$ alkyl), heteroaryl($C_{1-6}$ alkyl) and heterocyclyl($C_{1-6}$ alkyl). In other embodiments, $R^{1Dd}$ can be selected from alkyl, aryl, and aryl($C_{1-6}$ alkyl). When $R^{1A}$ is a N-sulfonamido having the formula —NHS(O)$_2$R$^{1Dd}$, $R^{1Dd}$ can be a substituted or unsubstituted group.

In some embodiments, $G^{1A}$ can be

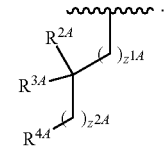

In some embodiments, $R^{2A}$ can be hydrogen. In other embodiments. $R^{2A}$ can be a $C_{1-6}$ alkyl. Examples of suitable $C_{1-6}$ alkyl include methyl, ethyl, n-propyl, isopropyl, n-butyl, isobutyl, tert-butyl, straight or branched pentyl and straight or branched hexyl. In some embodiments. $R^{3A}$ can be hydrogen. In other embodiments, $R^{3A}$ can be a $C_{1-6}$ alkyl. In some embodiments, $R^{2A}$ and $R^{3A}$ can be the same. In other embodiments, $R^{2A}$ and $R^{3A}$ can be different. In some embodiments, $R^{2A}$ and $R^{3A}$ can both be hydrogen. In other embodiments, $R^{2A}$ and $R^{3A}$ can both be a $C_{1-6}$ alkyl. For example, $R^{2A}$ and $R^{3A}$ can both be methyl. Alternatively, in some embodiments, $R^{2A}$ and $R^{3A}$ can be taken together to form an optionally substituted $C_{3-6}$ cycloalkyl. Suitable cycloalkyls include cyclopropyl, cyclobutyl, cyclopentyl and cyclohexyl. When $R^{2A}$ and $R^{3A}$ are taken together, the cycloalkyl group can be unsubstituted. In the alternative, the cycloalkyl group can be substituted with one or more substituents. In some embodiments, $R^{2A}$ and $R^{3A}$ can be taken together to form an optionally substituted $C_5$ cycloalkyl. In some embodiments, $R^{2A}$ and $R^{3A}$ can be taken together to form an unsubstituted $C_5$ cycloalkyl. In other embodiments, $R^{2A}$ and $R^{3A}$ can be taken together to form a mono-substituted or di-substituted $C_5$ cycloalkyl. In some embodiments, $R^{2A}$ and $R^{3A}$ can be taken together to form an optionally substituted 5 to 6 membered heterocyclyl. Examples of heterocyclyls that can be formed include, but are not limited to, optionally substituted nitrogen containing 5 to 6 membered heterocyclyls. In some embodiments, $R^{2A}$ and $R^{3A}$ can be taken together to form an optionally substituted 5 to 6 membered N-linked heterocyclyl, for example, an optionally substituted piperdino or an optionally substituted pyrrolidino.

Various groups can be $R^{4A}$. In some embodiments, $R^{4A}$ can be an optionally substituted aryl. In some embodiments, $R^{4A}$ can be an optionally substituted naphthyl. In other embodiments, $R^{4A}$ can be an optionally substituted phenyl. In some embodiments, $R^{4A}$ can be an unsubstituted phenyl. In other embodiments, $R^{4A}$ can be a substituted phenyl. One or more groups can be present on a substituted phenyl. For example, the substituted phenyl can be a mono-substituted phenyl, such as an ortho-substituted phenyl, a meta-substituted phenyl or a para-substituted phenyl. As another example, the substituted phenyl can be a di-substituted phenyl, such as a 2,5-di-substituted phenyl, 2,4-di-substituted phenyl and 2,3-di-substituted phenyl. In some embodiments, the substituted phenyl can be substituted with 3 or more substituent.

In other embodiments, $R^{4A}$ can be an optionally substituted cycloalkyl or an optionally substituted cycloalkenyl. For example, $R^{4A}$ can be an optionally substituted $C_{4-6}$ cycloalkyl. In some embodiments, $R^{4A}$ can be an unsubstituted cycloalkyl. In other embodiments, $R^{4A}$ can be a substituted cycloalkyl.

In still other embodiments, $R^{4A}$ can be an optionally substituted heteroaryl. In some embodiments, $R^{4A}$ can be an unsubstituted heteroaryl. In other embodiments, $R^{4A}$ can be a substituted heteroaryl. Examples of suitable heteroaryls are described herein. In some embodiments, $R^{4A}$ can be an optionally substituted monocyclic heteroaryl. In other embodiments, $R^{4A}$ can be an optionally substituted bicyclic heteroaryl, for example, an optionally substituted 1H-pyrrolo[2,3-b]pyridine.

In yet still other embodiments, $R^{4A}$ can be an optionally substituted heterocyclyl. In some embodiments, $R^{4A}$ can be an unsubstituted heterocyclyl. In other embodiments, $R^{4A}$ can be a substituted heterocyclyl. In some embodiments, $R^{4A}$ can be an optionally substituted monocyclic heterocyclyl. In other embodiments, $R^{4A}$ can be an optionally substituted bicyclic heterocyclyl.

When $R^{4A}$ is substituted, one or more groups can be present. When two or more of the substituents are present, two or more of the substituents can be the same. In some embodiments, when multiple substituents are present on $R^{4A}$, at least one of the substituents is different from the remaining substituents. In some embodiments, all of the substituents present on $R^{4A}$ are different. In some embodiments, $R^{4A}$ can be substituted with one or more substituents selected from halogen, $C_{1-6}$ alkyl, alkoxy, aryloxy, haloalkyl, haloalkoxy, hydroxyalkyl, N-sulfonamido, S-sulfonamido, sulfonyl, an optionally substituted aryl, an optionally substituted cycloalkyl, an optionally substituted heterocyclyl, carbonyl, C-carboxy, —$CH_2$-(mono-substituted amine) and $CH_2$-(di-substituted amine). In some embodiments, when $R^{4A}$ is a substituted aryl, the aryl can be substituted with one or more groups selected from $C_{1-6}$ alkyl, alkoxy, aryl (for example, phenyl), cyano, halogen, haloalkyl and haloalkoxy. In some embodiments, when $R^{4A}$ is a substituted cycloalkyl, the cycloalkyl can be substituted with $C_{1-6}$ alkyl, alkoxy, halogen and haloalkyl. In some embodiments, when $R^{4A}$ is a substituted heterocyclyl, the heterocyclyl can be substituted with $C_{1-6}$ alkyl, alkoxy, halogen, haloalkyl, aryl($C_{1-6}$ alkyl) and C-carboxy. In some embodiments, the substituted heterocyclyl of $R^{4A}$ can be substituted with a substituted or an unsubstituted benzyl.

The pyridazinone ring can be connected to $R^{4A}$ via a substituted or unsubstituted alkylene. In some embodiments. $Z^{1A}$ can be 0. In other embodiments. $Z^{1A}$ can be 1. In still other embodiments. $Z^{1A}$ can be 2. In yet still other embodiments, $Z^{1A}$ can be 3. In some embodiments, $Z^{1A}$ can be 4. In some embodiments, $Z^A$ can be 0. In other embodiments, $Z^{2A}$ can be 1. In still other embodiments, $Z^{2A}$ can be 2. In yet still other embodiments, $Z^{2A}$ can be 3. In some embodiments. $Z^{2A}$ can be 4. In some embodiments, $Z^{1A}$ can be 1, and $Z^{2A}$ can be 0. In other embodiments, $Z^{1A}$ and $Z^{2A}$ can be both 1. In still other embodiments, $Z^{1A}$ and $Z^{2A}$ can be both >1. In yet still other embodiments, at least one of $Z^{1A}$ and $Z^{2A}$ can be 1. In some embodiments, at least one of $Z^{1A}$ and $Z^{2A}$ can be 1, and the other of $Z^{1A}$ and $Z^{2A}$ can be >1.

In other embodiments, $G^{1A}$ can be $R^{5A}$. As with $R^{4A}$, $R^{5A}$ can be a variety of groups. In some embodiments, $R^{5A}$ can be an optionally substituted aryl. In some embodiments, $R^{5A}$ can be an optionally substituted naphthyl. In other embodiments, $R^{5A}$ can be an optionally substituted phenyl. In some embodiments, $R^{5A}$ can be an unsubstituted phenyl. In other embodiments, $R^{5A}$ can be a substituted phenyl. One or more groups can be present on a substituted phenyl. For example, the substituted phenyl can be a mono-substituted phenyl, such as an ortho-substituted phenyl, a meta-substituted phenyl or a para-substituted phenyl. As another example, the substituted phenyl can be a di-substituted phenyl, such as a 2,5-di-substituted phenyl. 2,4-di-substituted phenyl and 2,3-di-substituted phenyl. In some embodiments, the substituted phenyl can be substituted with 3 or more substituents.

In other embodiments, $R^{5A}$ can be an optionally substituted cycloalkyl or an optionally substituted cycloalkenyl. For example, $R^{5A}$ can be a substituted or an unsubstituted $C_{4-6}$ cycloalkyl. In some embodiments, $R^{5A}$ can be an unsubstituted cycloalkyl. In other embodiments, $R^{5A}$ can be a substituted cycloalkyl.

In still other embodiments, $R^{5A}$ can be an optionally substituted heteroaryl. In some embodiments, $R^{5A}$ can be an unsubstituted heteroaryl. In other embodiments, $R^{5A}$ can be a substituted heteroaryl. In some embodiments, $R^{5A}$ can be an optionally substituted monocyclic heteroaryl. In other embodiments, $R^{5A}$ can be an optionally substituted bicyclic heteroaryl.

In yet still other embodiments, $R^{5A}$ can be an optionally substituted heterocyclyl. In some embodiments. $R^{5A}$ can be an unsubstituted heterocyclyl. In other embodiments, $R^{5A}$ can be a substituted heterocyclyl. In some embodiments, $R^{5A}$ can be an optionally substituted monocyclic heterocyclyl. In other embodiments, $R^{5A}$ can be an optionally substituted bicyclic heterocyclyl.

When $R^{5A}$ is substituted, one or more groups can be present. When two or more of the substituents are present, two or more of the substituents can be the same. In some embodiments, when multiple substituents are present on $R^{5A}$, at least one of the substituents is different from the remaining substituents. In some embodiments, all of the substituents present on $R^{5A}$ are different. In some embodiments, $R^{5A}$ can be substituted with one or more substituents selected from halogen, $C_{1-6}$ alkyl, alkoxy, aryloxy, haloalkyl, haloalkoxy, hydroxyalkyl, N-sulfonamido, S-sulfonamido, sulfonyl, an optionally substituted aryl, an optionally substituted cycloalkyl, an optionally substituted heterocyclyl, carbonyl, C-carboxy, —CH$_2$-(mono-substituted amine) and CH$_2$-(di-substituted amine). In some embodiments, when $R^{5A}$ is a substituted aryl, the aryl can be substituted with one or more groups selected from $C_{1-6}$ alkyl, alkoxy, halogen and haloalkyl. In other embodiments, when $R^{5A}$ is a substituted aryl, the aryl can be substituted with one or more groups selected from $C_{1-4}$, alkyl, alkoxy, aryl (for example, phenyl), cyano, halogen, haloalkyl and haloalkoxy. In some embodiments, when $R^{5A}$ is a substituted cycloalkyl, the cycloalkyl can be substituted with $C_{1-6}$ alkyl, alkoxy, halogen and haloalkyl. In some embodiments, when $R^{5A}$ is a substituted heterocyclyl, the heterocyclyl can be substituted with $C_{1-6}$ alkyl, alkoxy, halogen, haloalkyl, aryl ($C_{1-6}$ alkyl) and C-carboxy. In some embodiments, the substituted heterocyclyl of $R^{5A}$ can be substituted with a substituted or an unsubstituted benzyl.

In some embodiments, $R^{1A}$ is not mono-substituted amine, such as —NH-alkyl. In other embodiments, $R^{1A}$ is not di-substituted amine. For example, in some embodiments, $R^{1A}$ is not —N(alkyl)$_2$, including —N(CH$_3$)$_2$. In some embodiments, $R^{6A}$ is not $C_{1-6}$ alkyl. In still other embodiments, $R^{1A}$ is not an optionally substituted heterocyclyl. In other embodiments, $R^{1A}$ is not an optionally substituted N-linked heterocyclyl.

In some embodiments, the fused bicyclic nitrogen-containing ring system of Formula (II) can be connected to $R^{4A}$ to form a cyclic compound, for example, a compound of Formula (Ih) In other embodiments, the fused bicyclic nitrogen-containing ring system of Formula (II) can be connected to $R^{5A}$ to form a cyclic compound, such as a compound of Formula (Ij). In some embodiments, when $R^{1A}$ is $R^{10A}$, then $R^{10A}$ and $R^{4A}$ can be taken together and include $L^{1A}$, where $L^{1A}$ connects $R^{10A}$ and $R^{4A}$ to form an 11- to 20-membered ring, or wherein when $R^{1A}$ then $R^{10A}$ and $R^{5A}$ can be taken together and include $L^{1A}$, where $L^{1A}$ connects $R^{1A}$ and $R^{5A}$ to form an 11- to 20-membered ring; wherein $R^{10A}$ can be an optionally substituted —CH$_2$—, an optionally substituted —CH=CH—. O (oxygen), S (sulfur), or $NR^{11A}$; and wherein $R^{11A}$ can be hydrogen or $C_{1-6}$ alkyl. In some embodiments, $R^{10A}$ can be $NR^{11A}$. For example, $R^{11A}$ can be NH. In other embodiments, $R^{10A}$ can be an optionally substituted —CH$_2$—. In still other embodiments, $R^{10A}$ can be O (oxygen). In yet still other embodiments, $R^{10A}$ can be S (sulfur).

With respect to $L^{1A}$, in some embodiments, $L^{1A}$ can be -$L^{2A}$-. In some embodiments, when $L^{1A}$ is -$L^{2A}$-, $L^{2A}$ can be selected from an optionally substituted alkylene, an optionally substituted alkenylene, an optionally substituted heteroalkylene and an optionally substituted heteroalkenylene. In some embodiments, $L^{2A}$ can be an optionally substituted alkylene, for example, an optionally substituted $C_{4-7}$ alkylene. In other embodiments, $L^{2A}$ can be an optionally substituted alkenylene, such as an optionally substituted $C_{4-7}$ alkenylene. In still other embodiments, $L^{2A}$ can be an optionally substituted heteroalkylene. Examples of suitable optionally substituted heteroalkylenes include the following: an optionally substituted —(CH$_2$)$_3$—O—, an optionally substituted —(CH$_2$)$_4$—O—, an optionally substituted —(CH$_2$)$_5$—O—, an optionally substituted —(CH$_2$)$_3$—S—, an optionally substituted —(CH$_2$)$_4$—S—, an optionally substituted —(CH$_2$)$_5$—S—, an optionally substituted —(CH$_2$)$_3$—NH—, an optionally substituted —(CH$_2$)$_4$—NH—, and an optionally substituted —(CH$_2$)$_5$—NH—. In yet still other embodiments, $L^{2A}$ can be an optionally substituted heteroalkenylene, such as an optionally substituted —(CH$_2$)(CH=CH)(CH$_2$)—O—, an optionally substituted —(CH$_2$)$_2$(CH=CH)(CH$_2$)—O—, an optionally substituted —(CH$_2$)(CH=CH)(CH$_2$)$_2$—O—, an optionally substituted —(CH$_2$)$_2$(CH=CH)(CH$_2$)$_2$—O—, an optionally substituted —(CH$_2$)$_2$(CH=CH)(CH$_2$)—S—, an optionally substituted —(CH$_2$)(CH=CH)(CH$_2$)$_2$—S—, an optionally substituted —(CH$_2$)$_2$(CH=CH)(CH$_2$)$_2$—S an optionally substituted —(CH$_2$)$_2$(CH=CH)(CH$_2$)—NH—, an optionally substituted —(CH$_2$)(CH=CH)(CH$_2$)$_2$—NH— and an optionally substituted —(CH$_2$)$_2$(CH=CH)(CH$_2$)$_2$—NH—. In some embodiments, $L^{2A}$ can be an optionally substituted —(CH$_2$)$_3$—O—, an optionally substituted —(CH$_2$)$_4$—O—, or an optionally substituted —(CH$_2$)$_5$—O—. In other embodiments, $L^{2A}$ can be an optionally substituted $C_3$ oxygen-containing heteroalkenylene, an optionally substituted $C_4$ oxygen-containing heteroalkenylene, or an optionally substituted $C_5$ oxygen-containing heteroalkenylene.

In other embodiments, $L^{1A}$ can be -$L^{3A}$-$L^{4A}$-$L^{5A}$-, wherein $L^{3A}$ can be an optionally substituted $C_{1-6}$ alkylene; $L^{4A}$ can be an optionally substituted cycloalkyl, an optionally substituted aryl, an optionally substituted heteroaryl, an optionally substituted heterocyclyl, O (oxygen), S (sulfur), or $NR^{11A}$; and $L^{5A}$ can be an optionally substituted $C_{1-6}$ alkylene or an optionally substituted heteroalkylene. In some embodiments, $L^{3A}$ can be an optionally substituted $C_{1-4}$ alkylene; $L^{4A}$ can be optionally substituted cycloalkyl, optionally substituted aryl, or optionally substituted heteroaryl; and $L^{5A}$ can be an optionally substituted $C_{1-4}$ alkylene. In other embodiments, $L^{3A}$ can be an optionally substituted $C_{1-4}$ alkylene; $L^{4A}$ can be O (oxygen), S (sulfur), or $NR^{11A}$; and $L^{5A}$ can be an optionally substituted $C_{1-4}$ alkylene. In still other embodiments, $L^{3A}$ can be optionally substituted $C_{2-4}$ alkylene; $L^{4A}$ can be optionally substituted cycloalkyl, optionally substituted aryl, optionally substituted heteroaryl, optionally substituted heterocyclyl, O (oxygen), S (sulfur), or $NR^{11A}$; and $L^{5A}$ can be optionally substituted $C_{2-4}$ alkylene.

In some embodiments, including those disclosed herewith respect to Formula (II), $W^A$ can be —N (nitrogen)-. In other embodiments, including those disclosed herewith respect to Formula (II), $W^A$ can be —CH$_2$—. In some embodiments, one or more of the carbon atoms of the fused-bicyclic nitrogen-containing ring system of Formula (II) can be substituted. For example, one or both of the carbon atoms adjacent to $W^A$ can be substituted carbon instead of —CH— and/or $W^A$ can be substituted carbon instead of —CH—.

In some embodiments, a compound of Formula (II) can be a compound selected from Formula (IIa), Formula (IIb), Formula (IIc) and Formula (IId):

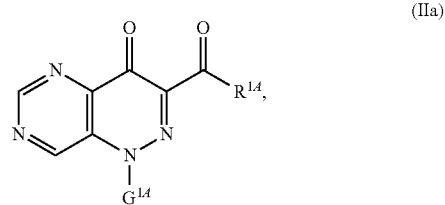

(IIa)

-continued

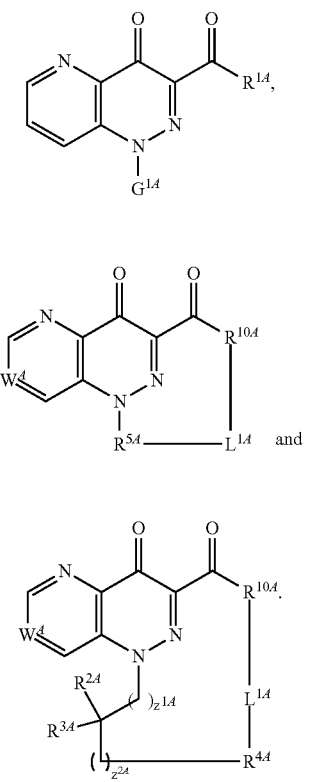

Examples of compounds of Formula (II) include the following:

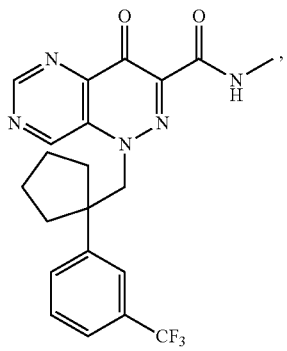

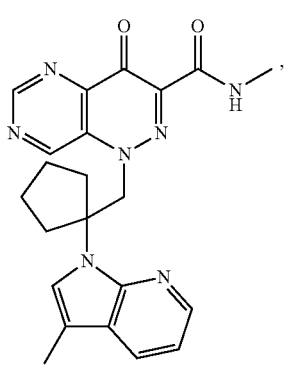

-continued

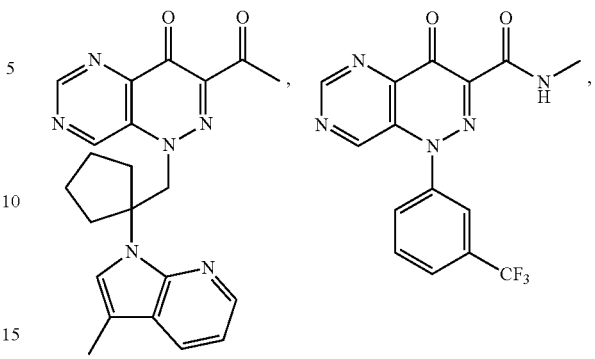

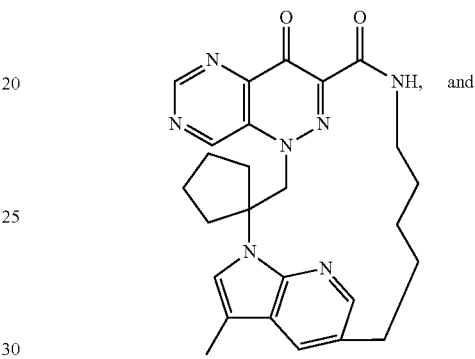

or a pharmaceutically acceptable salt of any of the foregoing.

Synthesis

Compounds of Formulae (I) and (II), and those described herein may be prepared in various ways. Some compounds of Formulae (I) and (II) can be obtained commercially and/or prepared utilizing known synthetic procedures. General synthetic routes to the compounds of Formulae (I) and (II), and some examples of starting materials used to synthesize the compounds of Formulae (I) and (II) are shown and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

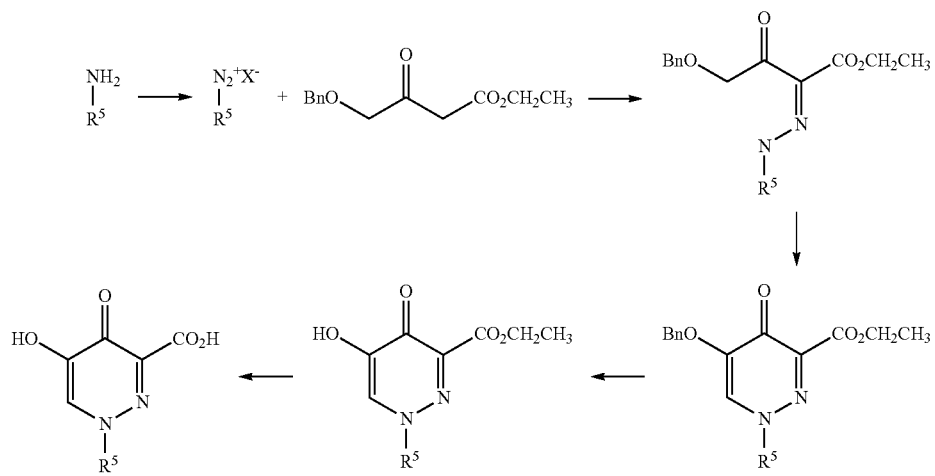

One method for forming a compound of Formula (I) where $G^1$ is $R^5$ is shown in Scheme 1. An amine having the formula of $R^5$—$NH_2$ can be converted to a diazonium salt having the formula $R^5$—$N_2^+X^-$, wherein $X^-$ is an inorganic or organic anion, using methods known to those skilled in the art (for example, $NaNO_2$, HCl). When $R^5$ is an optionally substituted phenyl group, the $R^5$—$NH_2$ can be an optionally substituted aniline. The diazonium salt can undergo a diazonium coupling reaction with a beta-keto ester using methods and conditions known to those skilled in the art. An example of a suitable beta-keto ester is shown in Scheme 1, and examples of suitable conditions include mildly acidic or neutral conditions. The 6-membered pyridazinone ring can be formed via a cyclization reaction with N,N-dimethylformamide-dimethyl acetal (DMF-DMA). The benzyl group can be cleaved, and the ester group can be undergo hydrolysis to form a compound of Formula (I). Cleavage of the benzyl group can be accomplished using palladium on carbon (Pd/C). Hydrolysis of the ester can be achieved using NaOH. In some instances, the benzyl group can be cleaved prior to the hydrolysis of the ester group. In other instances, the ester group can be hydrolyzed to a carboxylic acid prior to cleavage of the benzyl group.

When $R^5$ is substituted, a variety of methods can be used to add one or more substituents to $R^5$. For example, when $R^5$ is substituted with an optionally substituted heterocyclyl, the optionally substituted heterocyclyl can be added via an addition-elimination reaction to a halogen substituted compound having the formula $R^5$—$NO_2$. In some embodiments, a halogen substituted $R^5$—$NO_2$ can undergo ipso-substitution using an optionally substituted heterocyclyl. The resulting substituted nitro compound can be reduced to an amine using methods known to those skilled in the art (for example, Raney nickel, $PtO_2$ or Pd/C). A compound of Formula (I) can then be obtained following the general reaction scheme shown in Scheme 1. A general scheme starting with an example of a nitro compound is provided in Scheme 2. In Scheme 2, the phenyl ring can be further substituted with one or more substituents.

Scheme 2

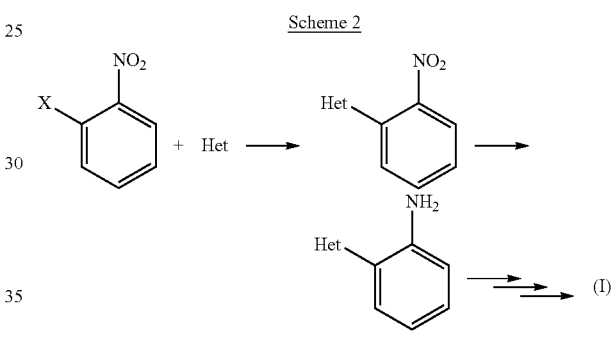

X = halogen and Het = optionally substituted heterocyclyl

Another method for adding one or more substituents to form a substituted $R^5$ is using a boronic acid or boronic ester. In some embodiments, a boronic acid or boronic ester can be used in a Suzuki coupling type-reaction to add one or more substituents to $R^5$. Suitable conditions include using a palladium catalyst and a base (for example, $Pd(PPh_3)_4$ and $K_2CO_3$). A non-limiting example using a boronic acid or boronic ester to form a substituted $R_5$ is shown in Scheme 3. In Scheme 3, the phenyl ring can be further substituted with one or more substituents. A compound of Formula (I) can be obtained via the general reaction scheme shown in Scheme 1. In Scheme 3, X can be a halogen and R" can be an optionally substituted alkyl or an optionally substituted aryl.

Scheme 3

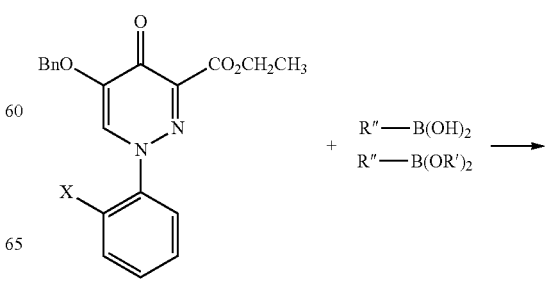

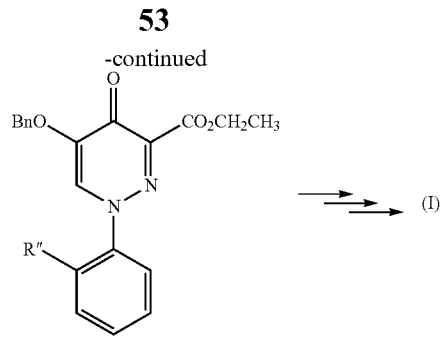

described herein, and a compound of Formula (I) can be obtained. Scheme 5 shows a general reaction scheme for obtaining compounds of Formula (I) where $R^1$ is a group other than a hydroxy or $C_{1-6}$ alkoxy, and $G^1$ and $G^2$ are as defined above. Additional information with respect to preparing compounds of Formula (I) is provided in U.S. Pat. No. 4,345,934. U.S. Publication No. U.S. 2009/281107A1, U.S. Publication No. U.S. 2010/197651A1. PCT Publication No. WO 2011/120153, Miyamoto et al., *Chem. Pharm. Bull.*, (1989) 37:93 and Miyamoto et al., *Chem. Pharm. Bull.*, (1988) 36:1321.

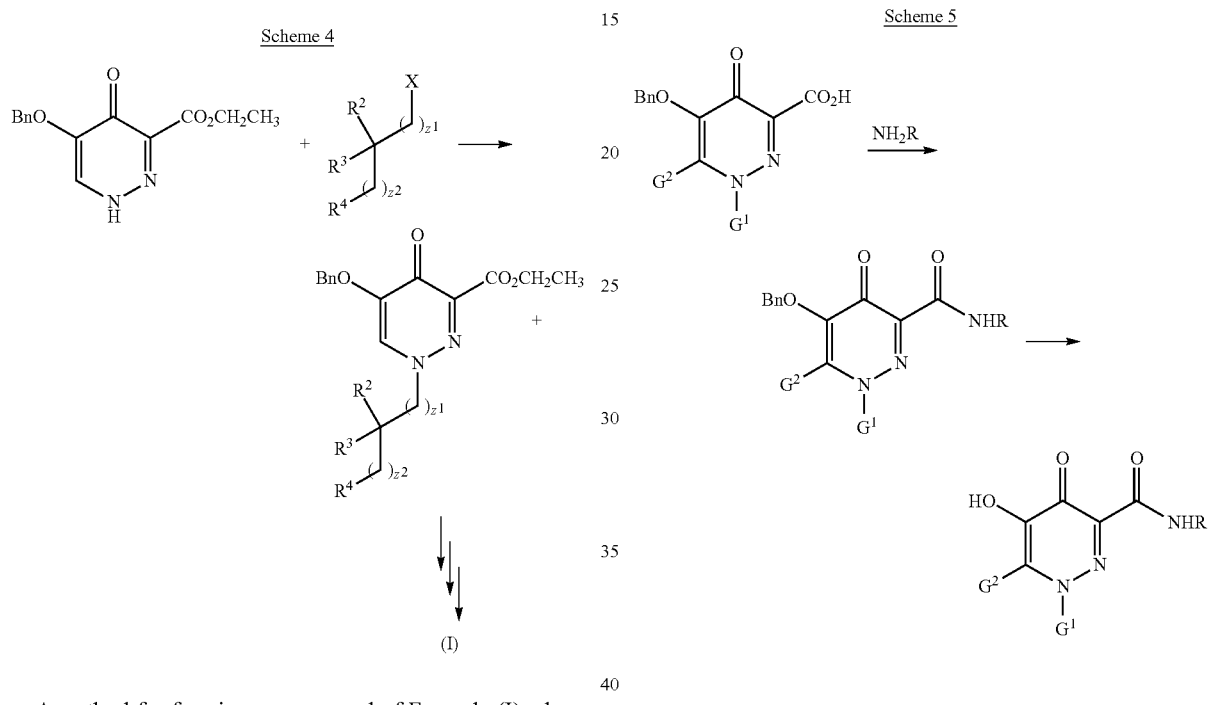

A method for forming a compound of Formula (I) where $G^1$ is

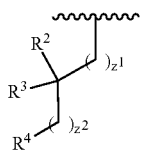

is shown in Scheme 4. As illustrated in Scheme 4, the nitrogen can be alkylated. A compound of Formula (I) can be obtained after the benzyl group is cleaved and the ester group undergoes hydrolysis.

Various methods can be used to form a group other than a hydroxy or $C_{1-6}$ alkoxy at $R^1$. The ester group can undergo hydrolysis to form a carboxylic acid. The carboxylic acid can then be transformed using methods known to those skilled in the art to form the desired $R^1$ group. For example, an optionally substituted amine and the carboxylic acid group can undergo a coupling reaction to form an optionally substituted amide group. Suitable coupling reagents can be used, including 2-(1H-Benzotriazole-1-yl)-1,1,3,3-tetramethyluronium hexafluorophosphate (HBTU). After formation of the $R^1$ group, the benzyl group can be cleaved using methods known to those skilled in the art, including those

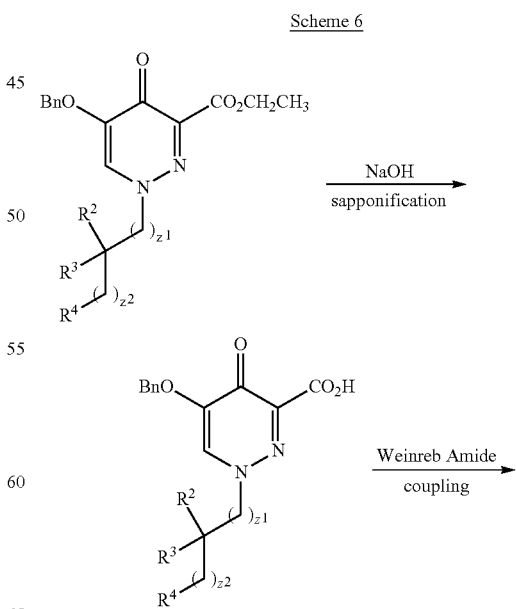

-continued

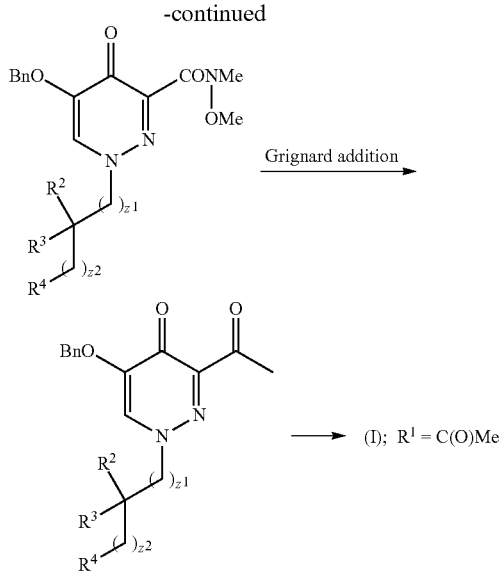

A method for forming a compound of Formula (I) where $G^1$ may be

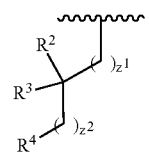

and $R^1$ may be an alkyl, such as methyl, is shown in Scheme 6. As illustrated in Scheme 6, the ester group can undergo hydrolysis to form a carboxylic acid. The carboxylic acid can then be transformed using methods known to those skilled in the art to form the desired $R^1$ group. For example, an amide and the carboxylic acid group can undergo a coupling reaction to form a substituted amide group. Examples of suitable amides include Weinreb amides, such as HNMe(OMe). Suitable coupling reagents are known to those skilled in the art and include 2-(1H-Benzotriazole-1-yl)-1,1,3,3-tetramethyluronium hexafluorophosphate (HBTU). The compound including the substituted amide group may be reacted with a suitable Grignard reagent to form Formula (I), where $G^1$ may be and $R^1$ may be an alkyl (for example, methyl). Additional information with respect to preparing compounds of Formula (I) is provided in Imada et al., *J. Med. Chem.*, 2006, 49(13): 3809-3825, and Clark et al., *Bioorg. Med. Chem. Lett.*, 2004, 14(12): 3299-3302.

Scheme 7

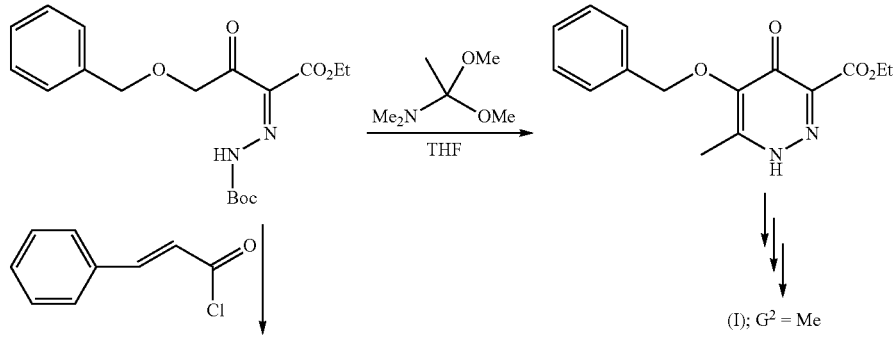

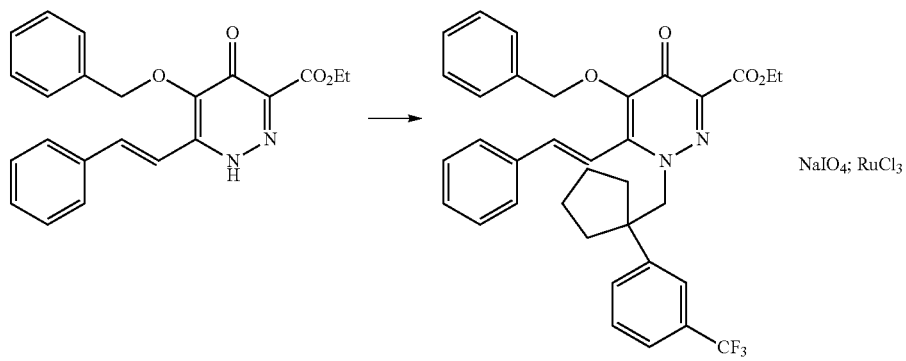

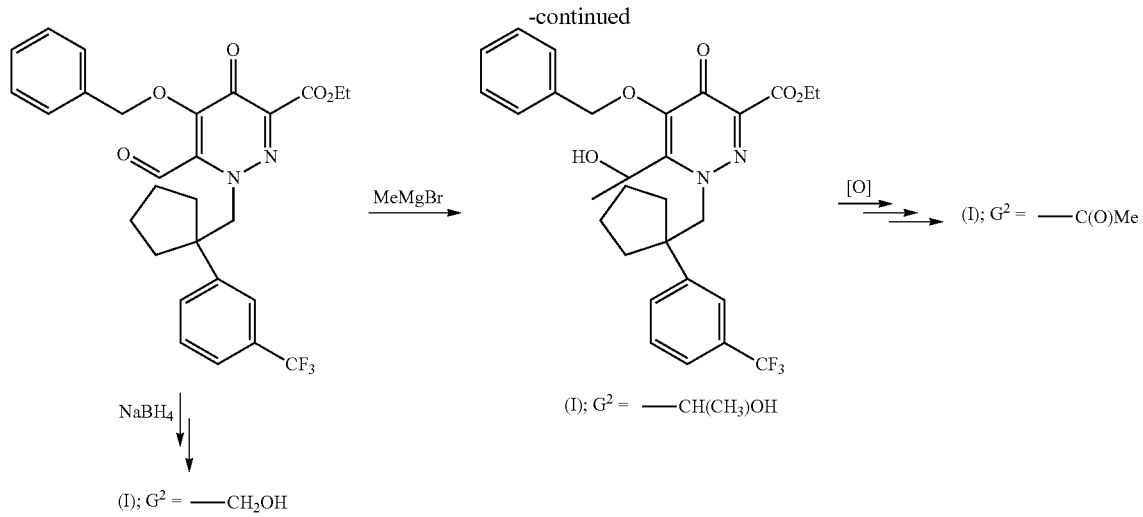

Example methods for forming a compound of Formula (I) where $G^2$ is an optionally substituted $C_{1-6}$ alkyl; —$CH_2OH$; —$CH(Y^1)(OH)$, —$C(O)Y^1$ are shown in Scheme 7. For instance, a 6-membered pyridazinone ring can be formed via a cyclization of the starting material with N,N-dimethylacetamide-dimethyl acetal or cinnamoyl chloride. An example of using cinnamoyl chloride is provided in U.S. Publication No. 2012/0022251, which is hereby incorporated by reference for the limited purpose of using cinnamoyl chloride. After cyclization, the 6-membered pyridazinone ring can be further modified to form a compound of Formula (I) where $G^2$ is an optionally substituted $C_{1-6}$ alkyl. The nitrogen of the 6-membered pyridazinone ring may be alkylated using methods known to those skilled in the art. To form compounds where $G^2$ is a $C_{1-6}$ alkyl; —$CH_2OH$; —$CH(Y^1)(OH)$, —$C(O)Y^1$, the exocyclic styrene alkene moiety may be oxidatively cleaved to afford an aldehyde, for example, via ozonolysis or using a sodium periodate—ruthenium trichloride mixture or the like. The aldehyde may be reduced to afford an alcohol or reacted with a Grignard reagent under appropriate conditions. For example, where $G^2$ is —$CH_2OH$, the aldehyde may be reduce using sodium borohydride; and where $G^2$=—$CH(CH_3)OH$, the aldehyde may be reacted with a Grignard reagent. The alcohol may be oxidized to form a ketone at $G^2$ (for example, $G^2$ is C(O)Me) using appropriate conditions known to those skilled in the art, such as ozonolysis.

Scheme 8

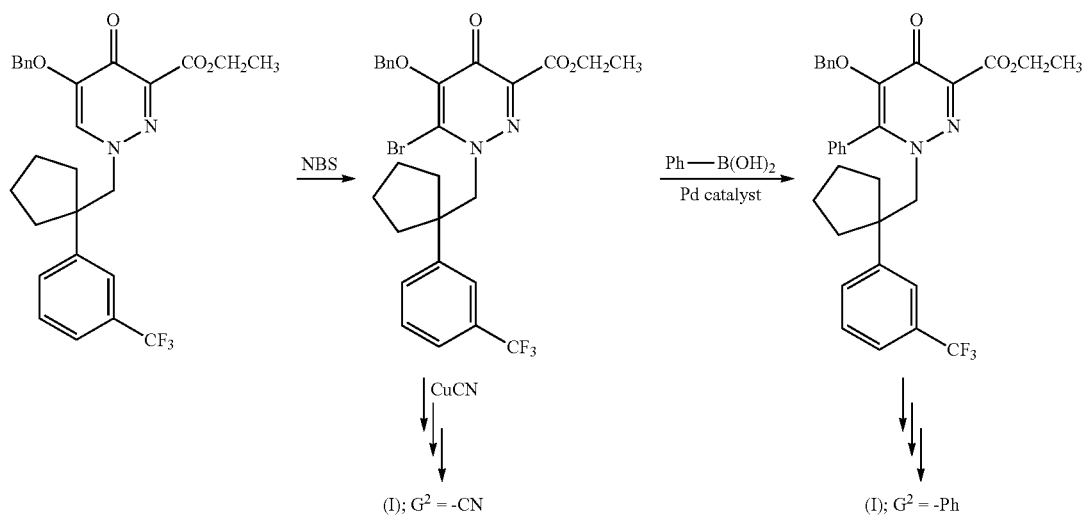

A method for forming a compound of Formula (I) where $G^2$ is —CN; or an optionally substituted aryl is shown in Scheme 8. For example, the β position of the α,β-unsaturated ketone in the 6-membered pyridazinone ring may be brominated using NBS (N-bromosuccinimide) under appropriate conditions to afford the vinyl bromide. An example of using NBS is described in WO 2012/039414, which is hereby incorporated by reference for the limited purpose of using NBS. The vinyl bromide may be treated with CuCN under appropriate conditions, for example as described in U.S. Pat. No. 5,202,323 to afford a compound of Formula (I) where $G^2$ is —CN. The vinyl bromide may be reacted with an aryl boronic acid (such as phenyl boronic acid) under appropriate conditions (for example, using a palladium catalyst) followed by further modification to afford a compound of Formula (I) where $G^2$ is an optionally substituted aryl.

Scheme 9

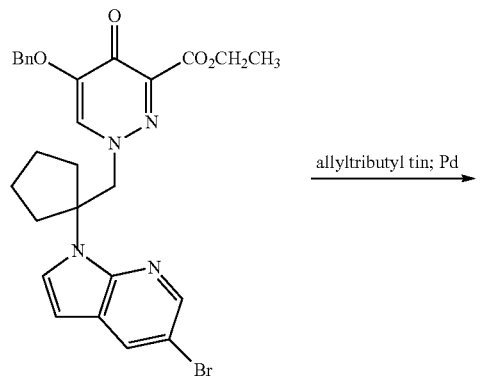

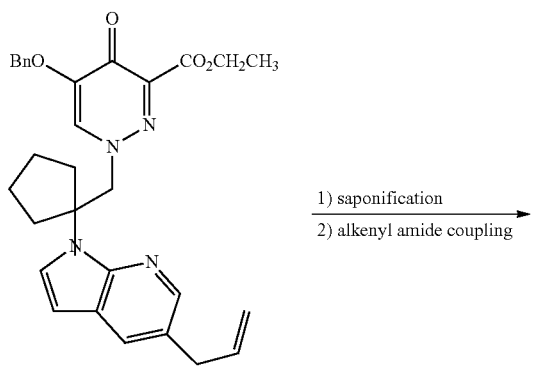

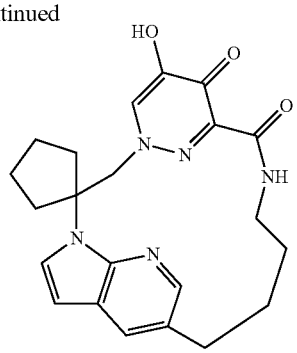

Example methods for forming a compound of Formula (I) that includes a macrocyclic ring formed from $R^{10}$-$L^1$-$R^4$ are shown in Schemes 9 and 10. In Scheme 9, the starting material may be reacted with allyltributyl tin in the presence of a metal catalyst, such a palladium, to afford the allyl intermediate. The ester of the allyl intermediate may be hydrolyzed to afford an intermediate that includes a carboxylic acid moiety, which can be then reacted with an allyl amine via a coupling reaction to afford a diene intermediate. Suitable coupling reagents can be used, including 2-(1H-Benzotriazole-1,1,3,3-tetramethyluronium hexafluorophosphate (HBTU). The diene intermediate can undergo a ring closing olefin metathesis macrocyclization using a suitable catalyst, for example, a Grubb's type catalyst to afford the alkene compound. Examples of suitable Grubb's type catalysts are described in in *Tetrahedron Letters* (2003), 44(10: 2401-2404, which is incorporated by reference for the limited purpose of its description of Grubb's type catalysts. The alkene may be hydrogenated, and the benzyl group may be cleaved, for example, using hydrogen ($H_2$) over Pd/C to afford to a compound of Formula (I).

Scheme 10

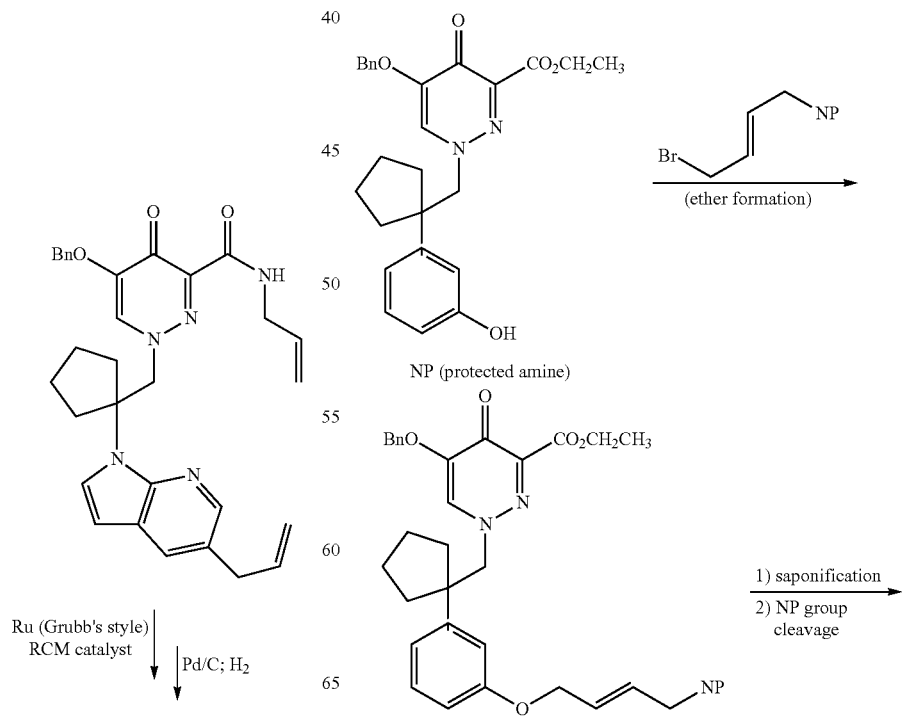

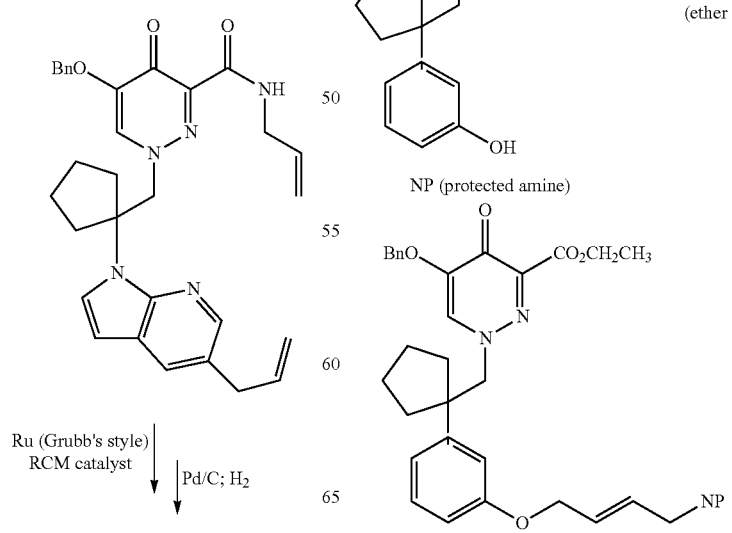

-continued

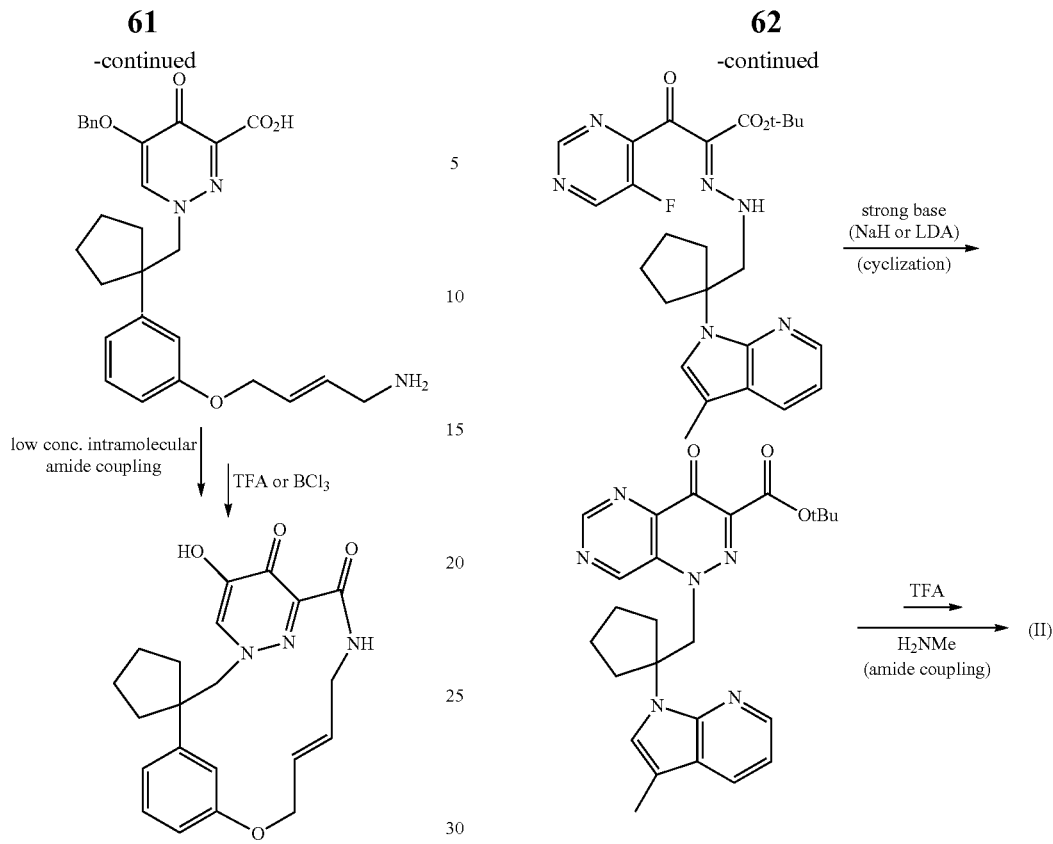

In Scheme 10, the starting material may be reacted with an ally bromide that includes a protected amine to afford a protected amine intermediate. The ester of the protected amine intermediate may be hydrolyzed to afford an intermediate that includes a carboxylic acid moiety and then the protecting group of the amine may be removed. The carboxylic acid moiety can be reacted with the amine via an intramolecular macrolactamization coupling reaction, for example as described in *Chemical Communications* (2002), (12):1280-1281, and WO 2009/004146, to afford the macrolactam intermediate. The benzyl group of the macrolactam intermediate may be cleaved, for example, using TFA or $BCl_3$ to afford to compounds of Formula (I).

Scheme 11

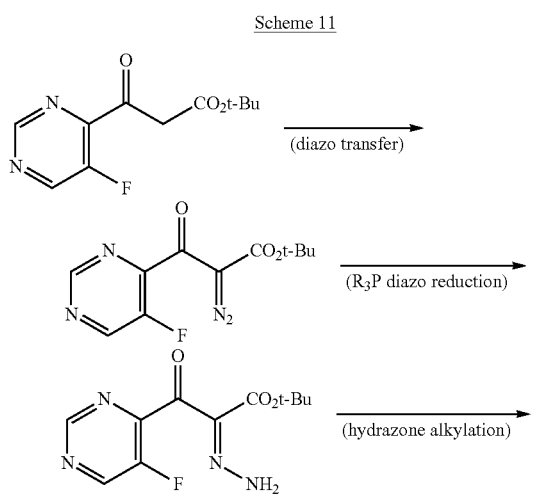

A method for forming a compound of Formula (II) where $R^{1A}$ is a mono-substituted amine is shown in Scheme 11. For example, the starting may be reacted with acetamidobenzenesulfonyl azide (ABSA) under appropriate conditions using methods and conditions known to those skilled in the art, for example, as described in WO 2011/120153, to afford the diazo intermediate. The diazo intermediate may be reduced under appropriate conditions using methods and conditions known to those skilled in the art, for example using trimethyl phosphine as described in WO 2011/120153 or tributyl phosphine as described in *Chem. Pharm. Bull.* (1988). 36:1321-1327, to afford the hydrazone intermediate. The hydrazone intermediate may be alkylated under appropriate conditions using methods and conditions known to those skilled in the art to afford the alkyl hydrazine intermediate. The alkyl hydrazone intermediate may be cyclized using a strong base (such as sodium hydride or LDA), for example as described in *Chem. Pharm. Bull.* (1989), 37:93-98, to afford the pyrimido[5,4-c]pyridazin-4(1H)-one intermediate. The tert-butyl ester of the pyrimido[5,4-c]pyridazin-4(1H)-one intermediate may be cleaved using an acid, such as TFA, to afford an intermediate that includes a carboxylic acid moiety. The carboxylic acid moiety can be reacted with methyl amine via a coupling reaction to afford the a compound of Formula (II). Suitable coupling reagents can be used, including 2-(1H-Benzotriazole-1-yl)-1,1,3,3-tetramethyluronium hexafluorophosphate (HBTU).

Pharmaceutical Compositions

Some embodiments described herein relate to a pharmaceutical composition, that can include an effective amount of one or more compounds described herein (e.g., a compound of Formulae (I) and/or (II), or a pharmaceutically acceptable salt thereof) and a pharmaceutically acceptable carrier, diluent, excipient or combination thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting, processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. In some embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intramuscular. In other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intranasal. In still other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering intradermal. In yet still other embodiments, an effective amount of one or more compounds of Formula (I), or a pharmaceutically acceptable salt thereof, and/or a pharmaceutical composition that includes one or more compounds described herein (e.g., a compound of Formula (I), or a pharmaceutically acceptable salt thereof) can be administering orally.

When administered orally, one or more compounds described herein (e.g., a compound of Formula (I), or a pharmaceutically acceptable salt thereof) can be formulated as tablets, pills, dragees, capsules, liquids, gels, syrups, slurries, suspensions and the like, for oral ingestion by a subject to be treated. Injectables can be prepared in conventional forms, either as liquid solutions or suspensions, solid forms suitable for solution or suspension in liquid prior to injection, or as emulsions. Pharmaceutical compositions for intranasal delivery may also include drops and sprays often prepared to assist in simulating nasal secretions.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use:

Some embodiments described herein relate to a method of ameliorating, treating and/or preventing an orthomyxovirus infection, which can include administering an effective amount of one or more compounds described herein, or a pharmaceutical composition that includes one or more compounds described herein (e.g., a compound of Formulae (I) and/or (II), or a pharmaceutically acceptable salt of the foregoing).

Other embodiments described herein relate to a method of inhibiting an orthomyxovirus viral replication, which can include contacting a cell infected with the orthomyxovirus virus with an effective amount of a compound of Formulae (I) and/or (II), or a pharmaceutically acceptable salt of the foregoing and/or a pharmaceutical composition that includes one or more compounds described herein (e.g., a compound of Formulae (I) and/or (II), or a pharmaceutically acceptable salt of the foregoing).

In some embodiments, an effective amount of one or more compounds of Formulae (I) and/or (II), or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used to treat and/or ameliorate an influenza viral infection. In other embodiments, an effective amount of one or more compounds of Formulae (I) and/or (II), or a pharmaceutically acceptable salt of the foregoing and/or a pharmaceutical composition that includes one or more compounds described herein (e.g., a compound of Formulae (I) and/or (II), or a pharmaceutically acceptable salt of the foregoing) can be used to prevent an influenza viral infection.

In some embodiments, an effective amount of one or more compounds of Formulae (I) and/or (II), or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used to inhibit the replication an influenza virus. In some embodiments, an effective amount of one or more compounds of Formulae (I), or a pharmaceutically acceptable salt of the foregoing and/or a pharmaceutical composition that includes one or more compounds described herein (e.g., a compound of Formulae (I) and/or (II), or a pharmaceutically acceptable salt of the foregoing) can be used to inhibit the influenza polymerase complex. In some embodiments, an effective amount of one or more compounds of Formulae (I) and/or (II), or a pharmaceutically acceptable salt of the foregoing and/or a pharmaceutical composition that includes one or more compounds described herein (e.g., a compound of Formulae (I) and/or (II), or a pharmaceutically acceptable salt of the foregoing) can be used for inhibiting and/or reducing the endonuclease activity of an influenza endonuclease that can include contacting the active site of the endonuclease with a compound of Formulae (I) and/or (II), or a pharmaceutically acceptable salt of the foregoing. In some embodiments, one or more compounds described herein inhibits and/or reduces the ability of the endonuclease to cleave the mRNA.

In some embodiments, including those embodiments in the previous paragraphs, the influenza viral infection can be an influenza A viral infection. In other embodiments, including those embodiments in the previous paragraphs, the influenza viral infection can be an influenza B viral infection. In still other embodiments, including those embodiments in the previous paragraphs, the influenza viral infection can be an influenza C viral infection. In some embodiments, a compound of Formulae (I) and/or (II), or a pharmaceutically acceptable salt of the foregoing, can be used to treat and/or ameliorate one or more subtypes of influenza. For example, a compound of Formula (I), or a pharmaceutically acceptable salt thereof, can be used to treat H1N1 and/or H3N2. In addition or in the alternative, a compound of Formulae (I) and/or (II), or a pharmaceutically acceptable salt of the foregoing, can be used to treat H2N2, H5N1 and/or H7N9. In some embodiments, a compound described herein (a compound of Formula (I), or a pharmaceutically acceptable salt thereof) can be effective against more than 1 subtype of influenza. For example, a compound described herein (a compound of Formula (I), or a pharmaceutically acceptable salt thereof can be effective against 2, 3, 4, and/or 5 or more subtypes of influenza.

In some embodiments, an effective amount of one or more compounds of Formulae (I) and/or (II), or a pharmaceutically acceptable of the foregoing, and/or a pharmaceutical composition that includes one or more compounds described herein (e.g., a compound of Formulae (I) and/or (II), or a pharmaceutically acceptable salt of the foregoing) can be used treat and/or ameliorate an upper respiratory viral infection attributed to (directly and/or indirectly) an influenza virus infection. In some embodiments, an effective amount of one or more compounds of Formulae (I) and/or (II), or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used treat and/or ameliorate a lower respiratory viral infection (directly and/or indirectly) an influenza virus infection. In some embodiments, an effective amount of one or more compounds of Formulae (I) and/or or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used treat and/or ameliorate one or more symptoms of an influenza virus infection (such as those described herein). In some embodiments, an effective amount of one or more compounds of Formulae (I) and/or (H), or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used treat and/or ameliorate bronchiolitis and/or tracheobronchitis due to an influenza virus infection. In some embodiments, an effective amount of one or more compounds of Formulae (I) and/or (II), or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used treat and/or ameliorate pneumonia due to an influenza virus infection. In some embodiments, an effective amount of one or more compounds of Formulae (I) and/or (II), or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used treat and/or ameliorate coup due to an influenza virus infection.

In some embodiments, an effective amount of one or more compounds of Formulae (I) and/or (II), or a pharmaceutically acceptable salt of the foregoing, and/or a pharmaceutical composition that includes one or more compounds described herein (e.g., a compound of Formulae (I) and/or (II), or a pharmaceutically acceptable salt of the foregoing) can be used lessen the severity of one or more symptoms of an influenza infection. Examples of symptoms include, but are not limited to, the following: fever, chills, cough, sore throat, runny nose, stuffy nose, muscle aches, body aches, headache, fatigue, vomiting and/or diarrhea.

As used herein, the terms "prevent" and "preventing," mean a subject does not develop an infection because the subject has an immunity against the infection, or if a subject becomes infected, the severity of the disease is less compared to the severity of the disease if the subject has not been administered/received the compound. Examples of forms of prevention include prophylactic administration to a subject who has been or may be exposed to an infectious agent, such as an orthomyxovirus (e.g., an influenza virus).

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

Various indicators for determining the effectiveness of a method for treating an orthomyxovirus viral infection are known to those skilled in the art. Example of suitable indicators include, but are not limited to, a reduction in viral load, a reduction in viral replication, a reduction in time to seroconversion (virus undetectable in patient serum), a reduction of morbidity or mortality in clinical outcomes, and/or other indicator of disease response.

In some embodiments, an effective amount of a compound of Formula (I), or a pharmaceutically acceptable salt thereof, is an amount that is effective to reduce viral titers to a lower level, for example, from about 10E4 TCID50/mL (TCID=tissue culture infectious dose) to about 10E3 TCID50/mL, or to about 100 TCID50/mL, or to about 10 TCID50/mL. In some embodiments, an effective amount of a compound of Formula (I), or a pharmaceutically acceptable salt thereof, is an amount that is effective to reduce viral load compared to the viral load before administration of the compound of Formula (I), or a pharmaceutically acceptable salt thereof. For example, wherein the viral load is measure before administration of the compound of Formula (I), or a pharmaceutically acceptable salt thereof, and again after initiation of the treatment regime with the compound of Formula (I), or a pharmaceutically acceptable salt thereof (for example, 10 days after initiation of treatment). In some embodiments, an effective amount of a compound of Formula (I), or a pharmaceutically acceptable salt thereof, can be an amount that is effective to reduce viral load to lower than about 10E4 TCID50/mL. In some embodiments, an effective amount of a compound of Formula (I), or a pharmaceutically acceptable salt thereof, is an amount that is effective to achieve a reduction in viral titer in a nasal/pharyngeal swab or nasal wash sample of the subject in the range of about 1.5-log to about a 2.5-log reduction or about a 3-log to about a 4-log reduction compared to the viral load before administration of the compound of Formula (I), or a pharmaceutically acceptable salt thereof. For example, wherein the viral load is measure before administration of the compound of Formula (I), or a pharmaceutically acceptable salt thereof, and again after initiation of the treatment regime with the compound of Formula (I), or a pharmaceutically acceptable salt thereof (for example, 10 days after initiation of treatment).

In some embodiments, a compound of Formula (I), or a pharmaceutically acceptable salt of the foregoing, can result in one or more overall quality of life health, such as reduced illness duration, reduced illness severity, reduced time to return to normal health and normal activity, and reduced time to alleviation of one or more symptoms of orthomyxovirus infection, compared to a subject who is untreated. In some embodiments, a compound of Formula (I), or a pharmaceutically acceptable salt of the foregoing, can result in a reduction in the length and/or severity of one or more symptoms associated with an orthomyxovirus infection compared to an untreated subject. Symptoms of an orthomyxovirus infection are described herein and include but not limited to cough, myalgia (muscle pain), nasal obstruction, sore throat, fatigue, headache and fever. In some embodiments, a compound of Formula (I), or a pharmaceutically acceptable salt of the thereof, can result in a reduction in one or more secondary complications associated with an orthomyxovirus infection, including but not limited to otitis media (ear inflammation), sinusitis, bronchitis and pneumonia compared to an untreated subject.

In some embodiments, a compound of Formula (I), or a pharmaceutically acceptable salt of the foregoing, can result in at least a 1, 2, 3, 4, 5, 10, 15, 20, 25, 50, 75, 100-fold or more reduction in the replication of an orthomyxovirus relative to pre-treatment levels in a subject, as determined after initiation of the treatment regime (for example, 10 days after initiation of treatment). In some embodiments, a compound of Formula (I), or a pharmaceutically acceptable salt of the foregoing, can result in a reduction of the replication of an orthomyxovirus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of orthomyxovirus replication in the range of 1 to 1.5 log. 1.5 log to 2 log, 2 log to 2.5 log, 2.5 to 3 log, or 3 to 3.5 log reduction of orthomyxovirus replication compared to the reduction of orthomyxovirus reduction achieved by oseltamivir (Tamiflu®), or may achieve the same reduction as that of oseltamivir (Tamiflu®) therapy in a shorter period of time, for example, in one day, two days, three days, or four days as compared to the reduction achieved after 5 days of oseltamivir (Tamiflu®) therapy.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formulae (I) and/or (II), or a pharmaceutically acceptable salt of the foregoing, can be administered to a subject infected with an influenza virus that is resistant to one or more different anti-influenza agents (for example, amantadine, rimantadine and/or oseltamivir). In some embodiments, a compound of Formulae (I) and/or (II), or a pharmaceutically acceptable salt of the foregoing, can be administered to a subject infected with an influenza virus that is resistant to a M2 protein inhibitor. In some embodiments, development of resistant influenza strains is delayed when subjects are treated with a compound of Formulae (I) and/or (II), or a pharmaceutically acceptable salt of the foregoing, compared to the development of influenza strains resistant to other influenza drugs.

In some embodiments, a compound of Formulae (I) and/or (II), or a pharmaceutically acceptable salt of the foregoing, can decrease the percentage of subjects that experience complications from an influenza viral infection compared to the percentage of subjects that experience complication being treated with oseltamivir. For example, the percentage of subjects being treated with a compound of Formulae (I) and/or (II), or a pharmaceutically acceptable salt of the foregoing, that experience complications can be 10%, 25%, 40%, 50%, 60%, 70%, 80% and 90% less compared to subjects being treated with oseltamivir.

In some embodiments, a compound of Formula (I), or a pharmaceutically acceptable salt thereof, or a pharmaceutical composition that includes a compound described herein, can be used in combination with one or more additional agent(s). In some embodiments, a compound of Formula (I), or a pharmaceutically acceptable salt thereof, can be used in combination with one or more agents currently used in a conventional standard of care for treating influenza. For example, the additional agent can be amantadine (adamantan-1-amine, rimantadine (Flumadine), zanamivir (Relenza) and oseltamivir (Tamiflu). For the treatment of influenza, additional agents include but are not limited to a neuraminidase inhibitor, a M2 protein inhibitor, a polymerase inhibitor, a PB2 inhibitor, peramivir ((1S,2S,3S,4R)-3-[(1S)-1-acetamido-2-ethylbutyl]-4-(diaminomethylideneamino)-2-hydroxycyclopentane-2-carboxylic acid, BioCryst Pharmaceuticals), laninamivir ((4S,5R,6R)-5-acetamido-4-carbamimidamido-6-[(1R,2R)-3-hydroxy-2-methoxypropyl]-5,6-dihydro-4H-pyran-2-carboxylic acid), favipiravir (T-705, 6-fluoro-3-hydroxy-2-pyrazinecarboxamide), laninamivir octanoate ((3R,4S)-3-acetamido-4-guanidino-2-((1S,2S)-2-hydroxy-1-methoxy-3-(octanoyloxy)propyl)-3,4-dihydro-2H-pyran-6-carboxylic acid) fludase (DAS181, NexBio), ADS-8902 (amantadine HCl/oseltamivir/ribavirin, Adamas Pharmaceuticals), an immuno-modulator (for example, a Type 1 interferon), beraprost (4-[2-hydroxy-1-[(E)-3-hydroxy-4-methyloct-1-en-6-ynyl]-2,3,3a,8b-tetrahydro-1H-cyclopenta[b][1]benzofuran-5-yl]butanoic acid), Neugene®, ribavirin, (R)-3-((5-fluoro-2-(5-fluoro-1H-pyrrolo[2,3-b]pyridin-3-yl)pyrimidin-4-yl)amino)-4,4-dimethylpentanoic acid (CAS Reg. No. 1422050-75-6), (2S,3S)-3-((5-fluoro-2-(5-fluoro-1H-pyrrolo[2,3-b]pyridin-3-yl)pyrimidin-4-yl)amino)bicyclo[2.2.2]octane-2-carboxylic acid (CAS Reg. No. 1259366-34-1. VX-787), FluMist Quadrivalent® (MedImmune), Fluarix® Quadrivalent (GlaxoSmithKline), Fluzone® Quadrivalent (Sanofi Pasteur), Flucelvax® (Novartis) and FluBlok® (Protein Sciences). In some embodiments, a compound of Formula (I), or a pharmaceutically acceptable salt thereof, or a pharmaceutical composition that includes a compound described herein, can be used in combination with oseltamivir.

Type 1 interferons are known to those skilled in the art. A non-limiting list of examples include: alpha-interferons, beta-interferons, delta-interferons, omega-interferons, tau-interferons, x-interferons, consensus interferons and asialo-interferons. Type 1 interferons can be pegylated. Examples of specific type 1 interferons include interferon alpha 1A, interferon alpha 1B, interferon alpha 2A, interferon alpha 2B, pegylated-interferon alpha 2a (PEGASYS, Roche), recombinant interferon alpha 2a (ROFERON, Roche), inhaled interferon alpha 2b (AERX, Aradigm), pegylated-interferon alpha 2b (ALBUFERON, Human Genome Sciences/Novartis, PEGINTRON, Schering), recombinant interferon alpha 2b (INTRON A, Schering), pegylated interferon alpha 2b (PEG-INTRON. Schering, VIRAFERON-PEG, Schering), interferon beta-1a (REBIF, Serono, Inc. and Pfizer), consensus interferon alpha (INFERGEN, Valeant Pharmaceutical).

In some embodiments, a compound of Formulae (I) and/or (II), or a pharmaceutically acceptable salt of the foregoing, can be administered with one or more additional agent(s) together in a single pharmaceutical composition. In some embodiments, a compound of Formulae (I) and/or (II), or a pharmaceutically acceptable salt of the foregoing, can be administered with one or more additional agent(s) as two or more separate pharmaceutical compositions. For example, a compound of Formulae (I) and/or (II), or a pharmaceutically acceptable salt of the foregoing, can be administered in one pharmaceutical composition, and at least one of the additional agents can be administered in a second pharmaceutical composition. If there are at least two additional agents, one or more of the additional agents can be in a first pharmaceutical composition that includes a compound of Formulae (I) and/or (II), or a pharmaceutically acceptable salt of the foregoing, and at least one of the other additional agent(s) can be in a second pharmaceutical composition.

The order of administration of a compound of Formulae (I) and/or (II), or a pharmaceutically acceptable salt of the foregoing, with one or more additional agent(s) can vary. In some embodiments, a compound of Formulae (I) and/or (II), or a pharmaceutically acceptable salt of the foregoing, can be administered prior to all additional agents. In other embodiments, a compound of Formulae (I) and/or (II), or a pharmaceutically acceptable salt of the foregoing, can be administered prior to at least one additional agent. In still other embodiments, a compound of Formulae (I) and/or (II), or a pharmaceutically acceptable salt of the foregoing, can be administered concomitantly with one or more additional agent(s). In yet still other embodiments, a compound of Formulae (I) and/or (II), or a pharmaceutically acceptable salt of the foregoing, can be administered subsequent to the administration of at least one additional agent. In some embodiments, a compound of Formulae (I) and/or (II), or a pharmaceutically acceptable salt of the foregoing, can be administered subsequent to the administration of all additional agents.

In some embodiments, the combination of a compound of Formula (I), or a pharmaceutically acceptable salt thereof, in combination with one or more additional agent(s) can result in an additive effect. In some embodiments, the combination of a compound of Formula (I), or a pharmaceutically acceptable salt thereof, in combination with one or more additional agent(s) can result in a synergistic effect. In some embodiments, the combination of a compound of Formula (I), or a pharmaceutically acceptable salt thereof, in combination with one or more additional agent(s) can result in a strongly synergistic effect. In some embodiments, the combination of a compound of Formula (I), or a pharmaceutically acceptable salt thereof, in combination with one or more additional agent(s) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formulae (I) and/or (II), or a pharmaceutically acceptable salt of the foregoing, in combination with one or more of the additional agent(s) described above, including pharmaceutically acceptable salts and prodrugs thereof, may be a reduction in the required amount(s) of the one or more additional agents, including pharmaceutically acceptable salts and prodrugs thereof, that is effective in treating a disease condition disclosed herein (for example, influenza), as compared to the amount required to achieve the same therapeutic result when one or more of the additional agents, including pharmaceutically acceptable salts and prodrugs thereof, are administered without a compound of Formulae (I) and/or (II), or a pharmaceutically acceptable salt of the foregoing. For example, the amount of an additional agent described above, including a pharmaceutically acceptable salt and prodrug thereof, can be less when administered in combination with a compound of Formulae (I) and/or (II), or a pharmaceutically acceptable salt of the foregoing, compared to the amount of additional agent, including a pharmaceutically acceptable salt and prodrug thereof, needed to achieve the same viral load reduction when administered as a monotherapy. Another potential advantage of utilizing a compound of Formulae (I) and/or (II), or a pharmaceutically acceptable salt of the foregoing, in combination with one or more of the additional agent(s) described above, including pharmaceutically acceptable salts and prodrugs thereof, is that the use of two or more compounds having different mechanisms of action can create a higher barrier to the development of resistant viral strains compared to the barrier when a compound is administered as monotherapy.

Additional advantages of utilizing, a compound of Formulae (I) and/or (II), or a pharmaceutically acceptable salt of the foregoing, in combination with one or more of the additional agent(s) described above, including pharmaceutically acceptable salts and prodrugs thereof, may include little to no cross resistance between a compound of Formulae (I) and/or (II), or a pharmaceutically acceptable salt of the foregoing, and the one or more additional agent(s) described above (including pharmaceutically acceptable salts and prodrugs thereof); different routes for elimination of a compound of Formulae (I) and/or (II), or a pharmaceutically acceptable salt of the foregoing, and the one or more additional agent(s) described above (including pharmaceutically acceptable salts and prodrugs thereof); little to no overlapping toxicities between a compound of Formulae (I) and/or (II), or a pharmaceutically acceptable salt of the foregoing, and the one or more additional agent(s) described above (including pharmaceutically acceptable salts and prodrugs thereof); little to no significant effects on cytochrome P450; and/or little to no pharmacokinetic interactions between a compound of Formulae (I) and/or (II), or a pharmaceutically acceptable salt of the foregoing, and the one or more additional agent(s) described above, including pharmaceutically acceptable salts and prodrugs thereof.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $EDS_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vi/ro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Example 1

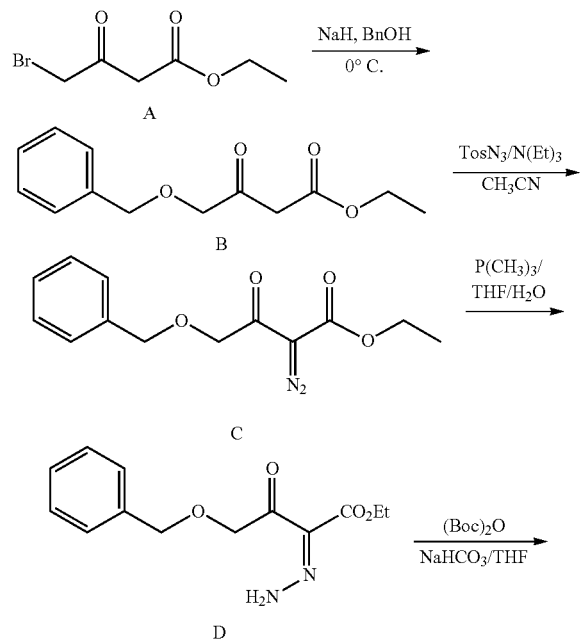

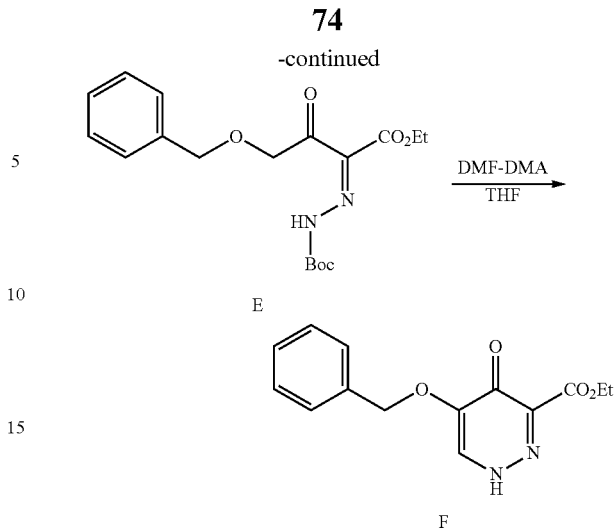

To a stirred solution of NaH (21.8 g. 912 mmol, 3.0 eq.) in THF (300 mL) was added BnOH (32.8 g, 304.0 mmol, 1.0 eq.) under a $N_2$ atmosphere at 0° C. After addition, the mixture was stirred for 30 min. Compound A (63.5 g. 304.0 mmol. 1.0 eq.) was added portionwise, and the mixture was allowed to warm to ambient temperature and stirred for 12 h. The product was followed by TLC using petroleum ether (PE):EtOAc=5:1. The mixture was poured into 2M HCl solution to adjust to ~pH 6. The solution was exacted with EtOAc (200 mL×3). The combined organic phases were dried over $Na_2SO_4$, filtered and concentrated. The residue was purified by column chromatography on silica gel (PE: EtOAc=30:1 to 5:1) to give B as a colorless oil (46 g, 88.5%). $^1$HNMR (CDCl$_3$) δ 7.39-7.29 (m, 5H), 4.59 (s, 2H), 4.17-4.24 (q, 2H), 4.14 (s, 2H), 3.53 (s, 2H), 1.31-1.22 (t, 3H).

To a stirred solution of B (10.0 g, 42.3 mmol, 1.0 eq.) in $CH_3CN$ (20 mL) under a $N_2$ atmosphere at 0° C., was added TosN$_3$ (8.35 g, 42.3 mmol, 1.0 eq.) and TEA (12.84 g, 127.1 mmol, 3.0 eq.). The mixture was stirred at 0° C. for 2 h. The mixture was warmed to room temperature (RT) and stirred for 6 h. The progress of the reaction was followed by TLC (PE:EtOAc=5:1). After complete conversion was observed, the solvent was removed under reduced pressure, and the residue was purified by column chromatography on silica gel (PE:EtOAc=30:1 to 5:1) to give C as a colorless oil (4.5 g, 40.5%). $^1$H NMR (CDCl$_3$) δ 7.39-7.26 (m, 5H), 4.64 (s, 2H). 4.60 (s, 2H), 4.29-4.24 (q, 2H), 1.32-1.28 (t, 3H).

To a solution of C (4.04 g, 15.4 mmol. 1.0 eq.) in THF (5 mL) was added P(CH$_3$)$_3$/THF solution (16.9 mL, 16.9 mM, 1.1 eq.) at RT. The mixture was stirred for 15 min (indicated by TLC, PE:EtOAc=2:1) and then quenched with water (2.8 mL). The mixture was stirred for 15 min and concentrated under reduced pressure. The crude residue was purified by column chromatography on silica gel (PE:EtOAc=5:1 to 2:1) to give D as a yellow solid (4.0 g, 98.2%). $^1$H NMR (CDCl$_3$) δ 7.39-7.24 (m, 5H), 4.66-4.66 (s, 1H), 4.66-4.61 (s, 2H), 4.53-4.53 (s, 1H), 4.31-4.24 (m, 2H), 1.35-1.29 (m, 3H).

To a stirred solution of D (20.0 g, 75.7 mmol, 1.0 eq.) in THF (100 mL) was added NaHCO$_3$ (19.1 g, 227.3 mmol, 3.0 eq.) and (Boc)$_2$O (22.84 g, 113.6 mmol, 1.5 eq.). The mixture was heated to reflux for 6 h and monitored by TLC (PE:EtOAc=2:1). After complete conversion was observed, the solution was concentrated under reduced pressure. The residue was dissolved in EtOAc (200 mL) and washed with water (80 mL×2). The organic layer was separated, dried over Na$_2$SO$_4$ and filtered. The mixture was concentrated under reduced pressure, and the residue was purified by column chromatography on silica gel (PE:EtOAc=8:1) to give E as a white solid (15 g, 54.30%). $^1$H NMR (CDCl$_3$) δ 11.59 (s, 1H), 7.40-7.26 (m, 5H), 4.71-4.61 (m, 2H), 4.39 (s, 2H), 4.71-4.27 (q, 2H), 1.70-1.48 (m, 9H). 1.38-1.24 (t, 3H).

To a solution of E (4.2 g, 11.5 mmol, 1 eq.) in THF (100 mL) at RT, was added DMF-DMA (6.15 g, 51.7 mmol, 4.5 eq.). The mixture was stirred at RT for 16 h. After complete conversion was observed as indicated by TLC, the reaction was treated with water (5-6 mL) and stirred for 30 min. The solvent was evaporated under reduced pressure at 40-50° C. The residue was crystallized from EtOAc to give the pure product as a white solid, (0.5 g). The mother liquor was concentrated and purified by column chromatography on silica gel (DCM:MeOH=50:1 to 10:1) to give F as a solid (2.4 g, 75.95%). $^1$H NMR (CD$_3$OD) δ 8.22 (s, 1H), 7.48-7.46 (m, 2H), 7.41-7.34 (m, 3H), 5.20 (s, 2H), 4.41-4.36 (q, 2H), 1.39-1.35 (t, 3H). LCMS (ESI) m/z [M+H]$^+$=275.2 (calc.=274.1). Retention Time=1.097 min.

Example 2

5-hydroxy-4-oxo-1-(3-(trifluoromethyl)phenyl)-1,4-dihydropyridazine-3-carboxylic acid

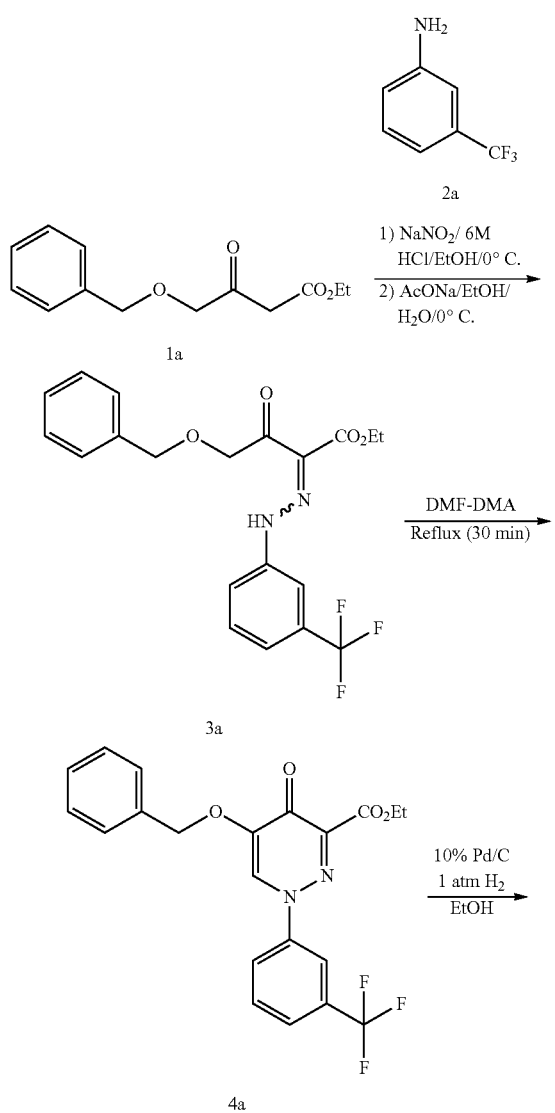

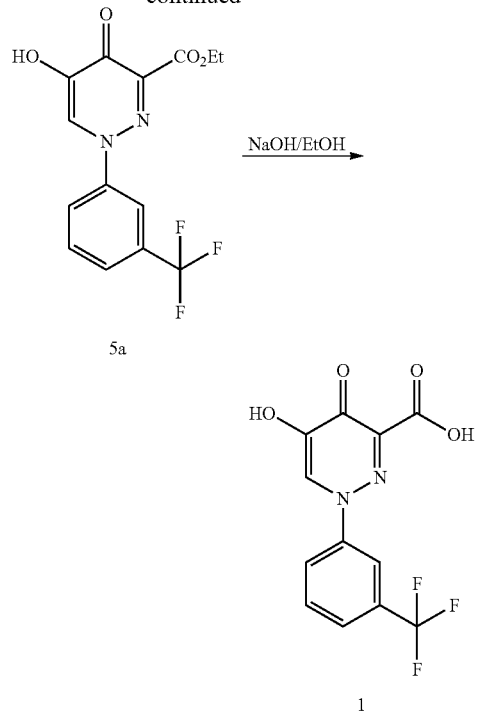

A mixture of 2a (3.2 g, 20 mmol) and 6 M HCl aqueous solution (20 mL, 120 mmol) was stirred at 0° C. To the mixture was added a solution of NaNO$_2$ (1.66 g, 24 mmol) in H$_2$O (5 mL) dropwise. After addition, the mixture was stirred for 15 min. The resulting aqueous solution was added to a suspension of 1a (4.7 g, 20 mmol) and NaOAc (9.84 g, 120 mmol) in EtOH (40 mL) at 0° C. After complete conversion, the mixture was poured into water and extracted with AcOEt (30 mL×3). The combined organic phases were washed with a sat. NaHCO$_3$ aqueous solution and brine, dried over MgSO$_4$, and concentrated under reduced pressure. Crude 3a (5.6 g) can be used without further purification. $^1$H NMR (400 MHz, CDCl$_3$) δ 14.79 (s, 0.5H), 12.94 (s, 0.5H), 7.70-7.30 (m, 9H), 4.76 (s, 1H), 4.73 (s, 1H), 4.70 (s, 1H), 4.67 (s, 1H), 4.39 (t, J=7.2 Hz, 1H), 4.32 (t, J=7.2 Hz, 1H), 1.43-1.37 (m, 3H).

A solution of 3a (4.8 g, 12 mmol) in DMF-DMA (33 mL) was heated to reflux for 2.5 h. After complete conversion, the reaction was cooled to RT. The precipitate was collected by suction-filtration. The filter cake was washed with a small amount of EtOAc and dried over in vacuum to give pure 4a as a white solid (3.5 g, 69.7%). $^1$H NMR (400 MHz, DMSO-d6) δ 8.89 (s, 1H), 8.16 (s, 1H), 8.11 (d, J=7.6 Hz, 1H), 7.89-7.82 (m, 2H), 7.49-7.39 (m, 5H), 5.52 (s. 2H), 4.33 (q, J=7.2 Hz, 2H). 1.29 (t, J=7.2 Hz, 3H).

A suspension of 4a (418 mg, 1.0 mmol) and Pd/C (50 mg) in EtOH/THF (1:1, 10 mL) was stirred at RT under H$_2$ atmosphere (15 psi.) for 30 min. After complete conversion, the mixture was filtered through a pad of celite. The filtrate was concentrated under reduced pressure. The crude product was crystallized in EtOAc to give pure 5a as a white solid (300 mg, 91.4%). $^1$H NMR (400 MHz, CD$_3$OD) δ 8.72 (s, 1H), 8.15 (s. 1H), 8.07 (d, J=7.2 Hz, 1H), 7.84-7.78 (m, 2H). 4.44 (q, J=7.2 Hz. 2H), 1.41 (t, J=7.2 Hz. 3H).

To a solution of 5a (328 mg, 1.0 mmol) in MeOH (5 mL) was added 1 N NaOH aqueous solution (3 mL, 3.0 mmol). The mixture was stirred at RT for 3 h. After complete conversion, MeOH was removed via vacuum. The aqueous phase was acidified with 1 N hydrochloride to pH=4. A white solid was precipitated from the mixture. The solid was collected by filtration, washed with water and dried over in vacuum to provide compound 1 as a white solid (120 mg, 40.0%). LCMS (ESI) m/z=300.8 [M+H]$^+$.

Example 3

1-(5-(N,N-diethylsulfamoyl)-2-methoxyphenyl)-5-hydroxy-4-oxo-1,4-dihydropyridazine-3-carboxylic acid (2)

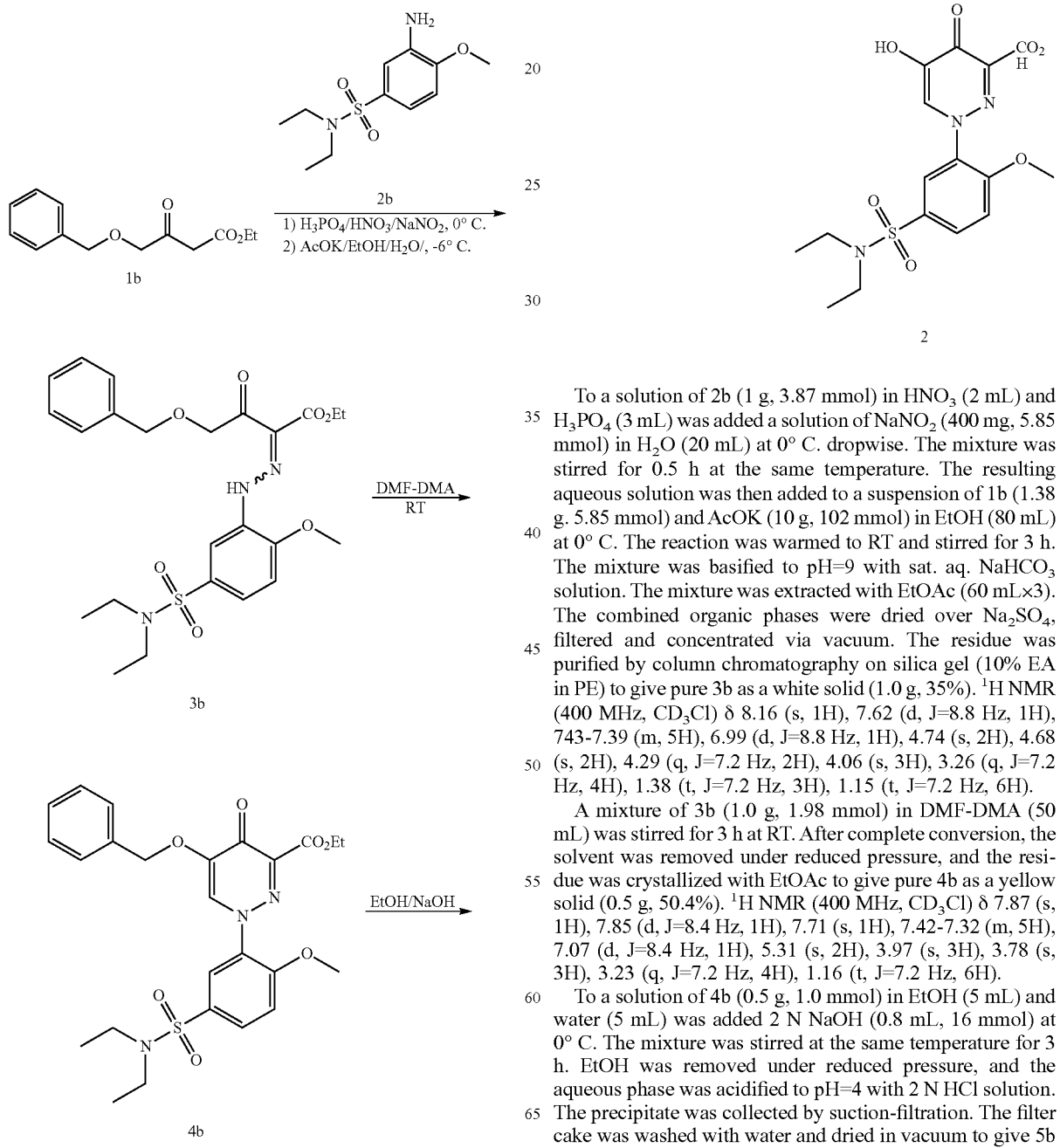

To a solution of 2b (1 g, 3.87 mmol) in HNO$_3$ (2 mL) and H$_3$PO$_4$ (3 mL) was added a solution of NaNO$_2$ (400 mg, 5.85 mmol) in H$_2$O (20 mL) at 0° C. dropwise. The mixture was stirred for 0.5 h at the same temperature. The resulting aqueous solution was then added to a suspension of 1b (1.38 g. 5.85 mmol) and AcOK (10 g, 102 mmol) in EtOH (80 mL) at 0° C. The reaction was warmed to RT and stirred for 3 h. The mixture was basified to pH=9 with sat. aq. NaHCO$_3$ solution. The mixture was extracted with EtOAc (60 mL×3). The combined organic phases were dried over Na$_2$SO$_4$, filtered and concentrated via vacuum. The residue was purified by column chromatography on silica gel (10% EA in PE) to give pure 3b as a white solid (1.0 g, 35%). $^1$H NMR (400 MHz, CD$_3$Cl) δ 8.16 (s, 1H), 7.62 (d, J=8.8 Hz, 1H), 743-7.39 (m, 5H), 6.99 (d, J=8.8 Hz, 1H), 4.74 (s, 2H), 4.68 (s, 2H), 4.29 (q, J=7.2 Hz, 2H), 4.06 (s, 3H), 3.26 (q, J=7.2 Hz, 4H), 1.38 (t, J=7.2 Hz, 3H), 1.15 (t, J=7.2 Hz, 6H).

A mixture of 3b (1.0 g, 1.98 mmol) in DMF-DMA (50 mL) was stirred for 3 h at RT. After complete conversion, the solvent was removed under reduced pressure, and the residue was crystallized with EtOAc to give pure 4b as a yellow solid (0.5 g, 50.4%). $^1$H NMR (400 MHz, CD$_3$Cl) δ 7.87 (s, 1H), 7.85 (d, J=8.4 Hz, 1H), 7.71 (s, 1H), 7.42-7.32 (m, 5H), 7.07 (d, J=8.4 Hz, 1H), 5.31 (s, 2H), 3.97 (s, 3H), 3.78 (s, 3H), 3.23 (q, J=7.2 Hz, 4H), 1.16 (t, J=7.2 Hz, 6H).

To a solution of 4b (0.5 g, 1.0 mmol) in EtOH (5 mL) and water (5 mL) was added 2 N NaOH (0.8 mL, 16 mmol) at 0° C. The mixture was stirred at the same temperature for 3 h. EtOH was removed under reduced pressure, and the aqueous phase was acidified to pH=4 with 2 N HCl solution. The precipitate was collected by suction-filtration. The filter cake was washed with water and dried in vacuum to give 5b as a white solid (0.3 g, 61.6%). $^1$H NMR (400 MHz. CD$_3$Cl)

δ 8.05 (s, 1H), 7.87-7.85 (m, 2H), 7.40-7.36 (m, 5H), 7.09 (d, J=8.0 Hz, 1H), 5.27 (s, 2H), 3.78 (s, 3H), 3.21 (q, J=7.2 Hz, 4H), 1.16 (t, J=7.2 Hz, 6H).

A mixture of 5b (0.3 g, 0.62 mmol) and Pd(OH)$_2$ (0.2 g) in MeOH (20 mL) was stirred for 4 h under H$_2$ atmosphere (30 psi). After complete conversion, the mixture was filtered through a pad of celite. The filtrate was concentrated under reduced pressure. The residue was purified by prep-HPLC to give compound 2 as a white solid (100 mg, 41.0%). LCMS (ESI) m/z=398.0 [M+H]$^+$.

Example 4

1-(4-tert-butylphenyl)-5-hydroxy-4-oxo-1,4-dihydro-pyridazine-3-carboxylic acid (3)

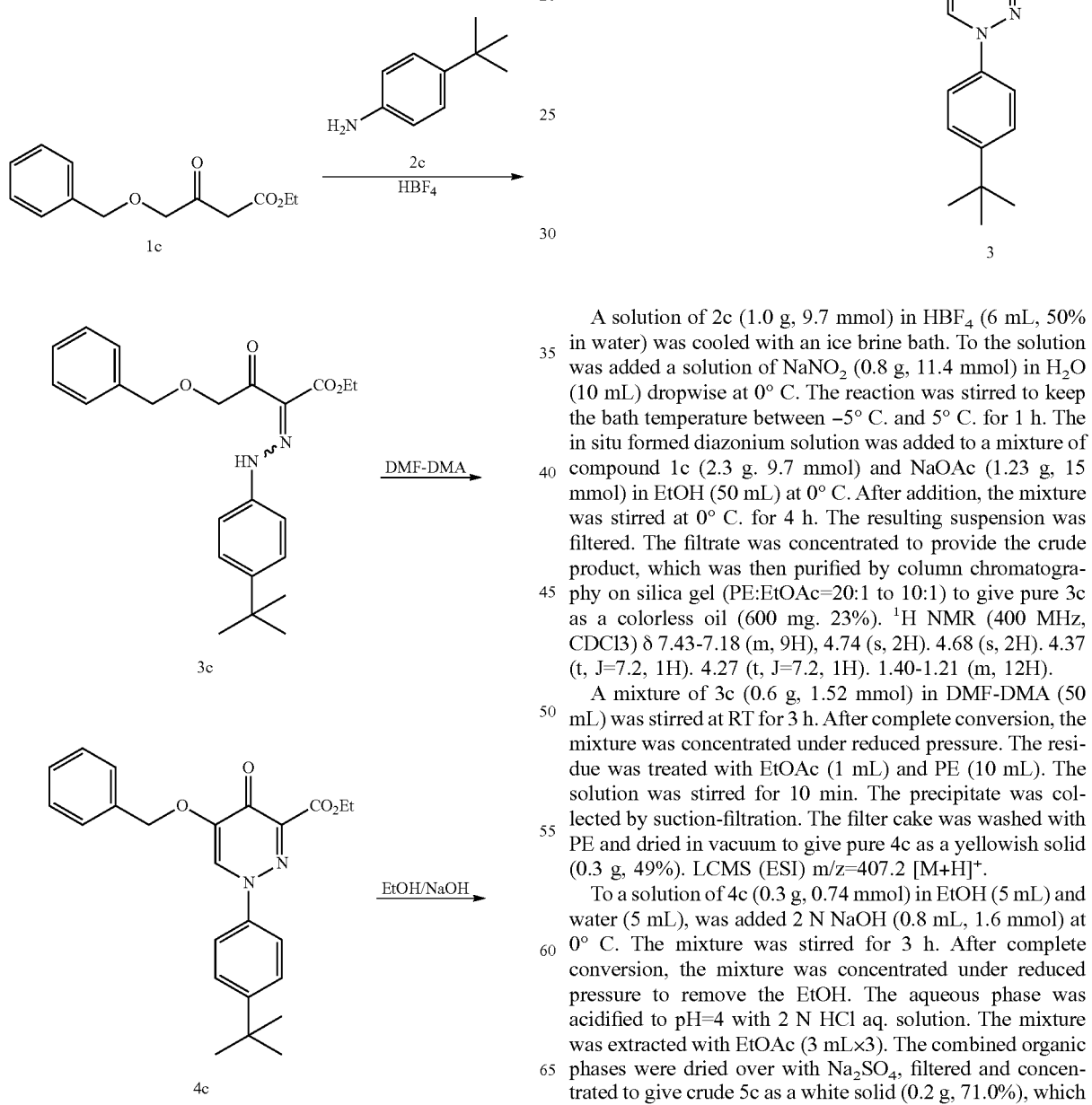

A solution of 2c (1.0 g, 9.7 mmol) in HBF$_4$ (6 mL, 50% in water) was cooled with an ice brine bath. To the solution was added a solution of NaNO$_2$ (0.8 g, 11.4 mmol) in H$_2$O (10 mL) dropwise at 0° C. The reaction was stirred to keep the bath temperature between −5° C. and 5° C. for 1 h. The in situ formed diazonium solution was added to a mixture of compound 1c (2.3 g. 9.7 mmol) and NaOAc (1.23 g, 15 mmol) in EtOH (50 mL) at 0° C. After addition, the mixture was stirred at 0° C. for 4 h. The resulting suspension was filtered. The filtrate was concentrated to provide the crude product, which was then purified by column chromatography on silica gel (PE:EtOAc=20:1 to 10:1) to give pure 3c as a colorless oil (600 mg. 23%). $^1$H NMR (400 MHz, CDCl3) δ 7.43-7.18 (m, 9H), 4.74 (s, 2H). 4.68 (s, 2H). 4.37 (t, J=7.2, 1H). 4.27 (t, J=7.2, 1H). 1.40-1.21 (m, 12H).

A mixture of 3c (0.6 g, 1.52 mmol) in DMF-DMA (50 mL) was stirred at RT for 3 h. After complete conversion, the mixture was concentrated under reduced pressure. The residue was treated with EtOAc (1 mL) and PE (10 mL). The solution was stirred for 10 min. The precipitate was collected by suction-filtration. The filter cake was washed with PE and dried in vacuum to give pure 4c as a yellowish solid (0.3 g, 49%). LCMS (ESI) m/z=407.2 [M+H]$^+$.

To a solution of 4c (0.3 g, 0.74 mmol) in EtOH (5 mL) and water (5 mL), was added 2 N NaOH (0.8 mL, 1.6 mmol) at 0° C. The mixture was stirred for 3 h. After complete conversion, the mixture was concentrated under reduced pressure to remove the EtOH. The aqueous phase was acidified to pH=4 with 2 N HCl aq. solution. The mixture was extracted with EtOAc (3 mL×3). The combined organic phases were dried over with Na$_2$SO$_4$, filtered and concentrated to give crude 5c as a white solid (0.2 g, 71.0%), which was used without further purification. $^1$H NMR (400 MHz, CDCl3) δ 8.19 (s. 1H), 7.52-7.50 (m, 2H), 7.45-7.36 (m, 7H), 5.39 (s, 2H). 1.34 (s, 9H).

A mixture of 5c (0.2 g, 0.53 mmol) and Pd(OH)$_2$ (0.2 g) in MeOH (20 mL) was stirred for 4 h under a H$_2$ atmosphere (15 psi). After the reaction was completed, the mixture was filtered through a pad of celite and concentrated to give the crude product. The crude product was purified by prep-HPLC to give compound 3 as a white solid (100 mg, 65.7%). LCMS (ESI) m/z=289.1 [M+H]$^+$.

Compound 4 was obtained following one of the procedures for obtaining compounds 1, 2 or 3 using 4-fluoroaniline. LCMS (ESI) m/z=249 [M−H] and 251 [M+H]$^+$.

Compound 5 was obtained following one of the procedures for obtaining compounds 1, 2 or 3 using 3-methoxyaniline. LCMS (ESI) m/z=261 [M−H] and 263 [M+H]$^+$.

Compound 6 was obtained following one of the procedures for obtaining compounds 1, 2 or 3 using 3-phenoxyaniline. LCMS (ESI) m/z=323 [M−H] and 324 [M+H]$^+$.

Compound 7 was obtained following one of the procedures for obtaining compounds 1, 2 or 3 using 2-(trifluoromethyl)aniline. LCMS (ESI)=301 [M+H]$^+$ and 323 [M+Na]$^+$.

Compound 8 was obtained following one of the procedures for obtaining compounds 1, 2 or 3 using 2-isopropylaniline. LCMS (ESI) m/z=275 [M+H]$^+$.

Compound 9 was obtained following one of the procedures for obtaining compounds 1, 2 or 3 using 2-phenoxyaniline. LCMS (ESI) m/z=325 [M+H]$^+$.

Compound 10 was obtained following one of the procedures for obtaining compounds 1, 2 or 3 using 2,3-dihydro-1H-inden-5-amine. LCMS (ESI) m/z=273 [M+H]$^+$.

Compound 11 was obtained following one of the procedures for obtaining compounds 1, 2 or 3 using 2-(piperidin-1-yl)aniline. LCMS (ESI) m/z=316 [M+H]$^+$.

Compound 12 was obtained following one of the procedures for obtaining compounds 1, 2 or 3 using 2,6-dimethylaniline. LCMS (ESI) m/z=261 [M+H]$^+$ and 283 [M+Na]$^+$.

Compound 13 was obtained following one of the procedures for obtaining compounds 1, 2 or 3 using 4-methoxy-[1,1'-biphenyl]-3-amine. LCMS (ESI) m/z=339 [M+H]$^+$.

Compound 14 was obtained following one of the procedures for obtaining compounds 1, 2 or 3 using 2-(difluoromethoxy)aniline. LCMS (ESI) m/z=299 [M+H]$^+$.

Compound 15 was obtained following one of the procedures for obtaining compounds 1, 2 or 3 using 2-methylquinolin-8-amine. LCMS (ESI) m/z=298 [M+H]$^+$.

Compound 16 was obtained following one of the procedures for obtaining compounds 1, 2 or 3 using 2-(tert-butyl)aniline. LCMS (ESI) m/z=289 [M+H]$^+$.

Compound 17 was obtained following one of the procedures for obtaining compounds 1, 2 or 3 using N-(3-aminophenyl)methanesulfonamide. LCMS (ESI) m/z=348 [M+Na]$^+$ and 673 [2M+Na]$^+$.

Compound 18 was obtained following one of the procedures for obtaining compounds 1, 2 or 3 using [1,1'-biphenyl]-2-amine. LCMS (ESI) m/z=309 [M+H]$^+$ and 331 [M+Na]$^+$.

Compound 19 was obtained following one of the procedures for obtaining compounds 1, 2 or 3 using 2-((cyclohexyl(methyl)amino)methyl)aniline. LCMS (ESI) m/z=358 [M+H]$^+$.

Compound 20 was obtained following one of the procedures for obtaining compounds 1, 2 or 3 using 3,5-bis(trifluoromethyl)aniline. LCMS (ESI) m/z=369 [M+H]$^+$ and 391 [M+Na]$^+$.

Compound 21 was obtained following one of the procedures for obtaining compounds 1, 2 or 3 using 2-(trifluoromethoxy)aniline. LCMS (ESI) m/z=317 [M+H]$^+$.

Compound 22 was obtained following one of the procedures for obtaining compounds 1, 2 or 3 using 3-amino-N-butylbenzenesulfonamide. LCMS (ESI) m/z=368 [M+H]$^+$.

Compound 23 was obtained following one of the procedures for obtaining compounds 1, 2 or 3 using 2-ethoxyaniline. LCMS (ESI) m/z=277 [M+H]$^+$, 299 [M+Na]$^+$ and 575 [2M+Na]$^+$.

Compound 24 was obtained following one of the procedures for obtaining compounds 1, 2 or 3 using 2-(phenylsulfonyl)aniline. LCMS (ESI) m/z=373 [M+H]$^+$ and 767 [2M+Na]$^+$.

Compound 25 was obtained following one of the procedures for obtaining compounds 1, 2 or 3 using 4-butoxyaniline. LCMS (ESI) m/z=305 [M+H]$^+$.

Compound 26 was obtained following one of the procedures for obtaining compounds 1, 2 or 3 using 3,5-dimethoxyaniline. LCMS (ESI) m/z=293 [M+H]$^+$.

Compound 27 was obtained following one of the procedures for obtaining compounds 1, 2 or 3 using 4-(trifluoromethyl)aniline. LCMS (ESI) m/z=301 [M+H]$^+$.

Compound 28 was obtained following one of the procedures for obtaining compounds 1, 2 or 3 using 4-(piperidin-1-yl)aniline. LCMS (ESI)=316 [M+H]$^+$.

Compound 29 was obtained following one of the procedures for obtaining compounds 1, 2 or 3 using 2-(2-aminophenyl)ethanol. LCMS (ESI) m/z=277 [M+H]$^+$.

Compound 30 was obtained following one of the procedures for obtaining compounds 1, 2 or 3 using 3-(trifluoromethoxy)aniline. LCMS (ESI) m/z=317 [M+H]$^+$.

Compound 31 was obtained following one of the procedures for obtaining compounds 1, 2 or 3 using 4-(methylsulfonyl)aniline. LCMS (ESI) m/z=311 [M+H]$^+$.

Compound 32 was obtained following one of the procedures for obtaining compounds 1, 2 or 3 using 2,3-dihydrobenzo[b][1,4]dioxin-6-amine. LCMS (ESI) m/z=291 [M+H]$^+$.

Compound 33 was obtained following one of the procedures for obtaining compounds 1, 2 or 3 using 1H-indazol-6-amine. LCMS (ESI) m/z=273 [M+H]$^+$.

Compound 34 was obtained following one of the procedures for obtaining compounds 1, 2 or 3 using 2'-ethyl-[1,1'-biphenyl]-2-amine. LCMS (ESI) m/z=337 [M+H]$^+$.

Compound 35 was obtained following one of the procedures for obtaining compounds 1, 2 or 3 using [1,1':2',1''-terphenyl]-2-amine. LCMS (ESI) m/z=385 [M+H]$^+$.

Compound 36 was obtained following one of the procedures for obtaining compounds 1, 2 or 3 using 2'-amino-[1,1'-biphenyl]-4-carbonitrile. LCMS (ESI) m/z=334 [M+H]$^+$ and 356 [M+Na]$^+$.

Compound 37 was obtained following one of the procedures for obtaining compounds 1, 2 or 3 using 4'-isobutyl-[1,1'-biphenyl]-2-amine. LCMS (ESI) m/z=365 [M+H]$^+$.

Compound 38 was obtained following one of the procedures for obtaining compounds 1, 2 or 3 using 2'-methyl-[1,1'-biphenyl]-2-amine. LCMS (ESI) m/z=323 [M+H]$^+$.

Compound 39 was obtained following one of the procedures for obtaining compounds 1, 2 or 3 using 2'-isopropyl-[1,1'-biphenyl]-2-amine. LCMS (ESI) m/z=351 [M+H]$^+$.

Compound 40 was obtained following one of the procedures for obtaining compounds 1, 2 or 3 using 2'-(trifluoromethoxy)-[1,1'-biphenyl]-2-amine. LCMS (ESI) m/z=393 [M+H]$^+$.

Compound 41 was obtained following one of the procedures for obtaining compounds 1, 2 or 3 using 2-morpholinoaniline. LCMS (ESI) m/z=318 [M+H]+.

Compound 42 was obtained following one of the procedures for obtaining compounds 1, 2 or 3 using 1H-indazol-5-amine. LCMS (ESI) m/z=273 [M+H]+.

Compound 43 was obtained following one of the procedures for obtaining compounds 1, 2 or 3 using 4-phenoxyaniline. LCMS (ESI) m/z=325 [M+H]+.

Compound 44 was obtained following the procedure for obtaining compound 24 except hydrolysis of the ethyl ester was not performed. LCMS (ESI) m/z=401 [M+H]+.

TABLE 1

Compounds of Formula (I)

| Structure | No. |
|---|---|
| | 4 |
| | 5 |
| | 6 |
| | 7 |
| 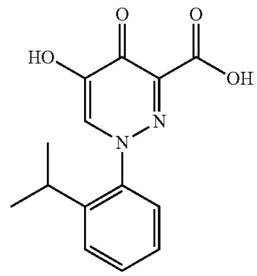 [SMILES: CC(C)c1ccccc1-n1cc(O)c(=O)c(C(=O)O)n1] | 8 |
| 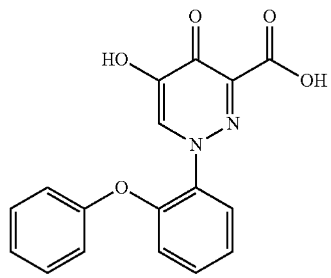 [SMILES: O=C(O)c1nn(-c2ccccc2Oc2ccccc2)cc(O)c1=O] | 9 |
| 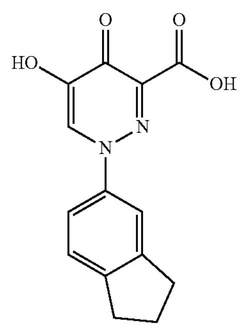 [SMILES: O=C(O)c1nn(-c2ccc3c(c2)CCC3)cc(O)c1=O] | 10 |
| 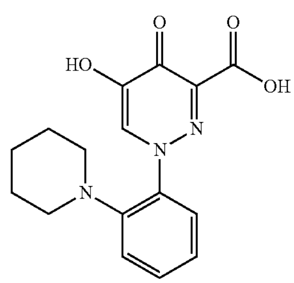 [SMILES: O=C(O)c1nn(-c2ccccc2N2CCCCC2)cc(O)c1=O] | 11 |
| 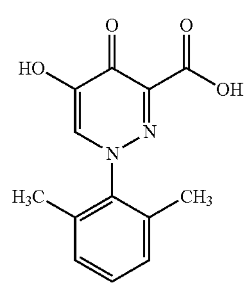 [SMILES: Cc1cccc(C)c1-n1cc(O)c(=O)c(C(=O)O)n1] | 12 |

TABLE 1-continued

Compounds of Formula (I)

| Structure | No. |
|---|---|
| (structure) | 13 |
| (structure) | 14 |
| (structure) | 15 |
| (structure) | 16 |
| (structure) | 17 |
| (structure) | 18 |
| (structure) | 19 |
| (structure) | 20 |
| (structure) | 21 |
| (structure) | 22 |

TABLE 1-continued

Compounds of Formula (I)

| Structure | No. |
|---|---|
| 5-hydroxy-4-oxo-1-(2-ethoxyphenyl)-1,4-dihydropyridazine-3-carboxylic acid | 23 |
| 5-hydroxy-4-oxo-1-(2-(phenylsulfonyl)phenyl)-1,4-dihydropyridazine-3-carboxylic acid | 24 |
| 5-hydroxy-4-oxo-1-(4-butoxyphenyl)-1,4-dihydropyridazine-3-carboxylic acid | 25 |
| 5-hydroxy-4-oxo-1-(3,5-dimethoxyphenyl)-1,4-dihydropyridazine-3-carboxylic acid | 26 |
| 5-hydroxy-4-oxo-1-(4-(trifluoromethyl)phenyl)-1,4-dihydropyridazine-3-carboxylic acid | 27 |
| 5-hydroxy-4-oxo-1-(4-(piperidin-1-yl)phenyl)-1,4-dihydropyridazine-3-carboxylic acid | 28 |
| 5-hydroxy-4-oxo-1-(2-(2-hydroxyethyl)phenyl)-1,4-dihydropyridazine-3-carboxylic acid | 29 |
| 5-hydroxy-4-oxo-1-(3-(trifluoromethoxy)phenyl)-1,4-dihydropyridazine-3-carboxylic acid | 30 |
| 5-hydroxy-4-oxo-1-(4-(methylsulfonyl)phenyl)-1,4-dihydropyridazine-3-carboxylic acid | 31 |

TABLE 1-continued

Compounds of Formula (I)

| Structure | No. |
|---|---|
| (5-hydroxy-4-oxo-1-(2,3-dihydro-1,4-benzodioxin-6-yl)-1,4-dihydropyridazine-3-carboxylic acid) | 32 |
| (5-hydroxy-4-oxo-1-(1H-indazol-6-yl)-1,4-dihydropyridazine-3-carboxylic acid) | 33 |
| (5-hydroxy-4-oxo-1-(2'-ethyl-[1,1'-biphenyl]-2-yl)-1,4-dihydropyridazine-3-carboxylic acid) | 34 |
| (5-hydroxy-4-oxo-1-([1,1':2',1''-terphenyl]-3-yl)-1,4-dihydropyridazine-3-carboxylic acid) | 35 |
| (5-hydroxy-4-oxo-1-(4'-cyano-[1,1'-biphenyl]-2-yl)-1,4-dihydropyridazine-3-carboxylic acid) | 36 |
| (5-hydroxy-4-oxo-1-(4'-isobutyl-[1,1'-biphenyl]-2-yl)-1,4-dihydropyridazine-3-carboxylic acid) | 37 |
| (5-hydroxy-4-oxo-1-(2'-methyl-[1,1'-biphenyl]-2-yl)-1,4-dihydropyridazine-3-carboxylic acid) | 38 |
| (5-hydroxy-4-oxo-1-(2'-isopropyl-[1,1'-biphenyl]-2-yl)-1,4-dihydropyridazine-3-carboxylic acid) | 39 |
| (5-hydroxy-4-oxo-1-(2'-trifluoromethoxy-[1,1'-biphenyl]-2-yl)-1,4-dihydropyridazine-3-carboxylic acid) | 40 |
| (5-hydroxy-4-oxo-1-(2-morpholinophenyl)-1,4-dihydropyridazine-3-carboxylic acid) | 41 |

TABLE 1-continued

Compounds of Formula (I)

| Structure | No. |
|---|---|
| 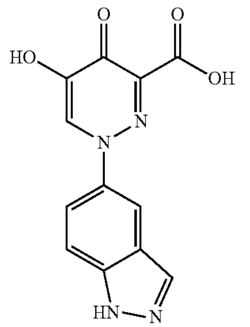 [SMILES: O=C(O)c1nn(-c2ccc3[nH]ncc3c2)cc(O)c1=O] | 42 |
| 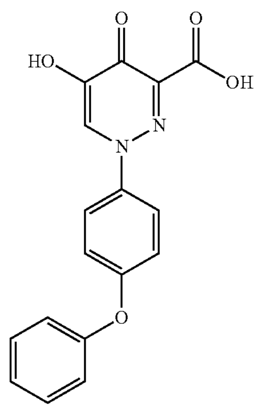 [SMILES: O=C(O)c1nn(-c2ccc(Oc3ccccc3)cc2)cc(O)c1=O] | 43 |
| 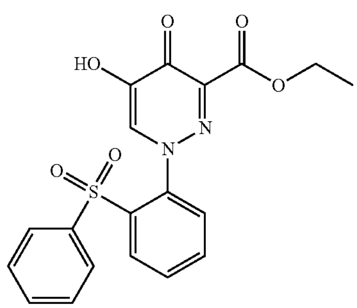 [SMILES: CCOC(=O)c1nn(-c2ccccc2S(=O)(=O)c2ccccc2)cc(O)c1=O] | 44 |

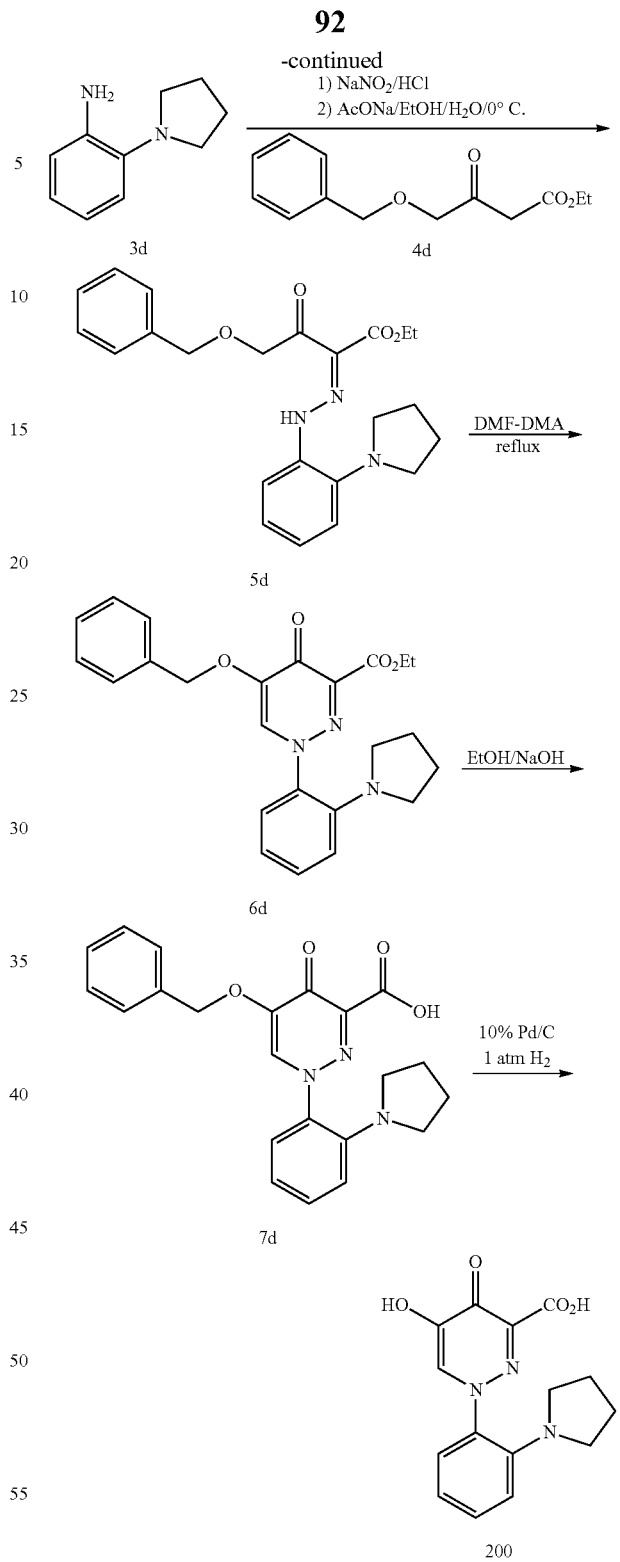

Example 5

5-hydroxy-4-oxo-1-(2-(pyrrolidin-1-yl)phenyl)-1,4-dihydropyridazine-3-carboxylic acid (200)

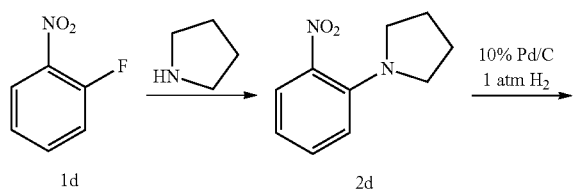

A solution of 1d (10.0 g, 70.9 mmol) in pyrrolidine (30 mL) was stirred at RT for 1 h. The solvent was evaporated under reduced pressure to give crude 2d as a colorless oil (10.0 g, 73.5%). The residue was used without further purification.

A mixture of 2d (10.0 g, 52.0 mmol) and Pd/C (1.0 g) in MeOH (20 mL) was stirred under $H_2$ atmosphere (15 psi) for 4 h. After complete conversion, the mixture was filtered through a pad of celite. The filtrate was concentrated under the reduced pressure. The residue was purified by column chromatography on silica gel (elution PE:EtOAc=50:1 to 20:1) to give pure 3d as a colorless oil (8.0 g, 95.2%). $^1$H NMR (400 MHz, CDCl$_3$) δ 6.94 (d, J=8.0 Hz, 1H), 6.88-6.81 (m, 1H), 6.71-6.66 (m, 2H), 3.79 (s, 2H), 3.01-2.98 (m, 4H), 1.88-1.85 (m, 4H).

To a stirred solution of 3d (743 mg, 4.59 mmol) in HCl (4.6 mL, 27.54 mmol) at 0° C. was added NaNO$_2$ (380 mg, 5.5 mmol) in H$_2$O (10 mL). The solution was stirred at 0° C. for 40 min. The resulting aqueous solution was added to a suspension of 4d (1.08 g. 4.59 mmol) and NaOAc (2.26 g, 27.54 mmol) in EtOH (10 mL) at 0° C. After addition, the solution was stirred at 0° C. for 30 min and then warmed to RT. The reaction was kept on stirring for another 4 h. After complete conversion, the mixture was treated with EtOAc (30 mL). The organic phase was separated, washed with water and brine, and dried over with Na$_2$SO$_4$. The solvent was removed under the reduced pressure. The residue, 5d, (4.0 g, 87.2%) was used without further purification.

A solution of 5d (0.8 g, 1.96 mmol) in DMF-DMA (10 mL) was stirred at RT for 4 h. The solution was concentrated in vacuum, and the residue was crystallized in EtOAc to give pure 6d as a yellowish solid (400 mg, 48.69%). $^1$H NMR (400 MHz, CD$_3$OD) δ 8.25 (s, 1H), 7.42-7.31 (m, 6H), 7.21 (d, J=7.6 Hz, 1H), 6.94 (d, J=8.4 Hz, 1H), 6.85-6.81 (m, 1H), 5.23 (s, 2H), 4.37 (q, J=7.2 Hz, 2H), 2.81-2.78 (m, 4H), 1.74-1.70 (m, 4H), 1.35 (t, J=7.2 Hz, 3H).

To a stirred solution of 6d (0.4 g, 0.95 mmol) in EtOH (10 mL) was added 2 N NaOH solution (1.4 mL, 2.86 mmol) dropwise. After addition, the mixture was stirred at RT for 1 h. After complete conversion, the EtOH was removed via vacuum. The resulting aqueous phase was acidified with 1 N HCl solution to pH=2. The precipitate was collected by suction-filtration. The filter cake was washed with water and dried in vacuo to give pure 7d as a white solid (250 mg, 67.3%).

A mixture of 7d (250 mg, 0.64 mmol) and Pd/C (50 mg) in MeOH (10 mL) was stirred under H$_2$ atmosphere (15 psi) for 15 min. After complete conversion, the mixture was filtered through a pad of celite. The filtrate was concentrated via vacuum. The residue was crystallized in EtOH (10 mL) to give compound 200 as a yellowish solid (50 mg, 25.91%). LCMS (ESI) m/z=302.0 [M+H]$^+$.

Compound 201 was obtained following the procedure for obtaining compound 200 using 1-chloro-2-nitro-4-(trifluoromethyl)benzene and pyrrolidine. LCMS (ESI) m/z=370 [M+H]$^+$.

Compound 202 was obtained following the procedure for obtaining compound 200 using 1-fluoro-2-nitrobenzene and 4-methylpiperidine. LCMS (ESI) m/z=330 [M+H]$^+$.

Compound 203 was obtained following the procedure for obtaining Compound 200 using 1-fluoro-2-nitrobenzene and 2-benzylpyrrolidine. LCMS (ESI) m/z=392 [M+H]$^+$.

Compound 204 was obtained following the procedure for obtaining compound 200 using 1-fluoro-2-nitrobenzene and 1-methylpiperazine. LCMS (ESI) m/z=331 [M+H]$^+$.

Compound 205 was obtained following the procedure for obtaining compound 200 using 1-fluoro-2-nitrobenzene and 1-ethylpiperazine. LCMS (ESI) m/z=345 [M+H]$^+$.

Compound 206 was obtained following the procedure for obtaining compound 200 using 1-fluoro-2-nitrobenzene and 4,4-dimethylpiperidine. LCMS (ESI) m/z=344 [M+H]$^+$.

Compound 207 was obtained following the procedure for obtaining compound 200 using 4-isopropylpiperidine. LCMS (ESI) m/z=358 [M+H]$^+$.

Compound 208 was obtained following the procedure for obtaining compound 200 using 4-(tert-butyl)piperidine hydrochloride. LCMS (ESI) m/z=372 [M+H]$^+$.

Compound 209 was obtained following the procedure for obtaining compound 200 using 3,3-dimethylpiperidine hydrochloride. LCMS (ESI) m/z344 [M+H]$^+$.

Compound 210 was obtained following the procedure for obtaining compound 200 using 3-methylpiperidine hydrochloride. LCMS (ESI) m/z=330 [M+H]$^+$.

Compound 211 was obtained following the procedure for obtaining compound 200 using 3-phenylpiperidine. LCMS (ESI) m/z=392 [M+H]$^+$.

TABLE 2

Compounds of Formula (I)

| Structure | No. |
|---|---|
| (structure with pyrrolidine, pyridazinone core, phenyl with CF$_3$) | 201 |
| (structure with 4-methylpiperidine, pyridazinone core, phenyl) | 202 |
| (structure with 2-benzylpyrrolidine, pyridazinone core, phenyl) | 203 |
| (structure with 1-methylpiperazine, pyridazinone core, phenyl) | 204 |

TABLE 2-continued

Compounds of Formula (I)

| Structure | No. |
|---|---|
| (structure) | 205 |
| (structure) | 206 |
| (structure) | 207 |
| (structure) | 208 |
| (structure) | 209 |
| (structure) | 210 |
| (structure) | 211 |

Example 6

1-(2',5'-dimethylbiphenyl-2-yl)-5-hydroxy-4-oxo-1,4-dihydropyidazine-3-carboxylic acid (300)

(reaction scheme: 3e + boronic acid → Pd(PPh$_3$)$_4$ K$_2$CO$_3$, Dioxane → 4e → Pd/C H$_2$, EtOH →)

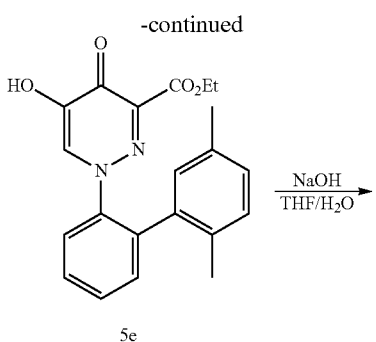

Compound 3e was prepared in accordance with the following reaction scheme as detailed below.

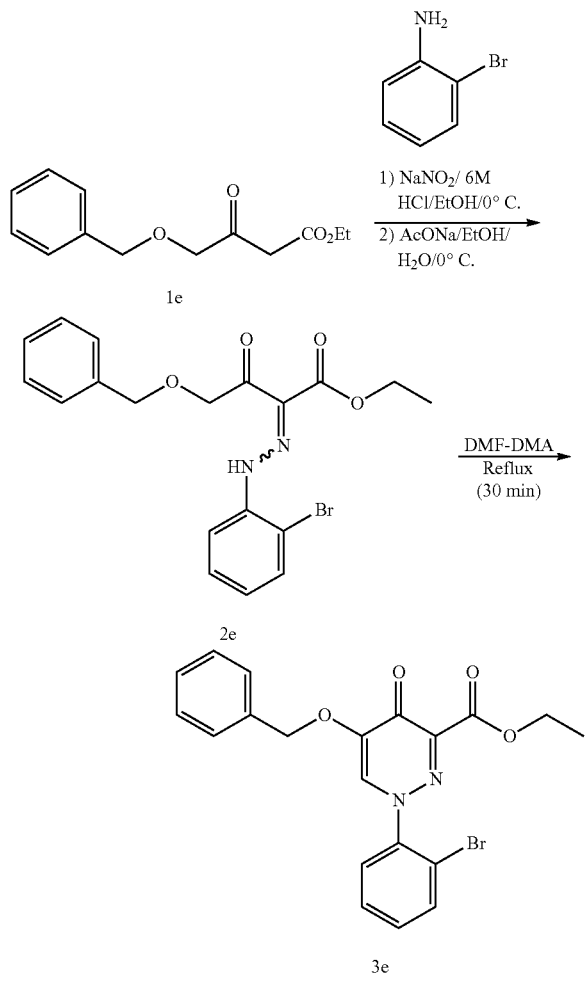

A mixture of 2-bromobenzenamine (3.4 g, 20 mmol) and 6 M HCl aqueous solution (20 mL, 120 mmol) was stirred at 0° C. To the mixture was added a solution of NaNO$_2$ (1.66 g, 24 mmol) in H$_2$O (5 mL) dropwise. After addition, the mixture was stirred for 15 min. The resulting aqueous solution was added to a suspension of 1e (4.7 g, 20 mmol) and NaOAc (9.84 g, 120 mmol) in EtOH (40 mL) at 0° C. dropwise. Water (about 15 mL) was added to dissolve the NaOAc. After complete conversion, the mixture was poured into water and extracted with AcOEt (50 mL×3). The combined organic phases were washed with sat. aq. NaHCO$_3$ solution and brine, dried over MgSO$_4$, and concentrated under reduced pressure. Crude 2e (6.3 g, 75.2%) was used without further purification. LCMS (ESI) m/z=418.8, 420.9 [M+H]$^+$.

A solution of 2e (3.3 g, 8 mmol) in DMF-DMA (22 mL) was heated to reflux for 2.5 h. After complete conversion, the reaction was cooled to RT. The precipitate was collected by suction-filtration, and the filter cake was washed with a small amount of EtOAc/PE (1:1, 6 mL) and dried over in vacuum to give pure 3e as a white solid (3.0 g, 87.4%). LCMS (ESI) m/z=429, 431 [M+H]$^+$.

To a suspension of 3e (500 mg, 1.16 mmol), 2,5-dimethylphenylboronic acid (210.3 mg, 1.40 mmol) and K$_2$CO$_3$ (322 mg, 2.33 mmol) in dioxane (10 mL) was added Pd(PPh$_3$)$_4$ (135 mg, 0.0168 mmol). The mixture was degassed for 5 min, and then refilled with N$_2$. The reaction was stirred at 100° C. under N$_2$ atmosphere for 2 h and then cooled to RT. The solid was filtered off, and the filtrate was concentrated under reduced pressure. The residue was purified by column chromatography on silica gel (PE:EA=5:1 to 2:1) to give pure 4e as a white solid (389 mg, 73.3%). $^1$H NMR (400 MHz, CDCl$_3$) δ 7.53-7.41 (m, 3H), 7.27-7.14 (m, 7H), 7.01 (s, 2H), 6.84 (s, 1H), 4.64-4.51 (m, 2H), 4.33 (q, J=7.2 Hz, 2H), 2.23 (s, 3H), 1.81 (s, 3H), 1.31 (t, J=7.2 Hz, 3H).

A mixture of 4e (389 mg. 0.85 mmol) and Pd/C (50 mg) in EtOH (20 mL) was stirred under a H$_2$ atmosphere (15 psi) for 30 min. The solution was filtered through a pad of celite. The filtrate was concentrated to give the crude product as a white solid (249 mg, 80.5%), which was used without further purification. LCMS (ESI) m/z=365.0 [M+H]$^+$.

To a solution of 5c (249 mg, 0.68 mmol) in THF (3 mL) was added 1N NaOH solution (1.36 mL, 1.36 mmol). The mixture was stirred at RT for 2 h. After complete conversion, THF was removed under reduced pressure, and the aqueous phase was acidified with 1 N HCl to pH=4. The precipitate was collected by suction-filtration. The filter cake was washed with water and dried in vacuum to give compound 300 as a white solid (130 mg, 56.9%). LCMS (ESI) m/z=336.9 [M+H]$^+$.

Compound 301 was obtained following the procedure for obtaining compound 300 using (3,5-dimethylphenyl)boronic acid. LCMS (ESI) m/z=337 [M+H]$^+$.

Compound 302 was obtained following the procedure for obtaining compound 300 using (4-(tert-butyl)phenyl)boronic acid. LCMS (ESI) m/z=365 [M+H]$^+$.

Compound 303 was obtained following the procedure for obtaining compound 300 using p-tolylboronic acid. LCMS (ESI) m/z=323 [M+H]$^+$.

Compound 304 was obtained following the procedure for obtaining compound 300 using tert-butyl 4-(4,4,5,5-tetramethyl-1,3,2-dioxaborolan-2-yl)-5,6-dihydropyridine-1(2H)-carboxylate. $^1$H NMR (CD$_3$OD): δ 1.45 (s, 9H). LCMS (ESI) m/z=316 [M-Boc+H]$^+$.

Compound 305 was obtained following the procedure for obtaining compound 300 using (4-fluoro-2-methylphenyl) boronic acid. LCMS (ESI) m/z=341 [M+H]$^+$.

Compound 306 was obtained following the procedure for obtaining compound 300 using (4-fluorophenyl)boronic acid. LCMS (ESI) m/z=327 [M+H]$^+$.

Compound 307 was obtained following the procedure for obtaining compound 300 using (4-(trifluoromethyl)phenyl) boronic acid. LCMS (ESI) m/z=377 [M+H]$^+$ and 399 [M+Na]$^+$.

Compound 308 was obtained following one of the procedures for obtaining compound 300 using 2-(cyclohex-1-en-1-yl)-4,4,5,5-tetramethyl-1,3,2-dioxaborolane. LCMS (ESI) m/z=315 [M+H]$^+$.

Compound 309 was obtained following the procedure for obtaining compound 300 using (2,3-dimethylphenyl)boronic acid. LCMS (ESI) m/z=337 [M+H]$^+$.

Compound 310 was obtained following the procedure for obtaining compound 300 using (2-isopropoxyphenyl)boronic acid. LCMS (ESI) m/z=367 [M+H]$^+$.

Compound 311 was obtained following the procedure for obtaining compound 300 using (2-phenoxyphenyl)boronic acid. LCMS (ESI) m/z=401 [M+H]$^+$.

Compound 312 was obtained following the procedure for obtaining compound 304 with the addition of a TFA/CH$_2$Cl$_2$ step to cleave the Boc group. LCMS (ESI) m/z=316 [M+H]$^+$.

Compound 313 was obtained following the procedure for obtaining compound 300 using (1H-indol-6-yl)boronic acid. LCMS (ESI) m/z=348 [M+H]$^+$.

Compound 314 was obtained following the procedure for obtaining compound 300 using 2-isopropoxy-5-methylphenyl)boronic acid. LCMS (ESI) m/z=381 [M+H]$^+$.

Compound 315 was obtained following the procedure for obtaining compound 300 using (2-methoxyphenyl)boronic acid. LCMS (ESI) m/z=339 [M+H]$^+$.

Compound 316 was obtained following the procedure for obtaining compound 300 using dibenzo[b,d]furan-4-ylboronic acid. LCMS (ESI) m/z=399 [M+H]$^+$.

Compound 317 was obtained following the procedure for obtaining compound 300 using (2-hydroxyphenyl)boronic acid with the modification that the boronic acid coupling product was alkylated using bromocyclohexane in DMF at RT using sodium iodide and potassium carbonate. LCMS (ESI) m/z=407 [M+H]$^+$.

Compound 318 was obtained following the procedure for obtaining compound 300 using (3-methoxyphenyl)boronic acid. LCMS (ESI) m/z=339 [M+H]$^+$.

Compound 319 was obtained following the procedure for obtaining compound 300 using (2-hydroxyphenyl)boronic acid with the modification that the boronic acid coupling product was alkylated using bromocyclopentane in DMF at RT using sodium iodide and postassium carbonate. LCMS (ESI) m/z=393 [M+H]$^+$.

Compound 320 was obtained following the procedure for obtaining compound 300 using (1H-indol-5-yl)boronic acid. LCMS (ESI) m/z=348 [M+H]$^+$.

Compound 321 was obtained following the procedure for obtaining compound 300 using 4-(4,4,5,5-tetramethyl-1,3,2-dioxaborolan-2-yl)-1H-indazole. LCMS (ESI) m/z=362 [M+H]$^+$.

Compound 322 was obtained following the procedure for obtaining compound 300 using (2-chloro-5-methoxyphenyl) boronic acid. LCMS (ESI) m/z=373 [M+H]$^+$.

Compound 323 was obtained following the procedure for obtaining compound 300 using (3-chloro-5-methoxyphenyl) boronic acid. LCMS (ESI) m/z=373 [M+H]$^+$.

Compound 324 was obtained following the procedure for obtaining compound 300 using (1-methyl-1H-indol-6-yl) boronic acid with the modification that the ester/ether precursor was treated with methyl iodide and potassium carbonate in DMF prior to debenzylation and ester hydrolysis. LCMS (ESI)=362 [M+H]$^+$.

Compound 325 was obtained following the procedure for obtaining compound 300 using (2-isobutoxyphenyl)boronic acid. LCMS (ESI) m/z=381 [M+H]$^+$.

Compound 326 was obtained following the procedure for obtaining compound 300 using (3-ethoxy-5-methylphenyl) boronic acid. LCMS (ESI) m/z=367 [M+H]$^+$.

TABLE 3

Compounds of Formula (I)

| Structure | No. |
|---|---|
| 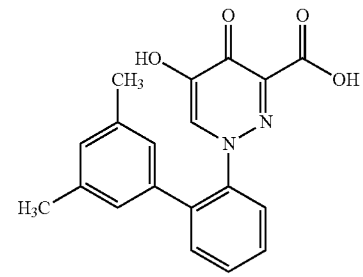 [SMILES: Cc1cc(C)cc(-c2ccccc2-n2cc(O)c(=O)c(C(=O)O)n2)c1] | 301 |
| 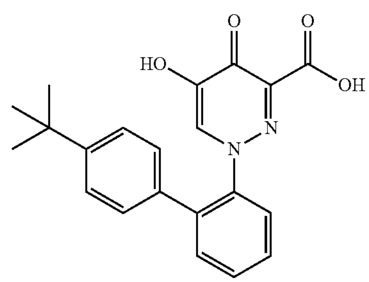 [SMILES: CC(C)(C)c1ccc(-c2ccccc2-n2cc(O)c(=O)c(C(=O)O)n2)cc1] | 302 |
| 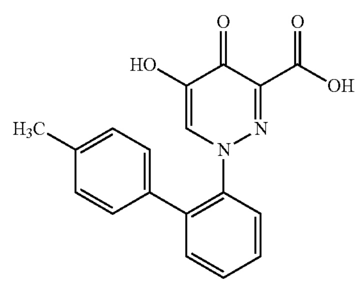 [SMILES: Cc1ccc(-c2ccccc2-n2cc(O)c(=O)c(C(=O)O)n2)cc1] | 303 |
| 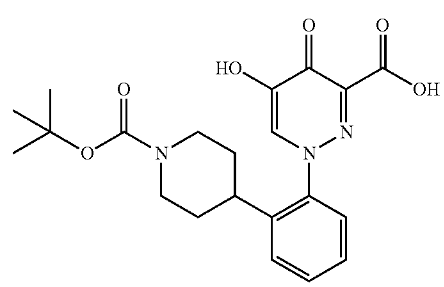 [SMILES: CC(C)(C)OC(=O)N1CCC(c2ccccc2-n2cc(O)c(=O)c(C(=O)O)n2)CC1] | 304 |

TABLE 3-continued

Compounds of Formula (I)

| Structure | No. |
|---|---|
| (4'-fluoro-2'-methylbiphenyl pyridazinone carboxylic acid) | 305 |
| (4'-fluorobiphenyl pyridazinone carboxylic acid) | 306 |
| (4'-trifluoromethylbiphenyl pyridazinone carboxylic acid) | 307 |
| (2'-cyclohexylphenyl pyridazinone carboxylic acid) | 308 |
| (2',3'-dimethylbiphenyl pyridazinone carboxylic acid) | 309 |
| (2'-isopropoxybiphenyl pyridazinone carboxylic acid) | 310 |
| (2'-phenoxybiphenyl pyridazinone carboxylic acid) | 311 |
| (2'-(piperidin-4-yl)phenyl pyridazinone carboxylic acid) | 312 |
| (2'-(1H-indol-6-yl)phenyl pyridazinone carboxylic acid) | 313 |
| (5'-methyl-2'-isopropoxybiphenyl pyridazinone carboxylic acid) | 314 |

TABLE 3-continued

Compounds of Formula (I)

| Structure | No. |
|---|---|
| (structure) | 315 |
| (structure) | 316 |
| (structure) | 317 |
| (structure) | 318 |
| (structure) | 319 |
| (structure) | 320 |
| (structure) | 321 |
| (structure) | 322 |
| (structure) | 323 |
| (structure) | 324 |

TABLE 3-continued

Compounds of Formula (I)

| Structure | No. |
|---|---|
| 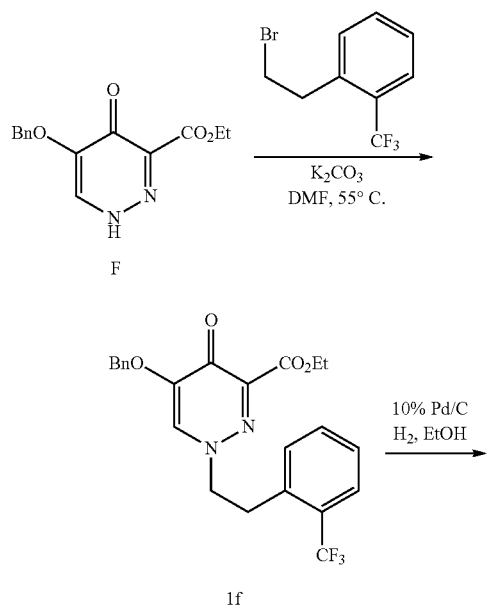 | 325 |
| 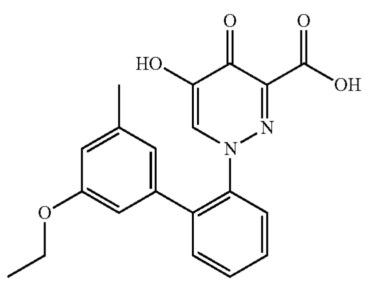 [SMILES: CCOc1cc(C)cc(-c2ccccc2-n2cc(O)c(=O)c(C(=O)O)n2)c1] | 326 |

Example 7

1-(2-(trifluoromethyl)phenethyl)-1,4-dihydro-5-hydroxy-4-oxopyridazine-3-carboxylic acid (400)

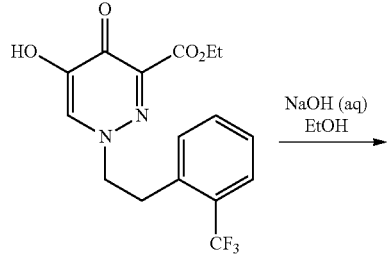

408

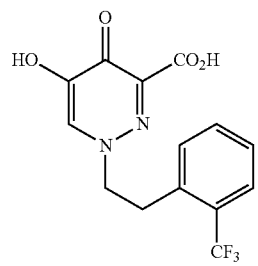

400

Potassium carbonate (0.20 g, 1.5 mmol) was added to a solution of compound F (80 mg. 2.9 mmol) and trifluoromethylphenethyl bromide (0.15 mL. 8.8 mmol), in DMF (1 mL). The reaction was heated at 55° C. for 30 min. The mixture was diluted with EtOAc (50 mL) and washed H$_2$O (3×), brine (1×), dried (Na$_2$SO$_4$), and concentrated. The crude mixture was chromatographed (SiO$_2$, EtOAc:hexane) to provide if (80 mg, 62%).

Compound if (80 mg, 1.8 mmol) was hydrogenated over 10% Pd/C (4 mg) in THF/EtOH mL, 50% v/v) for 2 h. The catalyst was removed by filtration, and the filtrate was concentrated. The crude product was recrystallized from hexane/CH$_1$Cl$_2$ to provide compound 408 (51 mg, 61%). LCMS (DUIS) m/z=357 [M+H]$^+$.

Sodium hydroxide (1.0 mL, 2.0 M in H$_2$O) was added to a solution of compound 408 (48 mg, 1.1 mmol) in EtOH (5 mL). The reaction was stirred at RT for 4 h. The mixture was concentrated and then acidified with 1M HCl to give a precipitate which was collected by filtration to give compound 400 as a white solid (3.7 mg, 10%). LCMS (ESI) m/z=329 [M+H]$^+$ and 392 [M+CH$_3$CN+Na]$^+$.

Compound 401 was obtained following the procedure for obtaining compound 400 using (2-bromoethyl)benzene. LCMS (ESI) m/z=261 [M+H]$^+$.

Compound 402 was obtained following the procedure for obtaining compound 400 using (3-bromopropyl)benzene. LCMS (ESI) m/z=275 [M+H]$^+$, 287 [M+Na]$^+$ and 338 [M+CH$_3$CN+Na]$^+$.

Compound 403 was obtained following the procedure for obtaining compound 400 using 3-(bromomethyl)-1,1'-biphenyl. LCMS (ESI) m/z=323 [M+H]$^+$, 345 [M+Na]$^+$ and 667 [2M+Na]$^+$.

Compound 404 was obtained following the procedure for obtaining compound 400 using tert-butyl 3-(2-bromoethyl)-1H-indole-1-carboxylate. LCMS (ESI) m/z=400 [M+H]$^+$, 422 [M+Na]$^+$ and 344 [M+H—C$_4$H$_8$]$^+$.

Compound 405 was obtained following the procedure for obtaining compound 400 using 1-(1-(bromomethyl)cyclopentyl)-3-(trilluoromethyl)benzene, with the modifications that step 1 of the reaction was heated at 85° C. for 24 h and step 3 was not performed. LCMS (ESI) m/z=409 [M−H]− and 455 [M+HCO$_2$]−.

Compound 406 was obtained following the procedure for obtaining compound 400 using 1-(1-(bromomethyl)cyclopentyl)-3-(trifluoromethyl)benzene, with the modification that step 1 of the reaction was heated at 85° C. for 24 h. LCMS (ESI) m/z=381 [M−H]⁻ and 763 [2M−H]⁻.

Compound 407 was obtained following the procedure for obtaining compound 404 with the modification that compound 404 was treated with trifluoroacetic acid in dichloromethane. LCMS (ESI) m/z=300 [M+H]⁺ and 322 [M+Na]⁺.

Compound 408 was obtained following the procedure for obtaining compound 400 using 1-(2-bromoethyl)-2-(trifluoromethyl)benzene with the modification that step 3 was not performed. LCMS (ESI) m/z=357 [M+H]⁺.

Compound 409 was obtained following the procedure for obtaining compound 400 using benzyl bromide. LCMS (ESI) m/z=247 [M+H]⁺.

Compound 410 was obtained following the procedure for obtaining compound 400 using (1-(bromomethyl)cyclopentyl)benzene with the modification that step 1 of the reaction was heated at 85° C. for 24 h. LCMS (ESI) m/z=315 [M+H]⁺.

Compound 411 was obtained following the procedure for obtaining compound 410 with the modification that step 3 was not performed. LCMS (ESI) m/z=343 [M+H]⁺.

Compound 412 was obtained following the procedure for obtaining compound 400 using 1-(2-bromoethyl)-3-(trifluoromethyl)benzene. LCMS (ESI)=327 [M−H]⁻.

Compound 413 was obtained following the procedure for obtaining compound 400 using 1-(2-bromoethyl)-2-methoxybenzene. LCMS (ESI) m/z=289 [M−H]⁻.

Compound 414 was obtained following the procedure for obtaining compound 400 using 1-(2-bromoethyl)-3-methoxybenzene. LCMS (ESI) m/z=289 [M−H]⁻.

Compound 415 was obtained following the procedure for obtaining compound 400 using 1-(2-bromoethyl)-4-methoxybenzene. LCMS (ESI) m/z=289 [M−H]⁻.

Compound 416 was obtained following the procedure for obtaining compound 400 using 1-(1-bromo-2-methylpropan-2-yl)-4-methylbenzene with the modification that step 1 of the reaction was heated at 95° C. for 96 h. LCMS (ESI) m/z=301 [M−H]⁻.

Compound 417 was obtained following the procedure for obtaining compound 400 using 4-(2-bromoethyl)-1,2-dimethoxybenzene. LCMS (ESI) m/z=319 [M−H]⁻.

Compound 418 was obtained following the procedure for obtaining compound 400 using 2-bromo-3,4-dihydronaphthalen-1(2H)-one with the modifications that step 1 of the reaction was performed at RT for 1 h and step 2 was stopped after 1 h. LCMS (ESI) m/z=301 [M+H]⁺.

Compound 419 was obtained following the procedure for obtaining compound 400 using 1-(1-(bromomethyl)cyclopentyl)-3,5-bis(trifluoromethyl)benzene with the modification that step 1 of the reaction was heated at 85° C., for 24 h. LCMS (ESI) m/z=449 [M−H]⁻.

Compound 420 was obtained following the procedure for obtaining compound 419 with the modification that step 3 was not performed. LCMS (ESI) m/z=477 [M−H]⁻ and 523 [M−HCO₂]⁻.

Compound 421 was obtained following the procedure for obtaining compound 400 using (2-bromoethyl)cyclohexane. LCMS (ESI) m/z=267 [M+H]⁺.

Compound 422 was obtained following the procedure for obtaining compound 400 using (1-(1H-pyrrolo[2,3-b]pyridin-1-yl)cyclopentyl)methanol with the modification that the alkylation was carried out under Mitsunobu conditions (Ph₃P; DEAD; THF; RT to 85° C. for 12 h). LCMS (ESI) m/z=353 [M−H]⁻.

Compound 423 was obtained following the procedure for obtaining compound 400 using 1-(2-bromoethyl)naphthalene. LCMS (ESI) m/z=311 [M+H]⁺.

Compound 424 was obtained following the procedure for obtaining compound 400 using 1-(1-(bromomethyl)cyclopropyl)-3-(trifluoromethyl)benzene. LCMS (ESI) m/z=353 [M−H]⁻.

Compound 425 was obtained following the procedure for obtaining compound 400 using (1-(3-methyl-1H-pyrrolo[2,3-b]pyridin-1-yl)cyclopentyl)methanol with the modification that the alkylation was carried out under Mitsunobu conditions (Ph₃P; DIAD; THF; RT to 80° C. for 8 h). LCMS (ESI) m/z=367 [M−H]⁻.

Compound 426 was obtained following the procedure for obtaining compound 400 using 1-(1-(bromomethyl)cyclopropyl)-4-chlorobenzene. LCMS (ESI) m/z=321 [M+H]⁺.

Compound 427 was obtained following the procedure for obtaining compound 400 using 2-(2-bromoethyl)naphthalene. LCMS (ESI) m/z=311 [M+H]⁺.

TABLE 4

Compounds of Formula (I)

| Structure | No. |
| --- | --- |
| 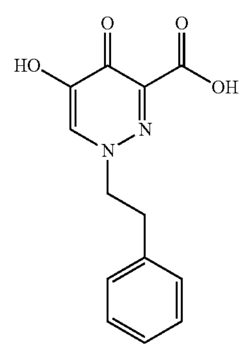 [SMILES: O=C(O)c1nn(CCc2ccccc2)cc(O)c1=O] | 401 |
| 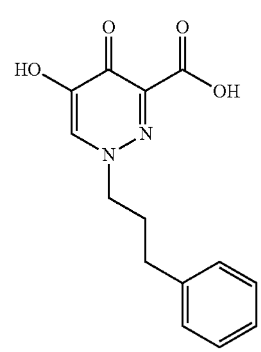 [SMILES: O=C(O)c1nn(CCCc2ccccc2)cc(O)c1=O] | 402 |

TABLE 4-continued

Compounds of Formula (I)

| Structure | No. |
|---|---|
| 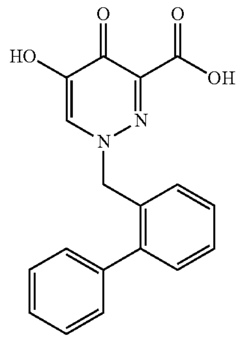 [SMILES: O=C(O)c1nn(Cc2ccccc2-c2ccccc2)cc(O)c1=O] | 403 |
| 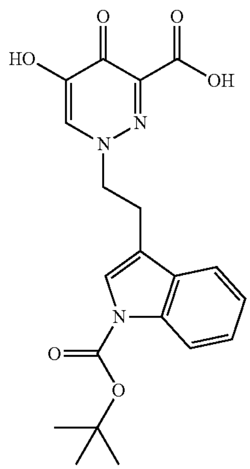 [SMILES: CC(C)(C)OC(=O)n1cc(CCn2cc(O)c(=O)c(C(=O)O)n2)c2ccccc21] | 404 |
| 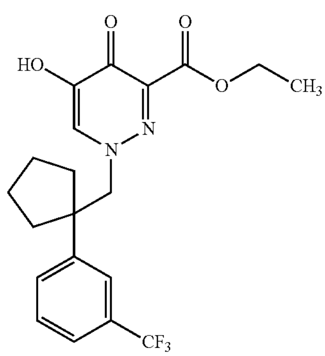 [SMILES: CCOC(=O)c1nn(CC2(c3cccc(C(F)(F)F)c3)CCCC2)cc(O)c1=O] | 405 |
| 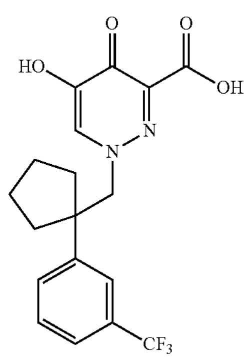 [SMILES: O=C(O)c1nn(CC2(c3cccc(C(F)(F)F)c3)CCCC2)cc(O)c1=O] | 406 |
| | 407 |
| | 408 |
| | 409 |
| | 410 |

TABLE 4-continued

Compounds of Formula (I)

| Structure | No. |
|---|---|
| (ethyl ester of 5-hydroxy-4-oxo-1-((1-phenylcyclopentyl)methyl)-1,4-dihydropyridazine-3-carboxylate) | 411 |
| 5-hydroxy-4-oxo-1-(3-(trifluoromethyl)phenethyl)-1,4-dihydropyridazine-3-carboxylic acid | 412 |
| 5-hydroxy-1-(2-methoxyphenethyl)-4-oxo-1,4-dihydropyridazine-3-carboxylic acid | 413 |
| 5-hydroxy-1-(3-methoxyphenethyl)-4-oxo-1,4-dihydropyridazine-3-carboxylic acid | 414 |
| 5-hydroxy-1-(4-methoxyphenethyl)-4-oxo-1,4-dihydropyridazine-3-carboxylic acid | 415 |
| 5-hydroxy-1-(2-methyl-2-(p-tolyl)propyl)-4-oxo-1,4-dihydropyridazine-3-carboxylic acid | 416 |
| 1-(3,4-dimethoxyphenethyl)-5-hydroxy-4-oxo-1,4-dihydropyridazine-3-carboxylic acid | 417 |
| 5-hydroxy-4-oxo-1-(1-oxo-1,2,3,4-tetrahydronaphthalen-2-yl)-1,4-dihydropyridazine-3-carboxylic acid | 418 |

TABLE 4-continued

Compounds of Formula (I)

| Structure | No. |
|---|---|
| (5-hydroxy-4-oxo-1-{[1-(3,5-bis(trifluoromethyl)phenyl)cyclopentyl]methyl}-1,4-dihydropyridazine-3-carboxylic acid) | 419 |
| (ethyl 5-hydroxy-4-oxo-1-{[1-(3,5-bis(trifluoromethyl)phenyl)cyclopentyl]methyl}-1,4-dihydropyridazine-3-carboxylate) | 420 |
| (5-hydroxy-4-oxo-1-(2-cyclohexylethyl)-1,4-dihydropyridazine-3-carboxylic acid) | 421 |
| (5-hydroxy-4-oxo-1-{[1-(7-azaindol-1-yl)cyclopentyl]methyl}-1,4-dihydropyridazine-3-carboxylic acid) | 422 |
| (5-hydroxy-4-oxo-1-[2-(naphthalen-1-yl)ethyl]-1,4-dihydropyridazine-3-carboxylic acid) | 423 |
| (5-hydroxy-4-oxo-1-{[1-(3-trifluoromethylphenyl)cyclopropyl]methyl}-1,4-dihydropyridazine-3-carboxylic acid) | 424 |
| (5-hydroxy-4-oxo-1-{[1-(3-methyl-7-azaindol-1-yl)cyclopentyl]}-1,4-dihydropyridazine-3-carboxylic acid) | 425 |
| (5-hydroxy-4-oxo-1-{[1-(4-chlorophenyl)cyclopropyl]methyl}-1,4-dihydropyridazine-3-carboxylic acid) | 426 |

TABLE 4-continued

Compounds of Formula (I)

| Structure | No. |
|---|---|
| 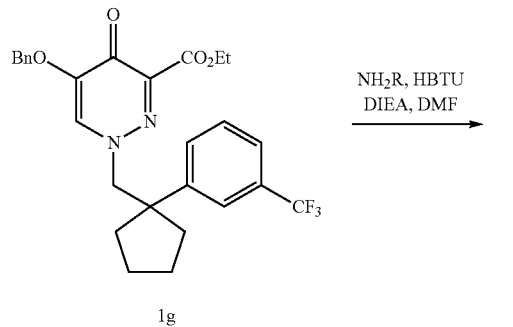 | 427 |

Example 8A 5-hydroxy-4-oxo-N-(1,1,1-trifluorobutan-2-yl)-1-((1-(3-(trifluoromethyl)phenyl)cyclopentyl)methyl)-1,4-dihydropyridazine-3-carboxamide (500)

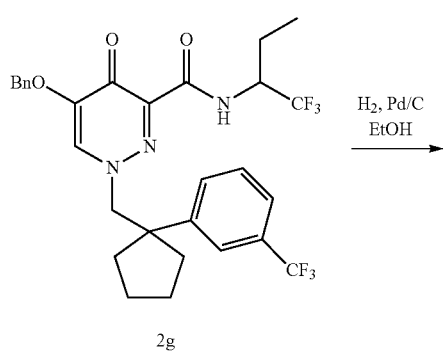

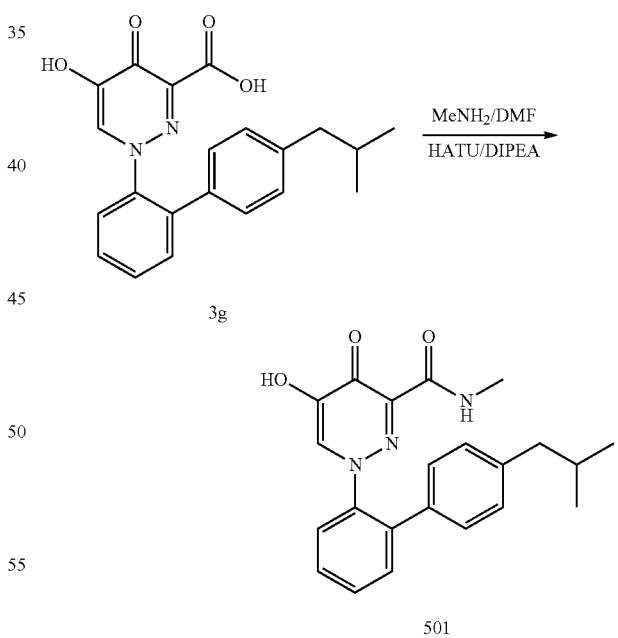

Diisopropylethylamine (52 μL, 0.30 mmol) was added to a solution of 1g (28 mg, 0.059 mmol), trifluorobutamine hydrochloride (30 mg. 0.18 mmol) and HBTU (33 mg, 0.89 mmol) in DMF (0.3 mL). The mixture was stirred at RT for 1.5 h. The reaction was diluted with EtOAc (20 mL) and washed successively with 1N HCl, water (3×) and brine. The reaction was purified by chromatography (10 g column, elution gradient 50% ethyl acetate/hexane–100% ethyl acetate to provide 2g (27 mg, 78%).

Compound 2g was deprotected by treatment with an atmospheric pressure (balloon) of $H_2(g)$ over 10% Pd/C (3 mg) in ethanol (10 mL) for 1.5 h. The mixture was filtered to remove the catalyst and concentrated to provide pure compound 500 (22.4 mg). LCMS (ESI) m/z=492 [M+H]$^+$.

Example 8B

To a stirred solution of 3g (182 mg, 0.50 mmol), HATU (380 mg, 1.0 mmol) and DIPEA (516 mg, 4.0 mmol) in DMF (20 mL) was added MeNH$_2$.HCl (134 mg, 2.0 mmol). The mixture was stirred at RT for 4 h. After complete conversion, the solvent was removed under reduced pressure. The residue was purified by prep-HPLC to give compound 501 as a white solid (50 mg, 26.5%). LCMS (ESI) m/z=378.1 [M+H]

Compound 502 was obtained following the procedure for obtaining compound 500 using 3,3-difluoropyrrolidine. LCMS (ESI) m/z=470 [M−H]⁻ and 941 [2M−H]⁻.

Compound 503 was obtained following the procedure for obtaining compound 500 using 1-(trifluoromethyl)cyclopentanamine. LCMS (ESI) m/z=516 [M−H]⁻ and 1033 [2M−H]⁻.

Compound 504 was obtained following the procedure for obtaining compound 500 using dimethylamine. LCMS (ESI) m/z=408 [M−H]⁻ and 454 [M−HCO$_2$]⁻.

Compound 505 was obtained following the procedure for obtaining compound 500 using 2,2,2-trifluoroethanamine. LCMS (ESI) m/z=462 [M−H]⁻.

Compound 506 was obtained following the procedure for obtaining compound 500 using methanamine and 1-((1-(3,5-bis(trifluoromethyl)phenyl)cyclopentyl)methyl)-5-hydroxy-4-oxo-1,4-dihydropyridazine-3-carboxylic acid. LCMS (ESI) m/z=462 [M−H]⁻.

Compound 507 was obtained following the procedure for obtaining Compound 500 using cyclopropanamine. LCMS (ESI) m/z=420 [M−H]⁻.

Compound 508 was obtained following the procedure for obtaining compound 500 using cyclopropanamine and 1-((1-(3,5-bis(trifluoromethyl)phenyl)cyclopentyl)methyl)-5-hydroxy-4-oxo-1,4-dihydropyridazine-3-carboxylic acid. LCMS (ESI) m/z=488 [M−H]⁻ and 977 [2M−H]⁻.

Compound 509 was obtained following the procedure for obtaining compound 500 using phenylmethanamine. LCMS (ESI) m/z=470 [M−H]⁻.

Compound 510 was obtained following the procedure for obtaining compound 500 using cyclopropylmethyl amine. LCMS (ESI) m/z=436 [M−H]⁻.

Compound 511 was obtained following the procedure for obtaining compound 500 using methanamine. LCMS (ESI) m/z=394 [M−H]⁻ and 789 [2M−H]⁻.

Compound 512 was obtained following the procedure for obtaining compound 500 using methanesulfonamide with the modification that a mixed anhydride was first prepared using ethyl chloroformate in place of HBTU and methanesulfonamide was subsequently added in a separate step. LCMS (ESI)=459 [M−H]⁻.

Compound 513 was obtained following the procedure for obtaining compound 500 using compound 406 and 3,4-dichlorobenzylamine with the modification that trifluoroacetic acid at 55° C. was used in place of Pd/C/H$_2$ to remove the O-benzyl group. LCMS (ESI) m/z=540 [M+H]⁺.

Compound 514 was obtained following the procedure for obtaining compound 500 using cyclopentanamine. LCMS (ESI) m/z=448 [M−H]⁻.

Compound 515 was obtained following the procedure for obtaining compound 500 using cyclobutanamine. LCMS (ESI) m/z=434 [M−H]⁻.

Compound 516 was obtained following the procedure for obtaining compound 500 using cyclohexanamine. LCMS (ESI) m/z=462 [M−H]⁻.

Compound 517 was obtained following the procedure for obtaining compound 500 using aniline. LCMS (ESI) m/z=456 [M−H]⁻.

Compound 518 was obtained following the procedure for obtaining compound 500 using compound 35 and methanamine. LCMS (ESI) m/z=398 [M+H]⁺.

Compound 519 was obtained following the procedure for obtaining compound 500 using compound 39 and methanamine. LCMS (ESI) m/z=364 [M+H]⁺.

Compound 520 was obtained following the procedure for obtaining compound 500 using compound 40 and methanamine. LCMS (ESI) m/z=406 [M+H]⁺.

compound 521 was obtained following the procedure for obtaining compound 500 using compound 313 and methanamine. LCMS (ESI) m/z=361 [M+H]⁺.

Compound 522 was obtained following the procedure for obtaining compound 500 using compound 314 and methanamine. LCMS (ESI) m/z=394 [M+H]⁺.

Compound 523 was obtained following the procedure for obtaining compound 500 using compound 406 and 4-chlorobenzylamine with the modification that trifluoroacetic acid at 55° C. was used in place of Pd/C/H$_2$ to remove the O-benzyl group. LCMS (ESI) m/z=504 [M+H]⁺.

Compound 524 was obtained following the procedure for obtaining compound 500 using compound 406 and 4-methylbenzylamine. LCMS (ESI) m/z=484 [M+H]⁺.

Compound 525 was obtained following the procedure for obtaining compound 500 using compound 406 and 4-methoxybenzyl amine. LCMS (ESI) m/z=500 [M−H]⁻.

TABLE 5

Compounds of Formula (I)

| Structure | No. |
|---|---|
| [structure] | 502 |
| [structure] | 503 |
| [structure] | 504 |

TABLE 5-continued

Compounds of Formula (I)

| Structure | No. |
|---|---|
| (structure) | 505 |
| (structure) | 506 |
| (structure) | 507 |
| (structure) | 508 |
| (structure) | 509 |
| (structure) | 510 |
| (structure) | 511 |
| (structure) | 512 |

TABLE 5-continued

Compounds of Formula (I)

TABLE 5-continued

Compounds of Formula (I)

| Structure | No. |
|---|---|
| 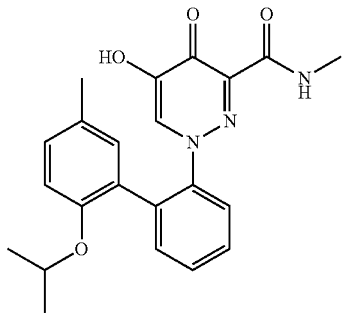 [SMILES: CNC(=O)c1nn(-c2ccccc2-c2cc(C)ccc2OC(C)C)cc(O)c1=O] | 522 |
| 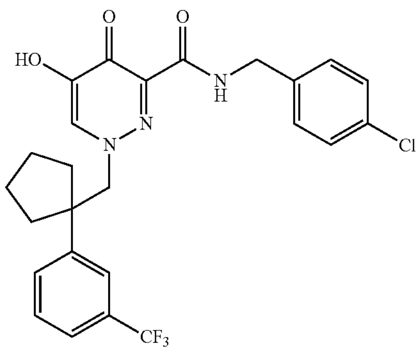 [SMILES: O=C(NCc1ccc(Cl)cc1)c1nn(CC2(c3cccc(C(F)(F)F)c3)CCCC2)cc(O)c1=O] | 523 |
| 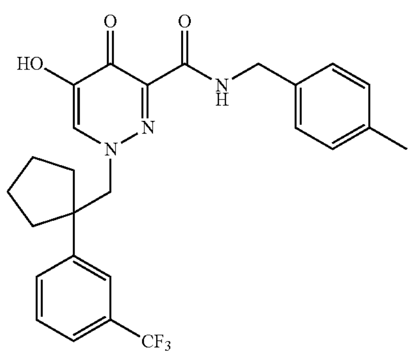 [SMILES: Cc1ccc(CNC(=O)c2nn(CC3(c4cccc(C(F)(F)F)c4)CCCC3)cc(O)c2=O)cc1] | 524 |
| 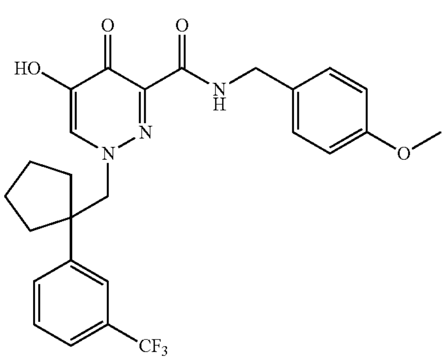 [SMILES: COc1ccc(CNC(=O)c2nn(CC3(c4cccc(C(F)(F)F)c4)CCCC3)cc(O)c2=O)cc1] | 525 |

Example 9A 1,4-dihydro-5-hydroxy-N-methyl-1-(2-(4-methylpiperazin-1-yl)phenyl)-4-oxopyridazine-3-carboxamide (600)

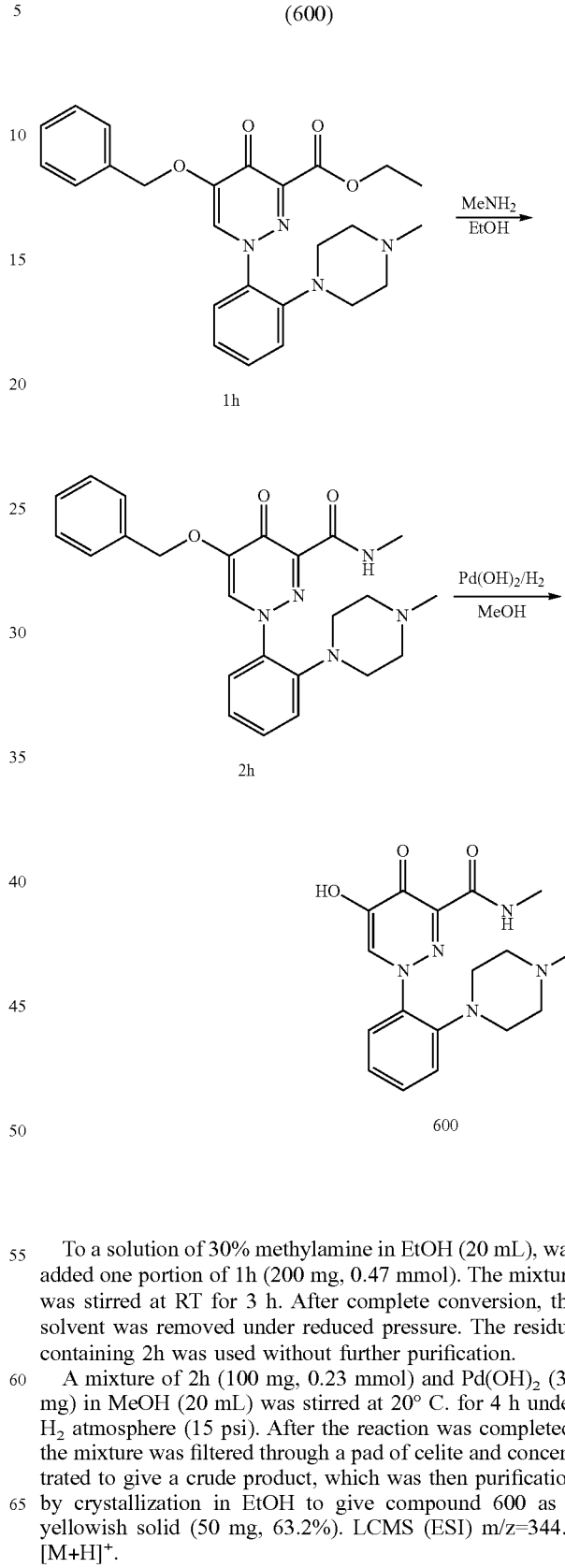

To a solution of 30% methylamine in EtOH (20 mL), was added one portion of 1h (200 mg, 0.47 mmol). The mixture was stirred at RT for 3 h. After complete conversion, the solvent was removed under reduced pressure. The residue containing 2h was used without further purification.

A mixture of 2h (100 mg, 0.23 mmol) and Pd(OH)$_2$ (30 mg) in MeOH (20 mL) was stirred at 20° C. for 4 h under H$_2$ atmosphere (15 psi). After the reaction was completed, the mixture was filtered through a pad of celite and concentrated to give a crude product, which was then purification by crystallization in EtOH to give compound 600 as a yellowish solid (50 mg, 63.2%). LCMS (ESI) m/z=344.2 [M+H]$^+$.

Example 9B 1,4-dihydro-1-(2,3-dihydrobenzo[b][1,4]dioxin-6-yl)-5-hydroxy-N-methyl-4-oxopyridazine-3-carboxamide (601)

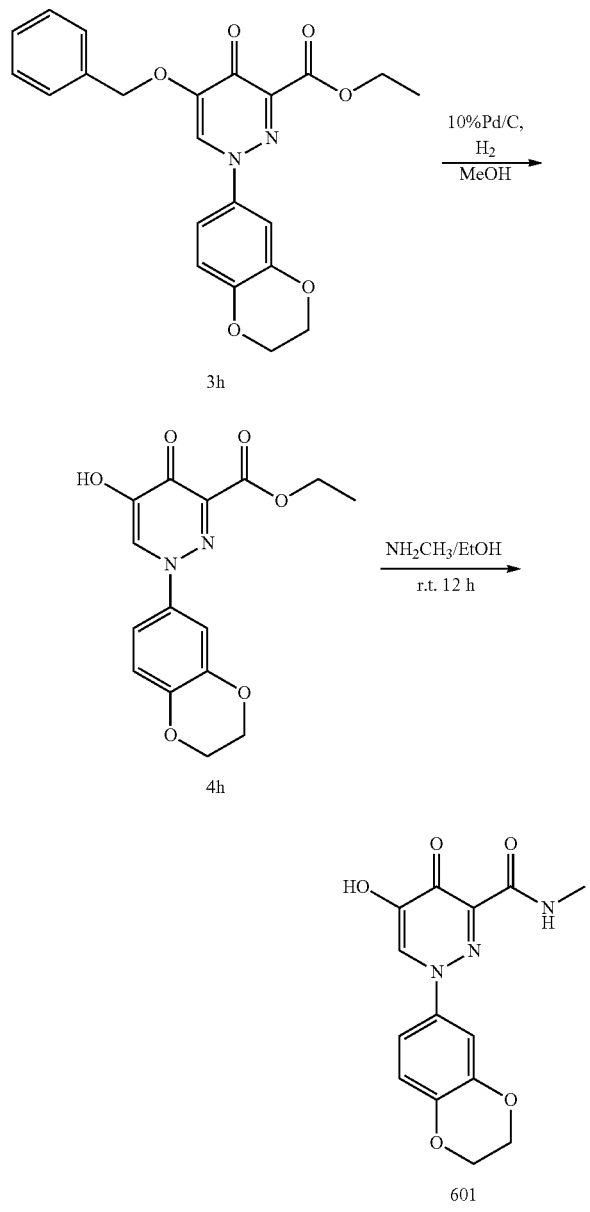 [SMILES: "MeOH" ; CCOC(=O)c1nn(-c2ccc3c(c2)OCCO3)cc(OCc2ccccc2)c1=O ; "10%Pd/C,H2" ; CCOC(=O)c1nn(-c2ccc3c(c2)OCCO3)cc(O)c1=O ; CNC(=O)c1nn(-c2ccc3c(c2)OCCO3)cc(O)c1=O]

A suspension of 3h (200 mg, 0.49 mmol) and 10% Pd/C (50 mg) in EtOH/DMF (1:1, 10 mL) was stirred at RT under H₂ atmosphere (1.0 atm.) for 30 min. After complete conversion, the mixture was filtered through a pad of celite. The filtrate was concentrated under reduced pressure. The residue was crystallized in PE:EtOAc (1:3) to give the pure 4h as a yellowish solid (130 mg, 83.4%).

To a solution of 30% methylamine in EtOH (10 mL), was added one portion of 4h (130 mg, 0.41 mmol). The mixture was stirred at RT for 12 h. After complete conversion, the solvent was removed under reduced pressure. The residue was re-dissolved by EtOH (10 mL) and concentrated in the vacuum to provide compound 601 as a yellowish solid (100 mg, 80.4%). LCMS (ESI) m/z=303.9 [M+H]⁺.

Compound 602 was obtained following the procedure for obtaining compound 601 using ammonia and the compound 1g. LCMS (ESI) m/z=380 [M−H]⁻ and 761 [2M−H]⁻.

Compound 603 was obtained following the procedure for obtaining compound 601 using methylamine and compound 24. LCMS (ESI) m/z=386 [M+H]⁺.

Compound 604 was obtained following the procedure for obtaining compound 600 using methylamine and compound 413. LCMS (ESI) m/z=304 [M+H]⁺.

Compound 605 was obtained following the procedure for obtaining compound 601 using benzylamine and compound 24. LCMS (ESI) m/z=462 [M+H]⁺.

Compound 606 was obtained following the procedure for obtaining compound 601 using methylamine and compound 421. LCMS (ESI) m/z=280 [M+H]⁺.

Compound 607 was obtained following the procedure for obtaining compound 600 using methylamine and compound 416. LCMS (ESI) m/z=314 [M−H]⁻.

Compound 608 was obtained following the procedure for obtaining compound 600 using methylamine and compound 412. LCMS (ESI)=340 [M−H]⁻.

Compound 609 was obtained following the procedure for obtaining compound 600 using methylamine and compound 422. LCMS (ESI) m/z=366 [M−H]⁻.

Compound 610 was obtained following the procedure for obtaining compound 601 using methylamine and compound 319. LCMS (ESI) m/z=406 [M+H]⁺.

Compound 611 was obtained following the procedure for obtaining compound 601 using methylamine and compound 318. LCMS (ESI) m/z=352 [M+H]⁺.

Compound 612 was obtained following the procedure for obtaining compound 601 using methylamine and compound 322. LCMS (ESI) m/z=386 [M+H]⁺.

Compound 613 was obtained following the procedure for obtaining compound 601 using methylamine and compound 320. LCMS (ESI) m/z=361 [M+H]⁺.

Compound 614 was obtained following the procedure for obtaining compound 601 using methylamine and compound 423. LCMS (ESI) m/z=324 [M+H]⁺.

Compound 615 was obtained following the procedure for obtaining compound 601 using methylamine and compound 205. LCMS (ESI) m/z=358 [M+H]⁺.

Compound 616 was obtained following the procedure for obtaining compound 601 using methylamine and compound 209. LCMS (ESI) m/z=357 [M+H]⁺.

Compound 617 was obtained following the procedure for obtaining compound 601 using methylamine and compound 24. LCMS (ESI) m/z=372 [M+H]⁺.

Compound 618 was obtained following the procedure for obtaining compound 601 using methylamine and compound 313 with the modification that the ester/ether precursor was treated with methyl iodide and potassium carbonate in DMF prior to debenzylation and amide formation. LCMS (ESI) m/z=375 [M+H]⁺.

Compound 619 was obtained following the procedure for obtaining compound 601 using methylamine and compound 316 or following the procedure for obtaining compound 300 using (5a,9a-dihydrodibenzo[b,d]furan-2-yl)boronic acid. LCMS (ESI) m/z=450 [M+H]⁺.

Compound 620 was obtained following the procedure for obtaining compound 601 using methylamine and compound 320 with the modification that the ester/ether precursor was treated with methyl iodide and potassium carbonate in DMF prior to debenzylation and amide formation. LCMS (ESI) m/z=375 [M+H]$^+$.

Compound 621 was obtained following the procedure for obtaining compound 600 using methylamine and compound 424. LCMS (ESI) m/z=366 [M−−H]$^−$.

Compound 622 was obtained following the procedure for obtaining compound 600 using methylamine and compound 425. LCMS (ESI) m/z=380 [M−H]$^−$.

Compound 623 was obtained following the procedure for obtaining compound 600 using 2-methylbenzyl amine and compound 406. LCMS (ESI) m/z=380 [M−H]$^−$.

Compound 624 was obtained following the procedure for obtaining compound 600 using 2-methoxybenzyl amine and compound 406. LCMS (ESI) m/z=500 [M−H]$^−$.

Compound 625 was obtained following the procedure for obtaining compound 600 using benzo[d][1,3]dioxol-5-yl-methanamine and compound 406. LCMS (ESI) m/z=514 [M−H]$^−$.

Compound 626 was obtained following the procedure for obtaining compound 601 using ammonia and compound 424. LCMS (ESI) m/z=352 [M−H]$^−$.

Compound 627 was obtained following the procedure for obtaining compound 601 using methylamine and compound 410. LCMS (ESI) m/z=328 [M+H]$^+$.

Compound 628 was obtained by first following the procedure for obtaining compound 6d using 1,2,3,4-tetrahydroquinoline and then following the procedure for obtaining compound 601 using methylamine. LCMS (ESI) m/z=377 [M+H]$^+$.

Compound 629 was obtained following the procedure for obtaining compound 601 using methylamine and compound 323. LCMS (ESI) m/z=386 [M+H]$^+$.

Compound 630 was obtained following the procedure for obtaining compound 601 using methylamine and compound 325. LCMS (ESI) m/z=394 [M+H]$^+$.

Compound 631 was obtained by first following the procedure for obtaining compound 3e using (2-(piperidin-1-yl)phenyl)boronic acid and then following the procedure for obtaining compound 601 using methylamine. LCMS (ESI) m/z=405 [M+H]$^+$.

Compound 632 was obtained by first following the procedure for obtaining compound 6d using indoline and then following the procedure for obtaining compound 601 using methylamine. LCMS (ESI) m/z=363 [M+H]$^+$.

Compound 633 was obtained following the procedure for obtaining compound 601 using methylamine and compound 326. LCMS (ESI) m/z=380 [M+H]$^+$.

Compound 634 was obtained following the procedure for obtaining compound 601 using methylamine and compound 426. LCMS (ESI) m/z=334 [M+H]$^+$.

Compound 635 was obtained following the procedure for obtaining compound 601 using methylamine and compound 427. LCMS (ESI) m/z=324 [M+H]$^+$.

Compound 636 was obtained following the procedure for obtaining compound 614 with the modification that compound 614 was treated with acetic anhydride and diisopropyl ethyl amine in dichloromethane at RT for 2 h. LCMS (ESI) m/z=366 [M+H]$^+$.

TABLE 6

| Compound of Formula (I) | |
|---|---|
| Structure | No. |
| (structure) | 602 |
| (structure) | 603 |
| (structure) | 604 |
| (structure) | 605 |

TABLE 6-continued

Compound of Formula (I)

| Structure | No. |
|---|---|
| (structure) | 606 |
| (structure) | 607 |
| (structure) | 608 |
| (structure) | 609 |
| (structure) | 610 |
| (structure) | 611 |
| (structure) | 612 |
| (structure) | 613 |
| (structure) | 614 |

TABLE 6-continued

Compound of Formula (I)

| Structure | No. |
|---|---|
| (structure) | 615 |
| (structure) | 616 |
| (structure) | 617 |
| (structure) | 618 |
| (structure) | 619 |
| (structure) | 620 |
| (structure) | 621 |
| (structure) | 622 |
| (structure) | 623 |
| (structure) | 624 |

TABLE 6-continued
| Compound of Formula (I) | |
|---|---|
| Structure | No. |
| 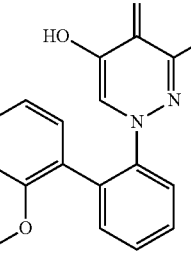 | 625 |
| | 626 |
| | 627 |
| | 628 |
| | 629 |
TABLE 6-continued
| Compound of Formula (I) | |
|---|---|
| Structure | No. |
| 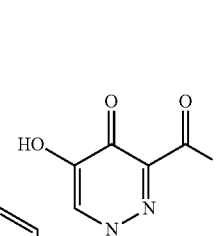 | 630 |
| | 631 |
| | 632 |
| | 633 |

TABLE 6-continued

Compound of Formula (I)

| Structure | No. |
|---|---|
| (structure) | 634 |
| (structure) | 635 |
| (structure) | 636 |

Example 10

Compounds of Formulae (I) and (II)

The foregoing syntheses are exemplary and can be used as a starting point to prepare additional compounds of Formulae (I) and (II). Examples of additional compounds of Formulae (I) and (II) are shown in Tables 7-9. These compounds can be prepared in various ways, including those synthetic schemes shown and described herein. Those skilled in the art will be able to recognize modifications of the disclosed syntheses and to devise routes based on the disclosures herein; all such modifications and alternate routes are within the scope of the claims.

TABLE 7

| Structure | No. | [M + H]$^+$ |
|---|---|---|
| (structure) | 637 | 486 |
| (structure) | 638 | 438 |
| (structure) | 639 | 390 |
| (structure) | 640 | 387 |
| (structure) | 641 | 400 |

TABLE 7-continued

| Structure | No. | [M + H]⁺ |
|---|---|---|
| (structure) | 642 | 392 |
| (structure) | 643 | 388 |
| (structure) | 644 | 420 |
| (structure) | 645 | 370 |
| (structure) | 646 | 476 |
| (structure) | 647 | 432 |
| (structure) | 648 | 476 |

TABLE 7-continued
| Structure | No. | [M + H]+ |
|---|---|---|
| 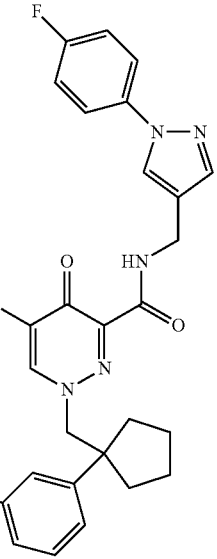 | 649 | 556 |
| 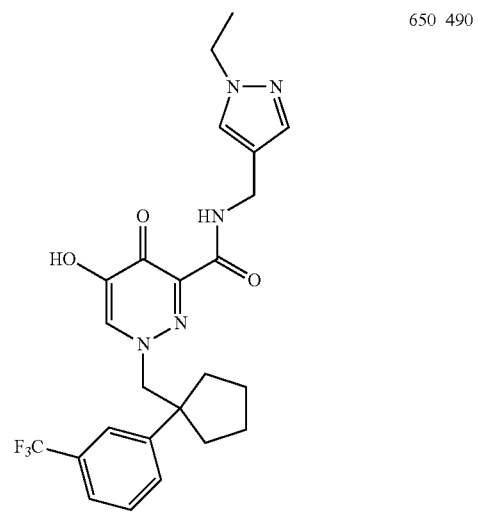 | 650 | 490 |
| 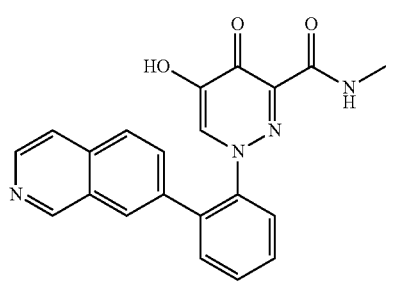 [SMILES: CNC(=O)c1nn(-c2ccccc2-c2ccc3ccncc3c2)cc(O)c1=O] | 651 | 373 |
TABLE 7-continued
| Structure | No. | [M + H]+ |
|---|---|---|
| 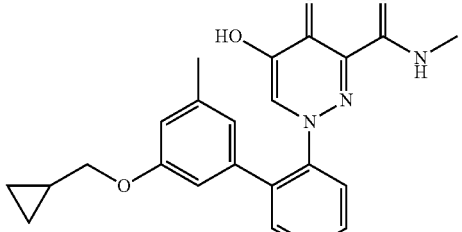 | 652 | 406 |
| 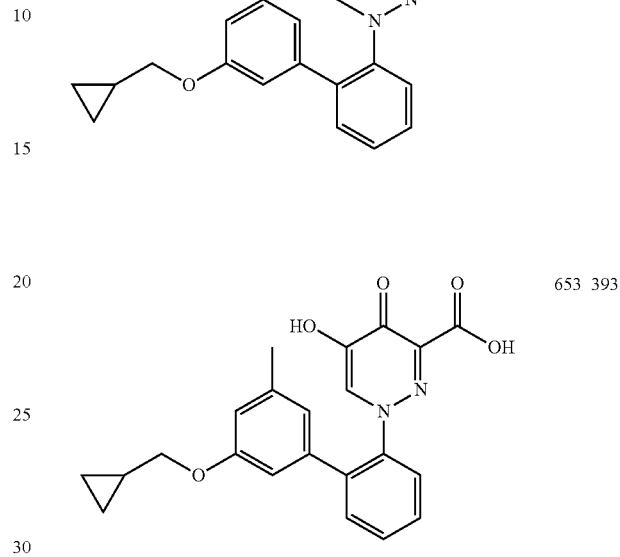 | 653 | 393 |
| 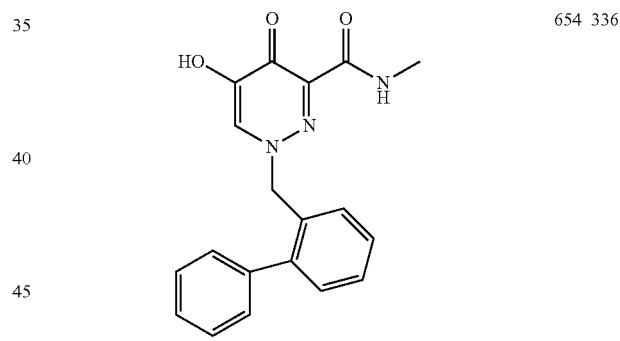 | 654 | 336 |
| 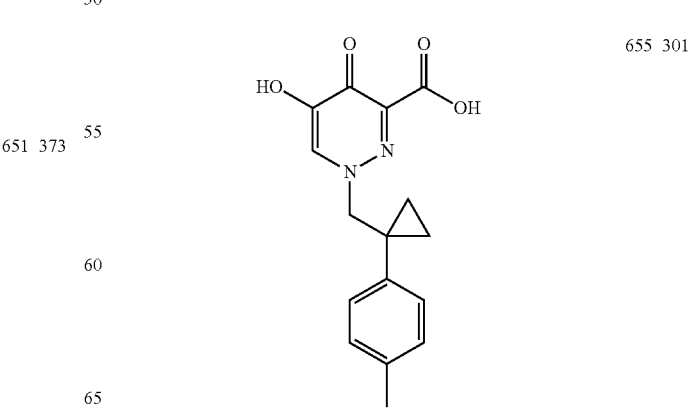 | 655 | 301 |

TABLE 7-continued
| Structure | No. | [M + H]+ |
|---|---|---|
| 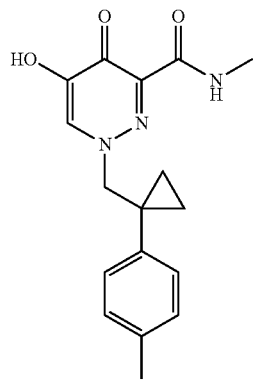 [SMILES: CNC(=O)c1nn(CC2(c3ccc(C)cc3)CC2)cc(O)c1=O] | 656 | 314 |
| 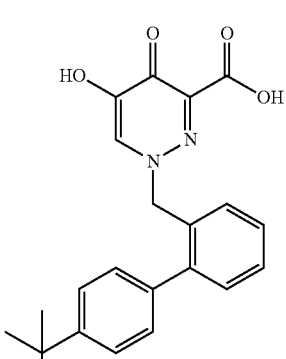 | 657 | 379 |
| 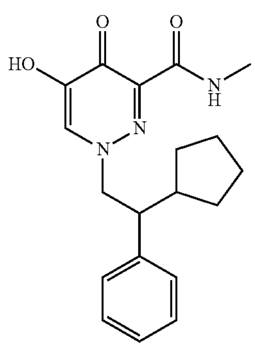 [SMILES: CNC(=O)c1nn(CC(c2ccccc2)C2CCCC2)cc(O)c1=O] | 658 | 342 |
| 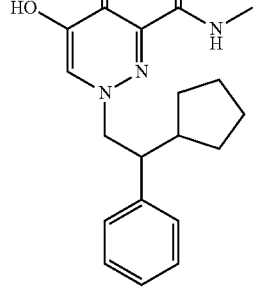 | 659 | 356 |
| 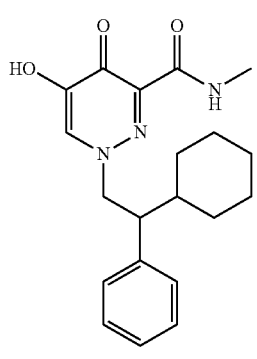 [SMILES: CNC(=O)c1nn(CC(c2ccccc2)C2CCCCC2)cc(O)c1=O] | 660 | 350 |
| 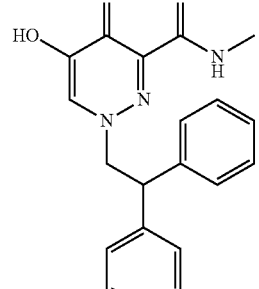 | 661 | 408 |
| 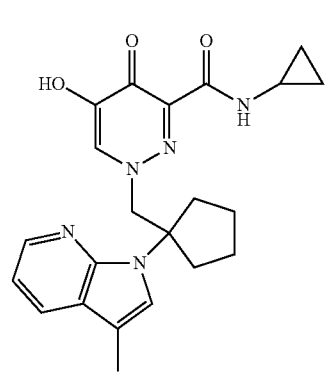 [SMILES: Cc1cn(C2(Cn3cc(O)c(=O)c(C(=O)NC4CC4)n3)CCCC2)c2ncccc12] | 662 | 424 |
| 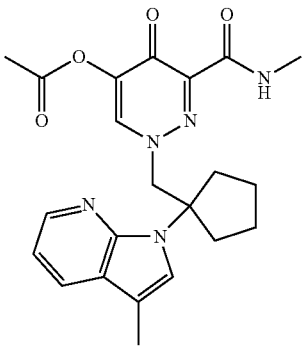 [SMILES: CNC(=O)c1nn(CC2(n3cc(C)c4cccnc43)CCCC2)cc(OC(C)=O)c1=O] | 663 | 492 |

TABLE 7-continued

| No. | Structure | [M+H]+ |
|---|---|---|
| 664 | 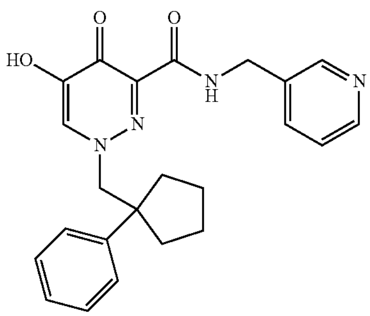 [SMILES: O=C(NCc1cccnc1)c1nn(CC2(c3ccccc3)CCCC2)cc(O)c1=O] | 405 |
| 665 | 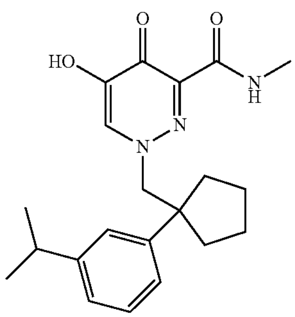 [SMILES: CNC(=O)c1nn(CC2(c3cccc(C(C)C)c3)CCCC2)cc(O)c1=O] | 370 |
| 666 | 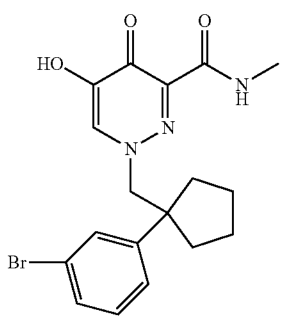 [SMILES: CNC(=O)c1nn(CC2(c3cccc(Br)c3)CCCC2)cc(O)c1=O] | 407 |
| 667 | 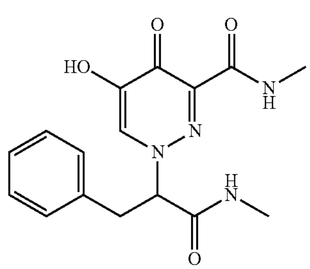 [SMILES: CNC(=O)c1nn(C(Cc2ccccc2)C(=O)NC)cc(O)c1=O] | 331 |
| 668 | 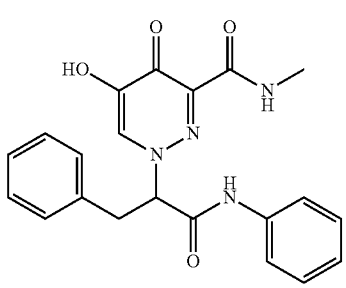 [SMILES: CNC(=O)c1nn(C(Cc2ccccc2)C(=O)Nc2ccccc2)cc(O)c1=O] | 393 |
| 669 | | 512 |
| 670 | | 376 |
| 671 | | 444 |
| 672 | | 539 |

TABLE 7-continued
| Structure | No. | [M + H]+ |
|---|---|---|
| 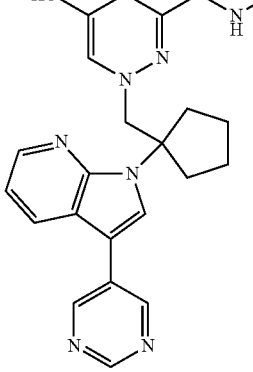 | 673 | 446 |
| 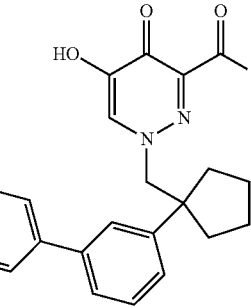 | 674 | 404 |
| 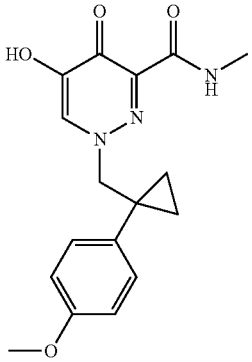 | 675 | 330 |
| 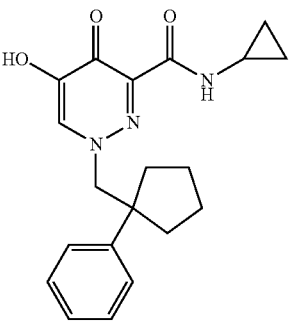 [SMILES: O=C(NC1CC1)c1nn(CC2(c3ccccc3)CCCC2)cc(O)c1=O] | 676 | 354 |
TABLE 7-continued
| Structure | No. | [M + H]+ |
|---|---|---|
| 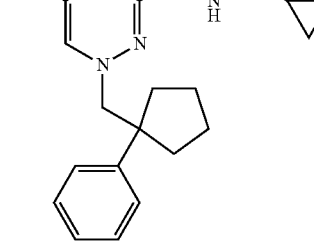 | 677 | 368 |
| 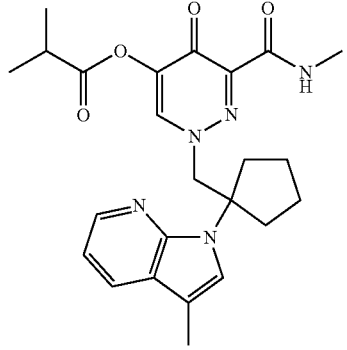 [SMILES: CNC(=O)c1nn(CC2(n3cc(C)c4cccnc43)CCCC2)cc(OC(=O)C(C)C)c1=O] | 678 | 452 |
| 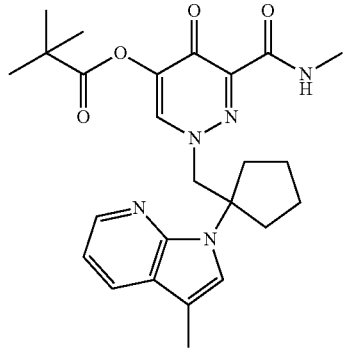 [SMILES: CNC(=O)c1nn(CC2(n3cc(C)c4cccnc43)CCCC2)cc(OC(=O)C(C)(C)C)c1=O] | 679 | 466 |
| 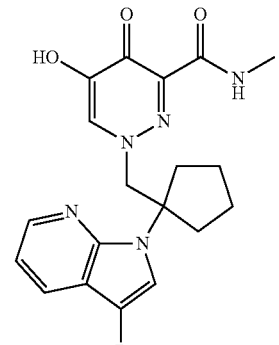 | 680 | 446 |

TABLE 7-continued
| No. | Structure | [M+H]+ |
|---|---|---|
| 681 | 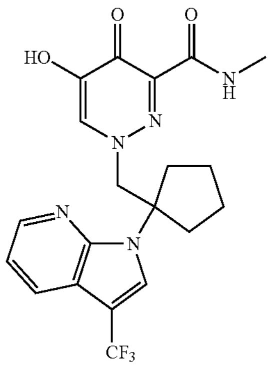 [SMILES: CNC(=O)c1nn(CC2(n3cc(C(F)(F)F)c4cccnc43)CCCC2)cc(O)c1=O] | 436 |
| 682 | 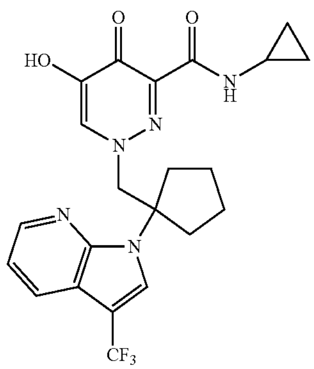 [SMILES: O=C(NC1CC1)c1nn(CC2(n3cc(C(F)(F)F)c4cccnc43)CCCC2)cc(O)c1=O] | 462 |
| 683 | 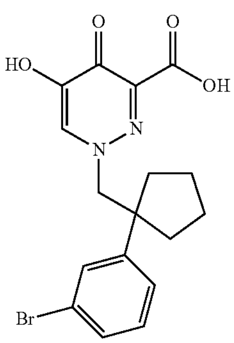 [SMILES: O=C(O)c1nn(CC2(c3cccc(Br)c3)CCCC2)cc(O)c1=O] | 393 |
| 684 | 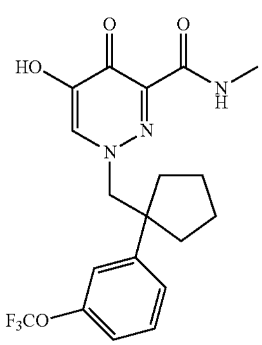 [SMILES: CNC(=O)c1nn(CC2(c3cccc(OC(F)(F)F)c3)CCCC2)cc(O)c1=O] | 412 |
| 685 | | 396 |
| 686 | | 404 |
| 687 | | 370 |
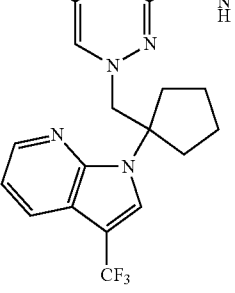
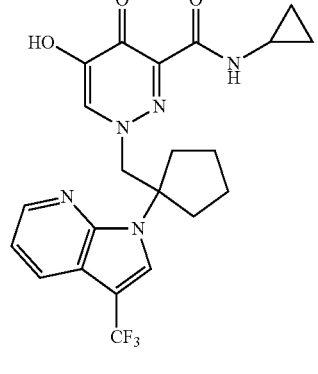
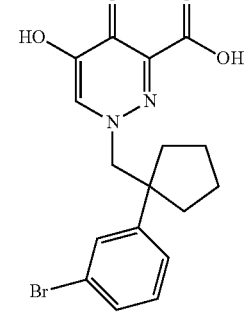
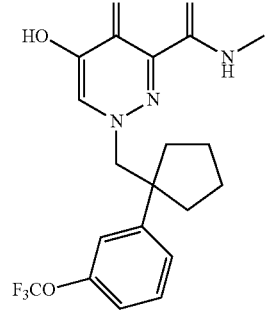

TABLE 7-continued

| No. | Structure | [M+H]+ |
|---|---|---|
| 688 | 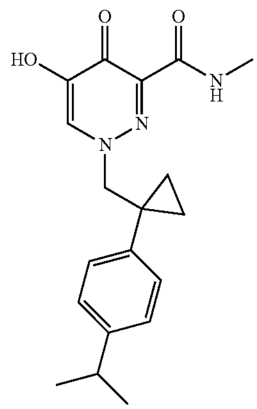 [SMILES: CNC(=O)c1nn(CC2(c3ccc(C(C)C)cc3)CC2)cc(O)c1=O] | 342 |
| 689 | 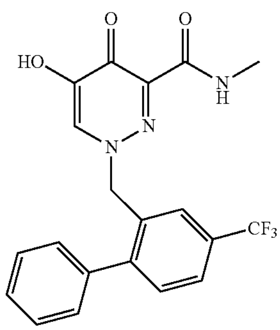 [SMILES: CNC(=O)c1nn(Cc2cc(C(F)(F)F)ccc2-c2ccccc2)cc(O)c1=O] | 404 |
| 690 | 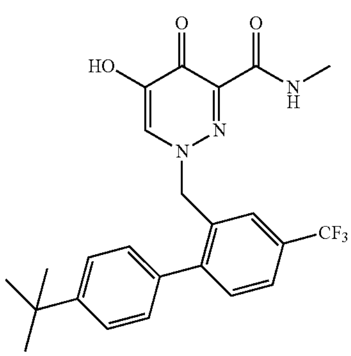 [SMILES: CNC(=O)c1nn(Cc2cc(C(F)(F)F)ccc2-c2ccc(C(C)(C)C)cc2)cc(O)c1=O] | 460 |
| 691 | 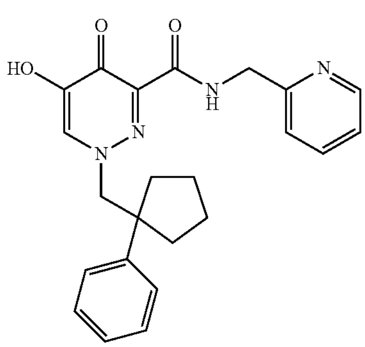 [SMILES: O=C(NCc1ccccn1)c1nn(CC2(c3ccccc3)CCCC2)cc(O)c1=O] | 405 |
| 692 | | 405 |
| 693 | | 406 |
| 694 | | 410 |
| 695 | | 520 |

TABLE 7-continued

| Structure | No. | [M + H]+ |
|---|---|---|
| (structure) | 696 | 482 |
| (structure) | 697 | 420 |
| (structure) | 698 | 404 |
| (structure) | 699 | 406 |
| (structure) | 700 | 362 |
| (structure) | 701 | 420 |
| (structure) | 702 | 342 |
| (structure) | 703 | 358 |

TABLE 7-continued
| No. | Structure | [M + H]+ |
|---|---|---|
| 704 | 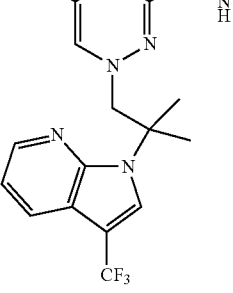 | 410 |
| 705 | 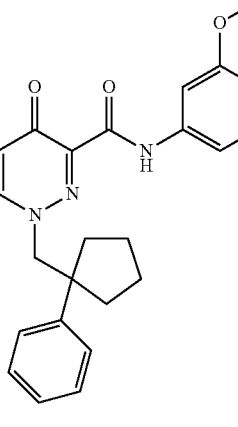 | 450 |
| 706 | 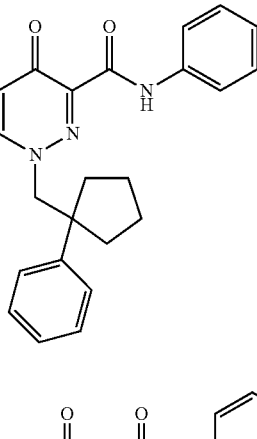 | 448 |
| 707 | 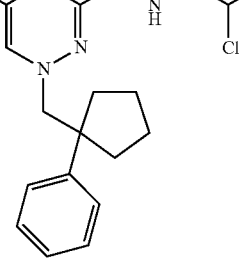 | 458 |
| 708 |  | 314 |
| 709 | 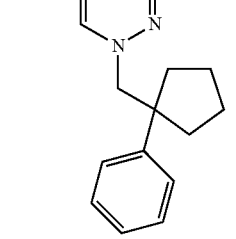 | 456 |
| 710 | 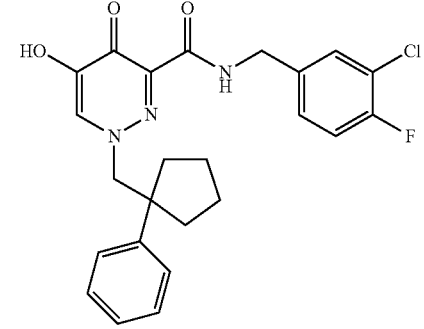 [SMILES: O=C(NCc1ccc(F)c(Cl)c1)c1nn(CC2(c3ccccc3)CCCC2)cc(O)c1=O] | 380 |
| 711 | 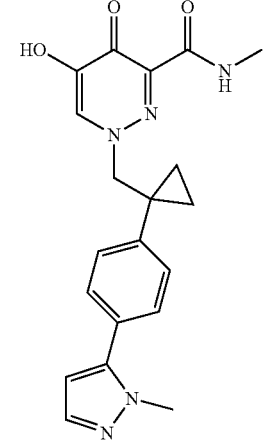 [SMILES: CNC(=O)c1nn(CC2(c3ccc(-c4ccnn4C)cc3)CC2)cc(O)c1=O] | 410 |

TABLE 7-continued

| Structure | No. | [M + H]+ |
|---|---|---|
| (structure) | 712 | 366 |
| (structure) | 713 | 380 |
| (structure) | 714 | 394 |
| (structure) | 715 | 391 |
| (structure) | 716 | 393 |
| (structure) | 717 | 319 |
| (structure) | 718 | 408 |

TABLE 7-continued

| No. | Structure | [M + H]+ |
|---|---|---|
| 719 | (5-hydroxy-4-oxo-1-((1-phenylcyclopentyl)methyl)-1,4-dihydropyridazine-3-carboxamide with 4-chloro-3-(trifluoromethyl)phenyl) | 492 |
| 720 | (5-hydroxy-4-oxo-1-((1-phenylcyclopentyl)methyl)-1,4-dihydropyridazine-3-carboxamide with 4-chlorophenyl) | 424 |
| 721 | (5-hydroxy-4-oxo-1-((1-phenylcyclopentyl)methyl)-1,4-dihydropyridazine-3-carboxamide with 4-(methylsulfonyl)phenyl) | 468 |
| 722 | (5-hydroxy-4-oxo-1-((1-(biphenyl-3-yl)cyclopentyl)methyl)-1,4-dihydropyridazine-3-carboxamide) | 390 |
| 723 | (5-hydroxy-1-((1-(3-isopropylphenyl)cyclopentyl)methyl)-4-oxo-1,4-dihydropyridazine-3-carboxylic acid) | 357 |
| 724 | (5-hydroxy-N-methyl-4-oxo-1-((1-(3-(thiophen-3-yl)phenyl)cyclopropyl)methyl)-1,4-dihydropyridazine-3-carboxamide) | 382 |
| 725 | (5-hydroxy-N-methyl-4-oxo-1-((1-(3-phenoxyphenyl)cyclopentyl)methyl)-1,4-dihydropyridazine-3-carboxamide) | 420 |

TABLE 7-continued
| Structure | No. | [M+H]+ |
|---|---|---|
| 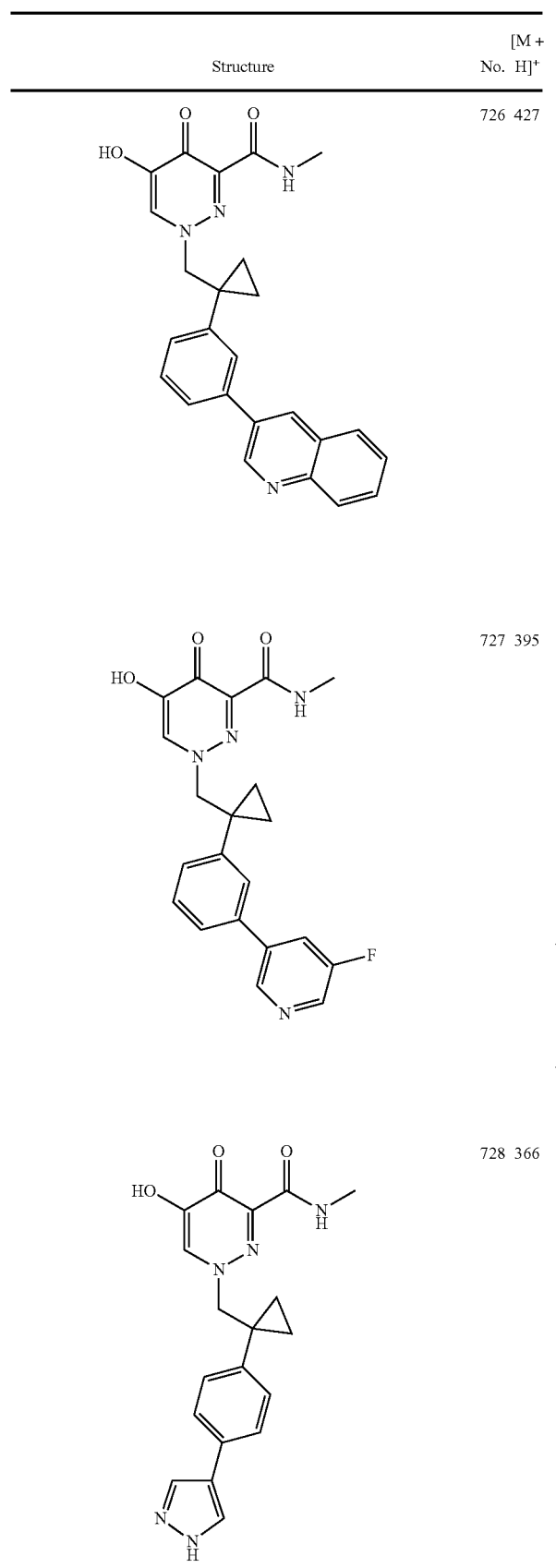 | 726 727 728 | 427 395 366 |
| 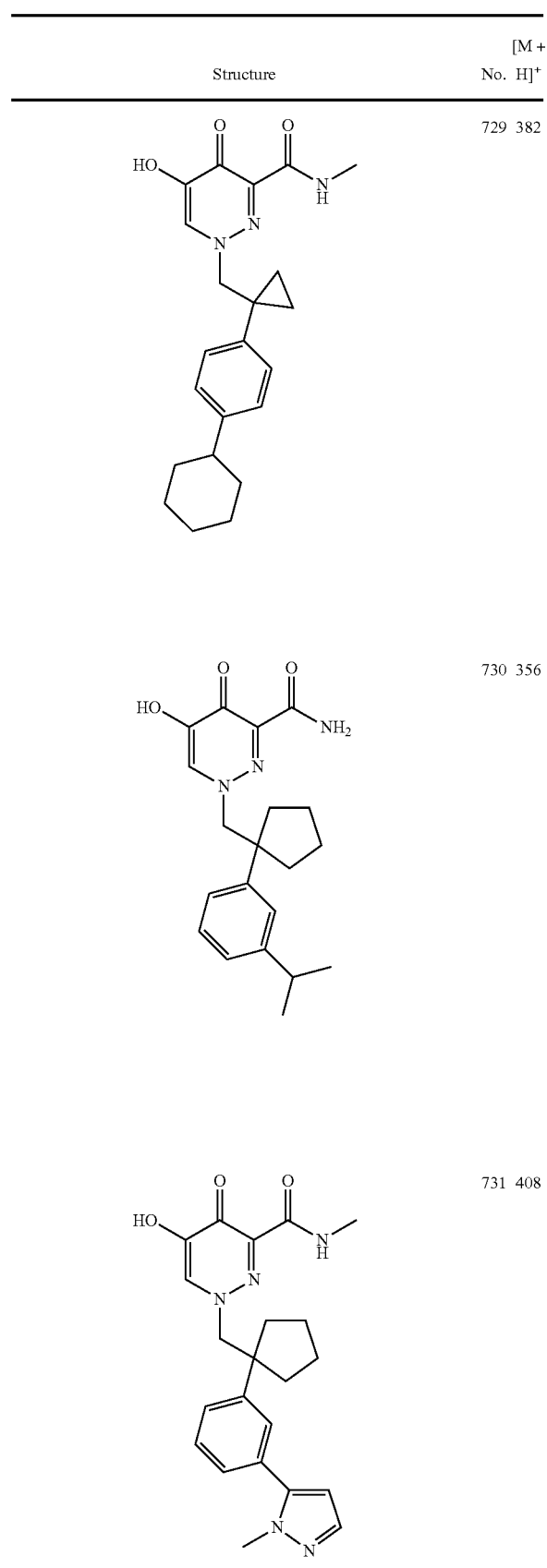 | 729 730 731 | 382 356 408 |

TABLE 7-continued
| Structure | No. | [M + H]+ |
|---|---|---|
| 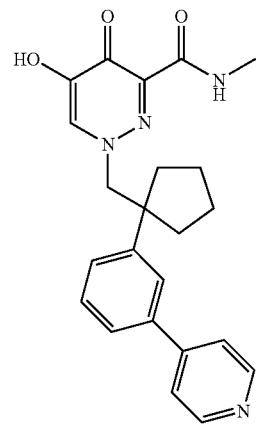 [SMILES: CNC(=O)c1nn(CC2(c3cccc(-c4ccncc4)c3)CCCC2)cc(O)c1=O] | 732 | 405 |
| 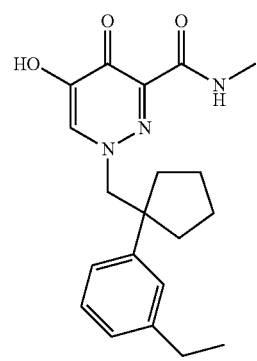 [SMILES: CCc1cccc(C2(Cn3cc(O)c(=O)c(C(=O)NC)n3)CCCC2)c1] | 733 | 356 |
| 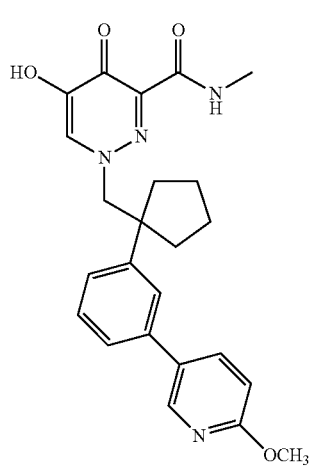 [SMILES: CNC(=O)c1nn(CC2(c3cccc(-c4ccc(OC)nc4)c3)CCCC2)cc(O)c1=O] | 734 | 435 |
TABLE 7-continued
| Structure | No. | [M + H]+ |
|---|---|---|
| 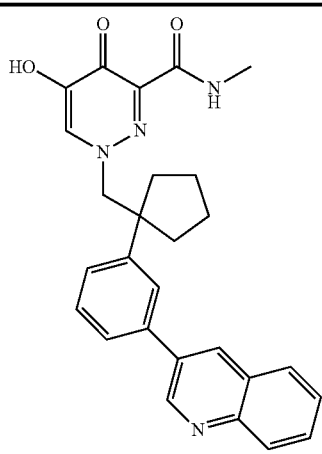 | 735 | 455 |
| 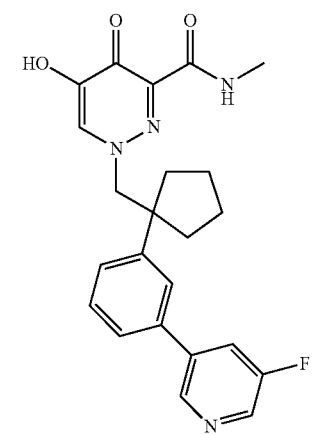 [SMILES: CNC(=O)c1nn(CC2(c3cccc(-c4cncc(F)c4)c3)CCCC2)cc(O)c1=O] | 736 | 423 |
| 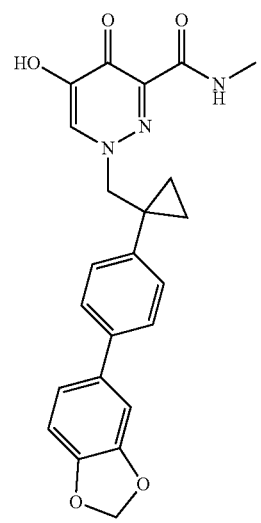 [SMILES: CNC(=O)c1nn(CC2(c3ccc(-c4ccc5c(c4)OCO5)cc3)CC2)cc(O)c1=O] | 737 | 420 |

TABLE 7-continued
| No. | Structure | [M+H]+ |
|---|---|---|
| 738 | 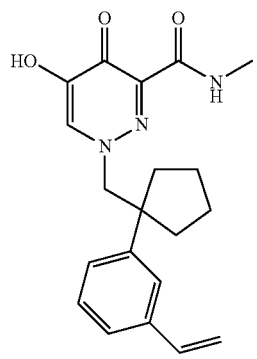 [SMILES: C=Cc1cccc(C2(Cn3cc(O)c(=O)c(C(=O)NC)n3)CCCC2)c1] | 354 |
| 739 | 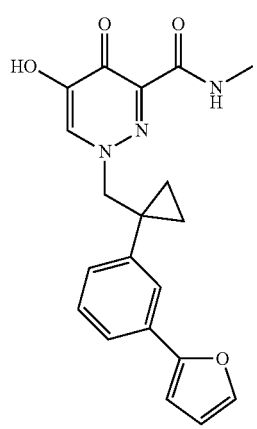 [SMILES: CNC(=O)c1nn(CC2(c3cccc(-c4ccco4)c3)CC2)cc(O)c1=O] | 366 |
| 740 | 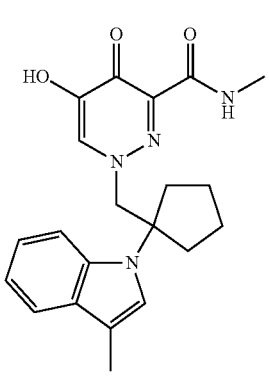 [SMILES: CNC(=O)c1nn(CC2(n3cc(C)c4ccccc43)CCCC2)cc(O)c1=O] | 381 |
| 741 | 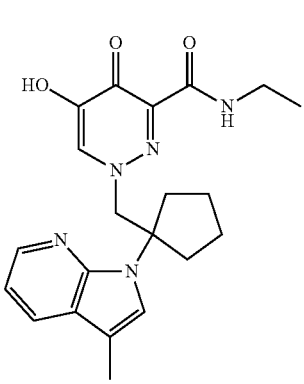 [SMILES: CCNC(=O)c1nn(CC2(n3cc(C)c4cccnc43)CCCC2)cc(O)c1=O] | 396 |
| 742 | 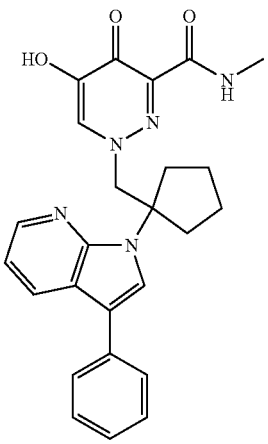 [SMILES: CNC(=O)c1nn(CC2(n3cc(-c4ccccc4)c4cccnc43)CCCC2)cc(O)c1=O] | 444 |
| 743 | 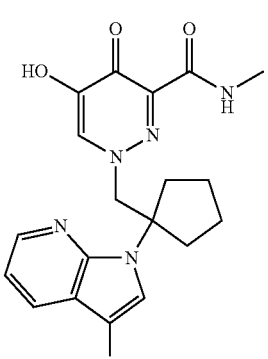 | 402 |
| 744 | 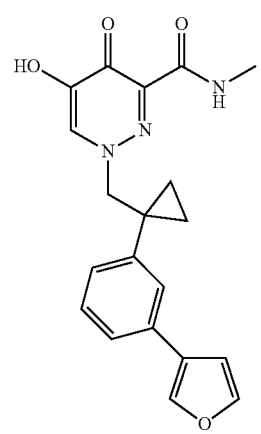 [SMILES: CNC(=O)c1nn(CC2(c3cccc(-c4ccoc4)c3)CC2)cc(O)c1=O] | 366 |

TABLE 7-continued

| No. | Structure | [M + H]+ |
|---|---|---|
| 745 | 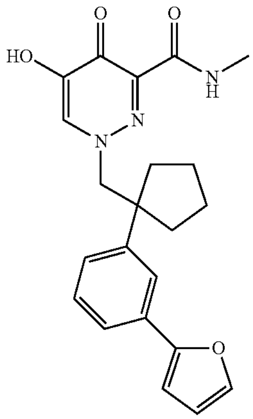 [SMILES: CNC(=O)c1nn(CC2(c3cccc(-c4ccco4)c3)CCCC2)cc(O)c1=O] | 394 |
| 746 | 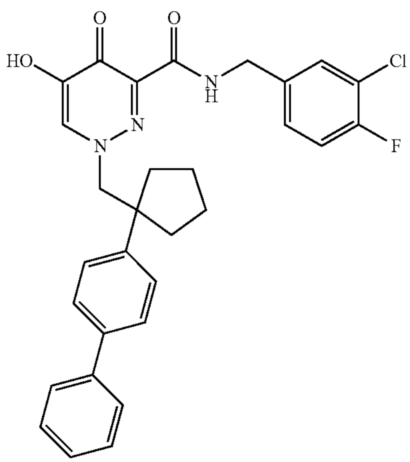 [SMILES: O=C(NCc1ccc(F)c(Cl)c1)c1nn(CC2(c3ccc(-c4ccccc4)cc3)CCCC2)cc(O)c1=O] | 533 |
| 747 | 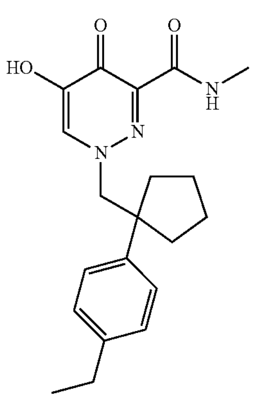 [SMILES: CCc1ccc(C2(Cn3cc(O)c(=O)c(C(=O)NC)n3)CCCC2)cc1] | 356 |
| 748 | 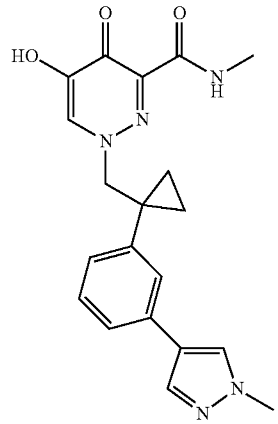 [SMILES: CNC(=O)c1nn(CC2(c3cccc(-c4cnn(C)c4)c3)CC2)cc(O)c1=O] | 380 |
| 749 | 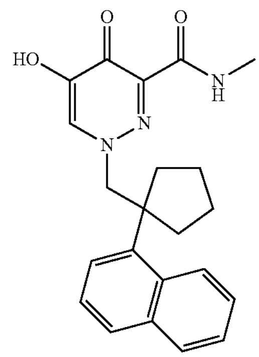 [SMILES: CNC(=O)c1nn(CC2(c3cccc4ccccc34)CCCC2)cc(O)c1=O] | 378 |
| 750 | 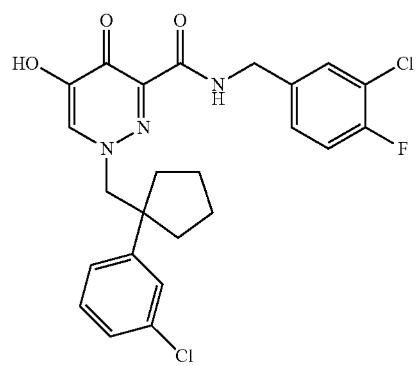 [SMILES: O=C(NCc1ccc(F)c(Cl)c1)c1nn(CC2(c3cccc(Cl)c3)CCCC2)cc(O)c1=O] | 490 |
| 751 | 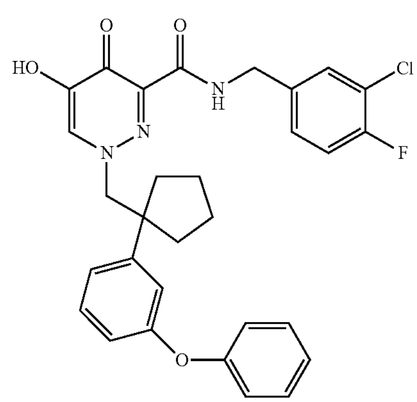 [SMILES: O=C(NCc1ccc(F)c(Cl)c1)c1nn(CC2(c3cccc(Oc4ccccc4)c3)CCCC2)cc(O)c1=O] | 549 |

TABLE 7-continued
| Structure | No. | [M + H]+ |
|---|---|---|
| 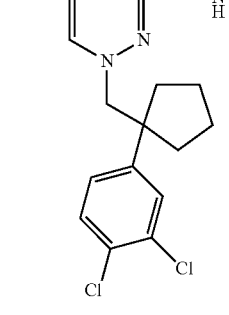 | 752 | 396 |
| 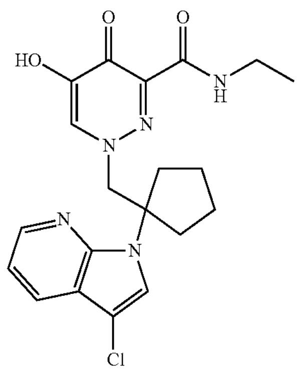 [SMILES: CCNC(=O)c1nn(CC2(n3cc(Cl)c4cccnc43)CCCC2)cc(O)c1=O] | 753 | 416 |
| 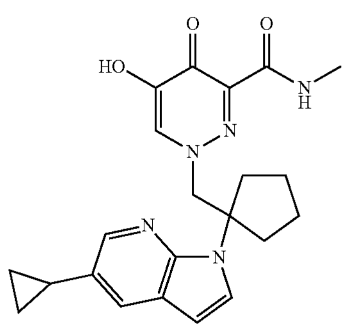 [SMILES: CNC(=O)c1nn(CC2(n3ccc4cc(C5CC5)cnc43)CCCC2)cc(O)c1=O] | 754 | 408 |
| 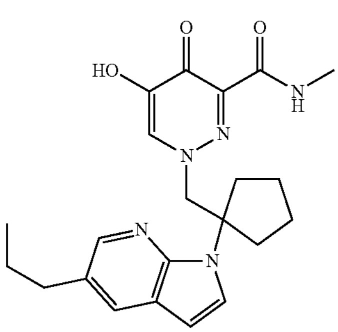 [SMILES: CCCc1cnc2c(ccn2C2(Cn3cc(O)c(=O)c(C(=O)NC)n3)CCCC2)c1] | 755 | 410 |
TABLE 7-continued
| Structure | No. | [M + H]+ |
|---|---|---|
| 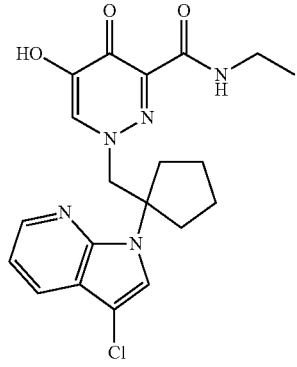 | 756 | 410 |
| 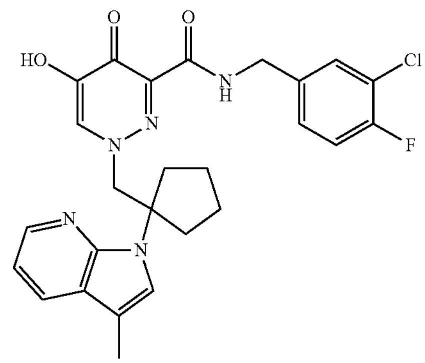 [SMILES: Cc1cn(C2(Cn3cc(O)c(=O)c(C(=O)NCc4ccc(F)c(Cl)c4)n3)CCCC2)c2ncccc12] | 757 | 510 |
| 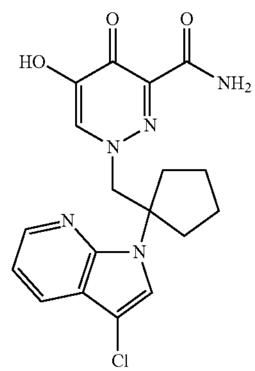 [SMILES: NC(=O)c1nn(CC2(n3cc(Cl)c4cccnc43)CCCC2)cc(O)c1=O] | 758 | 388 |
| 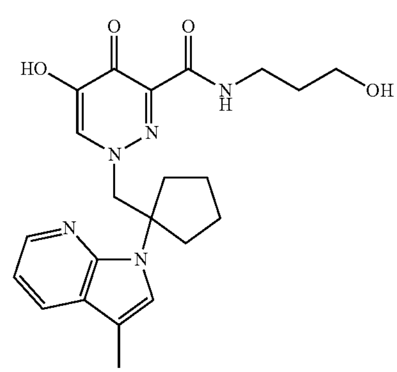 [SMILES: Cc1cn(C2(Cn3cc(O)c(=O)c(C(=O)NCCCO)n3)CCCC2)c2ncccc12] | 759 | 426 |

TABLE 7-continued

| No. | Structure | [M+H]+ |
|---|---|---|
| 760 | 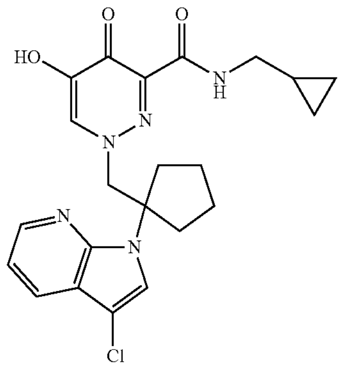 [SMILES: O=C(NCC1CC1)c1nn(CC2(n3cc(Cl)c4cccnc43)CCCC2)cc(O)c1=O] | 442 |
| 761 | 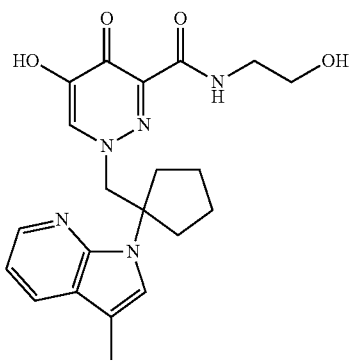 [SMILES: Cc1cn(C2(Cn3cc(O)c(=O)c(C(=O)NCCO)n3)CCCC2)c2ncccc12] | 412 |
| 762 | 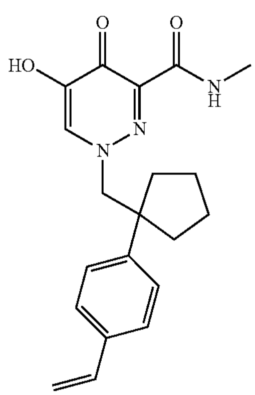 [SMILES: C=Cc1ccc(C2(Cn3cc(O)c(=O)c(C(=O)NC)n3)CCCC2)cc1] | 354 |
| 763 | 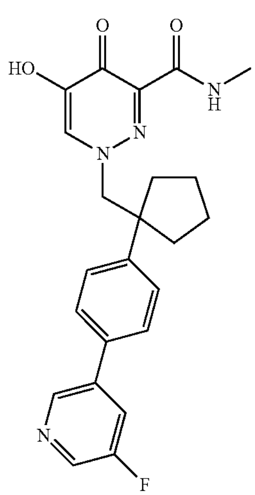 [SMILES: CNC(=O)c1nn(CC2(c3ccc(-c4cncc(F)c4)cc3)CCCC2)cc(O)c1=O] | 423 |
| 764 | 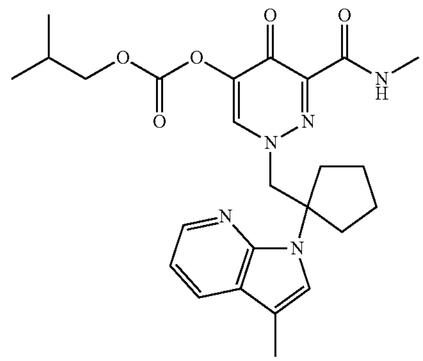 [SMILES: CNC(=O)c1nn(CC2(n3cc(C)c4cccnc43)CCCC2)cc(OC(=O)OCC(C)C)c1=O] | 482 |
| 765 | 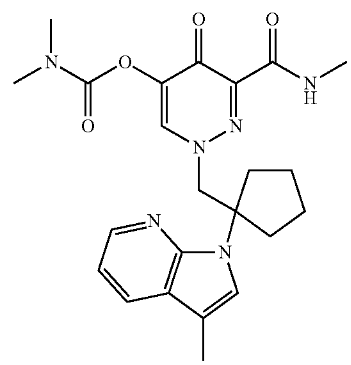 | 453 |
| 766 | 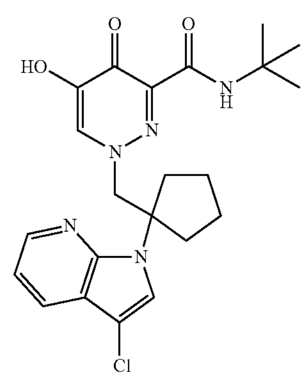 [SMILES: CC(C)(C)NC(=O)c1nn(CC2(n3cc(Cl)c4cccnc43)CCCC2)cc(O)c1=O] | 444 |
| 767 | 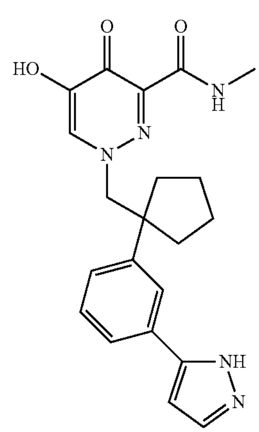 [SMILES: CNC(=O)c1nn(CC2(c3cccc(-c4ccn[nH]4)c3)CCCC2)cc(O)c1=O] | 394 |

TABLE 7-continued

| Structure | No. | [M + H]+ |
|---|---|---|
| (structure) | 768 | 430 |
| (structure) | 769 | 408 |
| (structure) | 770 | 435 |
| (structure) | 771 | 484 |
| (structure) | 772 | 484 |
| (structure) | 773 | 408 |
| (structure) | 774 | 412 |

TABLE 7-continued
| No. | Structure | [M + H]+ |
|---|---|---|
| 775 | 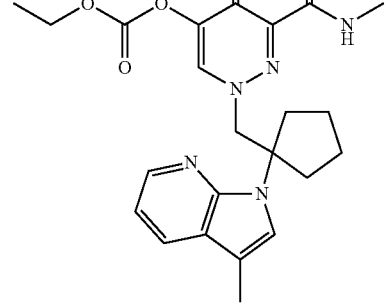 | 454 |
| 776 | 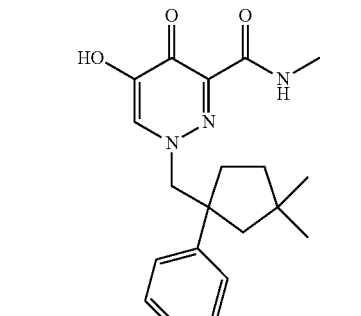 | 356 |
| 777 | 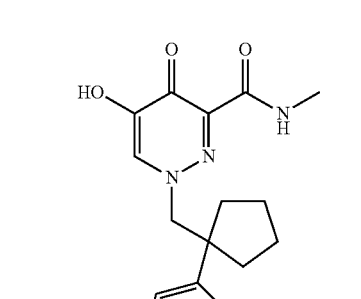 | 378 |
| 778 | 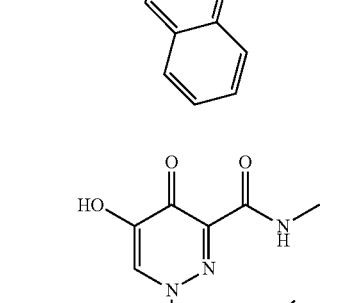 | 342 |
| 779 | 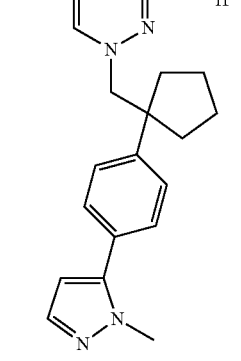 | 408 |
| 780 | 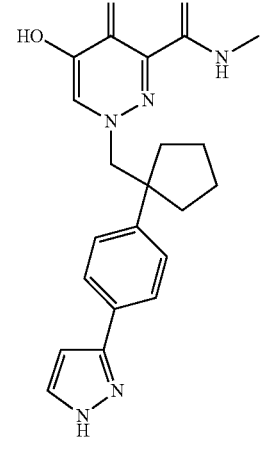 | 394 |
| 781 | 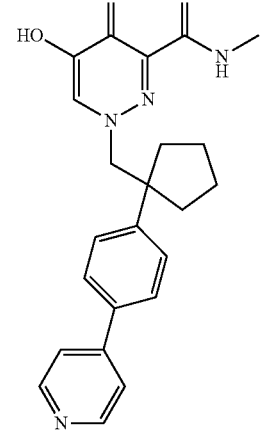 | 405 |

TABLE 7-continued

| No. | Structure | [M + H]+ |
|---|---|---|
| 782 | 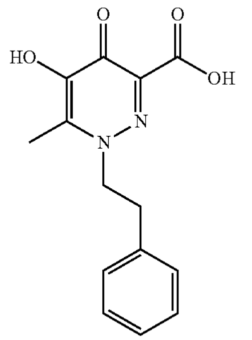 | 275 |
| 783 | 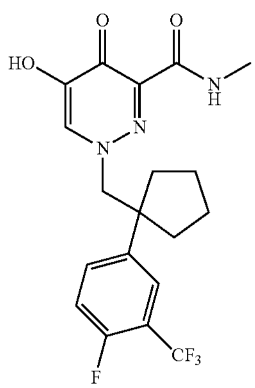 [SMILES: CNC(=O)c1nn(CC2(c3ccc(F)c(C(F)(F)F)c3)CCCC2)cc(O)c1=O] | 414 |
| 784 | 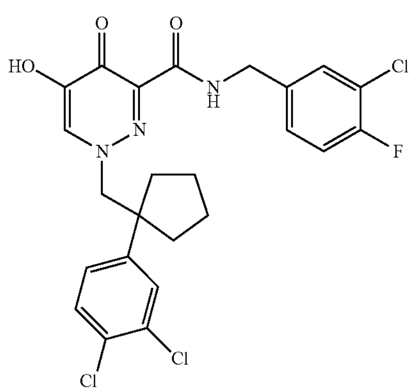 [SMILES: O=C(NCc1ccc(F)c(Cl)c1)c1nn(CC2(c3ccc(Cl)c(Cl)c3)CCCC2)cc(O)c1=O] | 524 |
| 785 | 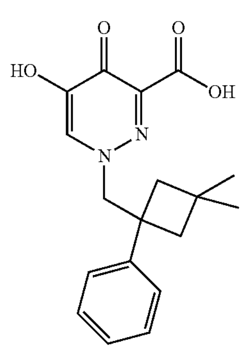 [SMILES: CC1(C)CC(Cn2cc(O)c(=O)c(C(=O)O)n2)(c2ccccc2)C1] | 329 |
| 786 | | 343 |
| 787 | | 401 |
| 788 | | 396 |
| 789 | | 482 |

TABLE 7-continued

| No. | Structure | [M + H]+ |
|---|---|---|
| 790 | 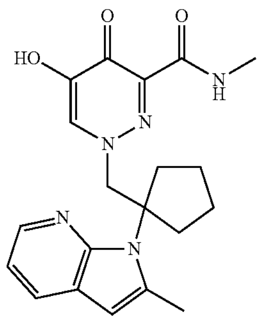 [SMILES: CNC(=O)c1nn(CC2(n3c(C)cc4cccnc43)CCCC2)cc(O)c1=O] | 382 |
| 791 | 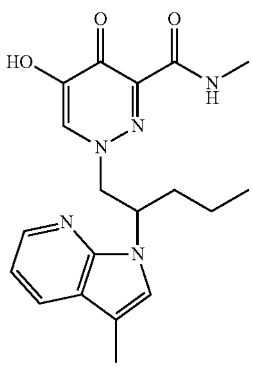 [SMILES: CCCC(Cn1cc(O)c(=O)c(C(=O)NC)n1)n1cc(C)c2cccnc21] | 370 |
| 792 | 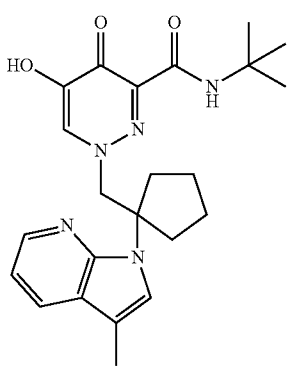 [SMILES: Cc1cn(C2(Cn3cc(O)c(=O)c(C(=O)NC(C)(C)C)n3)CCCC2)c2ncccc12] | 424 |
| 793 | 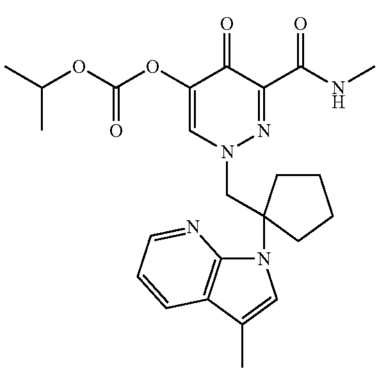 [SMILES: CNC(=O)c1nn(CC2(n3cc(C)c4cccnc43)CCCC2)cc(OC(=O)OC(C)C)c1=O] | 468 |
| 794 | | 428 |
| 795 | | 367 |
| 796 | | 432 |
| 797 | | 484 |

TABLE 7-continued

| Structure | No. | [M + H]+ |
|---|---|---|
| (structure 798) | 798 | 418 |
| (structure 799) | 799 | 470 |
| (structure 800) | 800 | 414 |
| (structure 801) | 801 | 496 |
| (structure 802) | 802 | 457 |
| (structure 803) | 803 | 490 |
| (structure 804) | 804 | 438 |
| (structure 805) | 805 | 492 |

TABLE 7-continued

| No. | Structure | [M + H]+ |
|-----|-----------|----------|
| 806 | 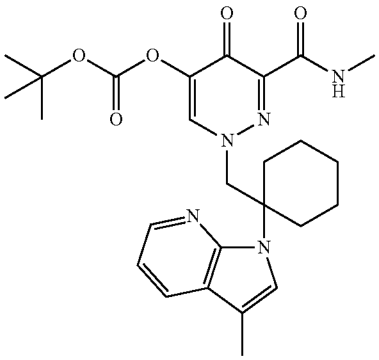 [SMILES: CNC(=O)c1nn(CC2(n3cc(C)c4cccnc43)CCCCC2)cc(OC(=O)OC(C)(C)C)c1=O] | 496 |
| 807 | 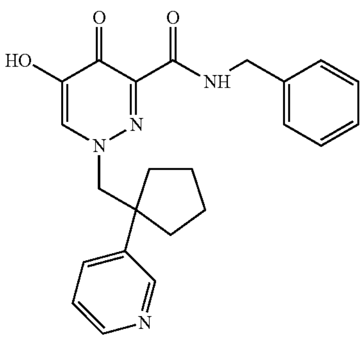 [SMILES: O=C(NCc1ccccc1)c1nn(CC2(c3cccnc3)CCCC2)cc(O)c1=O] | 405 |
| 808 | 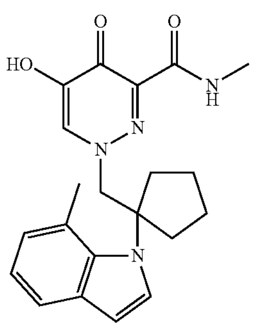 [SMILES: CNC(=O)c1nn(CC2(n3ccc4cccc(C)c43)CCCC2)cc(O)c1=O] | 381 |
| 809 | 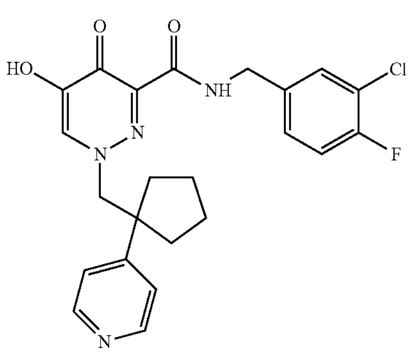 [SMILES: O=C(NCc1ccc(F)c(Cl)c1)c1nn(CC2(c3ccncc3)CCCC2)cc(O)c1=O] | 457 |
| 810 | 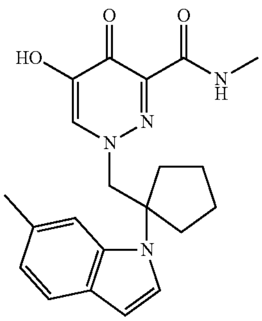 | 381 |
| 811 | 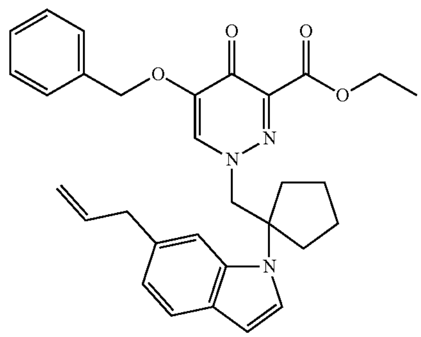 [SMILES: C=CCc1ccc2ccn(C3(Cn4cc(OCc5ccccc5)c(=O)c(C(=O)OCC)n4)CCCC3)c2c1] | 512 |
| 812 | 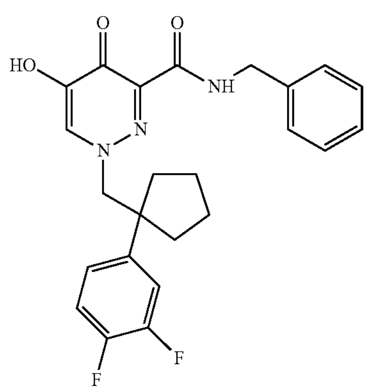 [SMILES: O=C(NCc1ccccc1)c1nn(CC2(c3ccc(F)c(F)c3)CCCC2)cc(O)c1=O] | 440 |
| 813 | 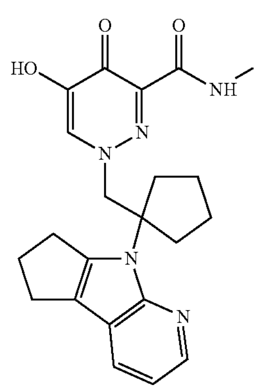 [SMILES: CNC(=O)c1nn(CC2(n3c4c(c5cccnc53)CCC4)CCCC2)cc(O)c1=O] | 408 |

TABLE 7-continued

| Structure | No. | [M + H]+ |
|---|---|---|
| (structure) | 814 | 368 |
| (structure) | 815 | 402 |
| (structure) | 816 | 385 |
| (structure) | 817 | 512 |
| (structure) | 818 | 402 |
| (structure) | 819 | 427 |
| (structure) | 820 | 440 |
| (structure) | 821 | 424 |

TABLE 7-continued
| Structure | No. | [M + H]+ |
|---|---|---|
| 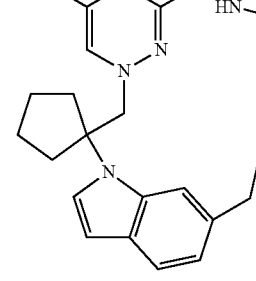 | 822 | 480 |
| 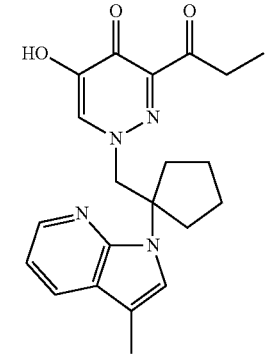 | 823 | 454 |
| 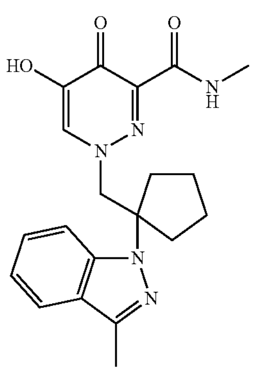 [SMILES: CNC(=O)c1nn(CC2(n3nc(C)c4ccccc43)CCCC2)cc(O)c1=O] | 824 | 382 |
| 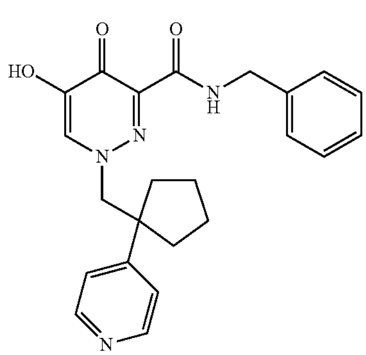 [SMILES: O=C(NCc1ccccc1)c1nn(CC2(c3ccncc3)CCCC2)cc(O)c1=O] | 825 | 405 |
TABLE 7-continued
| Structure | No. | [M + H]+ |
|---|---|---|
| 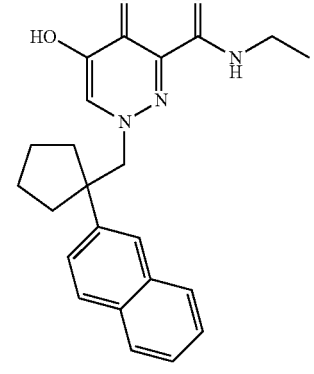 | 826 | 421 |
| 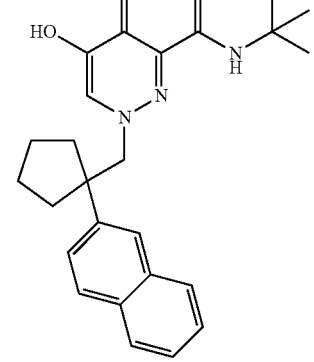 | 827 | 381 |
| 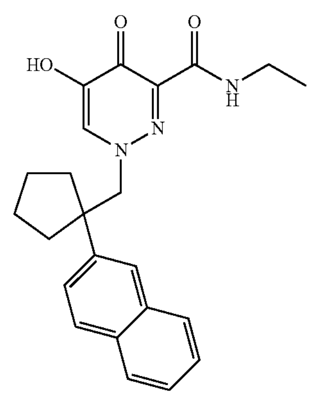 [SMILES: CCNC(=O)c1nn(CC2(c3ccc4ccccc4c3)CCCC2)cc(O)c1=O] | 828 | 392 |
| 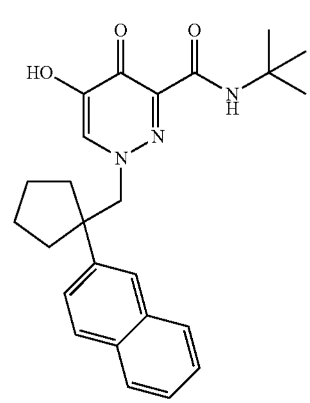 [SMILES: CC(C)(C)NC(=O)c1nn(CC2(c3ccc4ccccc4c3)CCCC2)cc(O)c1=O] | 829 | 420 |

TABLE 7-continued

| Structure | No. | [M + H]+ |
|---|---|---|
| (structure) | 830 | 381 |
| (structure) | 831 | 367 |
| (structure) | 832 | 406 |
| (structure) | 833 | 395 |
| (structure) | 834 | 365 |
| (structure) | 835 | 363 |
| (structure) | 836 | 515 |
| (structure) | 837 | 364 |

TABLE 7-continued

| Structure | No. | [M + H]+ |
|---|---|---|
| (structure 838) | 838 | 389 |
| (structure 839) | 839 | 390 |
| (structure 840) | 840 | 391 |
| (structure 841) | 841 | 419 |
| (structure 842) | 842 | 393 |
| (structure 843) | 843 | 379 |
| (structure 844) | 844 | 379 |
| (structure 845) | 845 | 379 |

TABLE 7-continued

| No. | Structure | [M + H]+ |
|---|---|---|
| 846 | 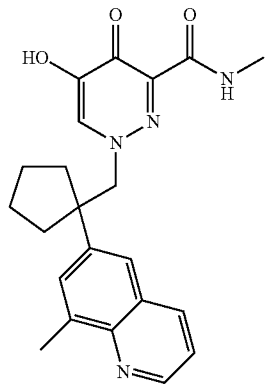 [SMILES: CNC(=O)c1nn(CC2(c3cc(C)c4ncccc4c3)CCCC2)cc(O)c1=O] | 393 |
| 847 | 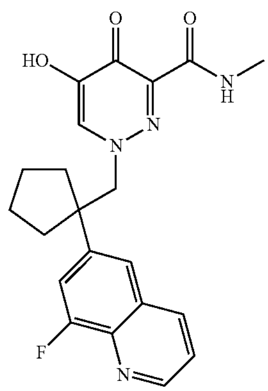 [SMILES: CNC(=O)c1nn(CC2(c3cc(F)c4ncccc4c3)CCCC2)cc(O)c1=O] | 397 |
| 848 | 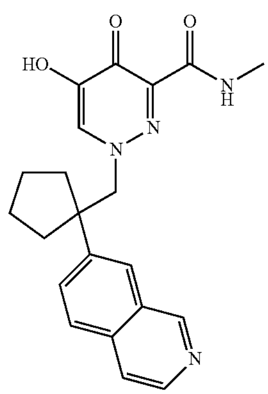 [SMILES: CNC(=O)c1nn(CC2(c3ccc4ccncc4c3)CCCC2)cc(O)c1=O] | 379 |
| 849 | 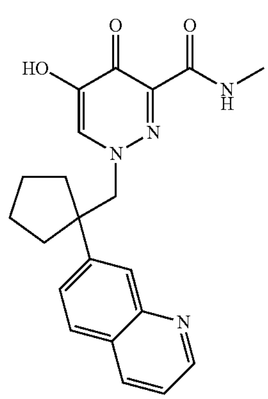 [SMILES: CNC(=O)c1nn(CC2(c3ccc4cccnc4c3)CCCC2)cc(O)c1=O] | 379 |
| 850 | | 367 |
| 851 | | 416 |
| 852 | | 472 |
| 853 | | 382 |

TABLE 7-continued

| No. | Structure | [M + H]+ |
|---|---|---|
| 854 | 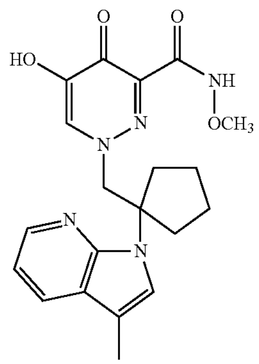 [SMILES: CONC(=O)c1nn(CC2(n3cc(C)c4cccnc43)CCCC2)cc(O)c1=O] | 398 |
| 855 | 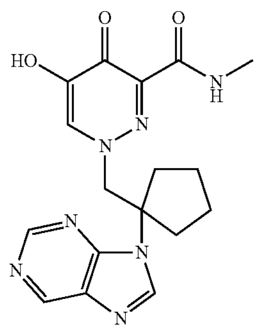 [SMILES: CNC(=O)c1nn(CC2(n3cnc4cncnc43)CCCC2)cc(O)c1=O] | 370 |
| 856 | 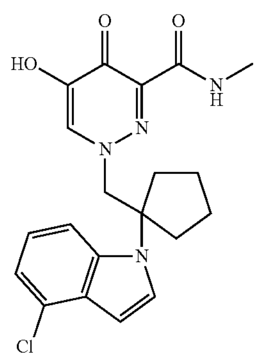 [SMILES: CNC(=O)c1nn(CC2(n3ccc4c(Cl)cccc43)CCCC2)cc(O)c1=O] | 401 |
| 857 | 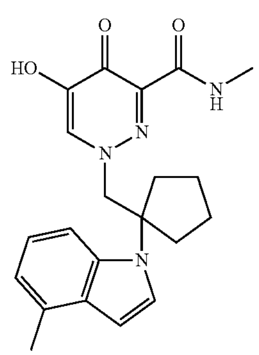 [SMILES: CNC(=O)c1nn(CC2(n3ccc4c(C)cccc43)CCCC2)cc(O)c1=O] | 381 |
| 858 | | 396 |
| 859 | | 385 |
| 860 | | 401 |
| 861 | | 385 |

TABLE 7-continued
| No. | Structure | [M+H]+ |
|---|---|---|
| 862 | 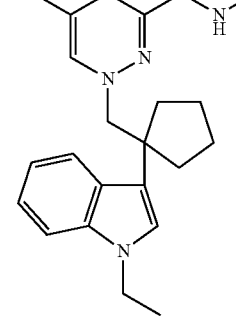 | 395 |
| 863 | 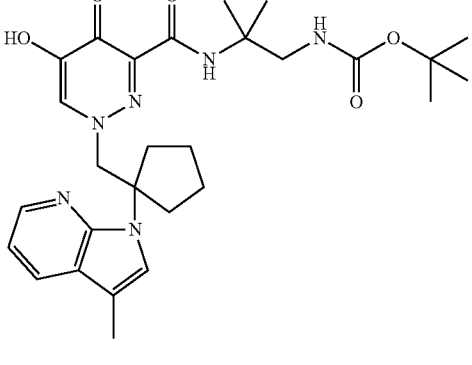 | 539 |
| 864 | 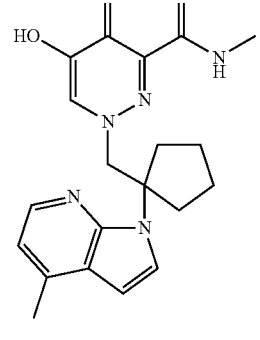 | 382 |
| 865 | 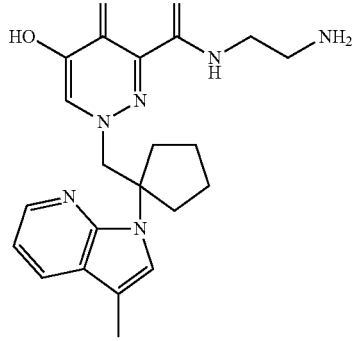 | 411 |
| 866 | 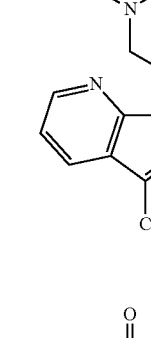 | 460 |
| 867 | 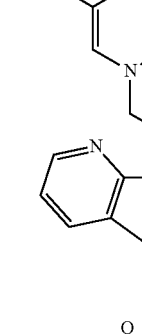 | 426 |
| 868 | 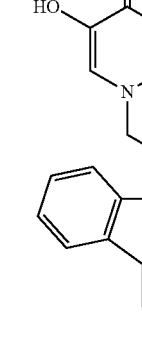 | 439 |
| 869 | 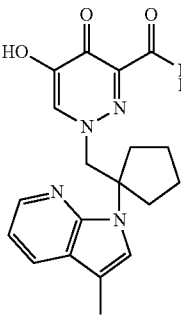 | 553 |

TABLE 7-continued
| No. | Structure | [M+H]+ |
|---|---|---|
| 870 | 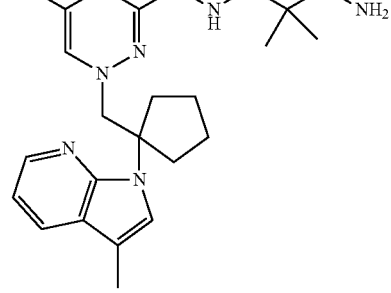 | 453 |
| 871 | 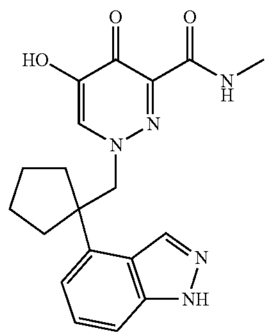 [SMILES: CNC(=O)c1nn(CC2(c3cccc4[nH]ncc34)CCCC2)cc(O)c1=O] | 368 |
| 872 | 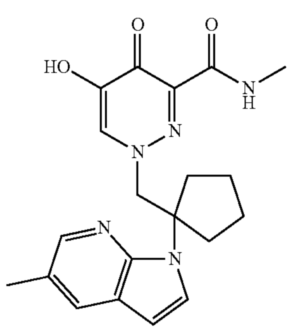 | 382 |
| 873 | 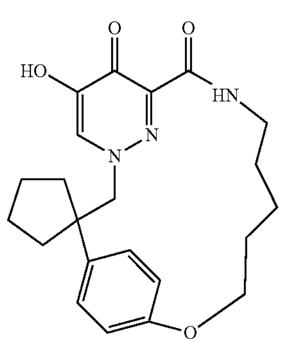 [SMILES: O=C1NCCCCCOc2ccc(cc2)C2(CCCC2)Cn2cc(O)c(=O)c1n2] | 398 |
| 874 | 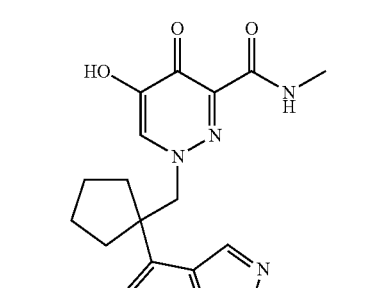 | 466 |
| 875 | | 406 |
| 876 | | 511 |
| 877 | | 438 |

TABLE 7-continued

| Structure | No. | [M+H]+ |
|---|---|---|
| (structure) | 878 | 581 |
| (structure) | 879 | 392 |
| (structure) | 880 | 425 |
| (structure) | 881 | 382 |
| (structure) | 882 | 382 |
| (structure) | 883 | 411 |
| (structure) | 884 | 443 |
| (structure) | 885 | 424 |

TABLE 7-continued

| Structure | No. | [M+H]+ |
|---|---|---|
| (5-hydroxy-4-oxo-1-((1-(5-methoxy-1H-pyrrolo[2,3-b]pyridin-1-yl)cyclopentyl)methyl)-1,4-dihydropyridazine-3-carboxamide, N-methyl) | 886 | 398 |
| (1-((1-(3,5-dichloro-1H-pyrrolo[2,3-b]pyridin-1-yl)cyclopentyl)methyl)-5-hydroxy-4-oxo-1,4-dihydropyridazine-3-carboxamide, N-methyl) | 887 | 437 |
| (5-hydroxy-1-((1-(5-methylquinolin-7-yl)cyclopentyl)methyl)-4-oxo-1,4-dihydropyridazine-3-carboxamide, N-methyl) | 888 | 393 |
| (5-hydroxy-1-((1-(7-methylquinolin-5-yl)cyclopentyl)methyl)-4-oxo-1,4-dihydropyridazine-3-carboxamide, N-methyl) | 889 | 393 |
| (5-hydroxy-1-((1-(3-methylquinolin-6-yl)cyclopentyl)methyl)-4-oxo-1,4-dihydropyridazine-3-carboxamide, N-methyl) | 890 | 393 |
| (1-((1-(2,3-dihydro-1H-cyclopenta[b]indol-4(1H)-yl)cyclopentyl)methyl)-5-hydroxy-4-oxo-1,4-dihydropyridazine-3-carboxamide, N-methyl) | 891 | 407 |
| (5-hydroxy-1-((1-(3-methoxy-1H-pyrrolo[2,3-b]pyridin-1-yl)cyclopentyl)methyl)-4-oxo-1,4-dihydropyridazine-3-carboxamide, N-methyl) | 892 | 398 |
| (1-((1-(3-chloronaphthalen-2-yl)cyclopentyl)methyl)-5-hydroxy-4-oxo-1,4-dihydropyridazine-3-carboxamide, N-methyl) | 893 | 412 |

TABLE 7-continued

| Structure | No. | [M+H]+ |
|---|---|---|
| (structure) | 894 | 424 |
| (structure) | 895 | 398 |
| (structure) | 896 | 417 |
| (structure) | 897 | 392 |
| (structure) | 898 | 415 |
| (structure) | 899 | 435 |

TABLE 8

Compounds of Formula (I)
Structure (structures)

TABLE 8-continued
Compounds of Formula (I)
Structure
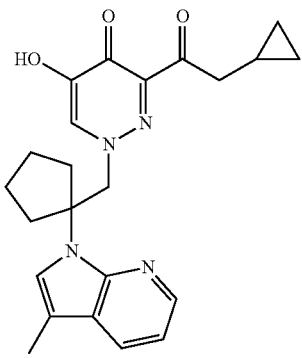 [SMILES: Cc1cn(C2(Cn3cc(O)c(=O)c(C(=O)CC4CC4)n3)CCCC2)c2ncccc12]
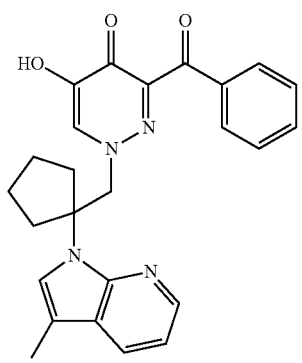 [SMILES: Cc1cn(C2(Cn3cc(O)c(=O)c(C(=O)c4ccccc4)n3)CCCC2)c2ncccc12]
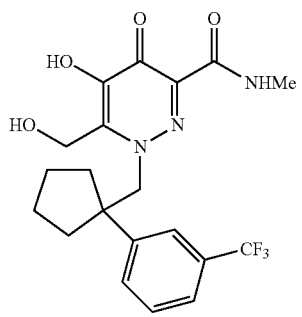 [SMILES: CNC(=O)c1nn(CC2(c3cccc(C(F)(F)F)c3)CCCC2)c(CO)c(O)c1=O]
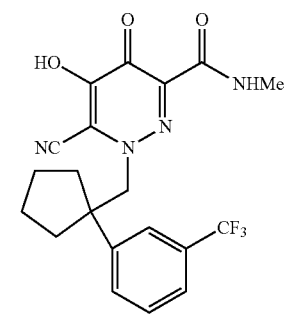 [SMILES: CNC(=O)c1nn(CC2(c3cccc(C(F)(F)F)c3)CCCC2)c(C#N)c(O)c1=O]
TABLE 8-continued
Compounds of Formula (I)
Structure
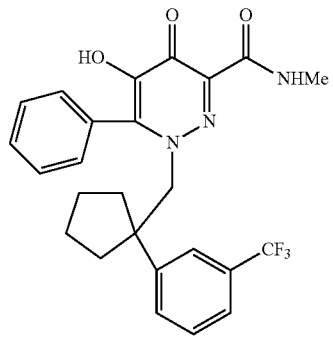 [SMILES: CNC(=O)c1nn(CC2(c3cccc(C(F)(F)F)c3)CCCC2)c(-c2ccccc2)c(O)c1=O]
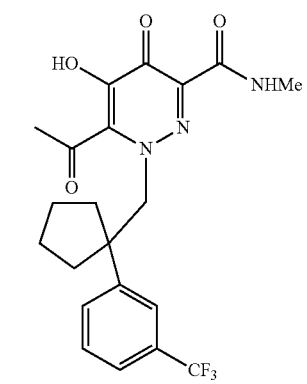 [SMILES: CNC(=O)c1nn(CC2(c3cccc(C(F)(F)F)c3)CCCC2)c(C(C)=O)c(O)c1=O]
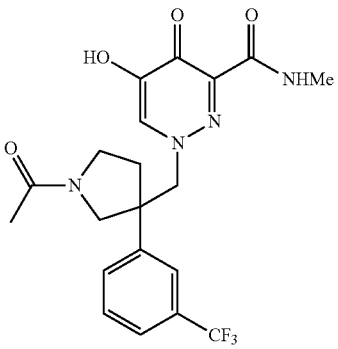 [SMILES: CNC(=O)c1nn(CC2(c3cccc(C(F)(F)F)c3)CCN(C(C)=O)C2)cc(O)c1=O]
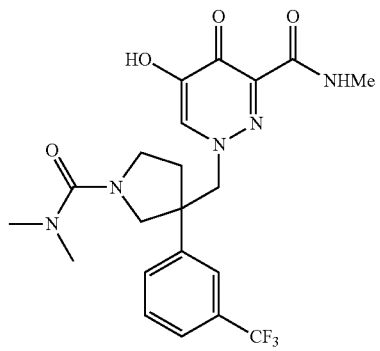 [SMILES: CNC(=O)c1nn(CC2(c3cccc(C(F)(F)F)c3)CCN(C(=O)N(C)C)C2)cc(O)c1=O]

TABLE 8-continued
Compounds of Formula (I)
Structure
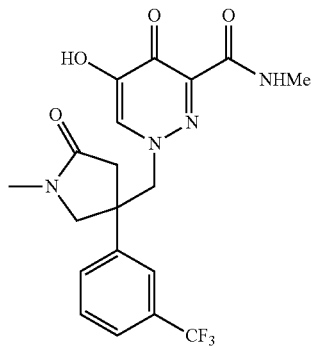 [SMILES: CNC(=O)c1nn(CC2(c3cccc(C(F)(F)F)c3)CC(=O)N(C)C2)cc(O)c1=O]
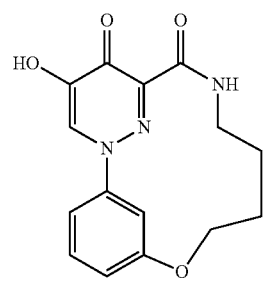 [SMILES: O=C1NCCCCOc2cccc(c2)-n2cc(O)c(=O)c1n2]
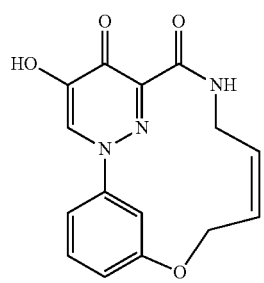 [SMILES: O=C1NC/C=C\COc2cccc(c2)-n2cc(O)c(=O)c1n2]
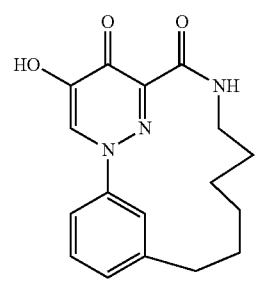 [SMILES: O=C1NCCCCCCc2cccc(c2)-n2cc(O)c(=O)c1n2]
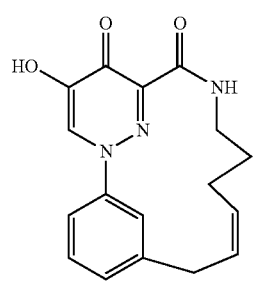
TABLE 8-continued
Compounds of Formula (I)
Structure
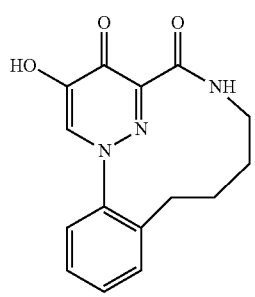 [SMILES: O=C1NCCCCc2ccccc2-n2cc(O)c(=O)c1n2]
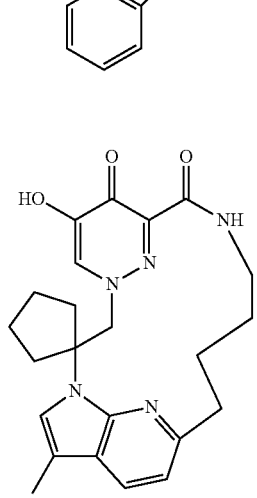
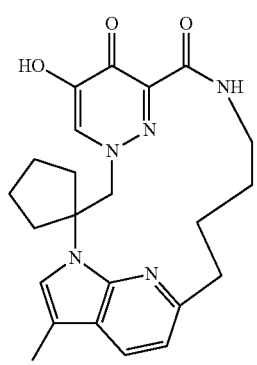 [SMILES: Cc1cn2c3nc(ccc13)CCCCNC(=O)c1nn(cc(O)c1=O)CC21CCCC1]

TABLE 8-continued

Compounds of Formula (I)
Structure

TABLE 8-continued
Compounds of Formula (I)
Structure
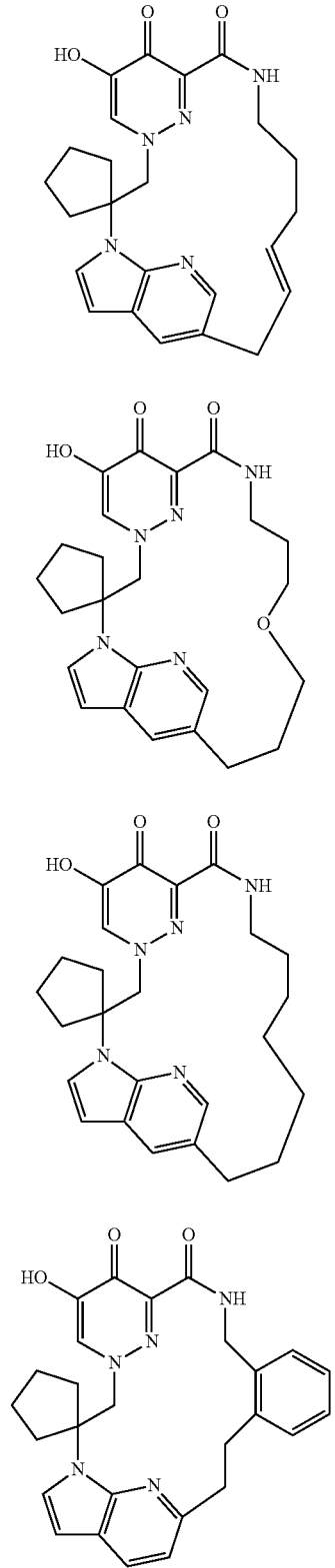
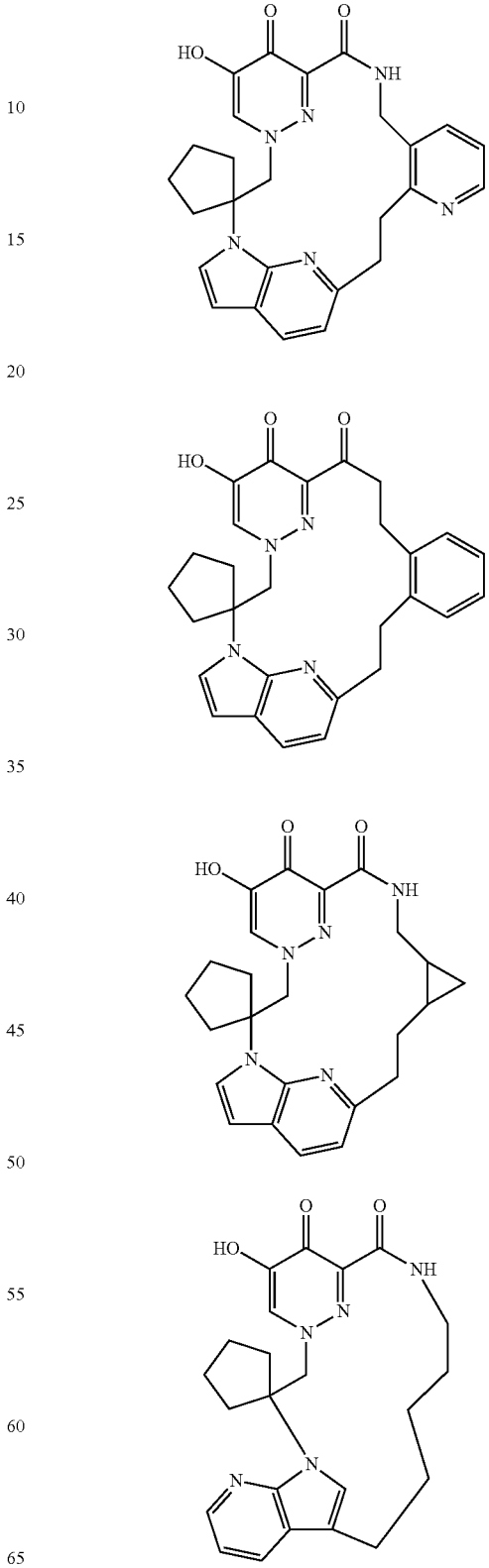

TABLE 8-continued
Compounds of Formula (I)
Structure
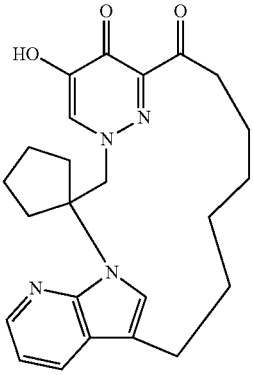 [SMILES: O=C1CCCCCCc2cn(c3ncccc23)C2(CCCC2)Cn2cc(O)c(=O)c1n2]
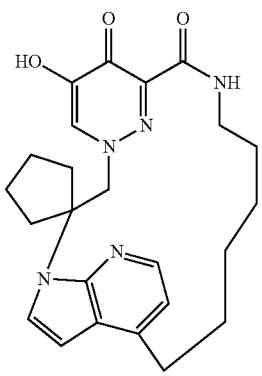 [SMILES: O=C1NCCCCCCc2ccnc3c2ccn3C2(CCCC2)Cn2cc(O)c(=O)c1n2]
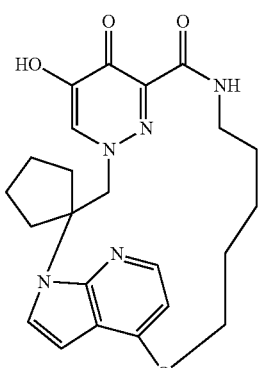
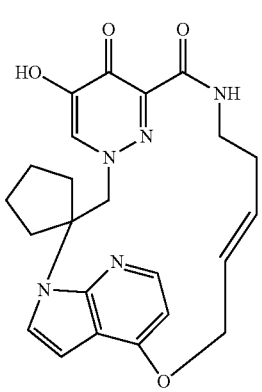 [SMILES: O=C1NCC/C=C/COc2ccnc3c2ccn3C2(CCCC2)Cn2cc(O)c(=O)c1n2]
TABLE 8-continued
Compounds of Formula (I)
Structure
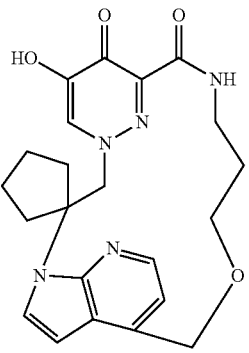 [SMILES: O=C1NCCCOCc2ccnc3c2ccn3C2(CCCC2)Cn2cc(O)c(=O)c1n2]
TABLE 9
Compounds of Formula (II)
Structure
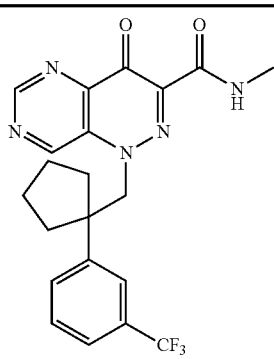
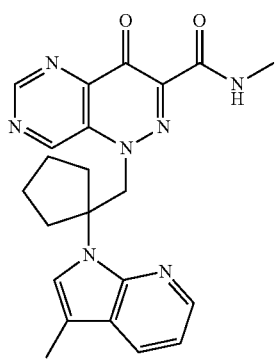 [SMILES: CNC(=O)c1nn(CC2(n3cc(C)c4cccnc43)CCCC2)c2cncnc2c1=O]
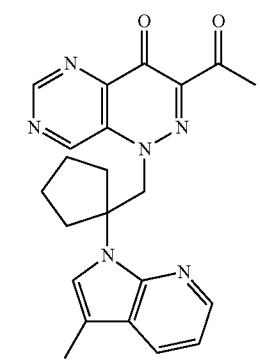 [SMILES: CC(=O)c1nn(CC2(n3cc(C)c4cccnc43)CCCC2)c2cncnc2c1=O]

TABLE 9-continued

Compounds of Formula (II)

Structure

Example 11

Influenza Antiviral Assay

Human lung carcinoma A549 cells (ATCC, Manassas, Va.) were plated at a density of $5\times10^4$ cells/mL ($5\times10^3$ cells/well) in assay media (Ham's F12 media supplemented with 0.3% FBS, 1% penicillin/streptomycin (all Mediatech, Manassas, Va.) and 1% DMSO (Sigma-Aldrich, St Louis, Mo.)) in black 96-well plates. Alternatively, Madin-Darby canine kidney epithelial cells (MDCK, ATCC), were plated at a density of $1\times10^5$ cells/mL ($1\times10^4$ cells/well) in assay media (DMEM supplemented with 0.3% FBS, 1% penicillin/streptomycin and 1% DMSO) in 96-well plates. After 24 hours, serially diluted test compounds were added to cells and incubated for an additional 24 hours. Cells were infected with 250 IU/well of Influenza strain A549 A/WSN/33 (H1N1) (Virapur, San Diego Calif.) and incubated for 20 hours at 37° C. 5% $CO_2$. The cell culture supernatant was aspirated off and 50 μL of 25 μM 2'-(4-Methylumbelliferyl)-a-D-N-acetylneuraminic acid (Sigma-Aldrich) dissolved in 33 mM MES, pH 6.5 (Emerald Biosystems. Bainbridge Island, Wash.) was added to the cells. After incubation for 45 mins at 30° C. reactions were stopped by addition of 150 μL stop solution (100 mM glycine, pH 10.5, 25% ethanol, all Sigma-Aldrich). Fluorescence was measured with excitation and emission filters of 355 and 460 nm, respectively, on a Victor X3 multi-label plate reader (Perkin Elmer. Waltham, Mass.). Cytotoxicity of uninfected parallel cultures was determined by addition of 100 μL of CellTiter-Glo® reagent (Promega, Madison, Wis.), and incubation for 10 mins at RT. Luminescence was measured on a Victor X3 multi-label plate reader.

Compounds of Formulae (I) and (II) are active in the assay as noted in Tables 10-17, where 'A' indicates an $EC_{50}<20$ μM, 'B' indicates an $EC_{50}$ of $\geq 20$ μM and $<100$ μM and 'C' indicates an $EC_{50}>100$ μM.

TABLE 10

Activity of compounds

| No. | % Inhibition |
| --- | --- |
| 1 | C |
| 2 | C |
| 4 | C |
| 6 | C |
| 7 | C |
| 9 | C |
| 10 | C |
| 11 | C |
| 17 | C |
| 18 | C |
| 19 | C |
| 20 | C |
| 21 | C |
| 24 | C |
| 35 | A |

TABLE 11

Activity of compounds

| No. | % Inhibition |
| --- | --- |
| 203 | B |
| 206 | B |
| 207 | B |
| 210 | C |
| 211 | B |

TABLE 12

Activity of compounds

| No. | % Inhibition |
| --- | --- |
| 314 | C |
| 319 | A |
| 320 | C |

TABLE 13

Activity of compounds

| No. | % Inhibition |
| --- | --- |
| 400 | C |
| 401 | C |
| 402 | C |

TABLE 13-continued

Activity of compounds

| No. | % Inhibition |
|---|---|
| 403 | C |
| 404 | C |
| 405 | A |
| 406 | A |
| 407 | C |
| 408 | B |
| 409 | C |
| 410 | A |
| 411 | A |
| 412 | C |
| 416 | B |
| 421 | C |
| 422 | A |
| 423 | C |
| 424 | B |

TABLE 14

Activity of compounds

| No. | % Inhibition |
|---|---|
| 500 | A |
| 501 | A |
| 502 | A |
| 503 | A |
| 504 | B |
| 505 | A |
| 506 | A |
| 507 | A |
| 509 | A |
| 510 | A |
| 511 | A |
| 512 | A |
| 513 | A |
| 514 | A |
| 515 | C |
| 516 | A |
| 517 | A |
| 518 | A |
| 519 | B |
| 523 | A |
| 524 | A |
| 525 | A |

TABLE 15

Activity of compounds

| No. | % Inhibition |
|---|---|
| 602 | A |
| 603 | C |
| 604 | C |
| 605 | B |
| 606 | B |
| 607 | A |
| 609 | A |
| 610 | B |
| 611 | C |
| 612 | B |
| 613 | C |
| 614 | B |
| 621 | A |
| 622 | A |
| 623 | A |
| 624 | A |
| 625 | A |
| 626 | B |
| 637 | A |
| 638 | A |

TABLE 15-continued

Activity of compounds

| No. | % Inhibition |
|---|---|
| 639 | B |
| 641 | C |
| 642 | C |
| 643 | C |
| 644 | C |
| 645 | A |
| 646 | A |
| 647 | A |
| 648 | A |
| 649 | A |
| 650 | A |
| 651 | B |
| 652 | C |
| 653 | C |
| 654 | C |
| 655 | C |
| 656 | C |
| 657 | C |
| 658 | C |
| 659 | C |
| 660 | C |
| 661 | A |
| 662 | A |
| 663 | C |
| 664 | C |
| 665 | A |
| 666 | A |
| 667 | C |
| 668 | C |
| 669 | C |
| 670 | C |
| 671 | A |
| 672 | A |
| 673 | C |
| 674 | A |
| 675 | C |
| 676 | A |
| 677 | A |
| 678 | A |
| 679 | A |
| 680 | A |
| 681 | A |
| 682 | A |
| 683 | C |
| 684 | A |
| 685 | A |
| 686 | A |
| 687 | A |
| 688 | A |
| 689 | C |
| 690 | C |
| 691 | A |
| 692 | A |
| 693 | A |
| 694 | A |
| 695 | A |
| 696 | C |
| 697 | C |
| 698 | A |
| 699 | A |

TABLE 16

Potency of compounds

| No. | % Inhibition |
|---|---|
| 700 | A |
| 701 | A |
| 702 | A |
| 703 | A |
| 704 | A |
| 705 | C |

TABLE 16-continued

Potency of compounds

| No. | % Inhibition |
|---|---|
| 706 | C |
| 707 | A |
| 708 | A |
| 709 | A |
| 710 | C |
| 711 | A |
| 712 | C |
| 713 | C |
| 714 | C |
| 718 | A |
| 719 | C |
| 720 | C |
| 721 | C |
| 722 | C |
| 723 | B |
| 724 | C |
| 725 | A |
| 726 | A |
| 727 | C |
| 728 | C |
| 729 | C |
| 730 | A |
| 731 | C |
| 732 | C |
| 733 | A |
| 734 | C |
| 735 | C |
| 736 | C |
| 737 | A |
| 738 | A |
| 739 | C |
| 740 | A |
| 741 | A |
| 742 | A |
| 743 | A |
| 744 | C |
| 745 | A |
| 746 | C |
| 747 | A |
| 748 | C |
| 749 | A |
| 750 | A |
| 751 | C |
| 752 | A |
| 753 | A |
| 754 | A |
| 755 | A |
| 756 | A |
| 757 | A |
| 758 | A |
| 759 | A |
| 760 | A |
| 761 | A |
| 762 | A |
| 763 | A |
| 764 | A |
| 765 | B |
| 766 | A |
| 767 | A |
| 768 | A |
| 769 | C |
| 770 | A |
| 771 | A |
| 772 | A |
| 773 | A |
| 774 | A |
| 775 | A |
| 776 | A |
| 777 | A |
| 778 | B |
| 779 | C |
| 780 | A |
| 781 | A |
| 782 | C |
| 783 | A |
| 784 | A |
| 785 | C |
| 786 | C |
| 787 | A |
| 788 | A |
| 789 | A |
| 790 | A |
| 791 | A |
| 792 | A |
| 793 | A |
| 794 | A |
| 795 | A |
| 796 | C |
| 797 | A |
| 798 | C |
| 799 | A |

TABLE 17

Potency of compounds

| No. | % Inhibition |
|---|---|
| 800 | A |
| 801 | A |
| 806 | A |
| 807 | A |
| 808 | A |
| 809 | A |
| 810 | A |
| 812 | A |
| 813 | A |
| 814 | A |
| 815 | A |
| 816 | A |
| 818 | A |
| 819 | A |
| 820 | A |
| 821 | A |
| 822 | A |
| 823 | A |
| 824 | A |
| 825 | A |
| 826 | A |
| 827 | A |
| 828 | A |
| 829 | A |
| 830 | C |
| 831 | C |
| 832 | C |
| 833 | A |
| 834 | C |
| 835 | C |
| 836 | C |
| 837 | C |
| 838 | A |
| 839 | C |
| 840 | C |
| 841 | A |
| 842 | C |
| 843 | A |
| 844 | A |
| 845 | A |
| 846 | A |
| 847 | C |
| 848 | C |
| 849 | A |
| 850 | A |
| 851 | A |
| 852 | C |
| 853 | A |
| 854 | A |
| 855 | C |
| 856 | A |

TABLE 17-continued

Potency of compounds

| No. | % Inhibition |
|---|---|
| 857 | A |
| 858 | C |
| 859 | A |
| 860 | A |
| 861 | A |
| 862 | C |
| 863 | A |
| 864 | A |
| 865 | A |
| 866 | A |
| 867 | A |
| 868 | A |
| 869 | A |
| 870 | B |
| 871 | C |
| 872 | A |
| 873 | C |
| 874 | C |
| 875 | A |
| 876 | A |
| 877 | C |
| 878 | A |
| 879 | A |
| 880 | C |
| 881 | A |
| 882 | A |
| 883 | C |
| 884 | A |
| 885 | C |
| 886 | A |
| 887 | A |
| 888 | A |
| 889 | A |
| 890 | A |
| 891 | A |
| 892 | A |
| 893 | A |
| 894 | A |
| 895 | A |
| 896 | A |
| 897 | A |
| 898 | A |
| 899 | A |

Example 12

EN PA FRET Inhibition Assay

EN PA FRET inhibition assay was performed using a 19 nucleotide synthetic oligoribonucleotide substrate: 5'-FAM-AUUUUGUUUUUAAUAUUUC-BHQ-3' (Integrated DNA Technologies, Inc., Coralville, Iowa) (SEQ. ID. NO. 1). Upon RNA cleavage, the fluorescent FAM group is released from the BHQ quencher. The PA sequence used to produce active enzyme is derived from any one of multiple influenza A virus strains (e.g., A/goose/Nanchang/3-120/01 (H3N2), A/Victoria/3/1975 (H3N2), A/Brisbane/10/2007 (H3N2), A/WSN/33 (H1N1), A/CA/4/2009 (H1N1), ND, A/CA/5/2009 (H1N1), A/Shanghai/1/2013 (H7N9), A/Guizhou/1/2009 (H5N1)). The full length recombinant protein was expressed from a baculovirus vector in insect cells. Full length EN PA was used in this assay at an effective concentration of 1 to 10 Nm, together with 50 Nm FRET probe with a final volume of 20 ml cleavage buffer (20 Mm Tris Ph8, 100 Mm NaCl, 5% Glycerol, 10 Mm β-ME, 0.01% Tween-20, 2 Mm $MnCl_2$).

Compounds described herein were added to a 384-well black polypropylene plate. Fluorescence was measured in a continuous mode up to 30 minutes with a Wallac 1420 Victor$^3$V multilabel counter (PerkinElmer Life Sciences, Shelton, Conn.) (excitation 485 nm; emission 535 nm). Measured $IC_{50}$ is defined as the concentration at which fluorescence is 50% that of the uninhibited control (DMSO). $IC_{50}$ was calculated by fitting the data to the sigmoidal equation Y=% Min+(% Max−% Min)/(1+X/$IC_{50}$), where Y corresponds to the percent relative enzyme activity, Max is the maximum enzyme activity in the presence of DMSO, Min is the inhibited activity at saturating concentration of compound, and X corresponds to the compound concentration. The $IC_{50}$ values were derived from the mean of a minimum of two independent experiments.

Compounds of Formulae (I) and (II) are potent in the assay as noted in Tables 18-25, where 'A' indicates an $IC_{50}$<100 nM, 'B' indicates an $IC_{50}$ of ≥100 nM and <1000 nM and 'C' indicates an $IC_{50}$≥1000 nM

TABLE 18

Potency of compounds

| No. | Potency |
|---|---|
| 1 | B |
| 2 | B |
| 3 | B |
| 4 | B |
| 5 | B |
| 6 | B |
| 7 | B |
| 8 | C |
| 9 | B |
| 10 | B |
| 11 | B |
| 12 | B |
| 13 | B |
| 14 | C |
| 15 | B |
| 16 | B |
| 17 | B |
| 18 | B |
| 19 | B |
| 20 | B |
| 21 | A |
| 22 | B |
| 23 | B |
| 24 | A |
| 25 | C |
| 26 | B |
| 27 | B |
| 28 | C |
| 29 | B |
| 30 | C |
| 31 | B |
| 32 | B |
| 33 | B |
| 34 | B |
| 35 | A |
| 36 | B |
| 37 | B |
| 38 | B |
| 39 | B |
| 40 | B |
| 41 | B |
| 42 | B |
| 43 | B |
| 44 | C |

TABLE 19

Potency of compounds

| No. | Potency |
|---|---|
| 200 | B |
| 201 | B |
| 202 | B |

TABLE 19-continued

Potency of compounds

| No. | Potency |
|---|---|
| 203 | B |
| 204 | C |
| 205 | C |
| 206 | B |
| 207 | B |
| 208 | B |
| 209 | B |
| 210 | B |
| 211 | B |

TABLE 20

Potency of compounds

| No. | Potency |
|---|---|
| 300 | B |
| 301 | B |
| 302 | B |
| 303 | B |
| 304 | C |
| 305 | B |
| 306 | B |
| 307 | B |
| 308 | B |
| 309 | C |
| 310 | B |
| 311 | A |
| 312 | C |
| 313 | B |
| 314 | B |
| 315 | B |
| 316 | B |
| 317 | A |
| 318 | B |
| 319 | B |
| 320 | B |
| 321 | C |
| 322 | B |
| 323 | B |
| 324 | B |
| 325 | A |

TABLE 21

Potency of compounds

| No. | Potency |
|---|---|
| 400 | A |
| 401 | B |
| 402 | B |
| 403 | A |
| 404 | A |
| 405 | C |
| 406 | A |
| 407 | B |
| 408 | C |
| 409 | B |
| 410 | A |
| 411 | B |
| 412 | A |
| 413 | A |
| 414 | A |
| 415 | B |
| 416 | A |
| 417 | B |
| 418 | B |
| 419 | A |
| 420 | B |
| 421 | B |

TABLE 21-continued

Potency of compounds

| No. | Potency |
|---|---|
| 422 | A |
| 423 | B |
| 424 | B |
| 425 | B |

TABLE 22

Potency of compounds

| No. | Potency |
|---|---|
| 500 | B |
| 501 | C |
| 502 | C |
| 503 | B |
| 504 | C |
| 505 | B |
| 506 | B |
| 507 | B |
| 508 | B |
| 509 | B |
| 510 | B |
| 511 | B |
| 512 | B |
| 513 | B |
| 514 | B |
| 515 | B |
| 516 | B |
| 517 | B |
| 518 | B |
| 519 | B |
| 520 | C |
| 521 | C |
| 522 | B |
| 523 | B |
| 524 | B |
| 525 | B |

TABLE 23

Potency of compounds

| No. | Potency |
|---|---|
| 600 | C |
| 601 | C |
| 602 | B |
| 603 | C |
| 604 | C |
| 605 | B |
| 606 | C |
| 607 | B |
| 608 | C |
| 609 | A |
| 610 | B |
| 611 | C |
| 612 | C |
| 613 | C |
| 614 | B |
| 615 | C |
| 616 | C |
| 617 | C |
| 618 | C |
| 619 | C |
| 620 | C |
| 621 | B |
| 622 | B |
| 623 | B |
| 624 | B |
| 625 | B |
| 626 | B |

TABLE 23-continued

Potency of compounds

| No. | Potency |
|---|---|
| 627 | B |
| 628 | C |
| 629 | C |
| 630 | B |
| 632 | C |
| 633 | C |
| 636 | C |
| 639 | B |
| 644 | B |
| 645 | A |
| 646 | A |
| 648 | A |
| 649 | A |
| 650 | A |
| 654 | B |
| 655 | A |
| 656 | B |
| 658 | B |
| 659 | B |
| 660 | B |
| 661 | A |
| 662 | A |
| 663 | B |
| 664 | B |
| 665 | A |
| 666 | A |
| 669 | A |
| 670 | B |
| 671 | B |
| 674 | A |
| 676 | A |
| 677 | A |
| 678 | A |
| 679 | A |
| 680 | A |
| 681 | A |
| 682 | A |
| 683 | A |
| 685 | A |
| 686 | B |
| 687 | A |
| 692 | A |
| 693 | A |
| 694 | B |
| 695 | A |

TABLE 24

Potency of compounds

| No. | Potency |
|---|---|
| 700 | A |
| 701 | A |
| 703 | A |
| 704 | A |
| 708 | A |
| 709 | A |
| 718 | A |
| 720 | A |
| 722 | A |
| 723 | A |
| 730 | A |
| 733 | A |
| 738 | A |
| 740 | A |
| 741 | A |
| 742 | A |
| 743 | A |
| 747 | A |
| 749 | A |
| 750 | A |

TABLE 24-continued

Potency of compounds

| No. | Potency |
|---|---|
| 752 | A |
| 753 | A |
| 754 | A |
| 755 | A |
| 756 | A |
| 757 | A |
| 758 | A |
| 759 | A |
| 760 | A |
| 761 | A |
| 762 | A |
| 764 | A |
| 765 | C |
| 766 | A |
| 768 | A |
| 771 | B |
| 772 | B |
| 773 | A |
| 774 | A |
| 775 | A |
| 776 | A |
| 777 | A |
| 778 | A |
| 782 | A |
| 783 | A |
| 784 | B |
| 785 | A |
| 786 | A |
| 787 | A |
| 788 | A |
| 789 | A |
| 790 | A |
| 791 | B |
| 792 | A |
| 793 | B |
| 794 | A |
| 795 | B |
| 796 | B |
| 797 | B |
| 798 | B |
| 799 | A |

TABLE 25

Potency of compounds

| No. | Potency |
|---|---|
| 800 | A |
| 801 | A |
| 802 | A |
| 803 | A |
| 804 | A |
| 805 | A |
| 806 | A |
| 807 | A |
| 808 | A |
| 809 | A |
| 810 | A |
| 812 | A |
| 813 | A |
| 814 | A |
| 815 | A |
| 816 | A |
| 818 | A |
| 819 | A |
| 820 | A |
| 821 | A |
| 822 | A |

TABLE 25-continued

Potency of compounds

| No. | Potency |
|-----|---------|
| 823 | A |
| 824 | B |
| 825 | B |
| 826 | A |
| 827 | A |
| 828 | A |
| 829 | A |
| 830 | B |
| 831 | B |
| 832 | A |
| 833 | A |
| 834 | B |
| 835 | B |
| 836 | C |
| 837 | B |
| 838 | A |
| 839 | B |
| 840 | B |
| 841 | B |
| 842 | B |
| 843 | A |
| 844 | A |
| 845 | A |
| 846 | A |
| 847 | A |
| 848 | A |
| 849 | A |
| 850 | A |
| 851 | A |
| 852 | C |
| 853 | A |
| 854 | A |
| 855 | B |
| 856 | A |
| 857 | A |
| 858 | B |
| 859 | A |
| 860 | A |
| 861 | A |
| 862 | B |
| 863 | B |
| 864 | A |
| 865 | A |
| 866 | A |
| 867 | A |
| 868 | A |
| 869 | B |
| 870 | A |
| 871 | A |
| 872 | A |
| 873 | B |
| 874 | B |
| 875 | A |
| 876 | A |
| 877 | B |
| 878 | A |
| 879 | A |
| 880 | A |
| 881 | A |
| 882 | A |
| 883 | A |
| 884 | A |
| 885 | B |
| 886 | A |
| 887 | A |
| 888 | A |
| 889 | A |
| 890 | A |
| 891 | A |
| 892 | A |
| 893 | A |
| 894 | A |
| 895 | A |
| 896 | A |
| 897 | A |
| 898 | A |
| 899 | A |

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof:

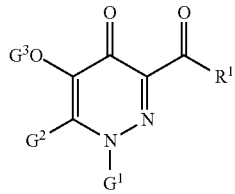
(I)

wherein:

G¹ is selected from the group consisting of

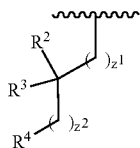

and R⁵;

G² is hydrogen, halogen, —CN, an optionally substituted C$_{1-6}$ alkyl, an optionally substituted aryl, an optionally substituted heteroaryl, —CH$_2$OH, —CH(Y¹)(OH) or —C(O)Y¹;

G³ is selected from the group consisting of hydrogen, —C(O)Y², —C(O)O—Y², —(CH$_2$)—OC(O)Y², —(CH$_2$)—OC(O)OY², —(CHCH$_3$)—OC(O)Y² and —(CHCH$_3$)—OC(O)OY²;

Y¹ and Y² are independently an optionally substituted C$_{1-6}$ alkyl or an optionally substituted aryl;

R¹ is selected from the group consisting of OR⁶, NH$_2$, an optionally substituted alkyl, an optionally substituted aryl, an optionally substituted mono-substituted amine, an optionally substituted di-substituted amine, an optionally substituted heterocyclyl, an optionally substituted N-sulfonamido and an optionally substituted alkoxyamine, or R¹ is R¹⁰;

R² is hydrogen, C$_{1-6}$ alkyl, an optionally substituted C$_{3-6}$ cycloalkyl, an optionally substituted aryl, an optionally substituted aryl(C$_{1-6}$ alkyl) or an optionally substituted C-amido;

R³ is hydrogen or C$_{1-6}$ alkyl;

or R² and R³ are taken together with the carbon to which they are attached to form an optionally substituted C$_{3-6}$ cycloalkyl or an optionally substituted 5 to 6 membered heterocyclyl, or R² and R³ are taken together to form =O;

R⁴ is selected from the group consisting of an optionally substituted aryl, an optionally substituted cycloalkyl, an optionally substituted cycloalkenyl, an optionally substituted heteroaryl and an optionally substituted heterocyclyl;

or R⁴ is A¹R$^{A4}$R$^{B4}$, wherein A¹ is CH or N; and R$^{A4}$ and R$^{B4}$ are each independently an optionally substituted phenyl;

R⁵ is selected from the group consisting of an optionally substituted aryl, an optionally substituted cycloalkyl, an optionally substituted cycloalkenyl, an optionally substituted heteroaryl and an optionally substituted heterocyclyl;

R⁶ is selected from the group consisting of hydrogen, C$_{1-6}$ alkyl, —C(O)R⁷ and —C(O)NR⁸R⁹;

R⁷ is selected from the group consisting of hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl); and R⁸ and R⁹ are independently selected from the group consisting of hydrogen, alkyl, alkenyl, alkynyl, cycloalkyl, cycloalkenyl, cycloalkynyl, aryl, heteroaryl, heterocyclyl, aryl(C$_{1-6}$ alkyl), heteroaryl(C$_{1-6}$ alkyl) and heterocyclyl(C$_{1-6}$ alkyl);

or R⁸ and R⁹ are taken together with the nitrogen to which they are attached to form an optionally substituted heterocyclyl;

wherein when R¹ is R¹⁰, then the compound of Formula (I) has the structure of Formula (Ih) or (Ij),

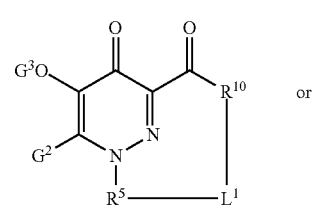
(Ih)

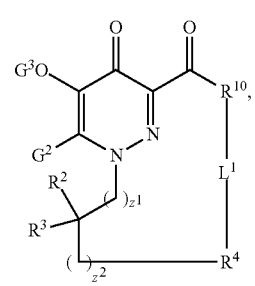
(Ij)

wherein the ring containing R¹⁰, L¹, and R⁴ is an 11- to 20-membered ring, and the ring containing R¹⁰, L¹, and R⁵ is an 11- to 20-membered ring;

R¹⁰ is optionally substituted —CH$_2$—, optionally substituted —CH═CH—, O (oxygen), S (sulfur) or NR¹¹;

R¹¹ is hydrogen or C$_{1-6}$ alkyl;

L¹ is -L²- or -L³-L⁴-L⁵-;

L² is selected from the group consisting of an optionally substituted alkylene, an optionally substituted alkenylene, an optionally substituted heteroalkylene and an optionally substituted heteroalkenylene, L³ is an optionally substituted C$_{1-6}$ alkylene, L⁴ is an optionally substituted cycloalkyl, an optionally substituted aryl, an optionally substituted heteroaryl, an optionally substituted heterocyclyl, O (oxygen), S (sulfur) or NR¹¹; and L⁵ is an optionally substituted C1.6 alkylene or an optionally substituted heteroalkylene, and Z¹ and Z² are independently 0, 1, 2, 3 or 4.

2. The compound of claim 1, or a pharmaceutically acceptable salt thereof, wherein:

G² is hydrogen or C$_{1-6}$ alkyl;

G³ is selected from the group consisting of hydrogen, —C(O)Y², —C(O)O—Y², —(CH$_2$)—OC(O)Y², —(CH$_2$)—OC(O)OY², —(CHCH$_3$)—OC(O)Y² and —(CHCH$_3$)—OC(O)OY²;

$Y^2$ is $C_{1-6}$ alkyl;

$R^1$ is selected from the group consisting of $OR^6$, $NH_2$, an optionally substituted mono-substituted amine, an optionally substituted di-substituted amine, an optionally substituted heterocyclyl and an optionally substituted N-sulfonamido, said an optionally substituted mono-substituted amine, an optionally substituted di-substituted amine, an optionally substituted heterocyclyl and an optionally substituted N-sulfonamido are each optionally substituted with one or more substituents selected from the group consisting of alkyl, alkenyl, alkynyl, cycloalkyl, cycloalkenyl, cycloalkynyl, aryl, heteroaryl, heterocyclyl, aryl(alkyl), heteroaryl (alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino;

$R^2$ is hydrogen or $C_{1-6}$ alkyl;

$R^3$ is hydrogen or $C_{1-6}$ alkyl;

or $R^2$ and $R^3$ are taken together with the carbon to which they are attached to form an optionally substituted $C_{3-6}$ cycloalkyl or an optionally substituted 5 to 6 membered heterocyclyl.

3. The compound of claim 1, or a pharmaceutically acceptable salt thereof, wherein:

$G^1$ is

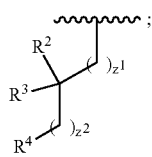

and $R^2$ and $R^3$ are taken together with the carbon to which they are attached to form an optionally substituted piperidino or an optionally substituted pyrrolidino.

4. The compound of claim 1, or a pharmaceutically acceptable salt thereof, having the structure of Formula (Ih) or Formula (Ij), or a pharmaceutically acceptable salt thereof:

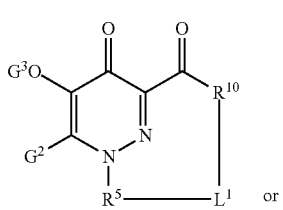

(Ih)

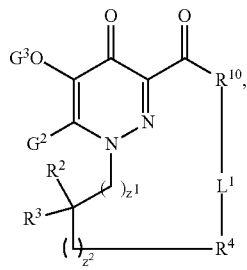

(Ij)

5. The compound of claim 4, or a pharmaceutically acceptable salt thereof, wherein $L^2$ is an optionally substituted alkylene or an optionally substituted alkenylene.

6. The compound of claim 4, or a pharmaceutically acceptable salt thereof, wherein $L^2$ is an optionally substituted heteroalkylene or an optionally substituted heteroalkenylene.

7. The compound of claim 4, or a pharmaceutically acceptable salt thereof, wherein $L^2$ is an optionally substituted $-(CH_2)_3-O-$, an optionally substituted $-(CH_2)_4-O-$, an optionally substituted $-(CH_2)_5-O-$, an optionally substituted $-(CH_2)_3-S-$, an optionally substituted $-(CH_2)_4-S-$, an optionally substituted $-(CH_2)_5-S-$, an optionally substituted $-(CH_2)_3-NH-$, an optionally substituted $-(CH_2)_4-NH-$, an optionally substituted $-(CH_2)_5-NH-$, an optionally substituted $-(CH_2)(CH=CH)(CH_2)-O-$, an optionally substituted $-(CH_2)_2(CH=CH)(CH_2)-O-$, an optionally substituted $-(CH_2)(CH=CH)(CH_2)_2-O-$, an optionally substituted $-(CH_2)_2(CH=CH)(CH_2)_2-O-$, an optionally substituted $-(CH_2)_2(CH=CH)(CH_2)-S-$, an optionally substituted $-(CH_2)(CH=CH)(CH_2)_2-S-$, an optionally substituted $-(CH_2)_2(CH=CH)(CH_2)_2-S$ an optionally substituted $-(CH_2)_2(CH=CH)(CH_2)-NH-$, an optionally substituted $-(CH_2)(CH=CH)(CH_2)_2-NH-$ or an optionally substituted $-(CH_2)_2(CH=CH)(CH_2)_2-NH-$.

8. The compound of claim 4, or a pharmaceutically acceptable salt therof, wherein $L^2$ is an optionally substituted $C_3$ oxygen containing heteroalkenylene, an optionally substituted $C_4$ oxygen containing heteroalkenylene or an optionally substituted $C_5$ oxygen containing heteroalkenylene.

9. The compound of claim 1, or a pharmaceutically acceptable salt thereof, wherein $R^1$ is $OR^6$.

10. The compound of claim 9, or a pharmaceutcially acceptable salt thereof, wherein $R^6$ is hydrogen or $C_{1-6}$ alkyl.

11. The compound of claim 9, or a pharmaceutically acceptable salt thereof, wherein $R^6$ is $-C(O)R^7$ or $-C(O)NR^8R^9$.

12. The compound of claim 1, or a pharmaceutically acceptable salt thereof, wherein $R^1$ is $NH_2$, an optionally substituted mono-substituted amine or an optionally substituted di-substituted amine.

13. The compound of claim 1, or a pharmaceutically accceptable salt thereof, wherein $R^1$ is an optionally substituted heterocyclyl or an optionally substituted N-sulfonamido.

14. The compound of claim 1, or a pharmaceutically acceptable salt thereof, wherein $R^1$ is $R^{10}$.

15. The compound of claim 14, or a pharmaceutically acceptable salt thereof, wherein $R^{10}$ is $CH_2$.

16. The compound of claim 14, or a pharmaceutically acceptable salt thereof, wherein $R^{10}$ is $NR^{11}$.

17. The compound of claim 1, or a pharmaceutically acceptable salt thereof, wherein G¹ is

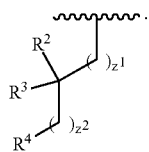

18. The compound of claim 17, or a pharmaceutically acceptable salt thereof, wherein R² is hydrogen; and R³ is hydrogen.

19. The compound of claim 17, or a pharmaceutically accetpable salt thereof, wherein R² is $C_{1-6}$ alkyl; and R³ is hydrogen.

20. The compound of claim 17, or a pharmaceutically acceptable salt thereof, wherein R² and R³ are taken together with the carbon to which they are attached to form an optionally substituted $C_{3-6}$ cycloalkyl or an optionally substituted 5 to 6 membered heterocyclyl.

21. The compound of claim 17, or a pharmaceutically acceptable salt thereof, wherein R⁴ is selected from the group consisting of an optionally substituted aryl, an optionally substituted heteroaryl and an optionally substituted heterocyclyl.

22. The compound of claim 21, or a pharmaceutically acceptable salt thereof, wherein R⁴ is an optionally substituted aryl.

23. The compound of claim 22, or a pharmaceutically acceptable salt thereof, wherein the optionally substituted aryl is an optionally substituted phenyl.

24. The compound of claim 21, or a pharmaceutically acceptable salt thereof, wherein R⁴ is an optionally substituted heteroaryl or an optionally substituted heterocyclyl.

25. The compound of claim 21, or a pharmaceutically acceptable salt thereof, wherein R⁴ is substituted with one or more substituents selected from the group consisting of halogen, $C_{1-6}$ alkyl, alkoxy, aryloxy, cyano, haloalkyl, haloalkoxy, hydroxyalkyl, N-sulfonamido, S-sulfonamido, sulfonyl, an optionally substituted aryl, aryl($C_{1-6}$ alkyl), an optionally substituted cycloalkyl, an optionally substituted heterocyclyl, carbonyl, C-carboxy, —CH₂-(mono-substituted amine) and CH₂-(di-substituted amine).

26. The compound of claim 17, or a pharmaceutically acceptable salt thereof, wherein Z¹ is 1; and Z² is 0.

27. The compound of claim 17, or a pharmaceutically acceptable salt thereof, wherein Z¹ is 1; and Z² is 1.

28. The compound of claim 1, or a pharmaceutically acceptable salt thereof, wherein G¹ is R⁵.

29. The compound of claim 28, or a pharmaceutically acceptable salt thereof, wherein R⁵ is selected from the group consisting of an optionally substituted aryl, an optionally substituted heteroaryl and an optionally substituted heterocyclyl.

30. The compound of claim 28, or a pharmaceutically acceptable salt thereof, wherein R⁵ is an optionally substituted aryl or an optionally substituted cycloalkyl.

31. The compound of claim 30, or a pharmaceutically acceptable salt thereof, wherein the optionally substituted aryl is an optionally substituted phenyl.

32. The compound of claim 28, or a pharmaceutically acceptable salt thereof, wherein R⁵ is an optionally substituted heteroaryl or an optionally substituted heterocyclyl.

33. The compound of claim 29, or a pharmaceutically acceptable salt thereof, wherein R⁵ is substituted with one or more substituents selected from the group consisting of halogen, $C_{1-6}$ alkyl, alkoxy, aryloxy, cyano, haloalkyl, haloalkoxy, hydroxyalkyl, N-sulfonamido, S-sulfonamido, sulfonyl, an optionally substituted aryl, aryl($C_{1-6}$ alkyl), an optionally substituted cycloalkyl, an optionally substituted heterocyclyl, carbonyl, C-carboxy, —CH₂-(mono-substituted amine) and CH₂-(di-substituted amine).

34. The compound of claim 1, or a pharmaceutically acceptable salt thereof, wherein G³ is hydrogen.

35. The compound of claim 1, wherein the compound is selected from the group consisting of:

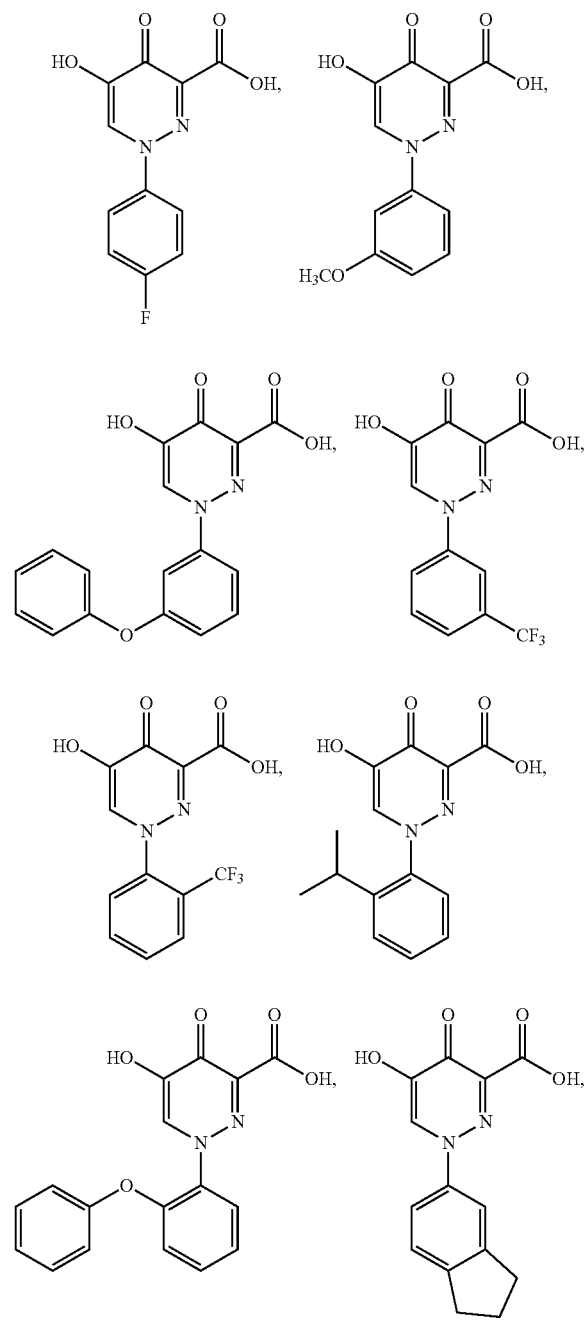

235
-continued
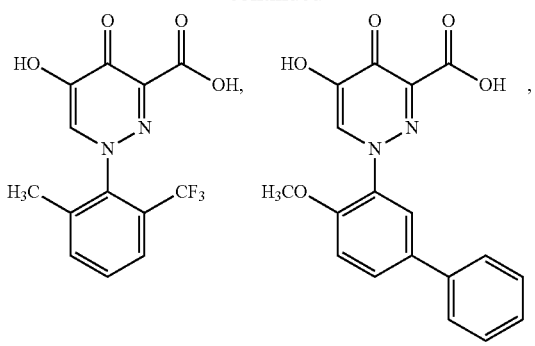
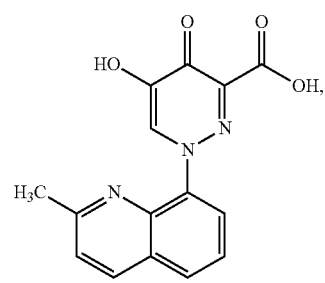
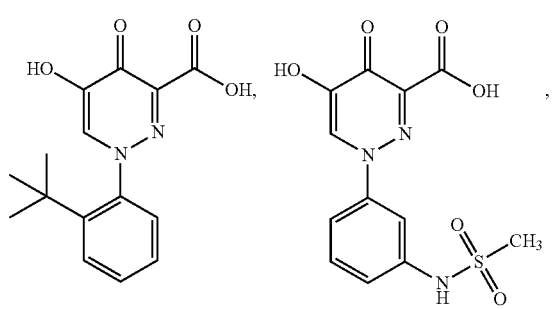
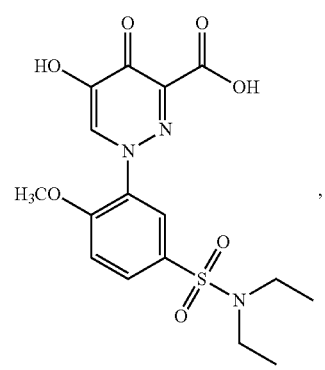
236
-continued
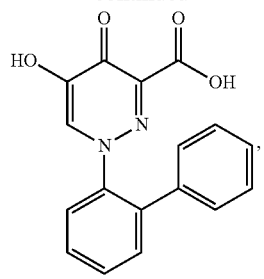
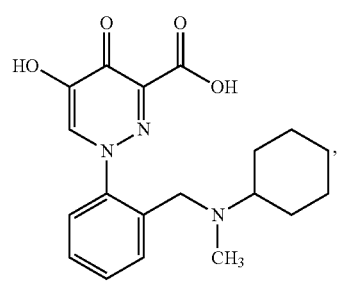
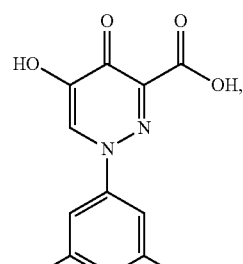
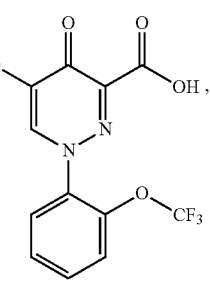
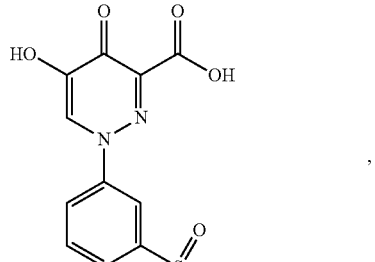

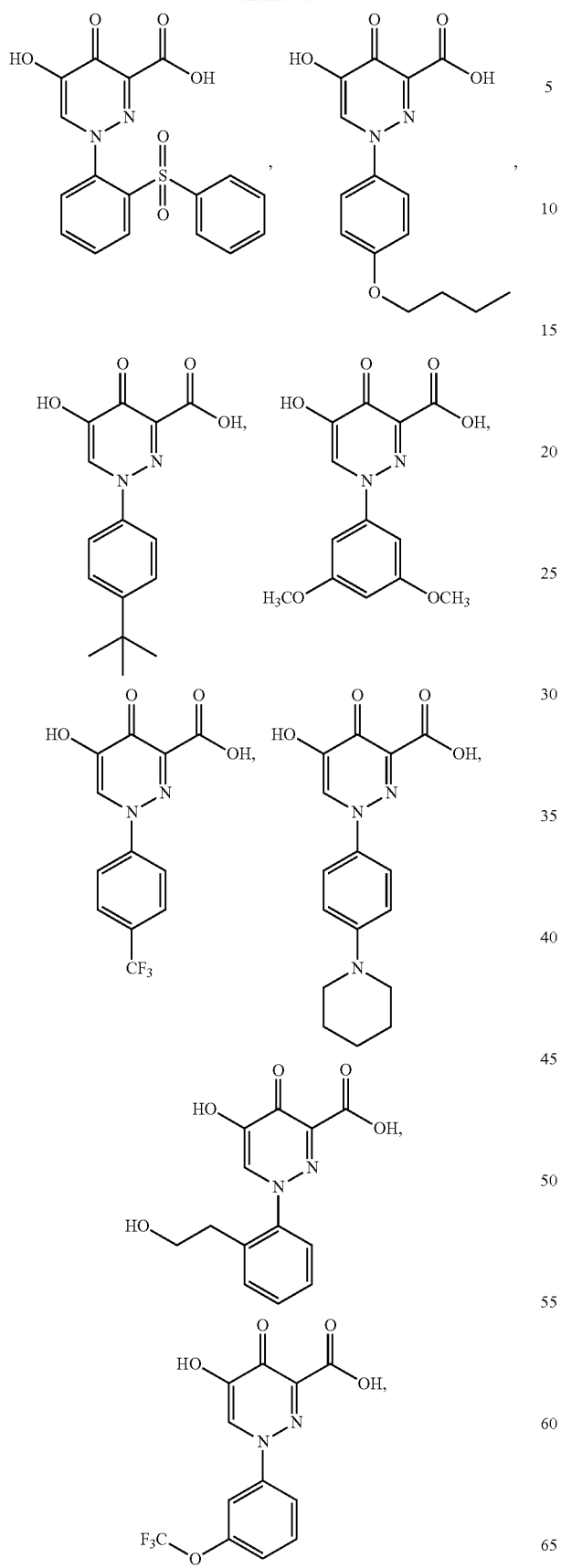
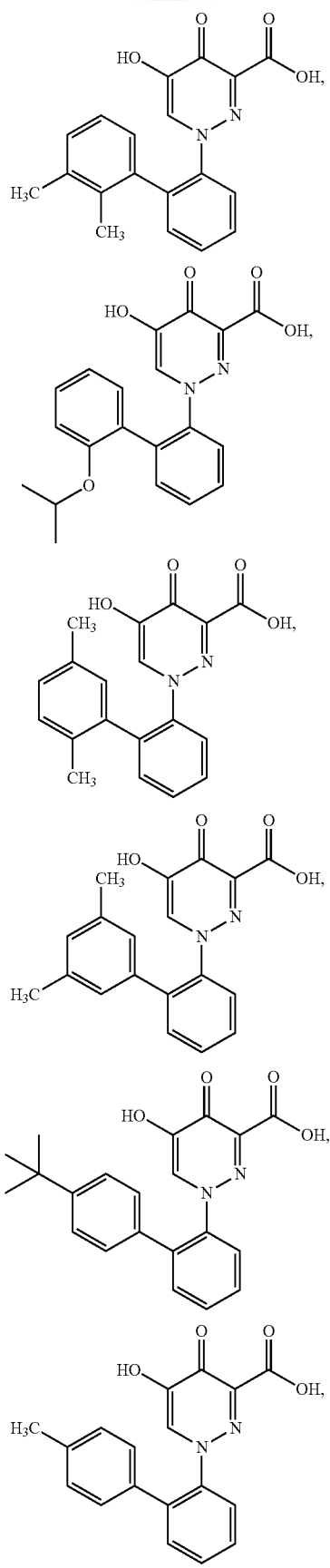

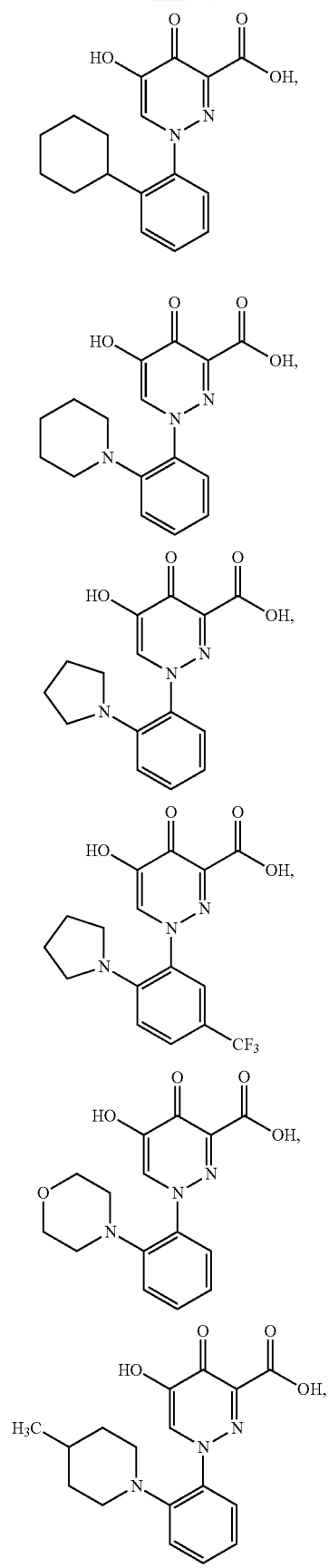
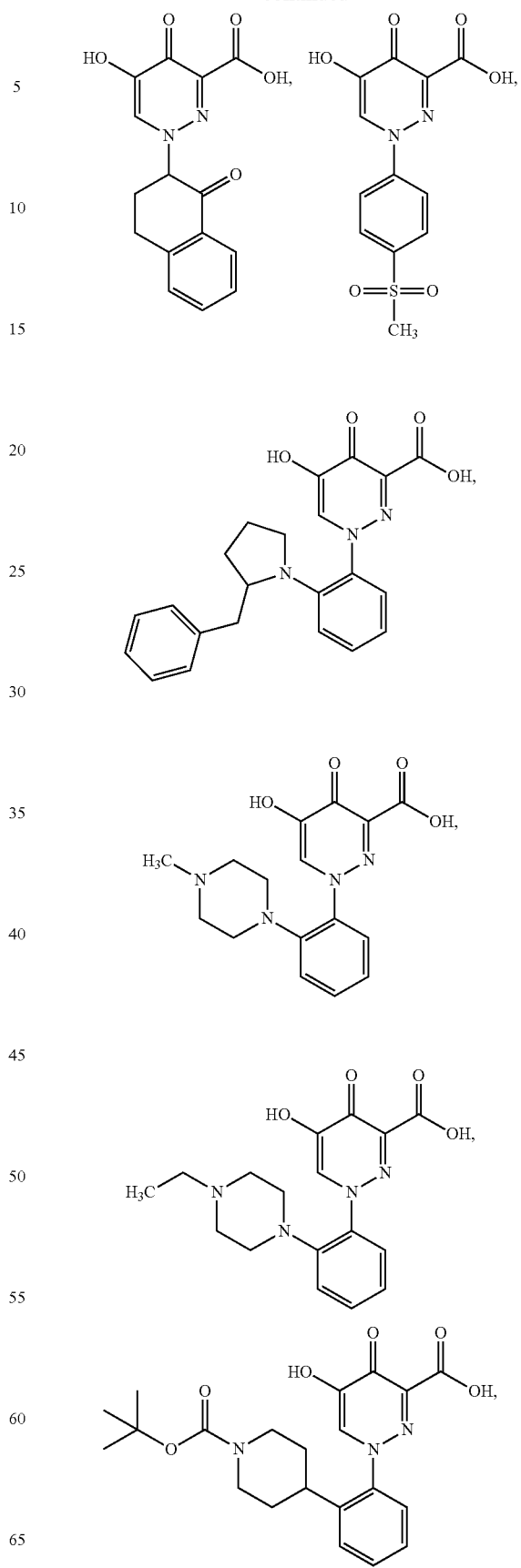

-continued
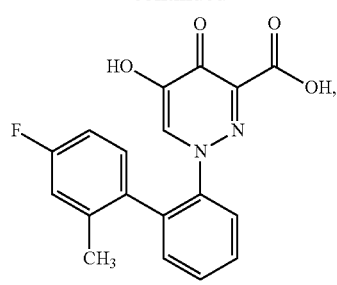
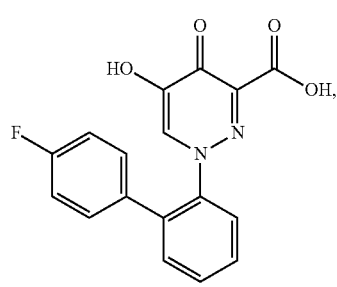
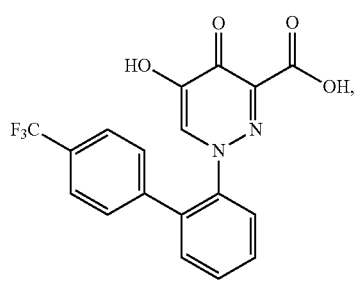
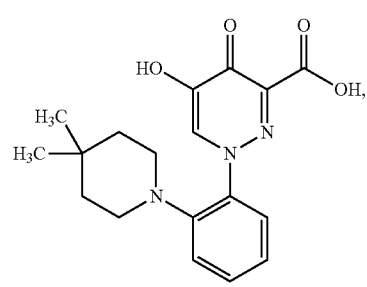
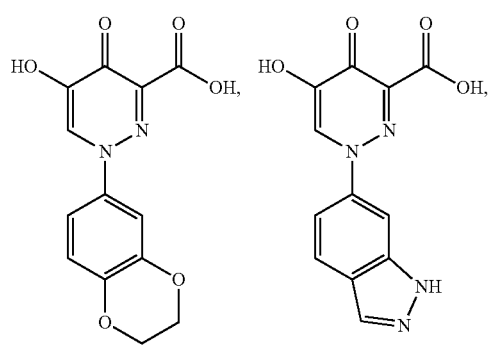
-continued
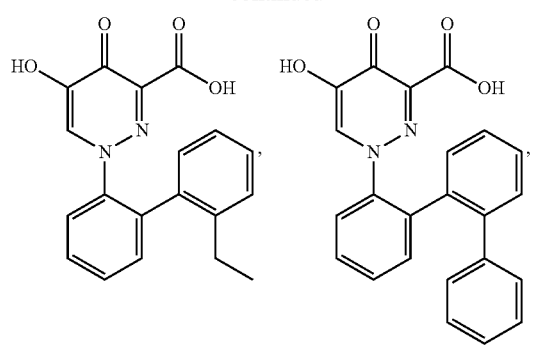
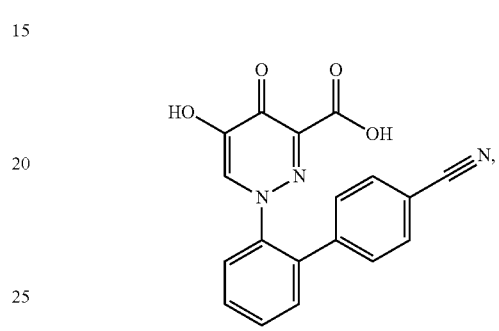
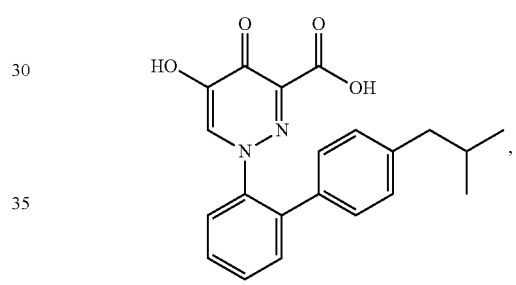
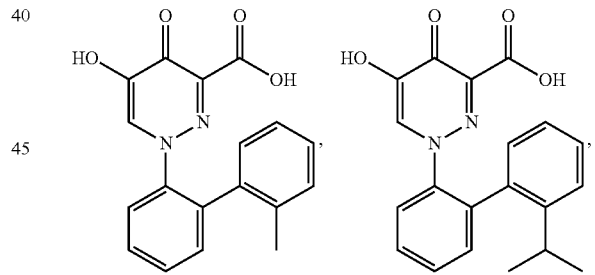
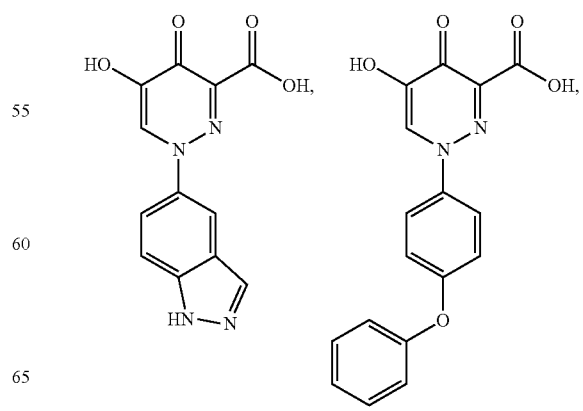

-continued
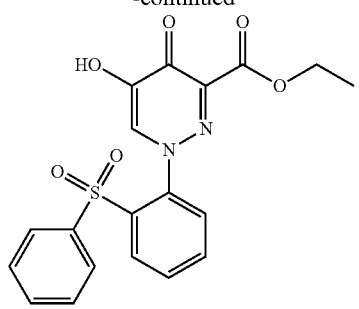
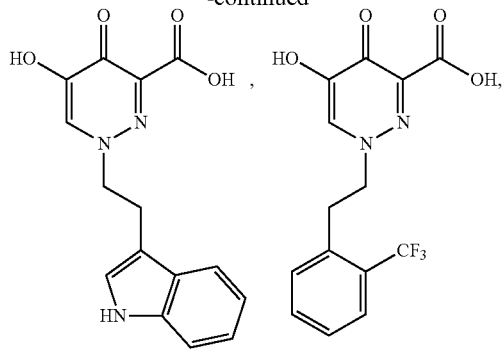
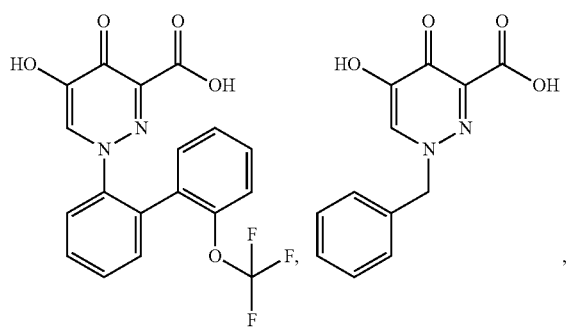
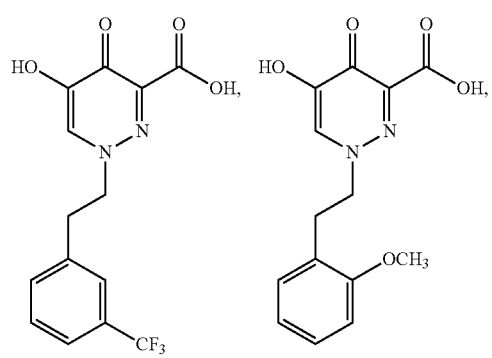
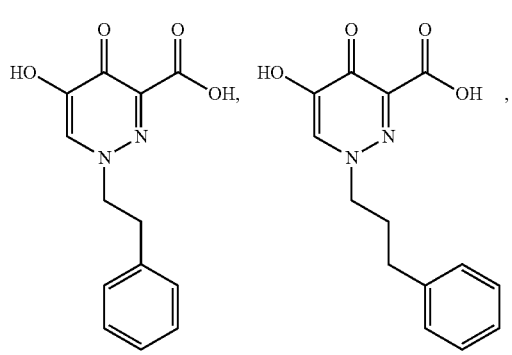
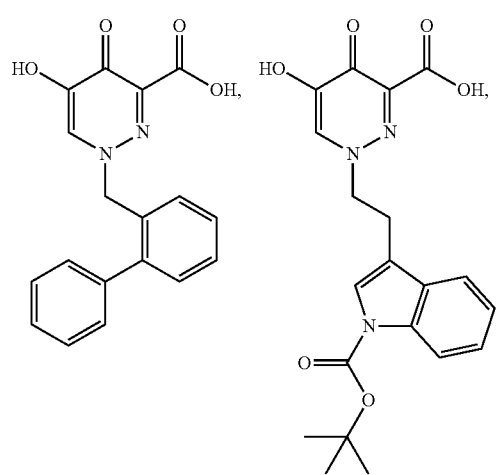
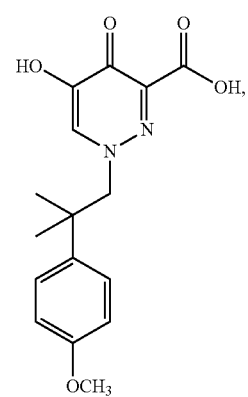

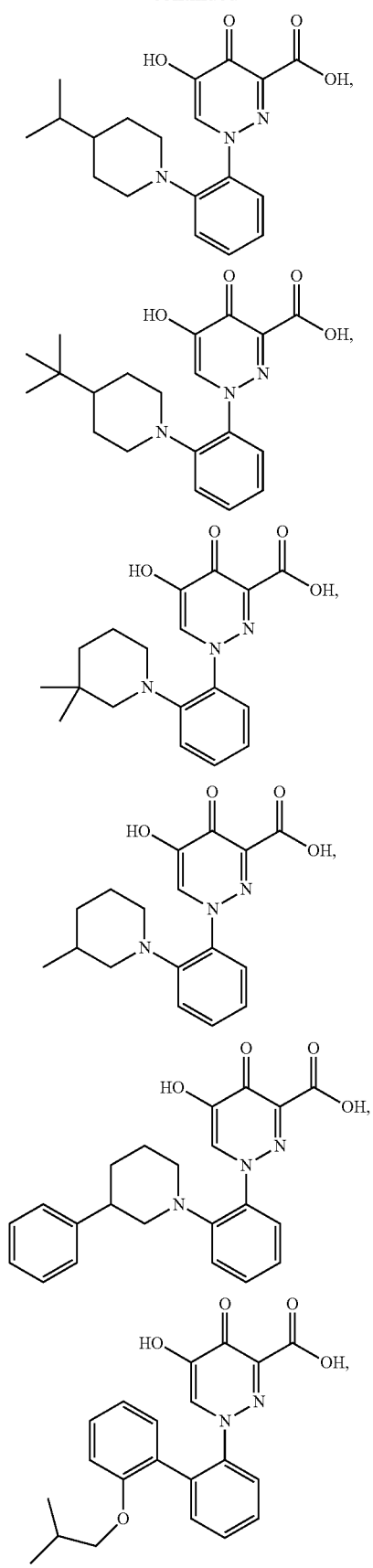
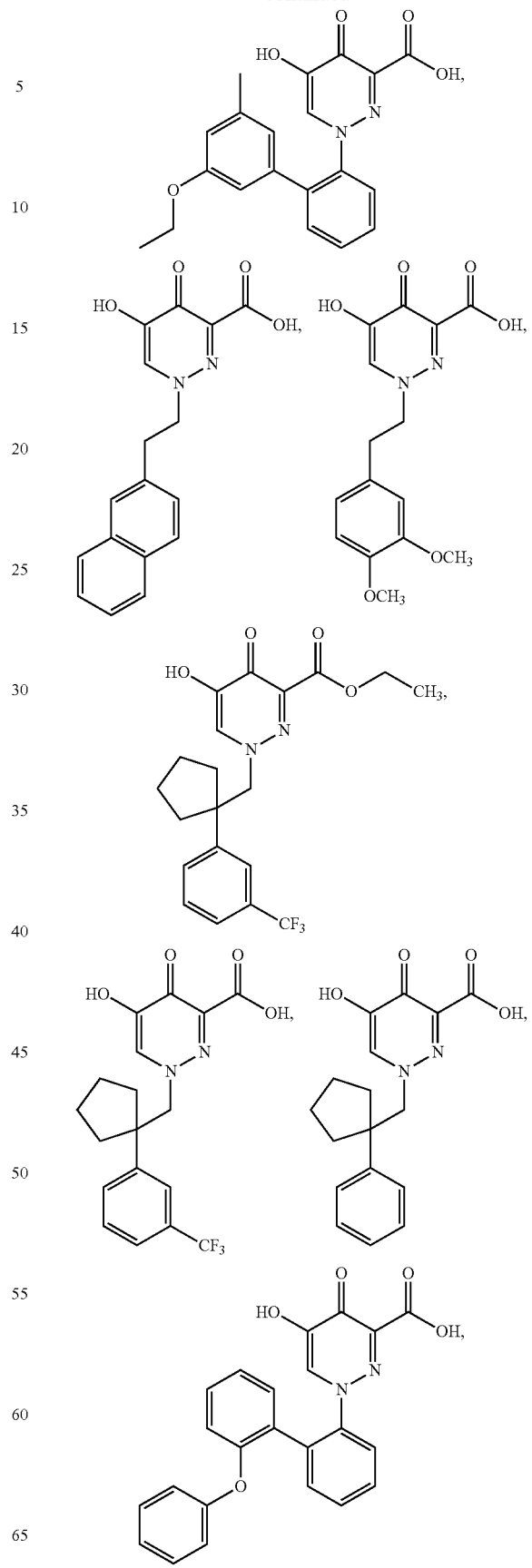

247
-continued
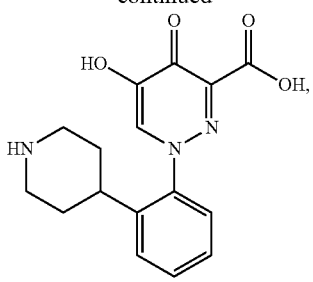
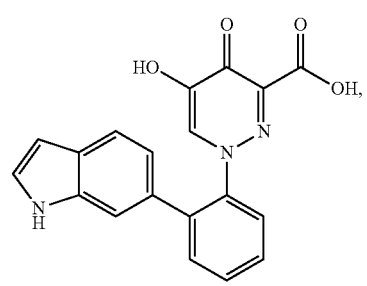
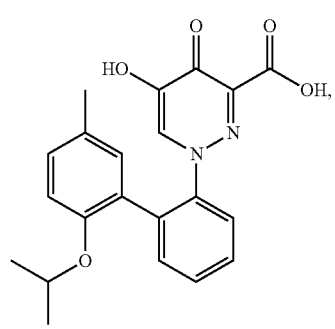
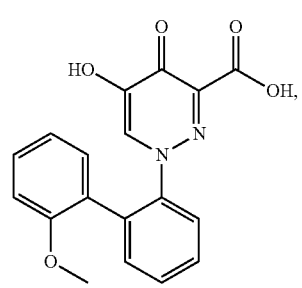
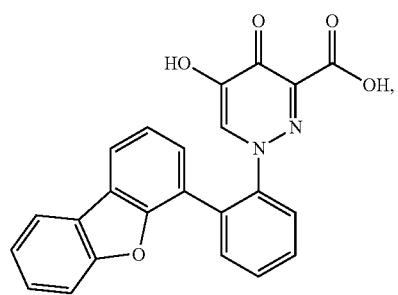
248
-continued
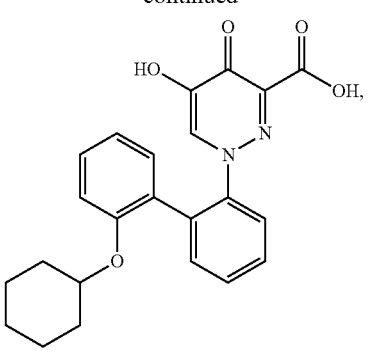
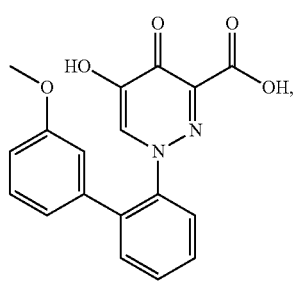
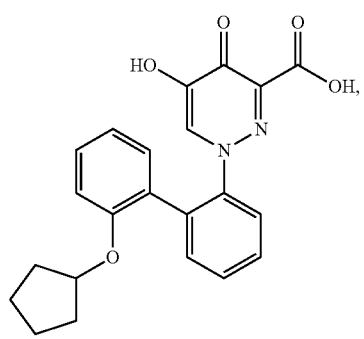
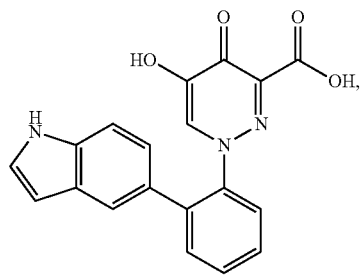
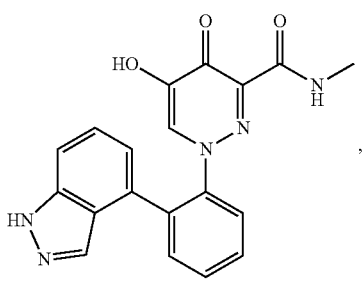

249
-continued
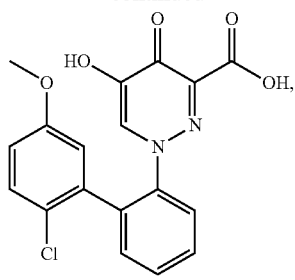
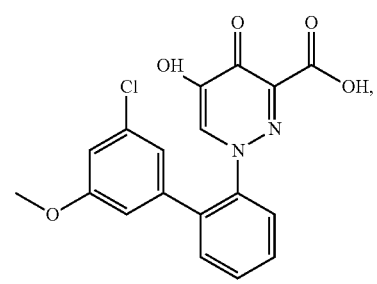
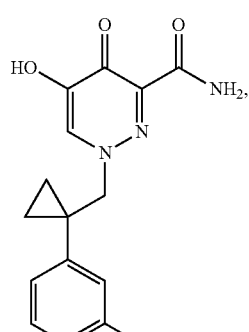
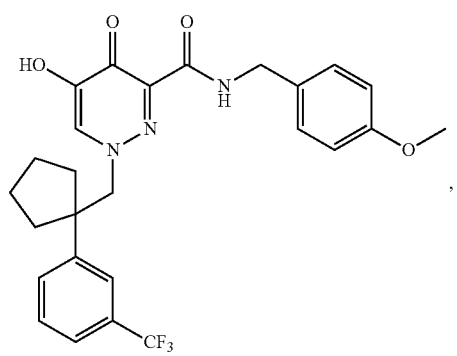
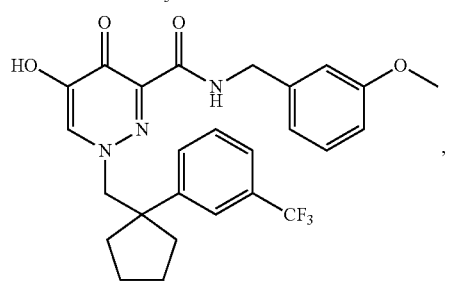
250
-continued
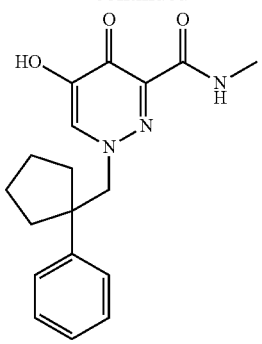
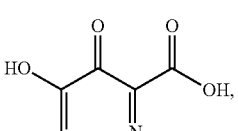 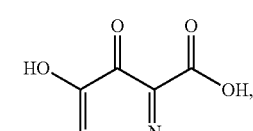
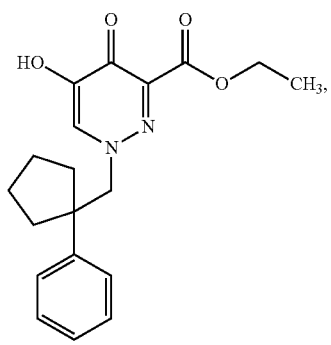
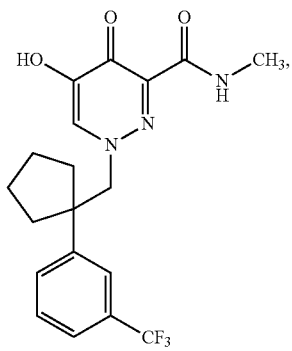

251
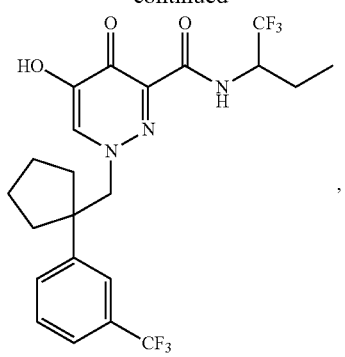
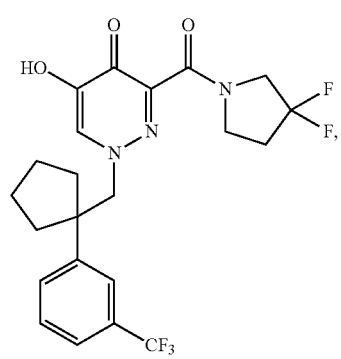
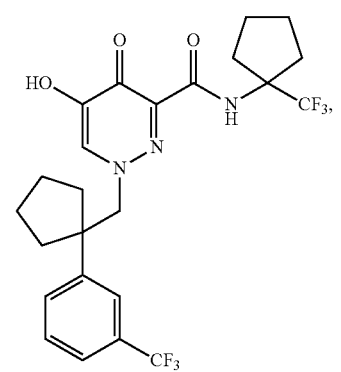
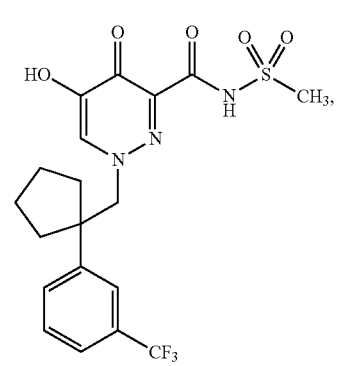
252
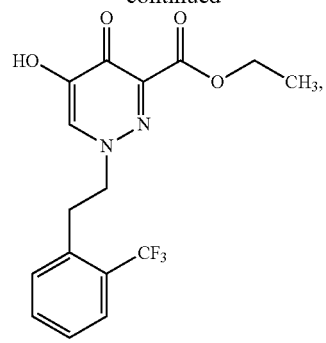
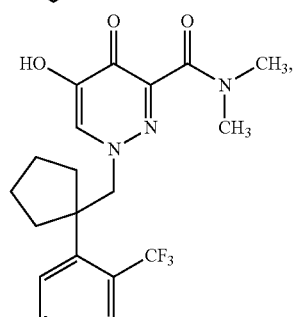
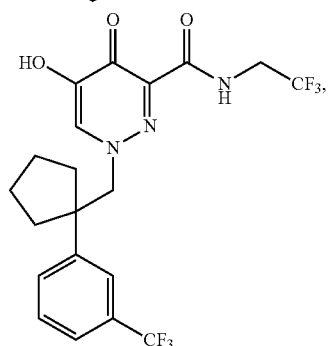
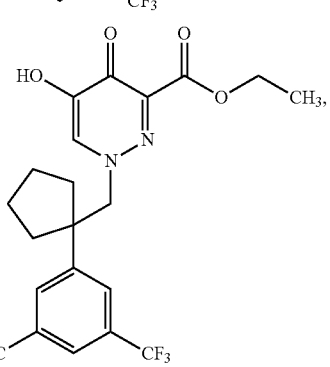
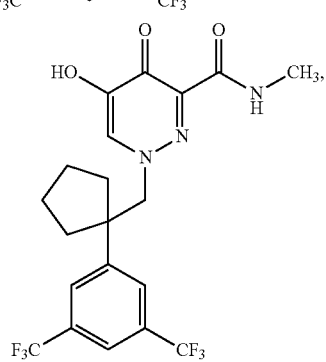

253
-continued
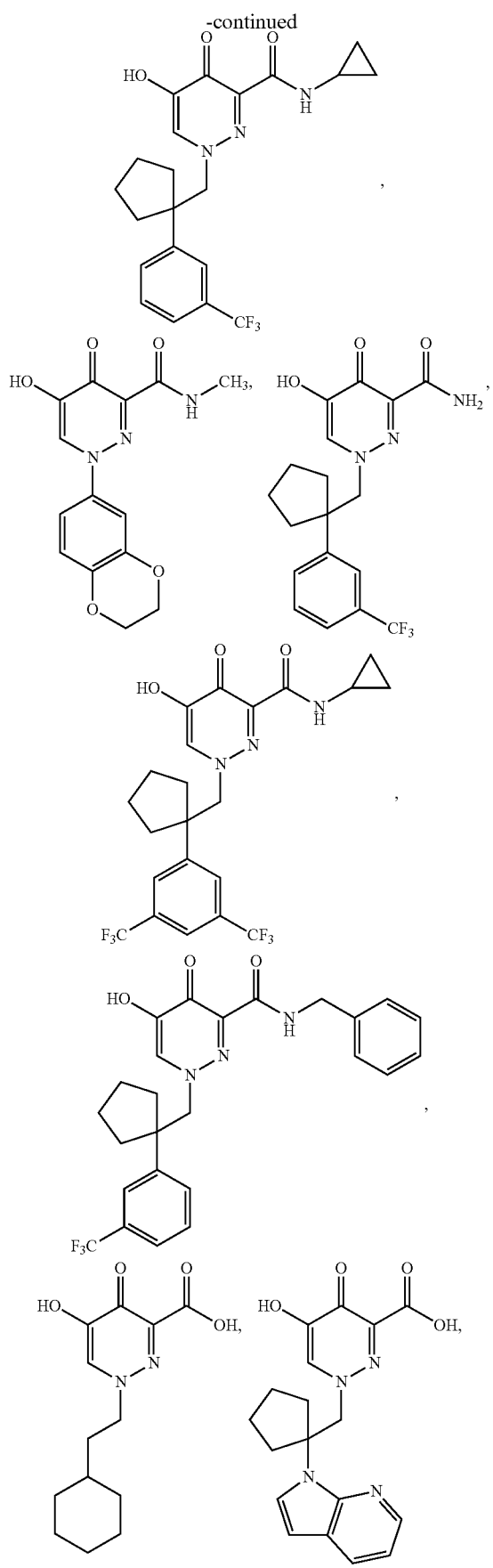
254
-continued
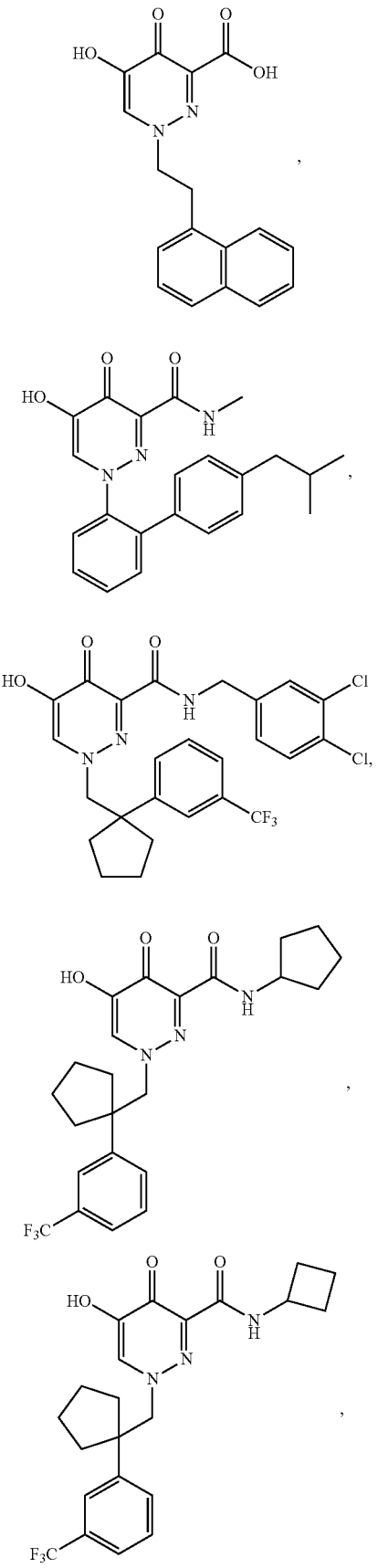

-continued
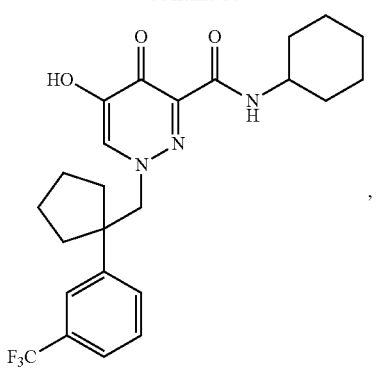
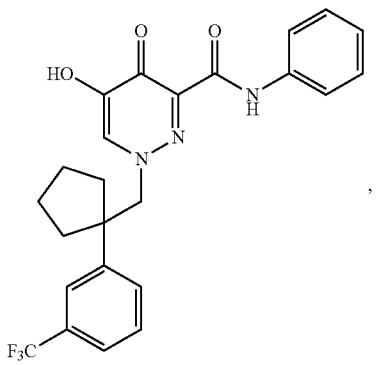
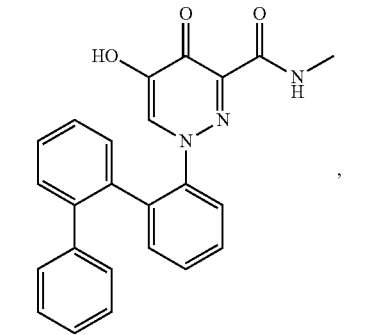
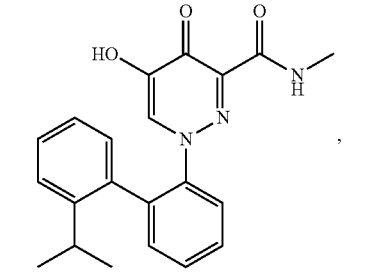
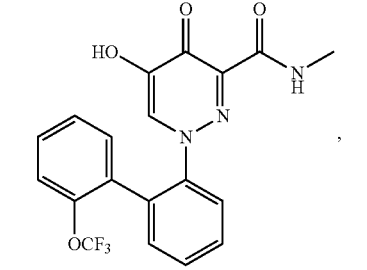
-continued
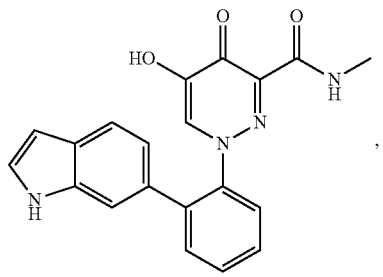
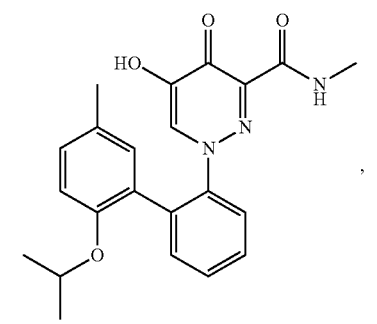
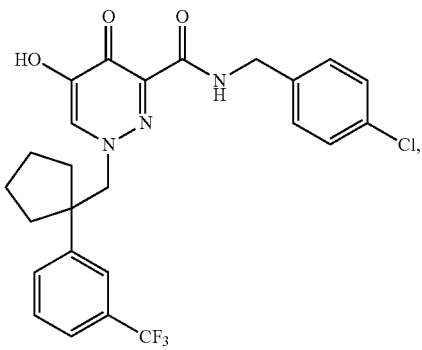
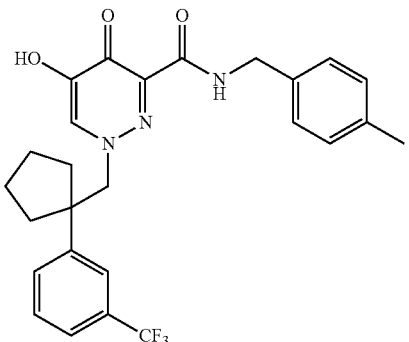
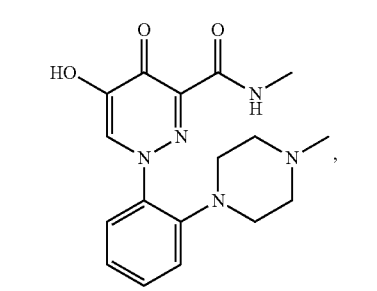

257
-continued
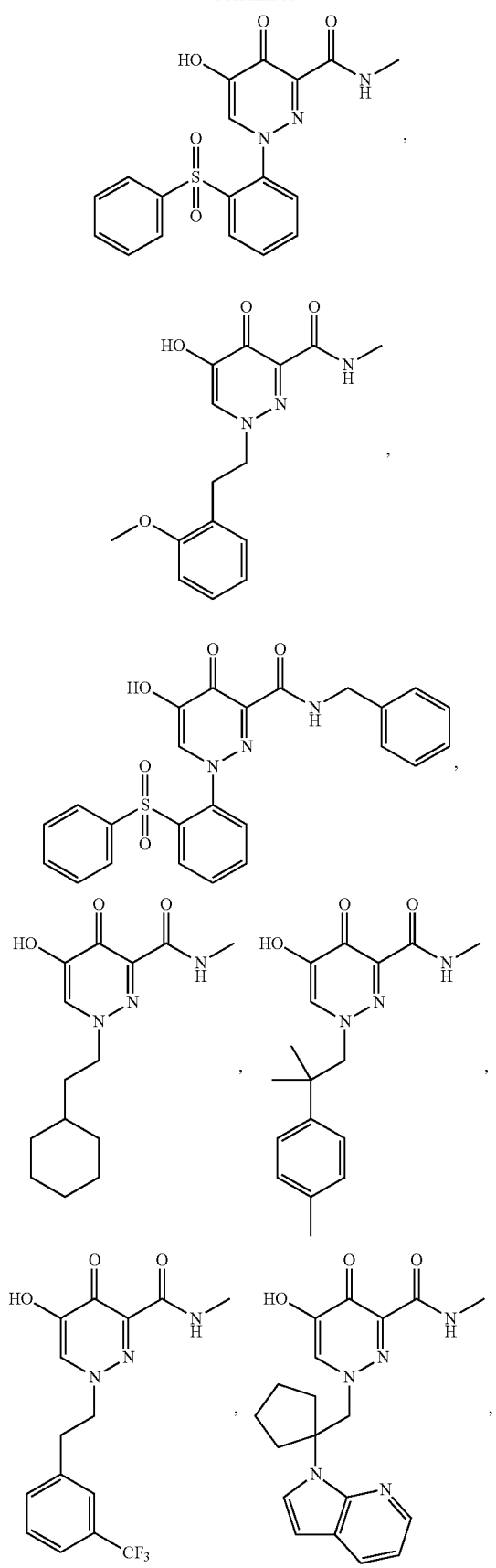
258
-continued
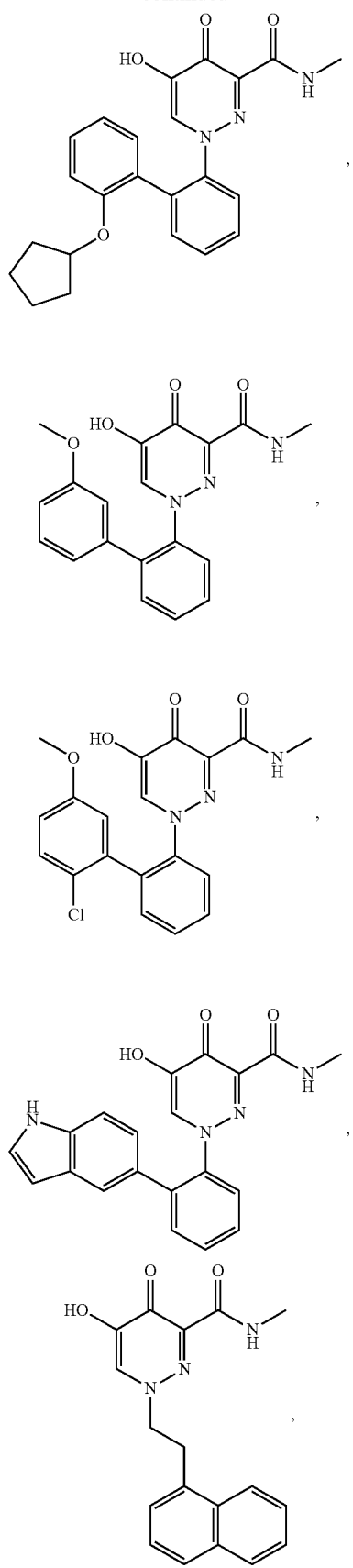

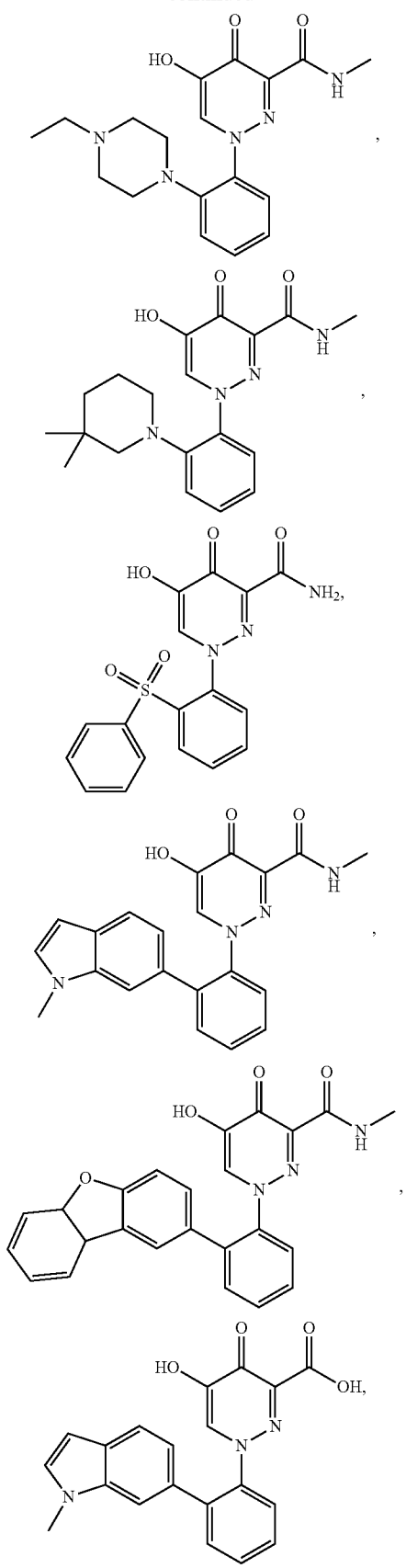
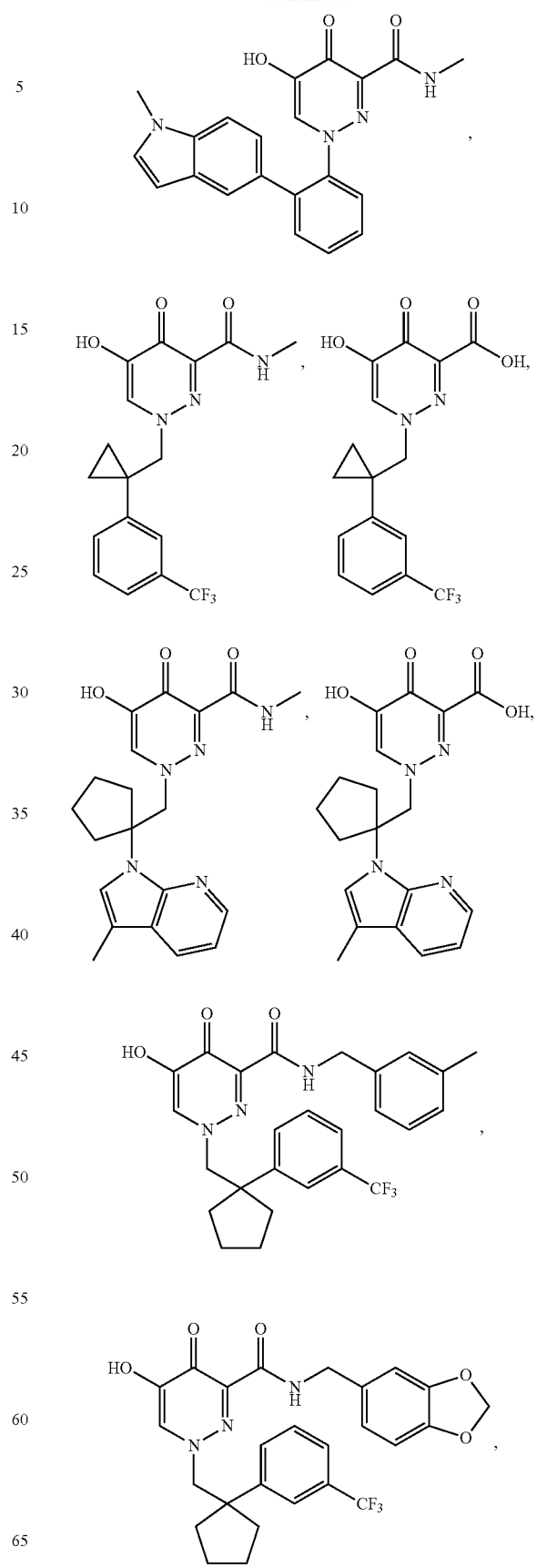

261
-continued
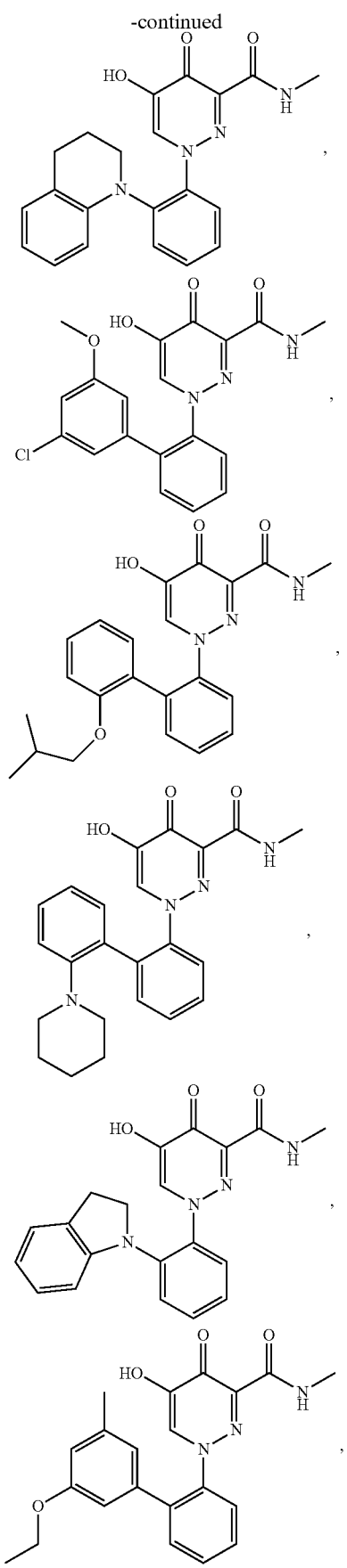
262
-continued
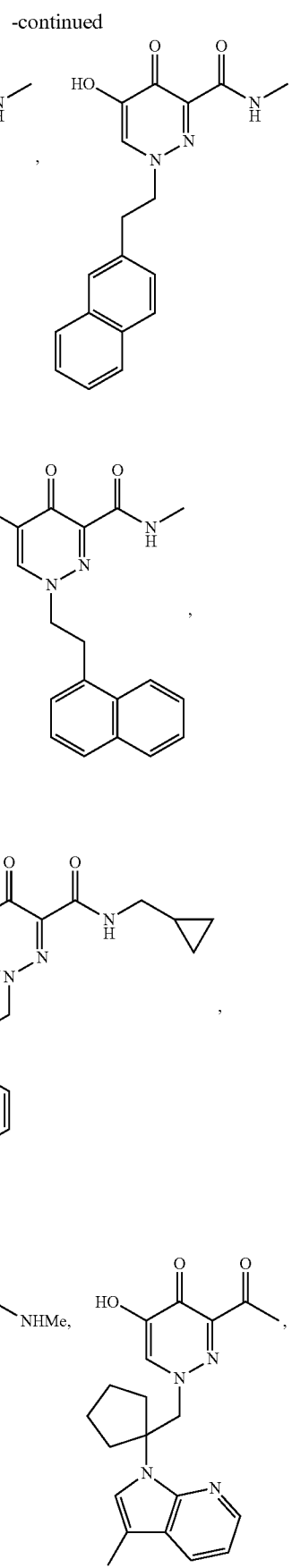

-continued
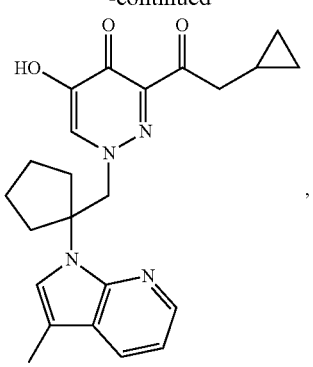
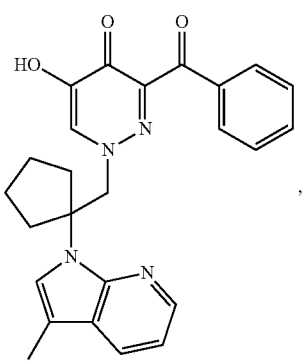
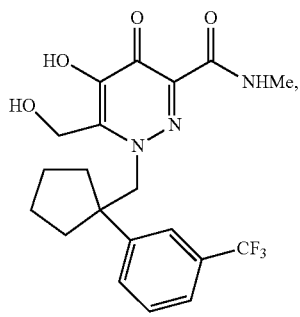
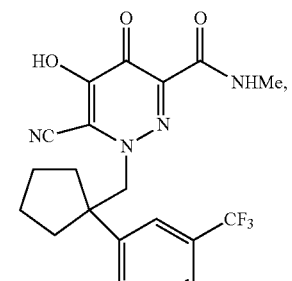
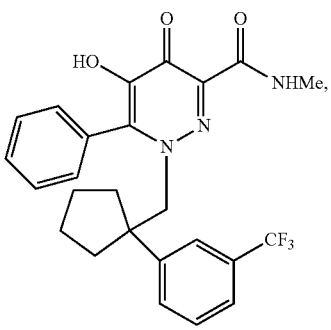
-continued
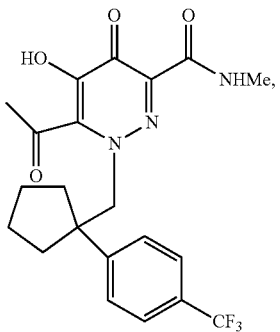
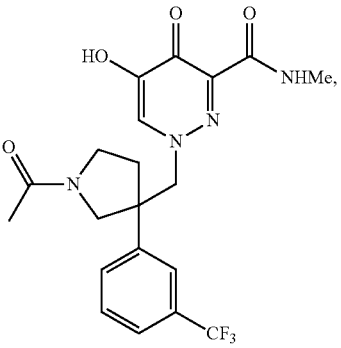
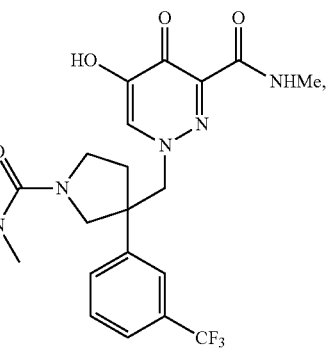
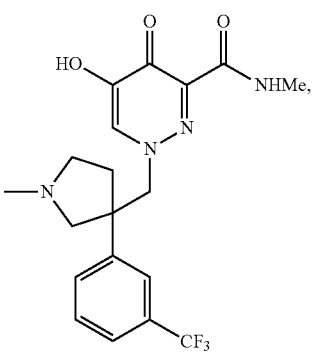
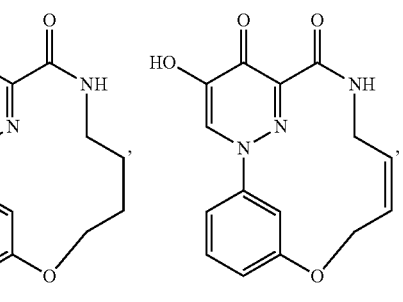

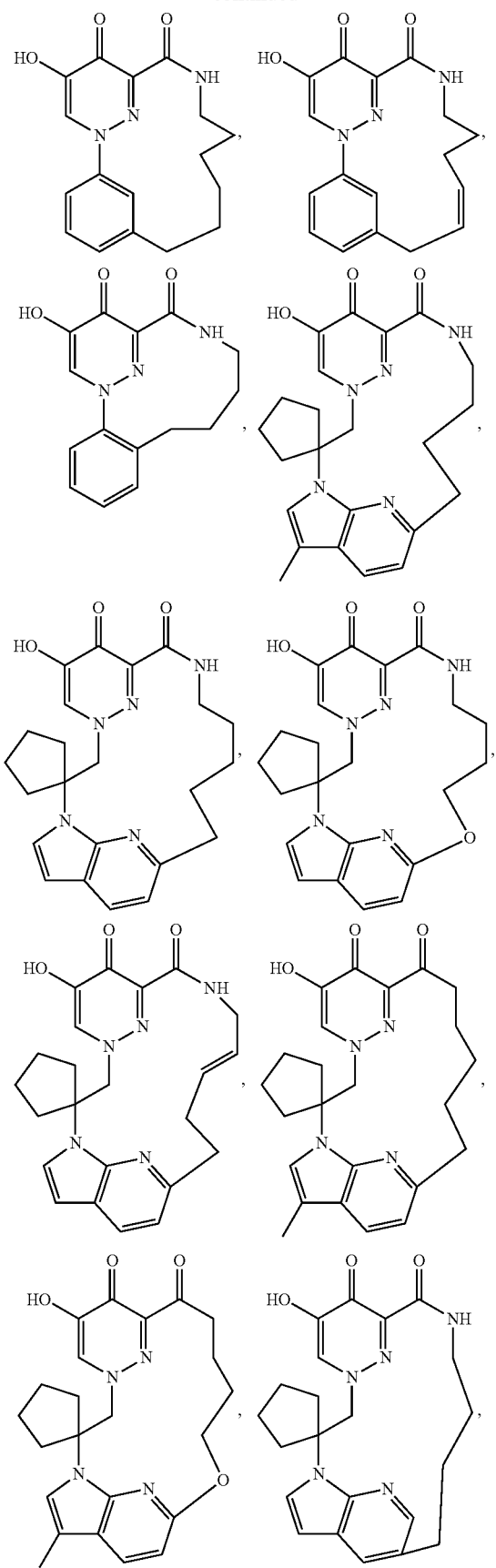
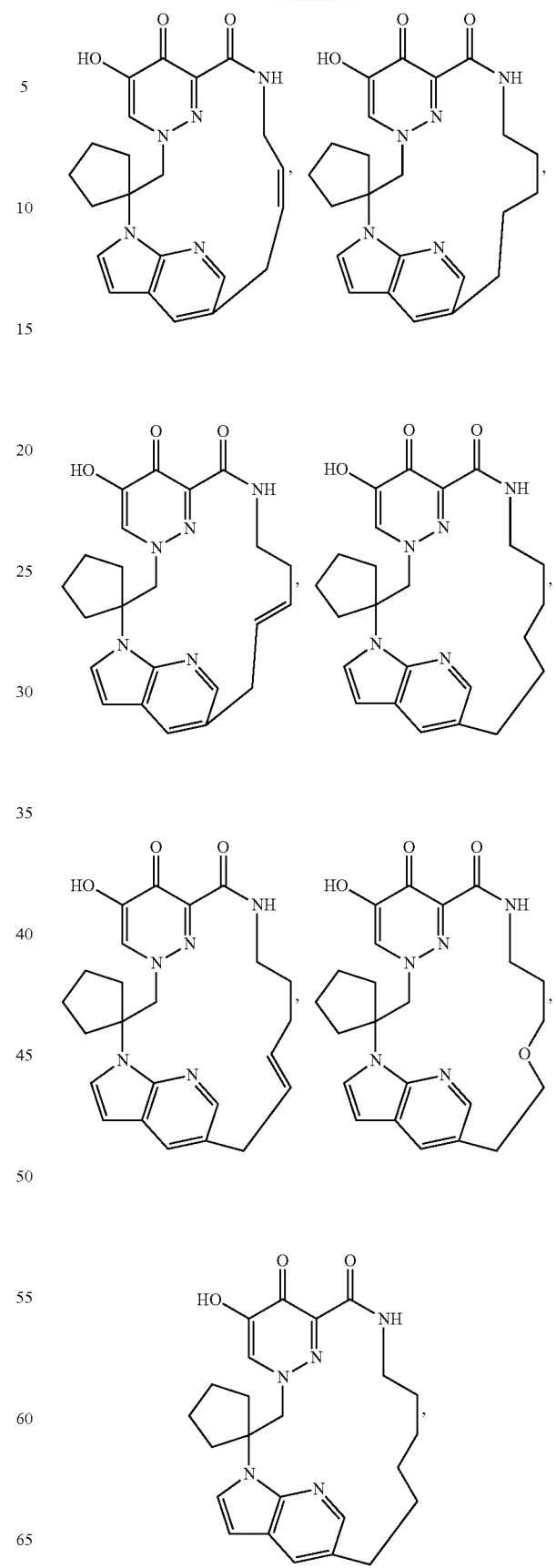

267
-continued
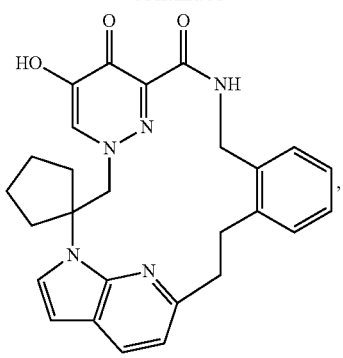
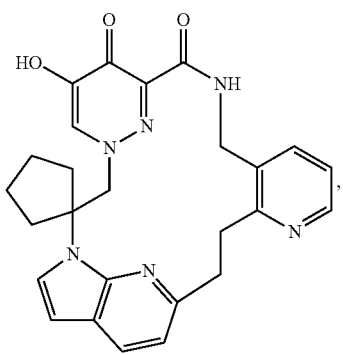
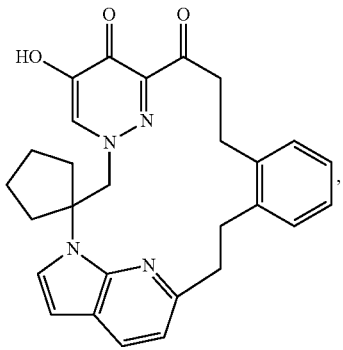
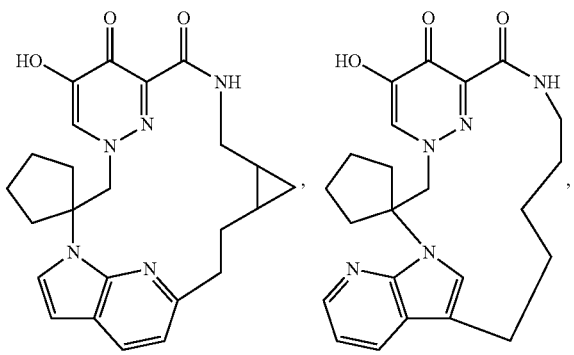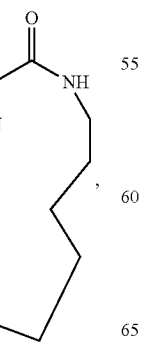
268
-continued
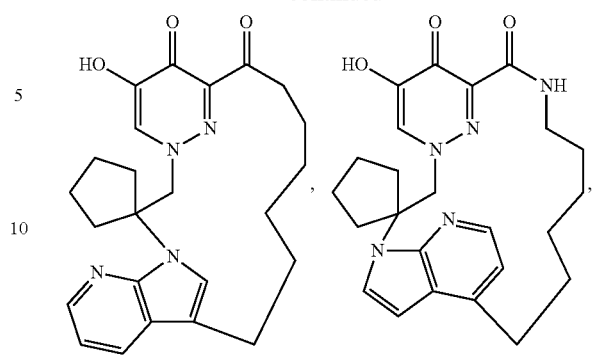
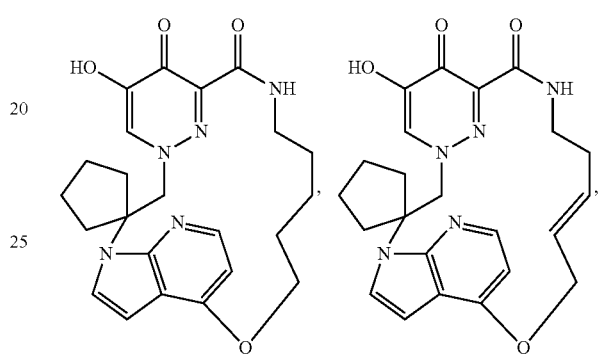
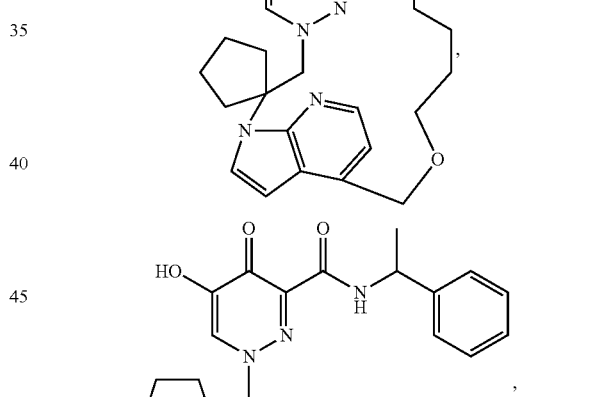
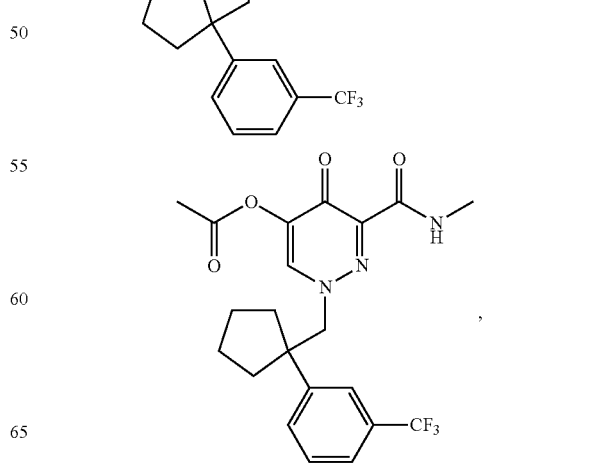

269
-continued
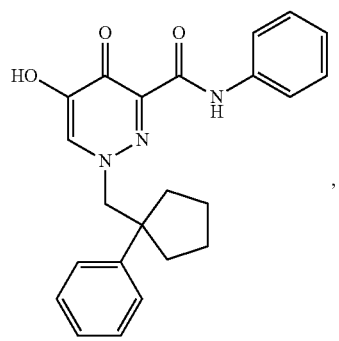
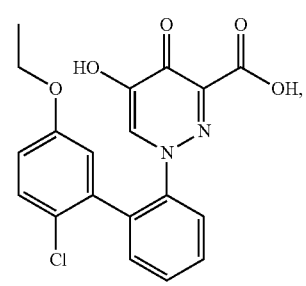
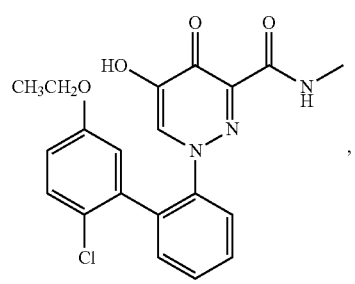
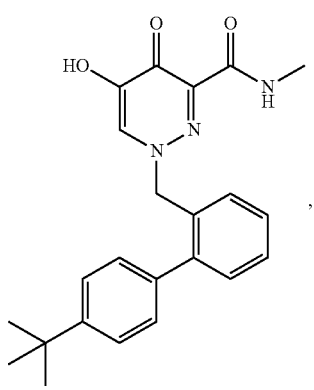
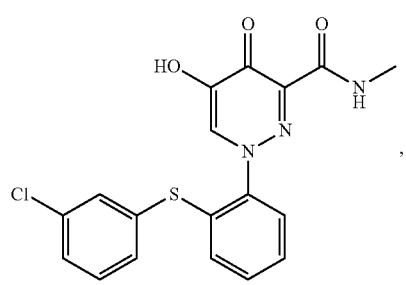
270
-continued
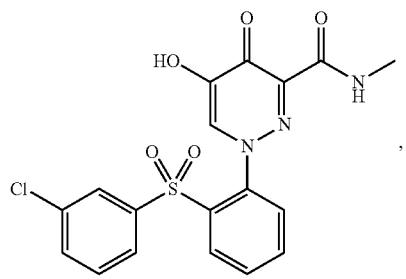
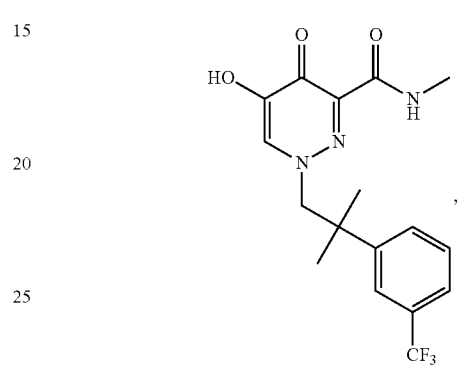
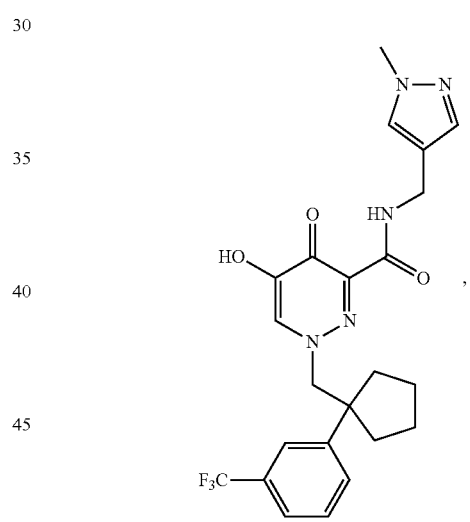
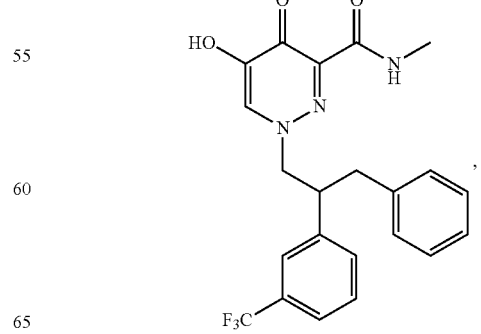

271
-continued
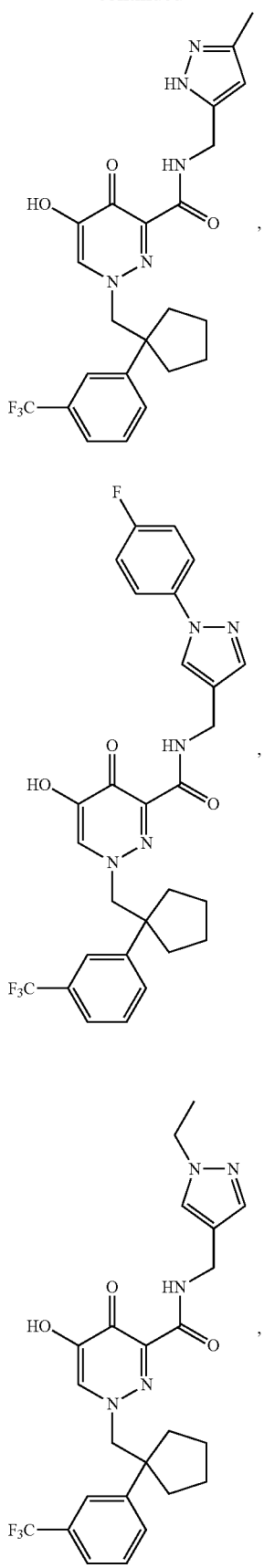
272
-continued
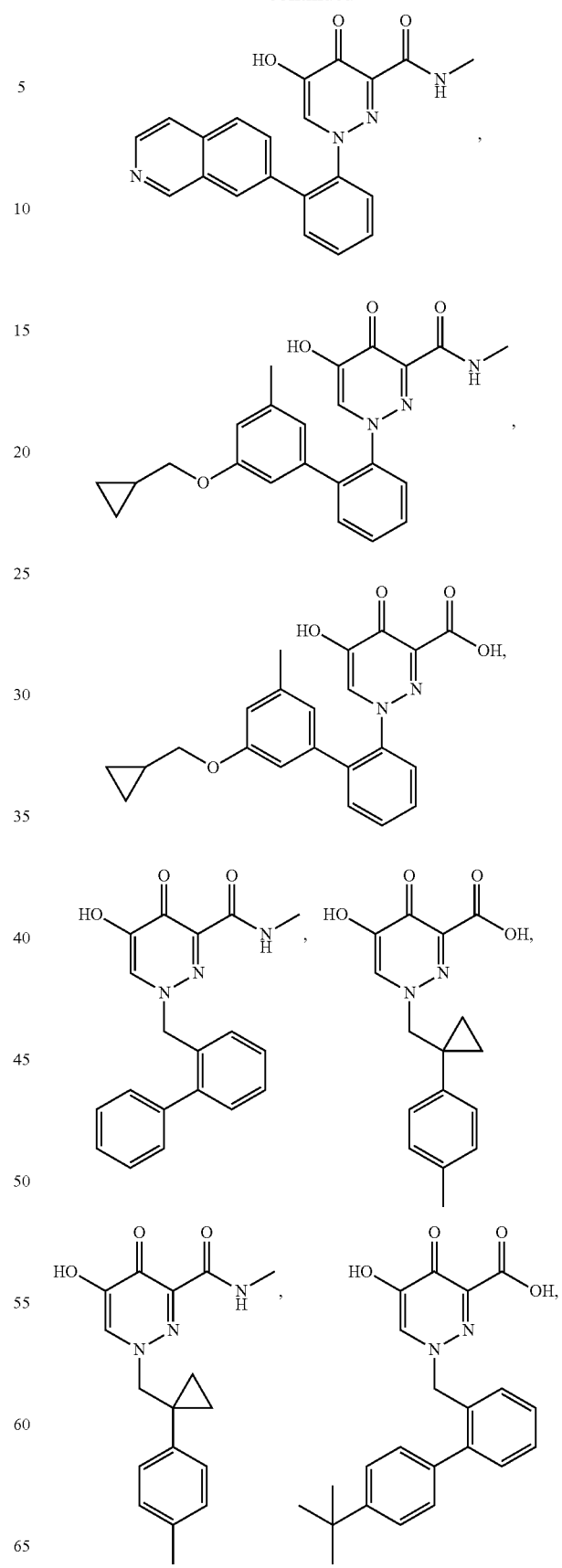

273
-continued
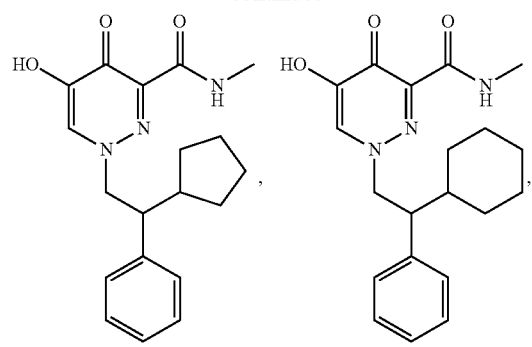
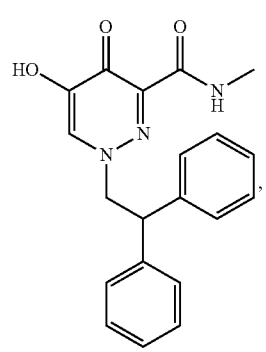
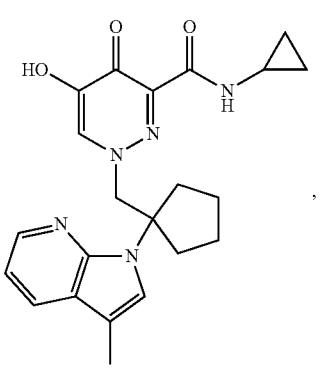
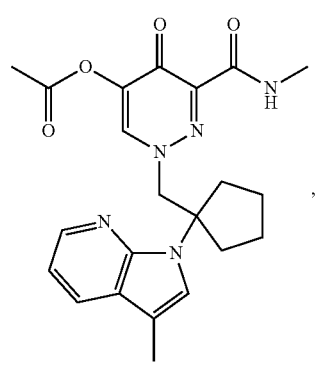
274
-continued
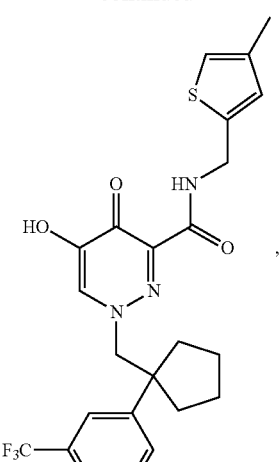
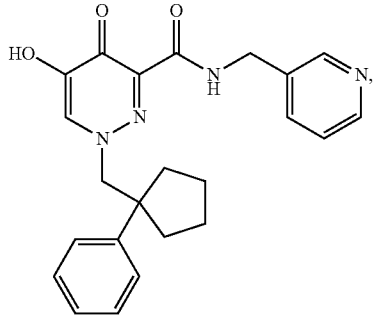
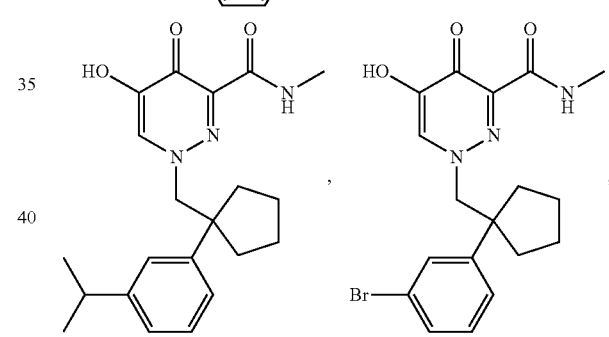
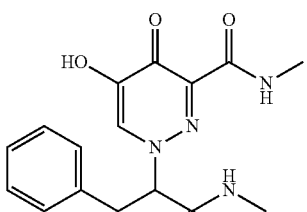
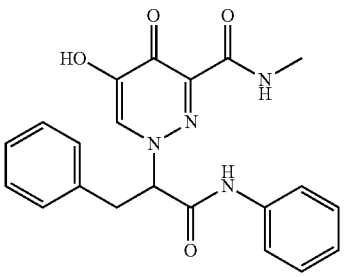

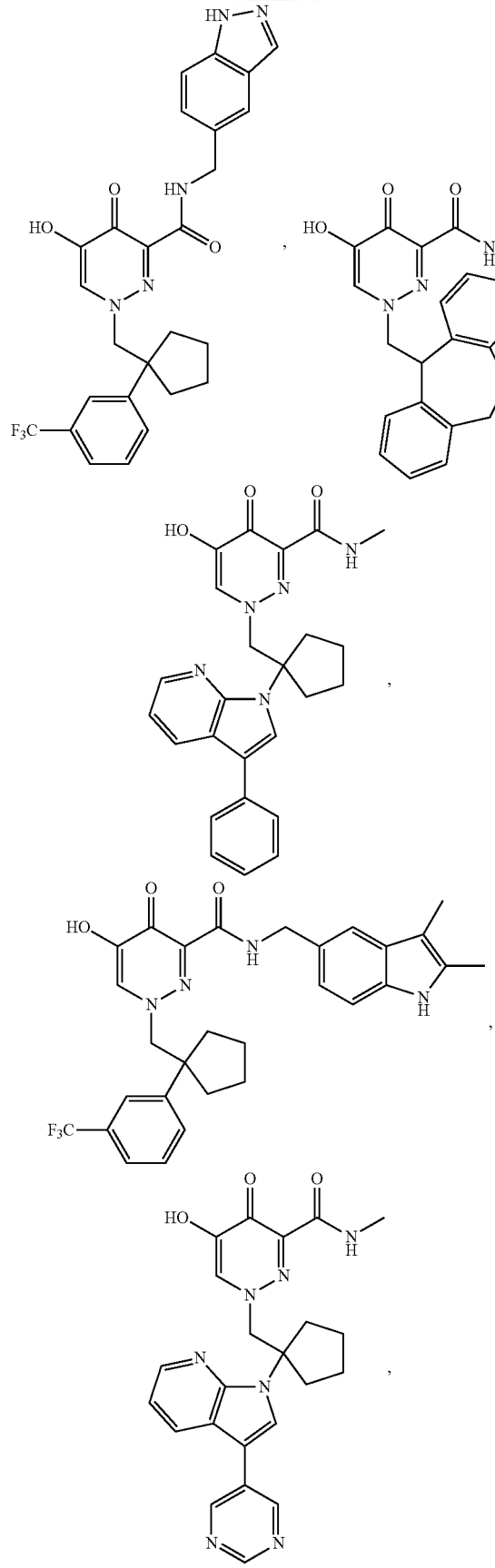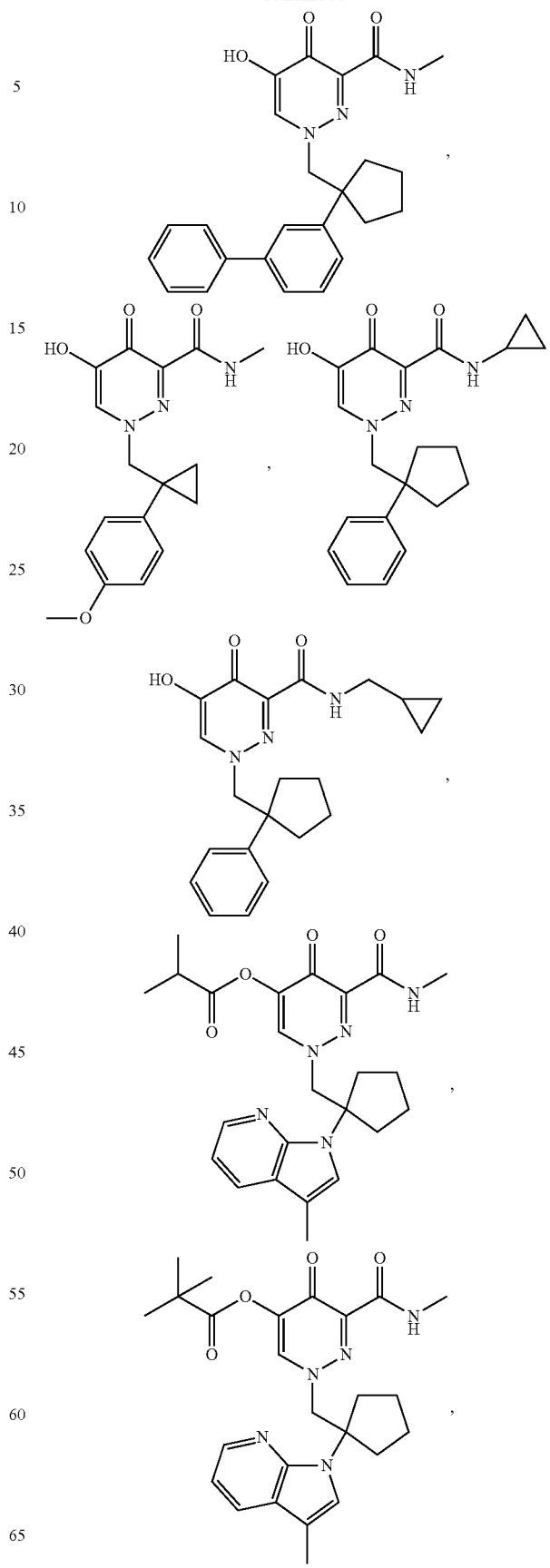

277
-continued
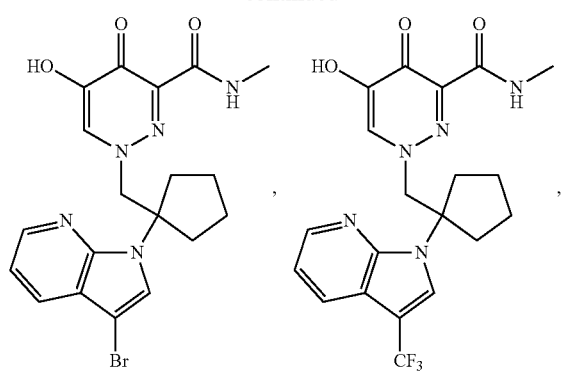
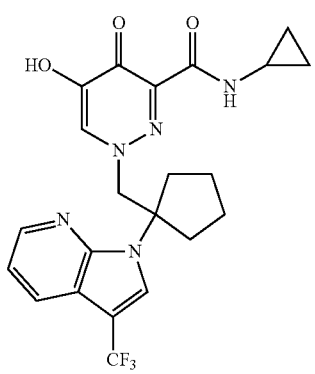
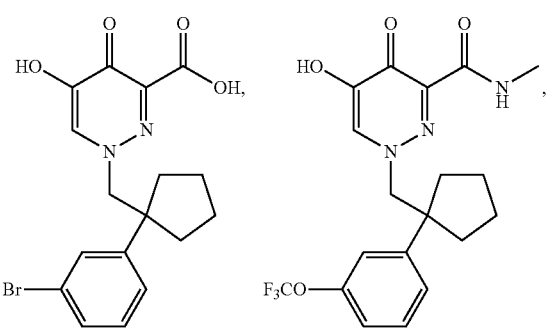
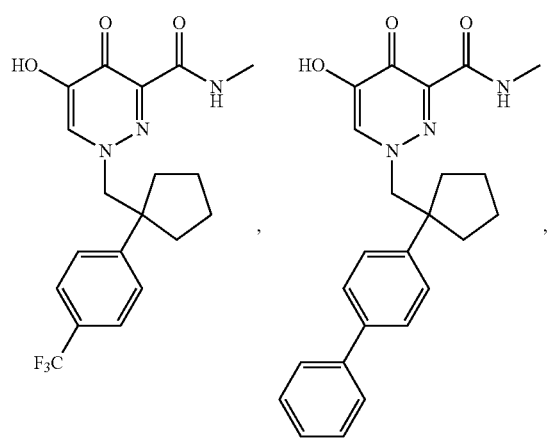
278
-continued
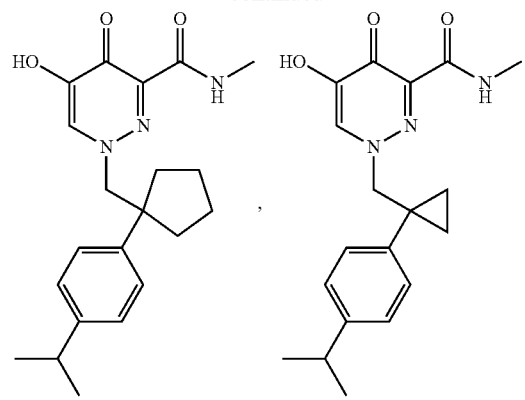
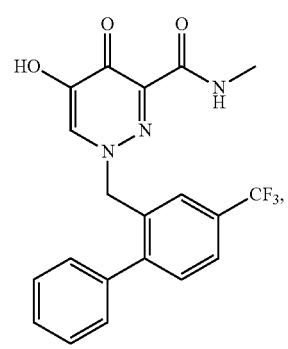
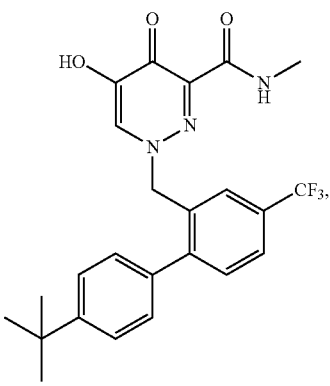
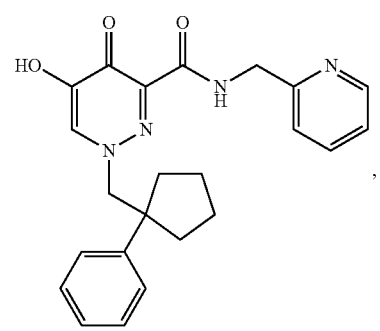

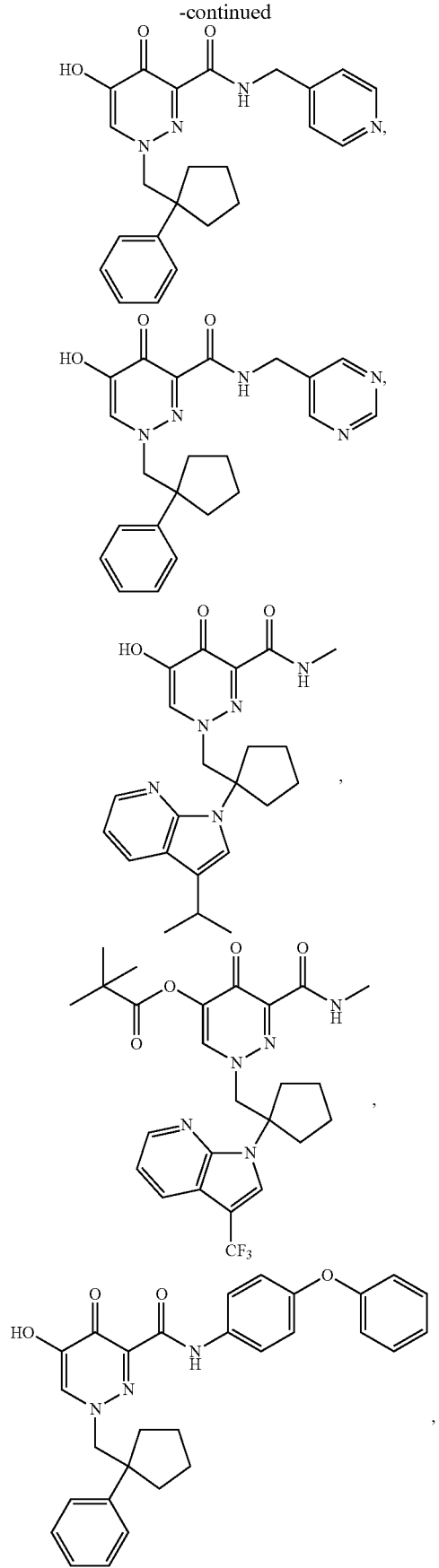
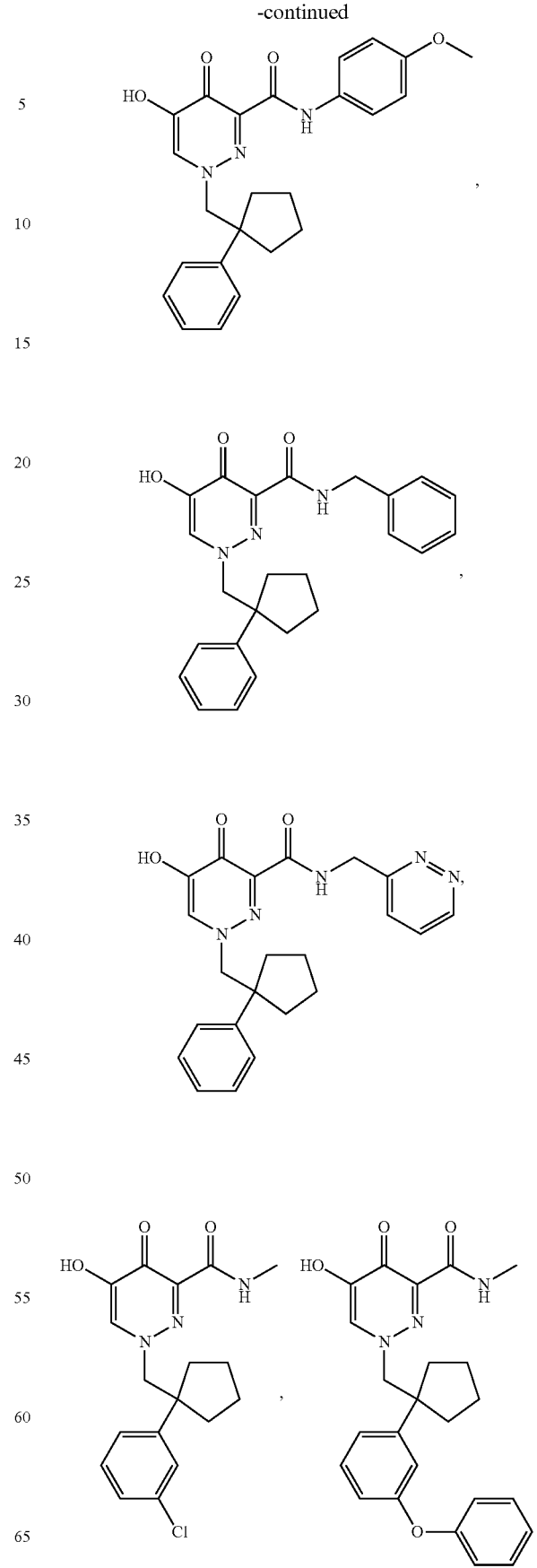

281
-continued
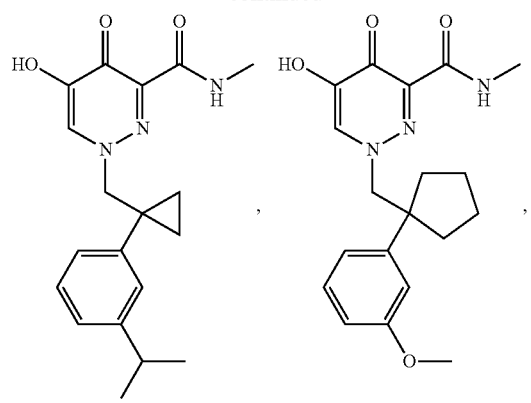
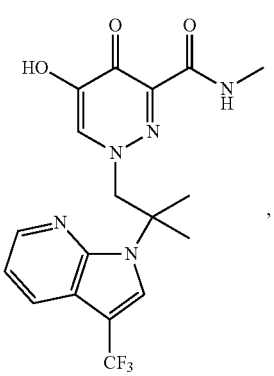
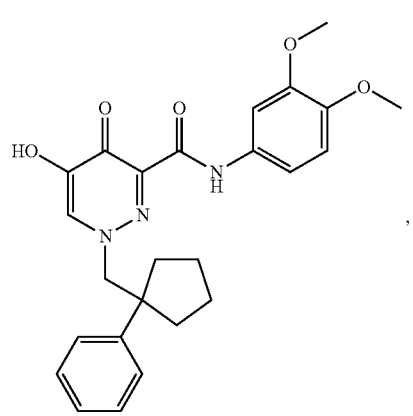
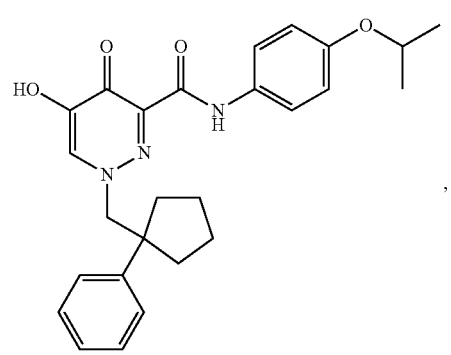
282
-continued
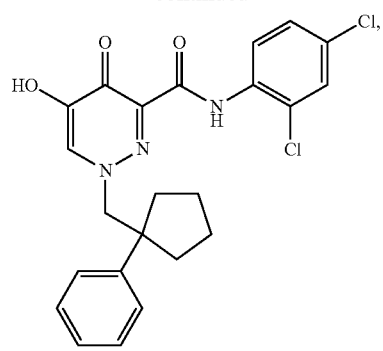
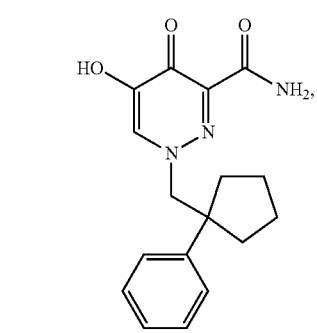
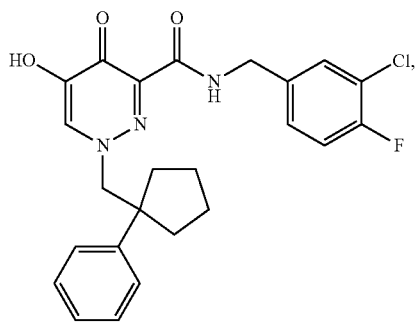
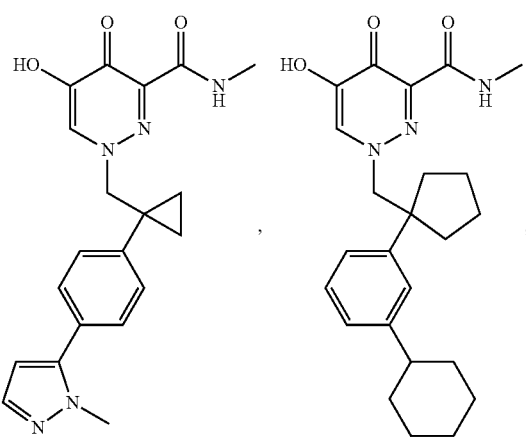

283
-continued
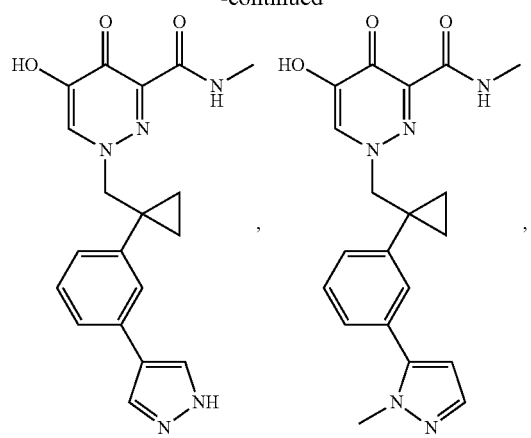
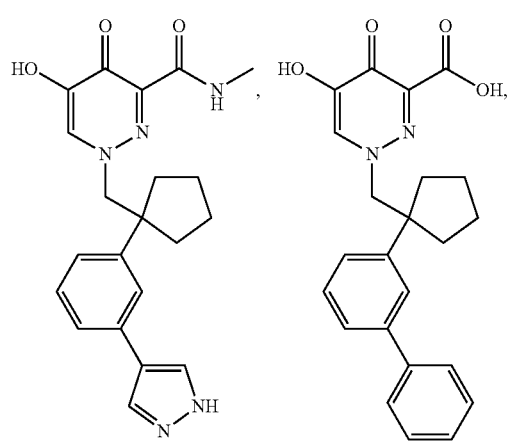
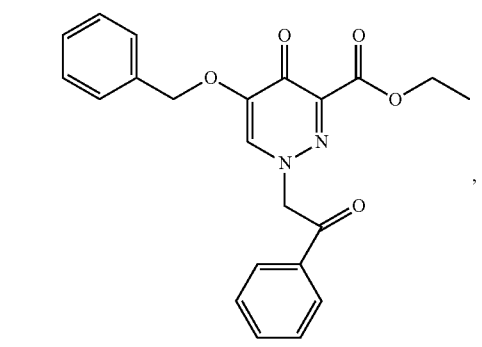
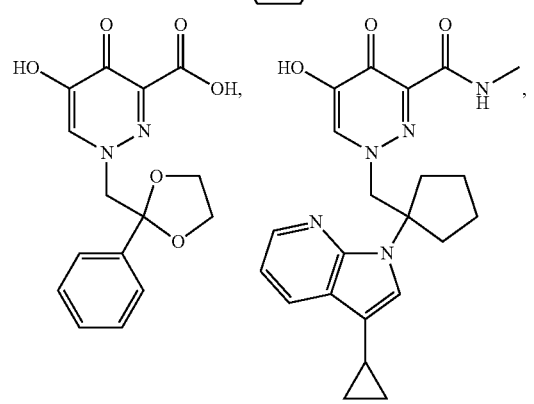
284
-continued
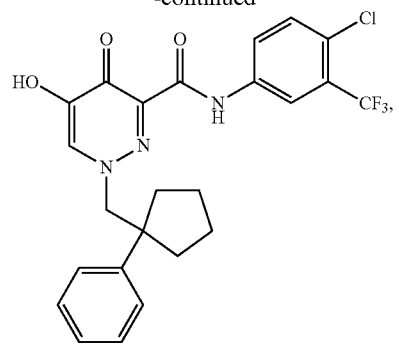
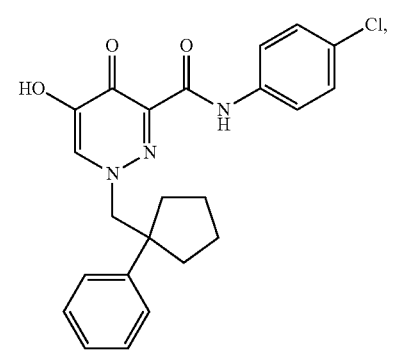
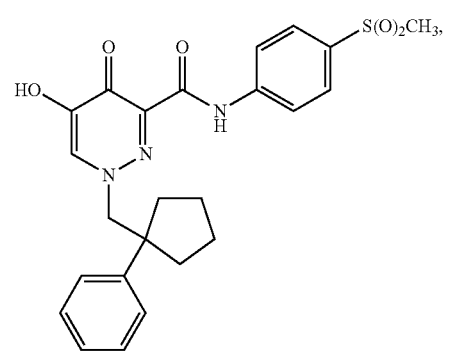
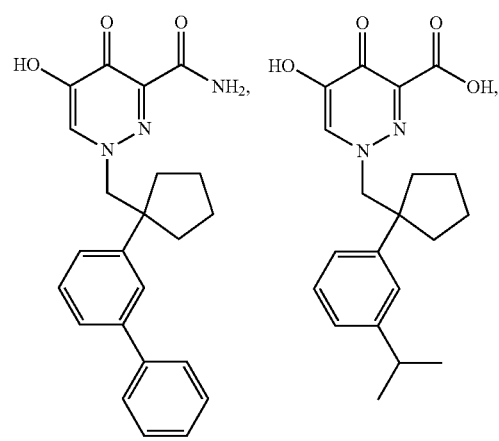

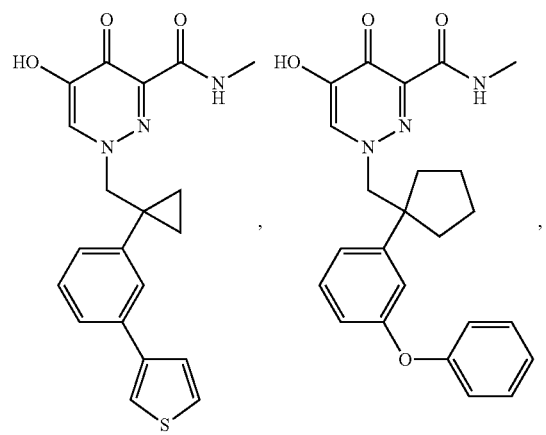
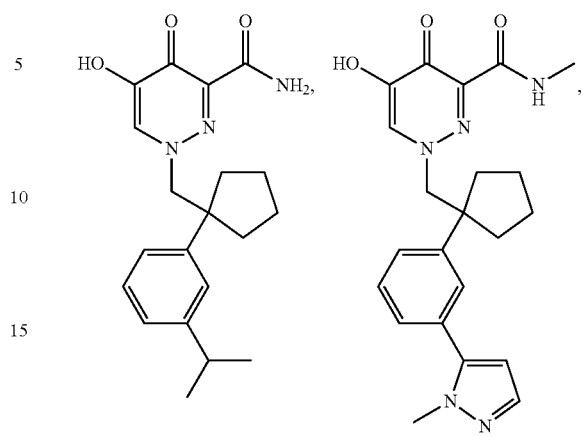
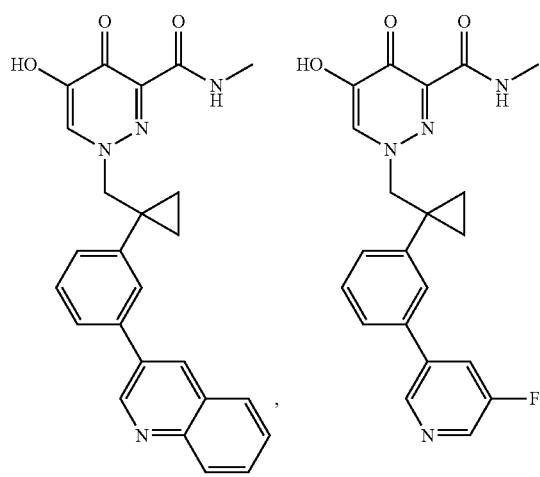
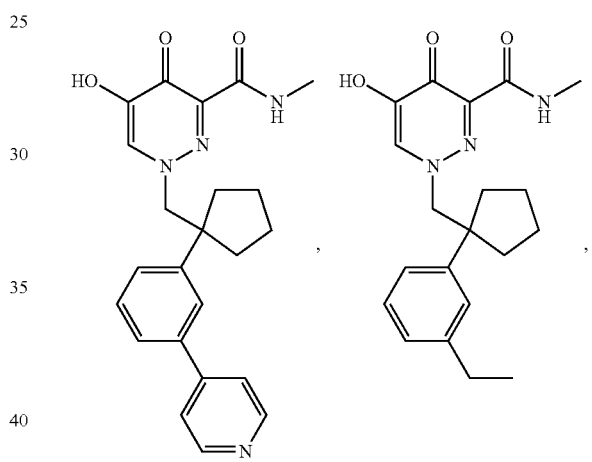
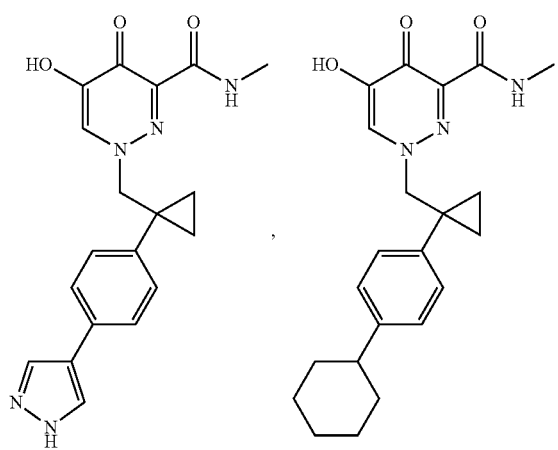
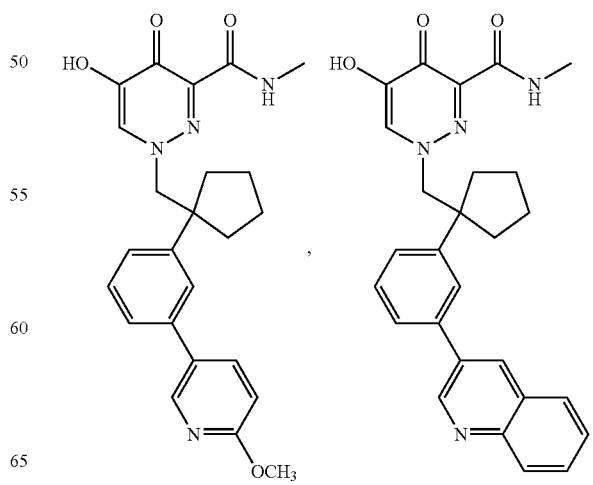

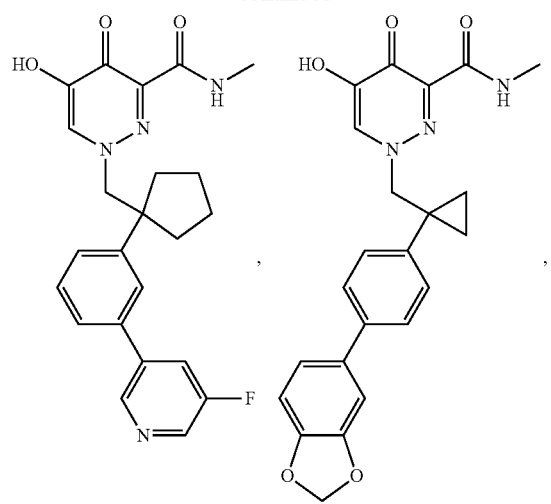
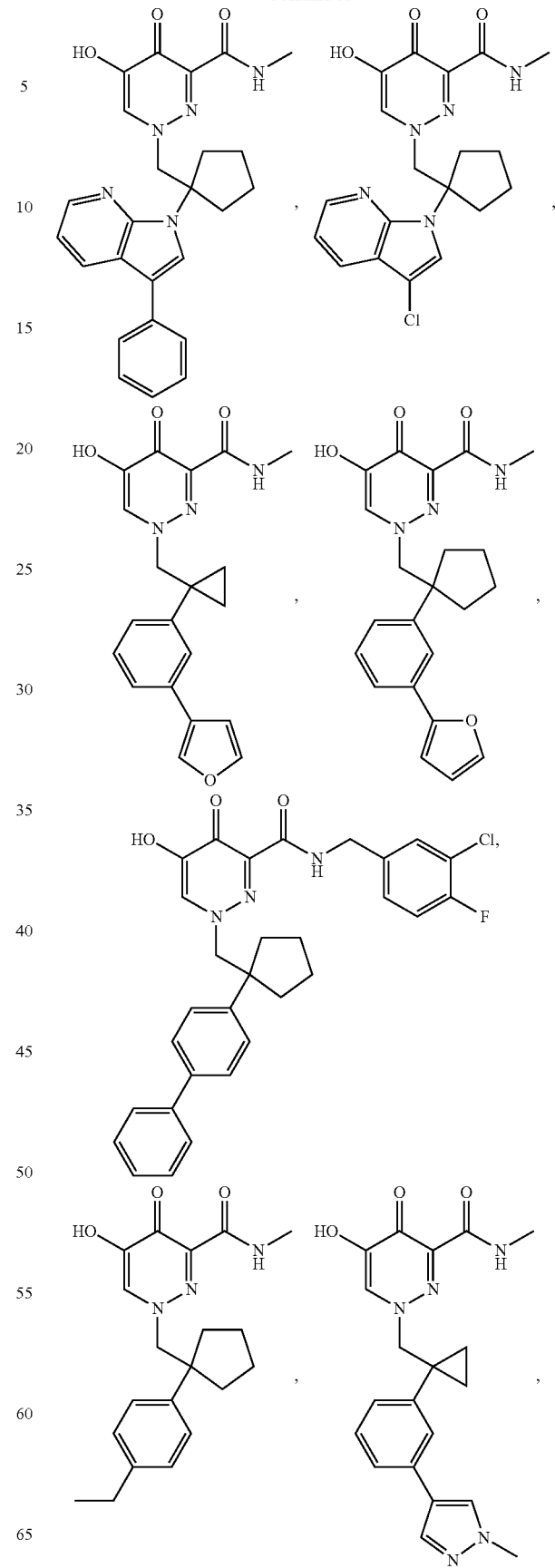

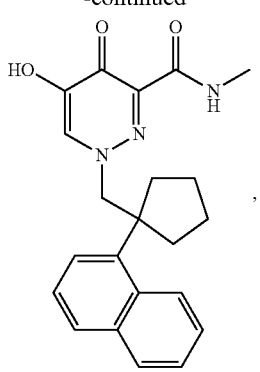
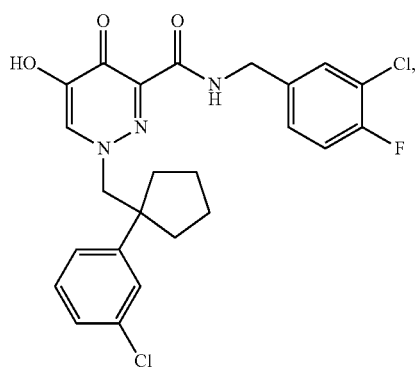
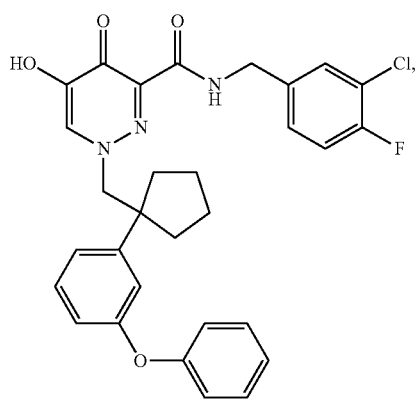
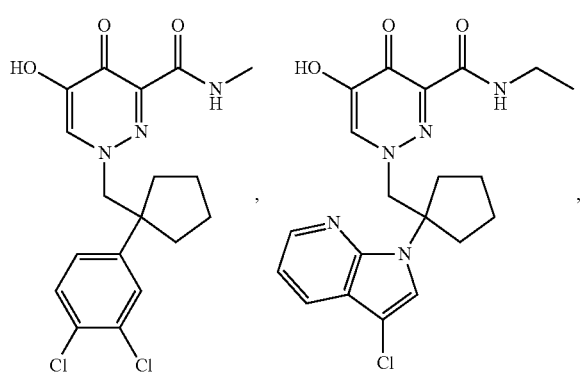
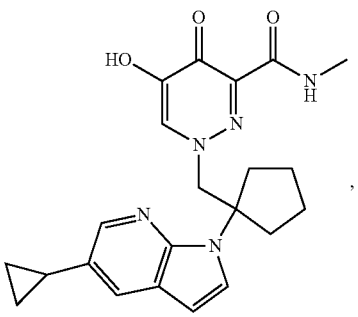
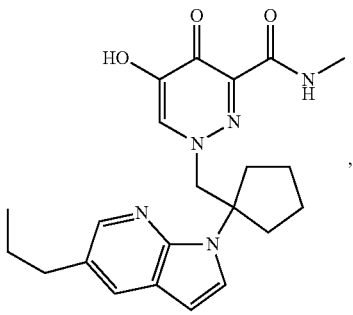
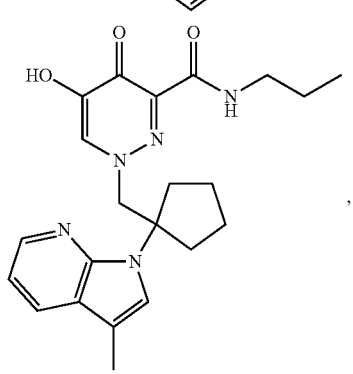
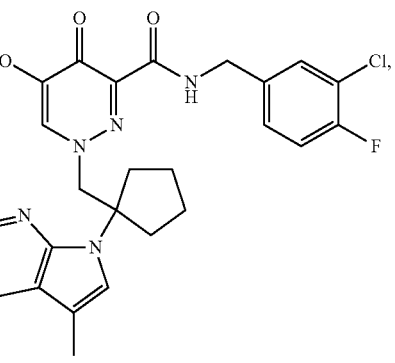
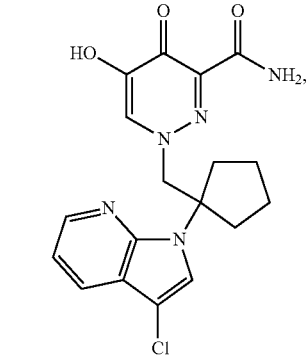

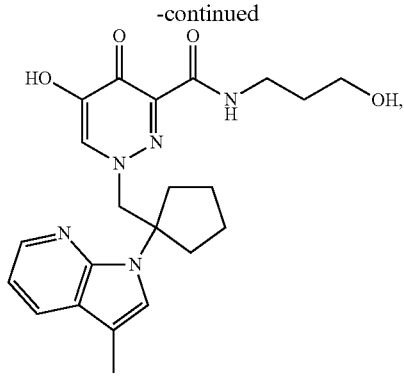
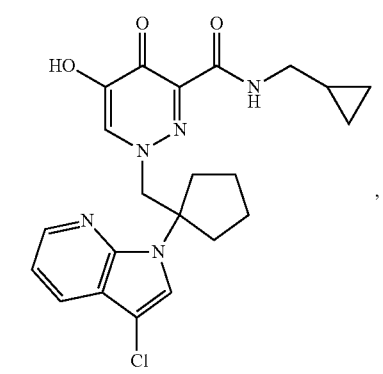
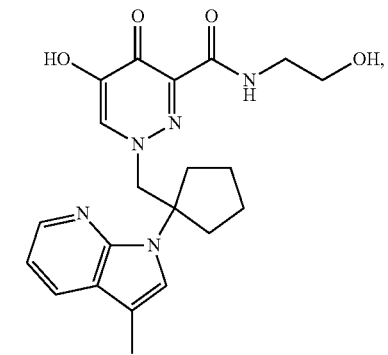
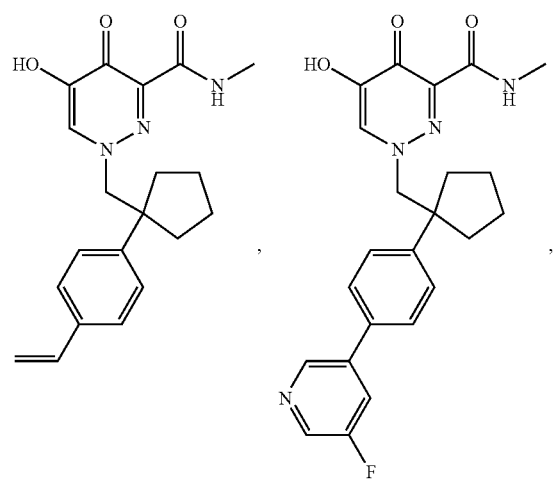
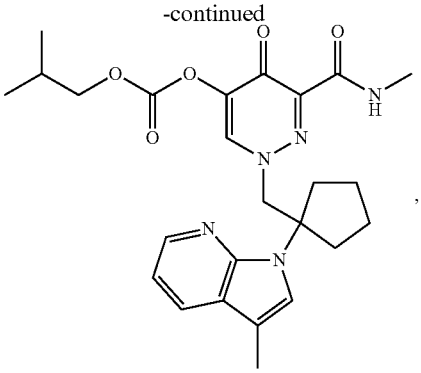
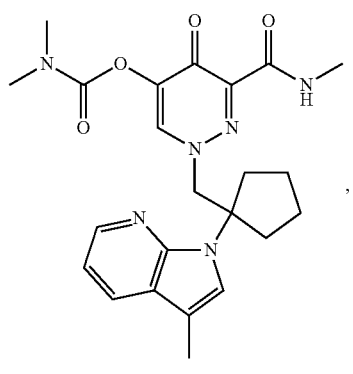
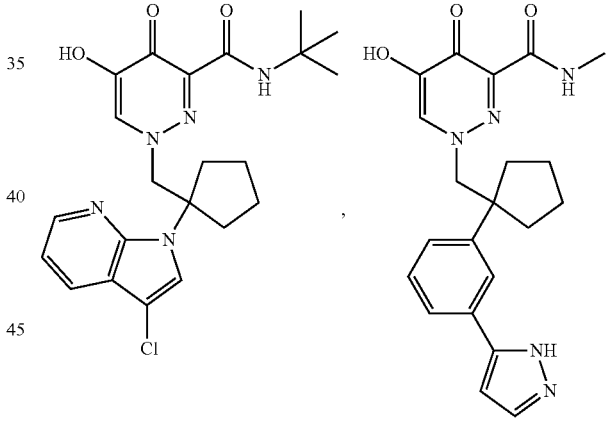
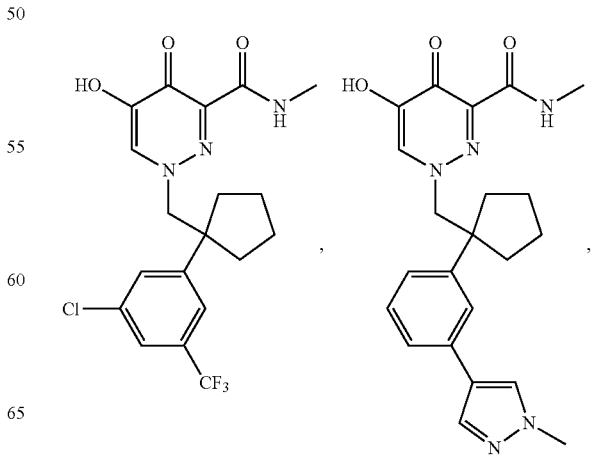

293
-continued
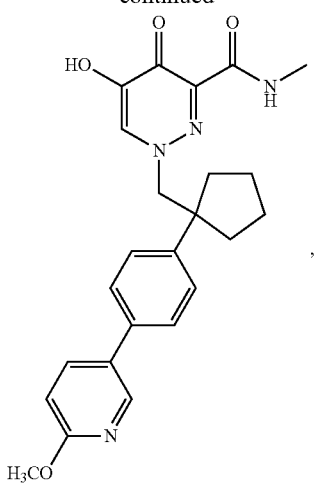
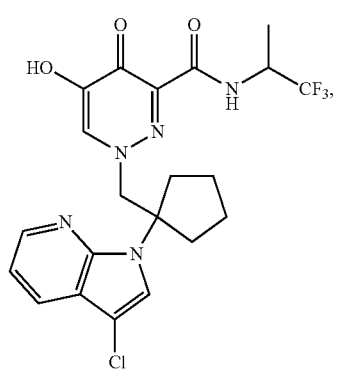
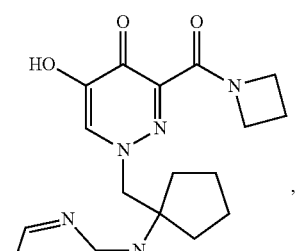
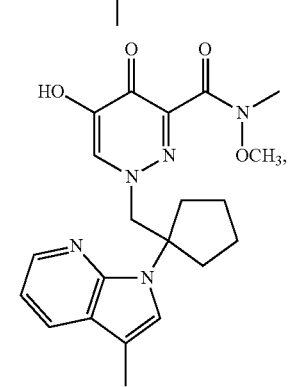
294
-continued
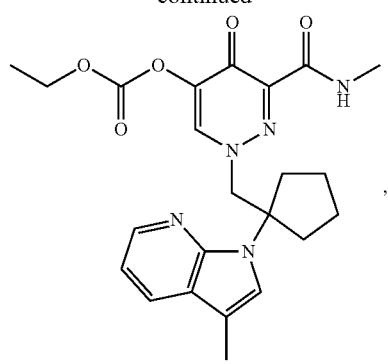
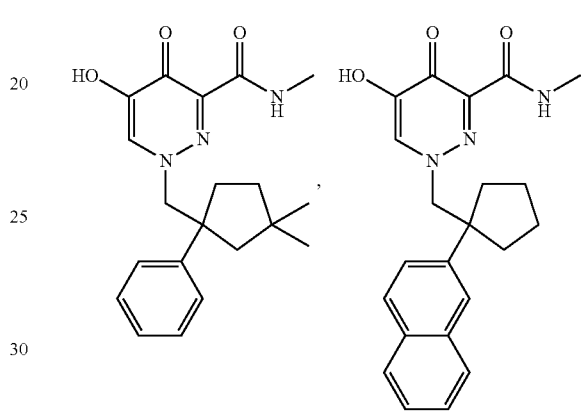
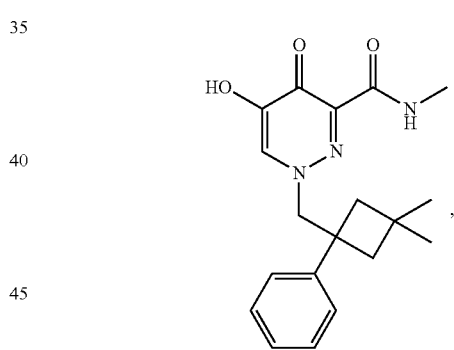
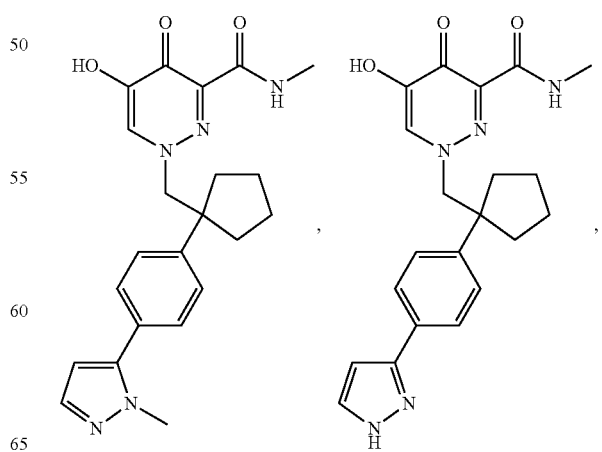

295
-continued
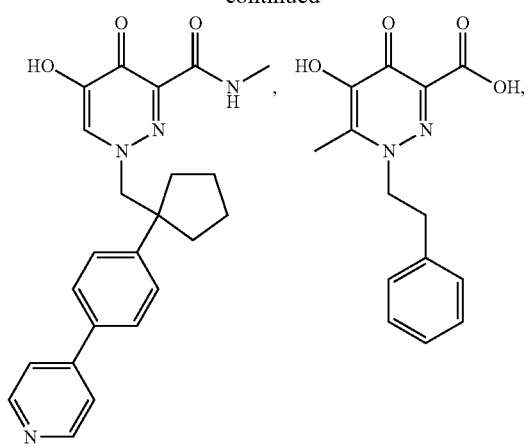
296
-continued
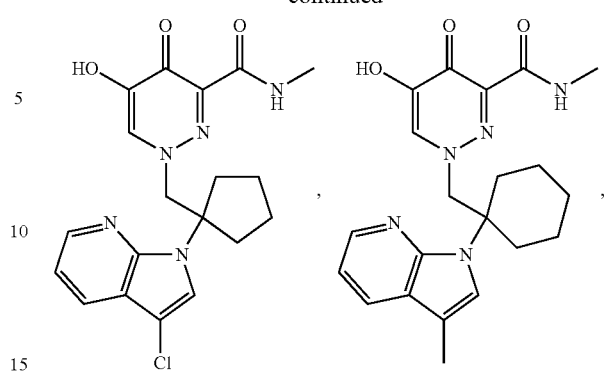
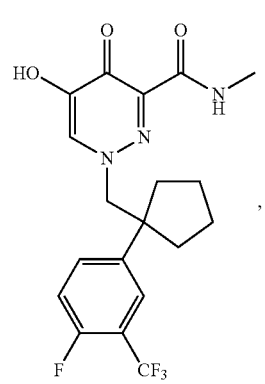
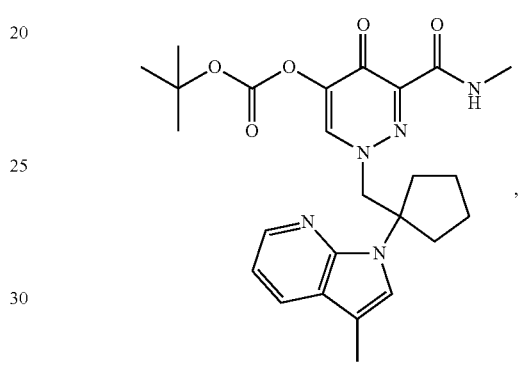
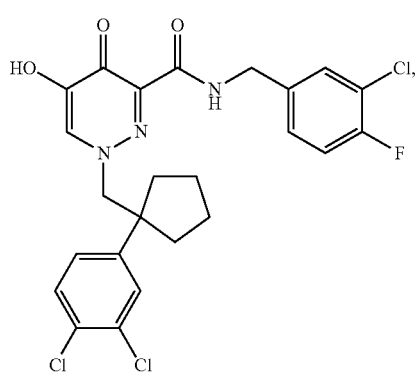
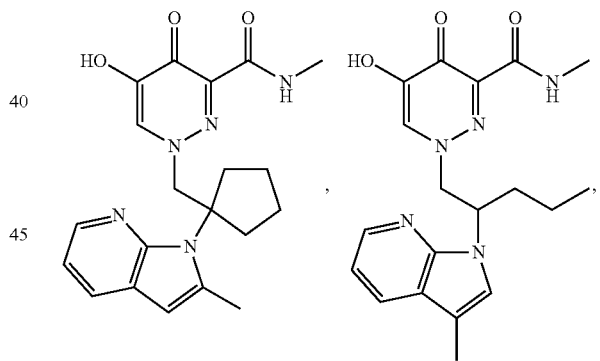
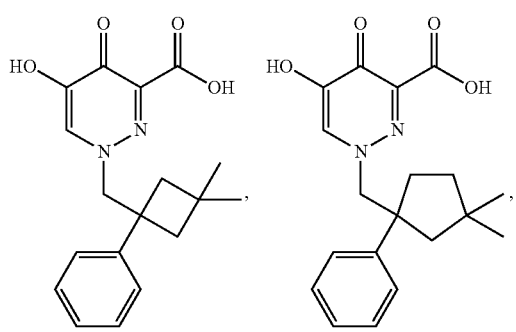
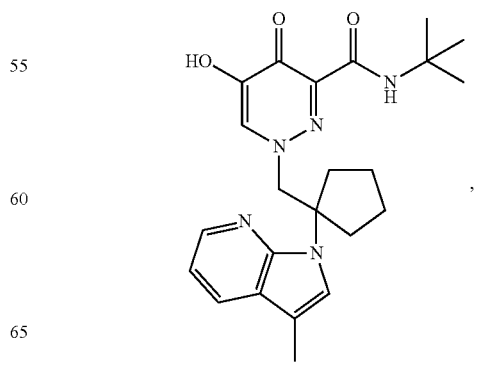

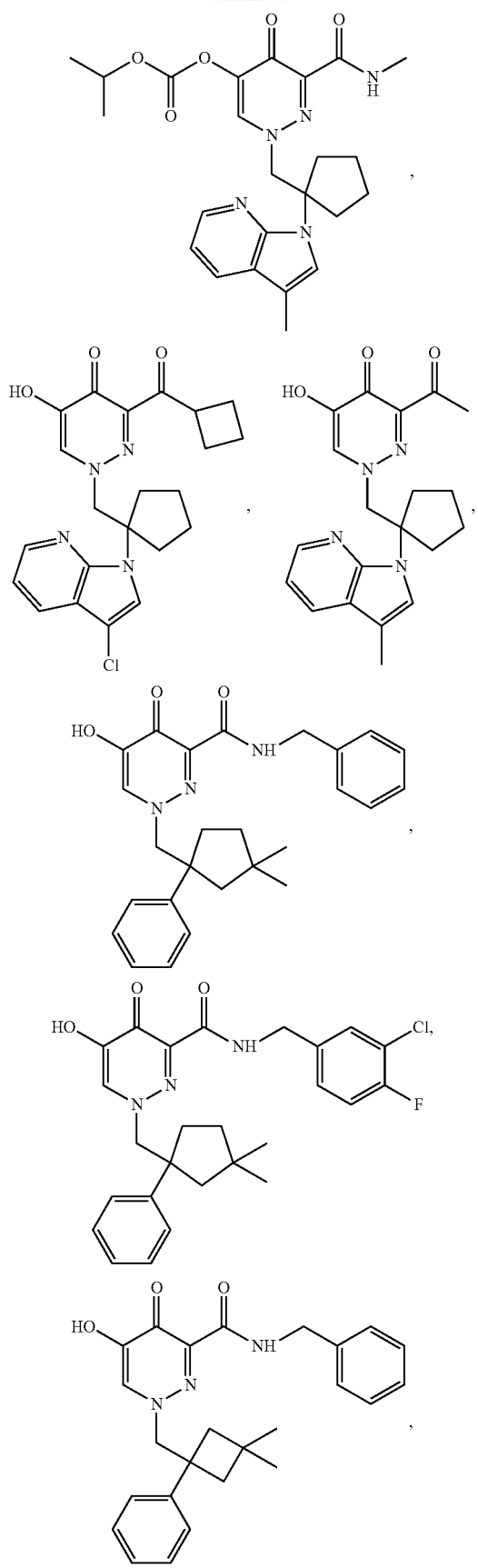
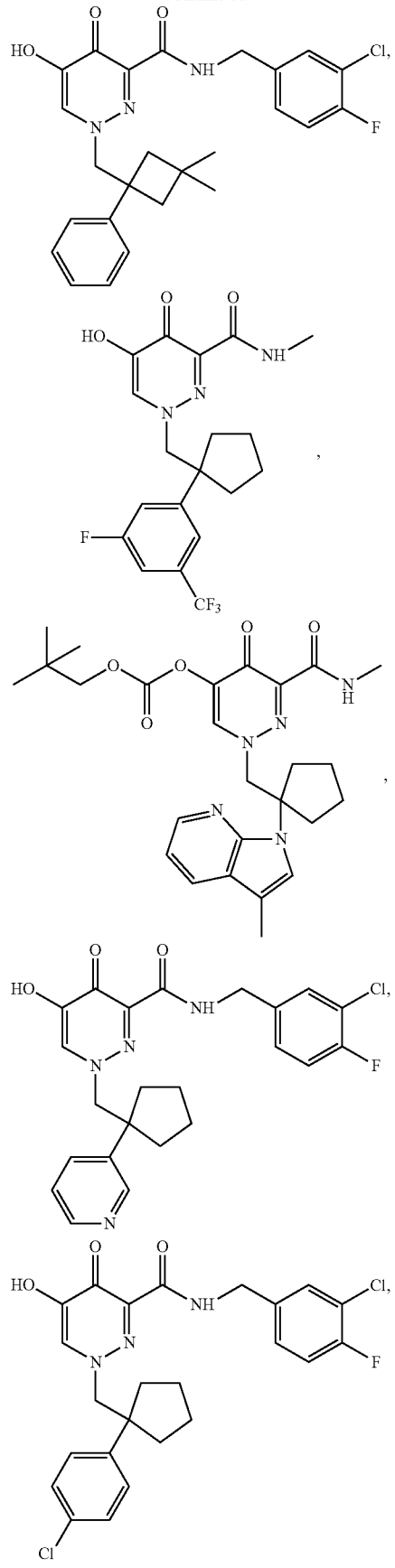

299
-continued
300
-continued
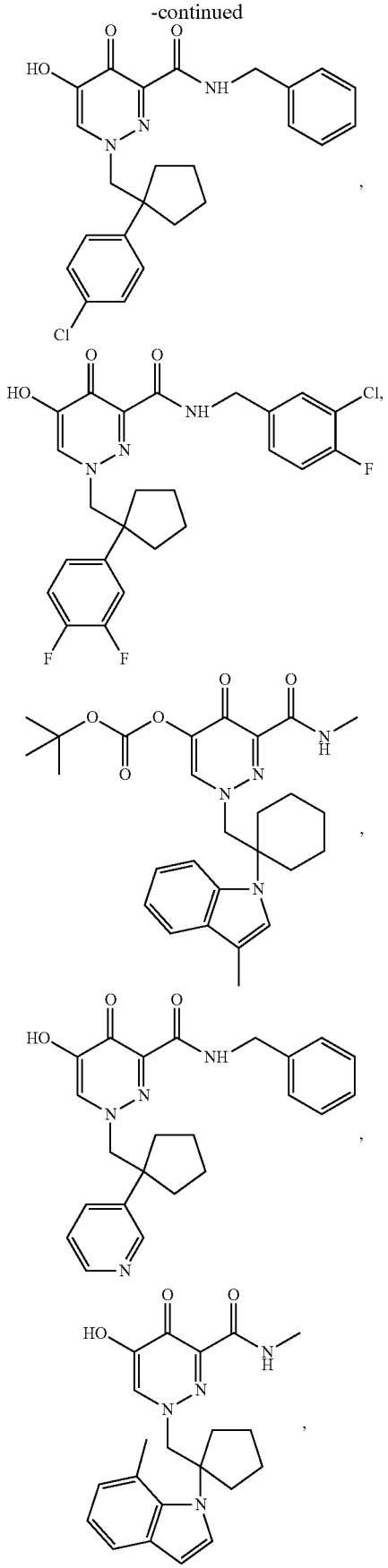
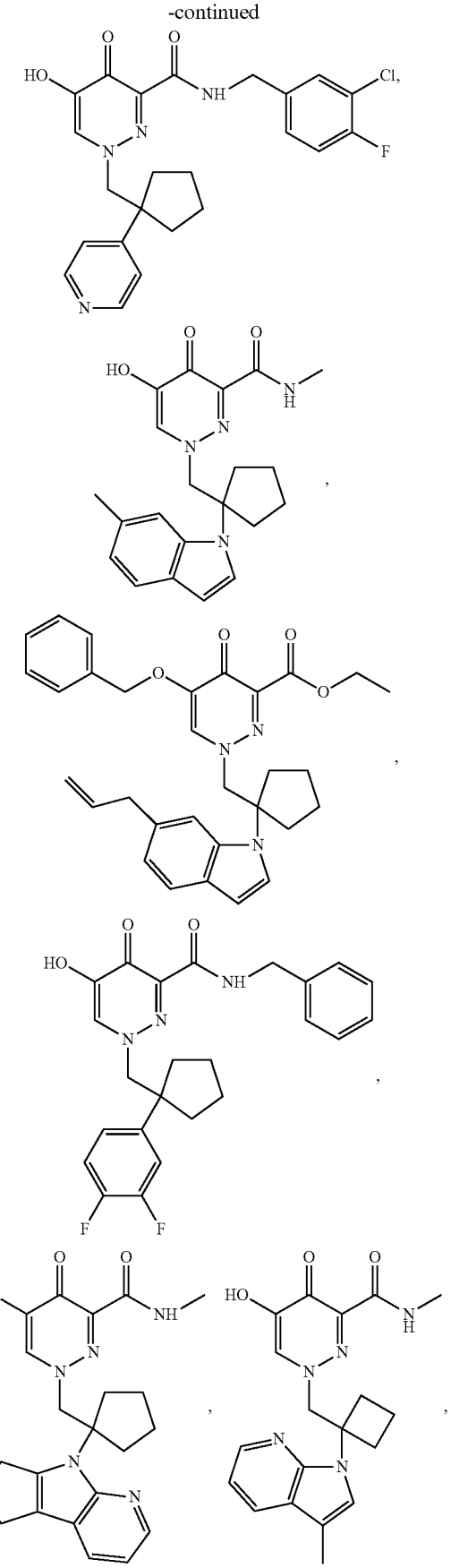

301
-continued
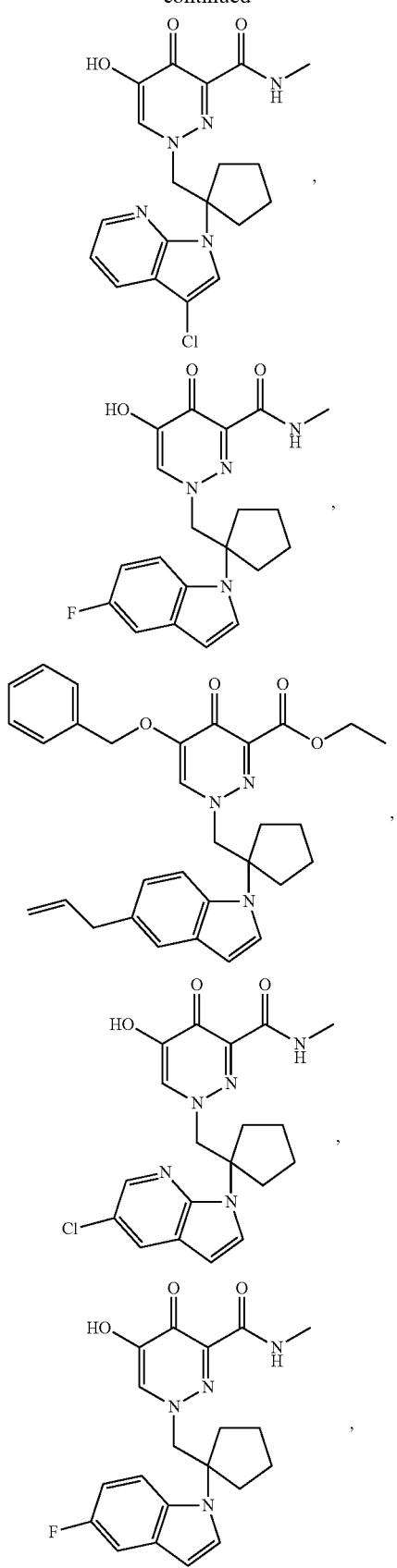
302
-continued
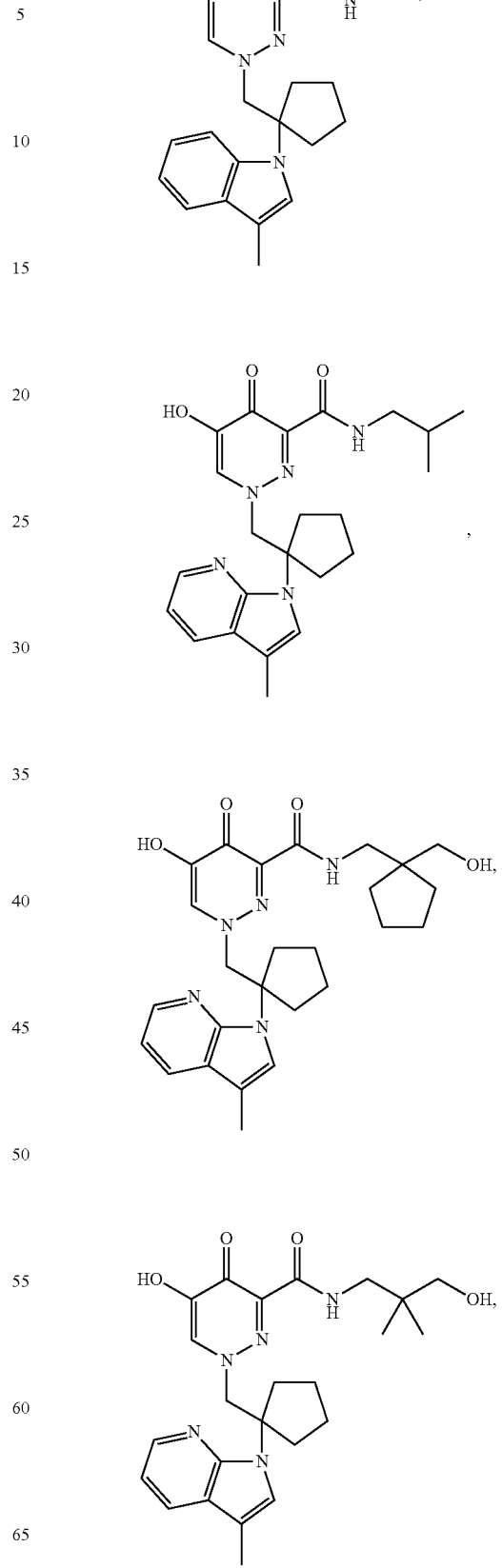

303
-continued
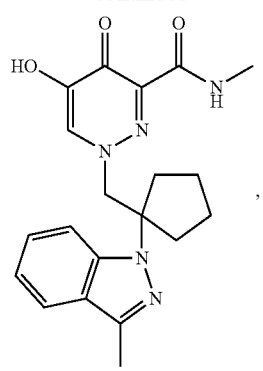
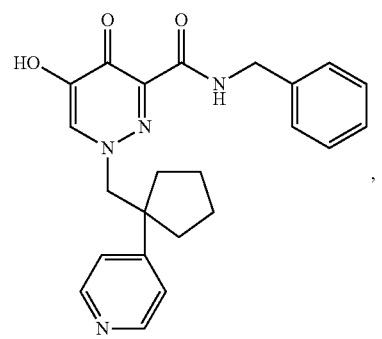
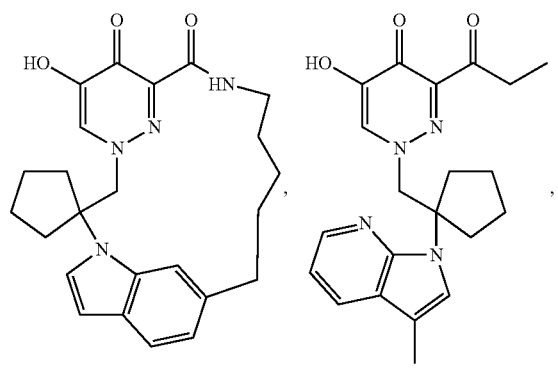
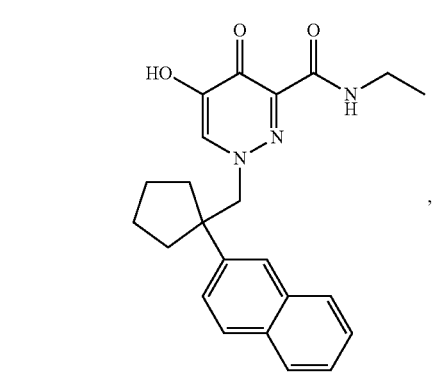
304
-continued
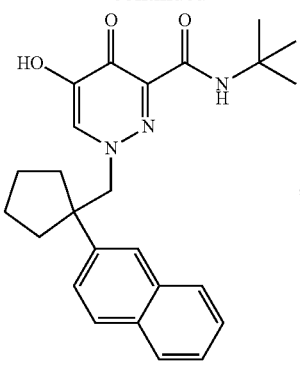
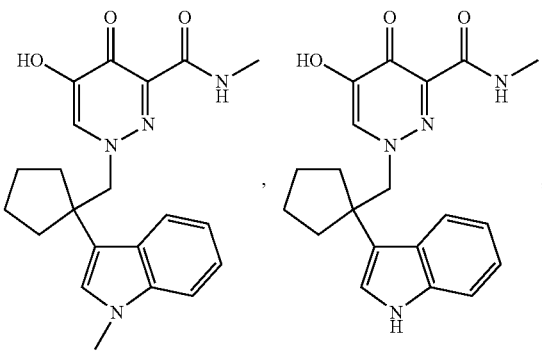
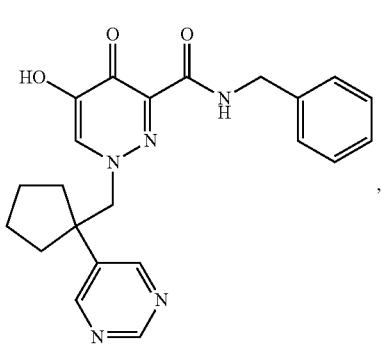
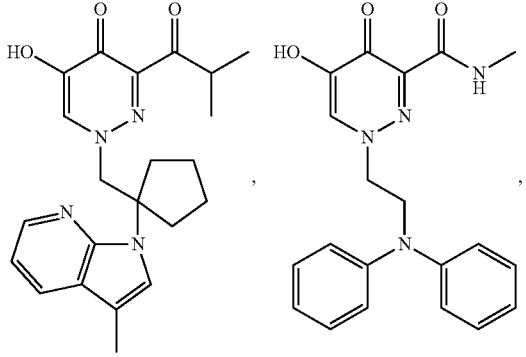

305
-continued
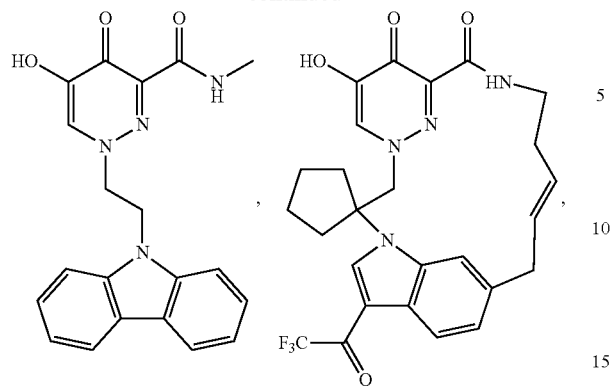
306
-continued
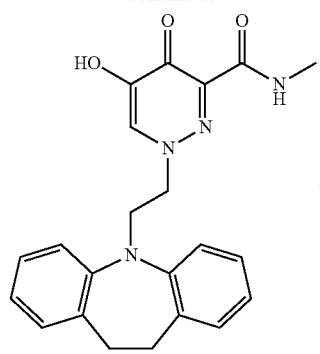
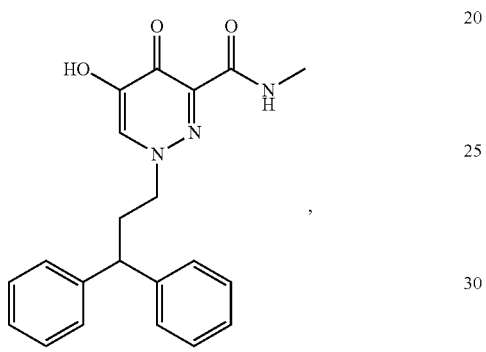
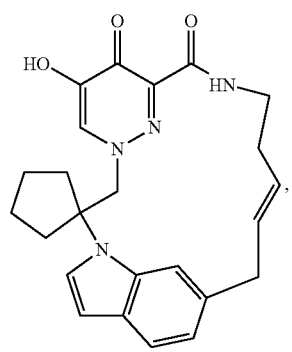
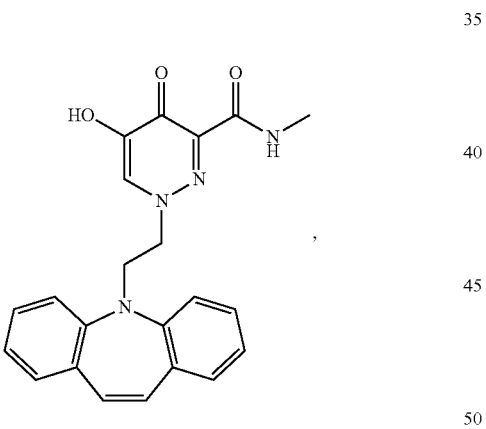
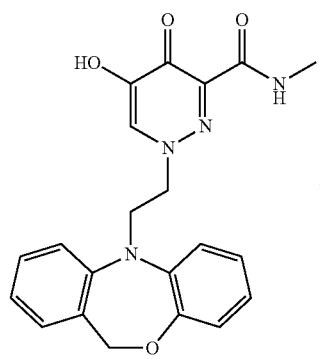
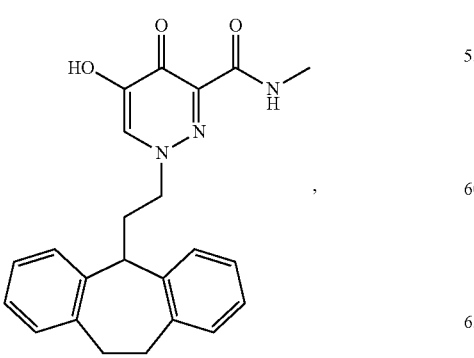
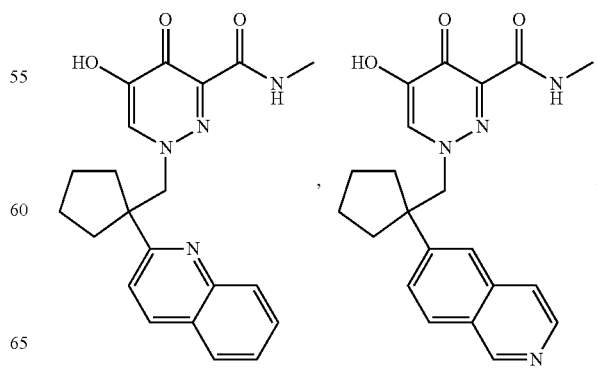

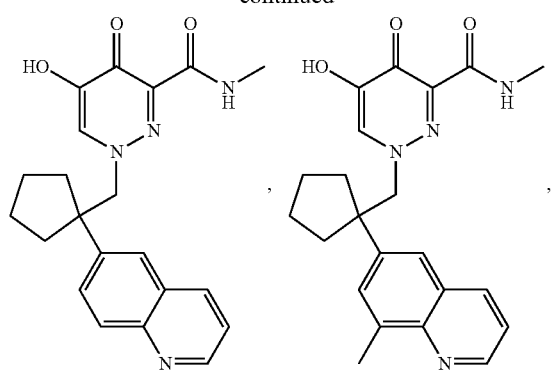
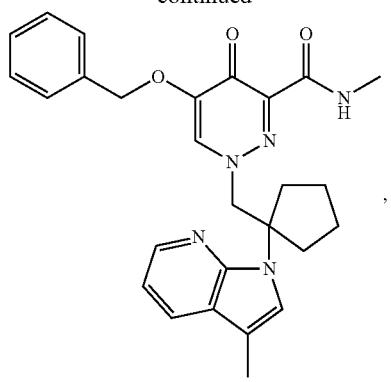
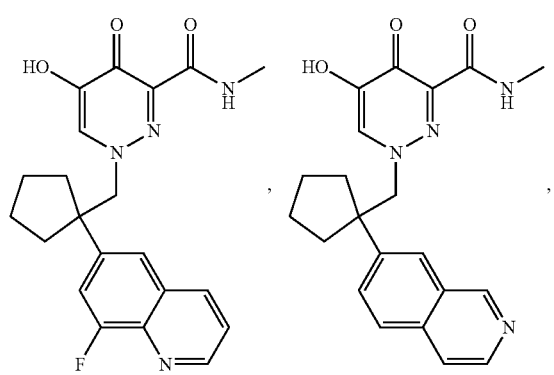
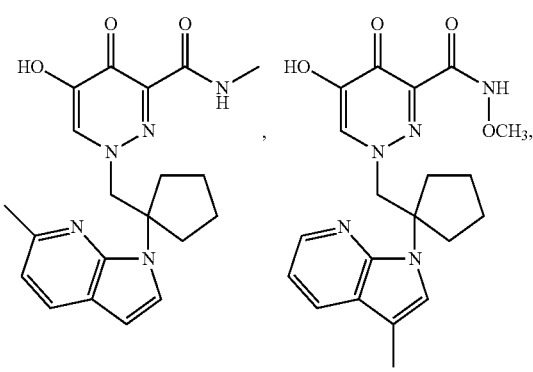
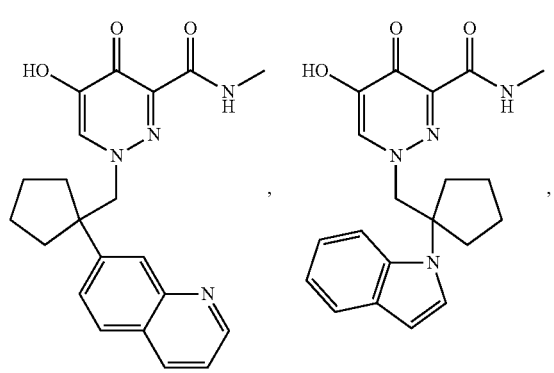
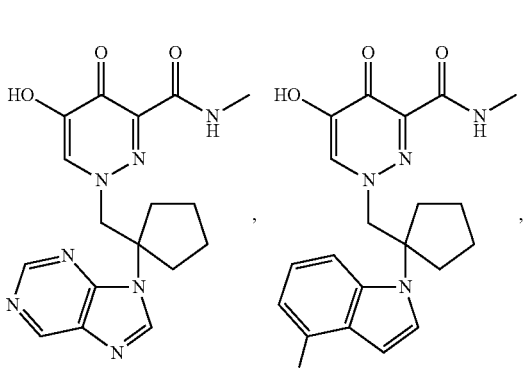
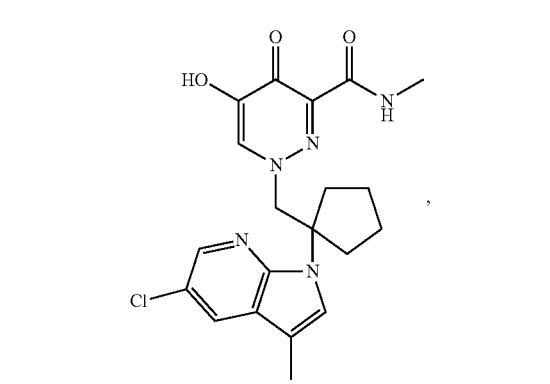
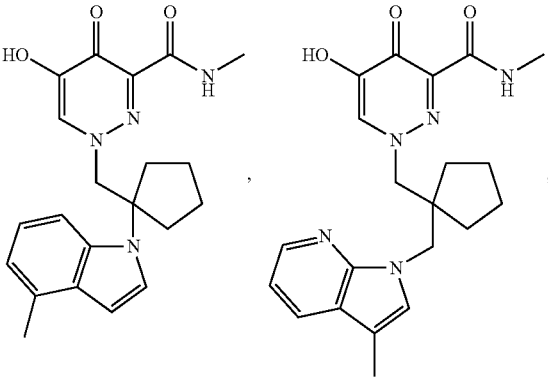

309
-continued
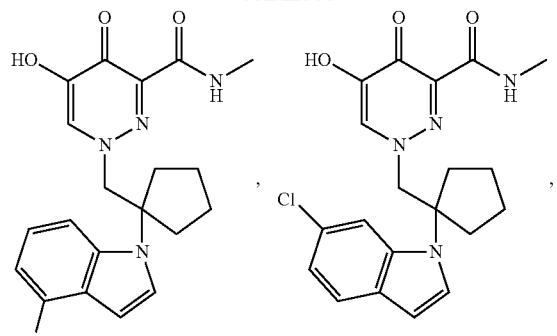
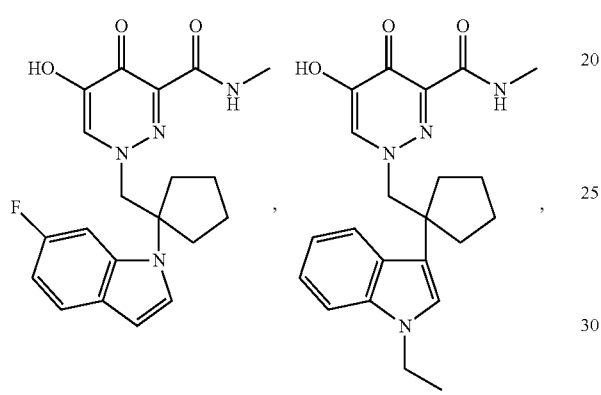
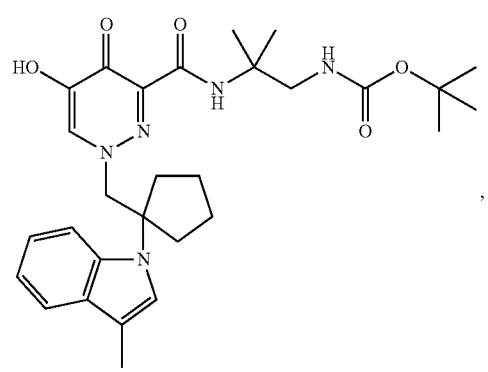
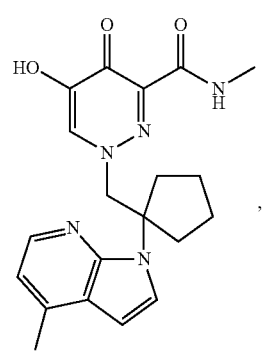
310
-continued
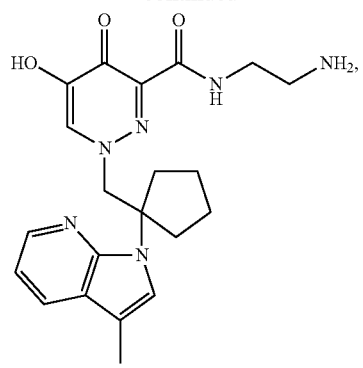
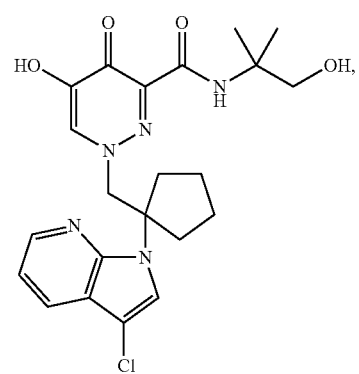
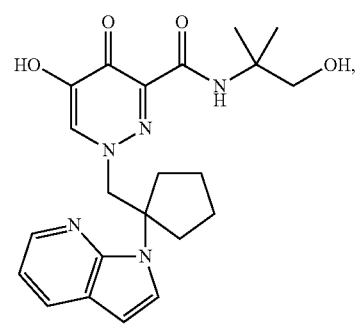
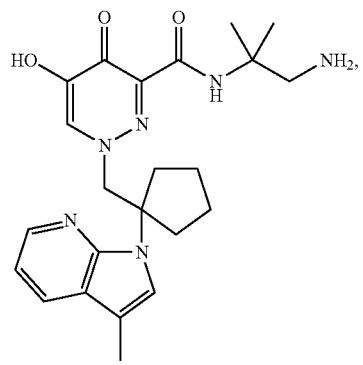

311
-continued
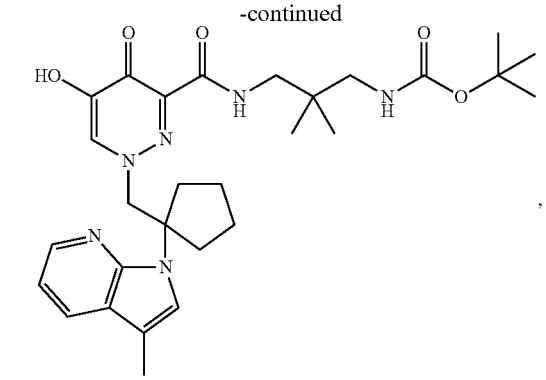
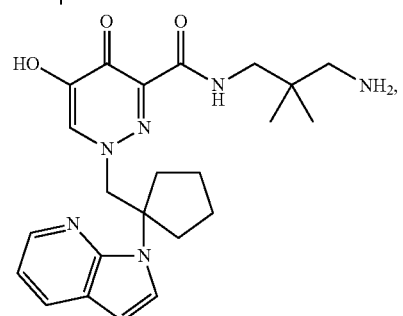
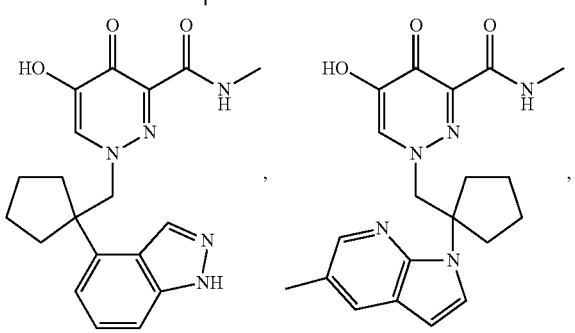
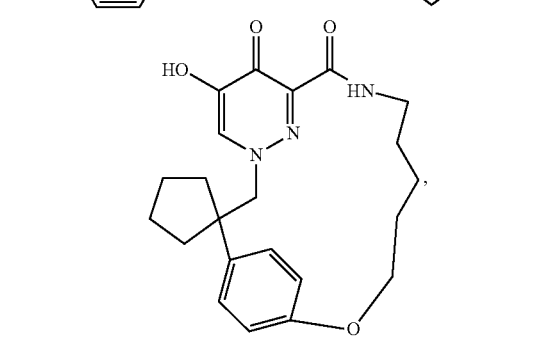
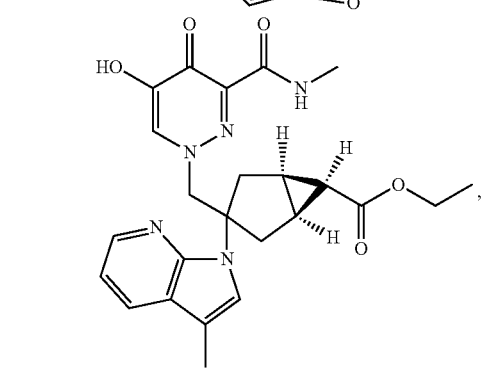
312
-continued
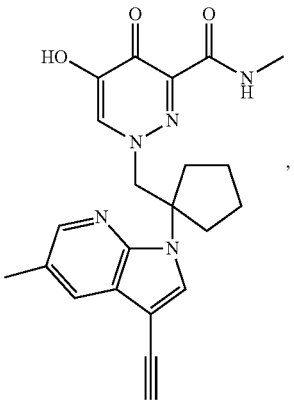
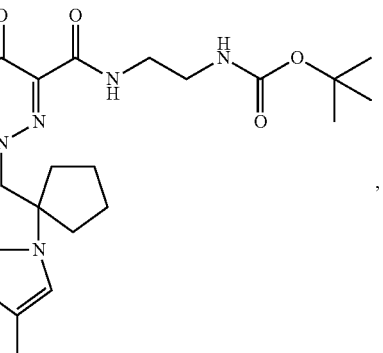
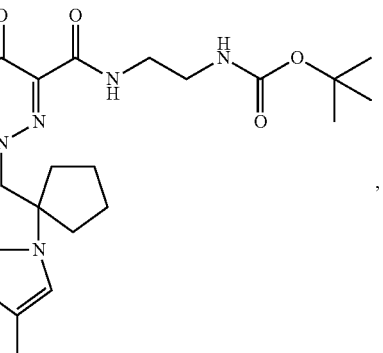
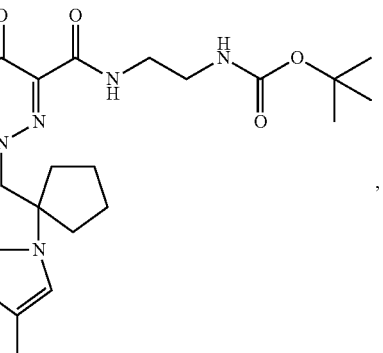

313
-continued
314
-continued
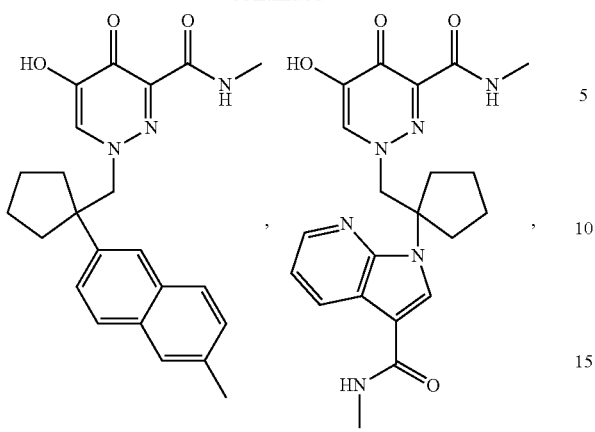
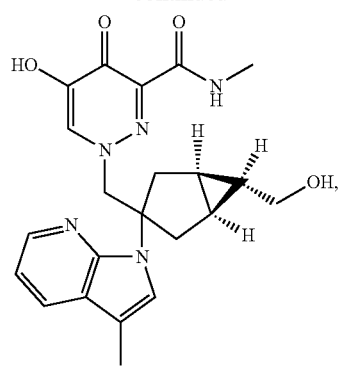
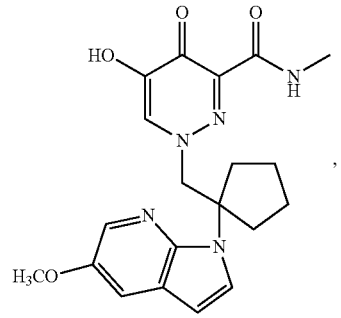
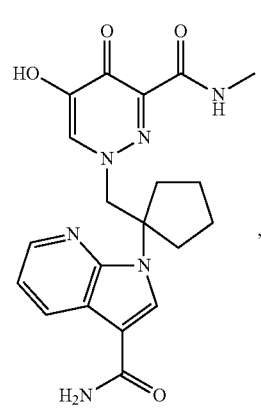
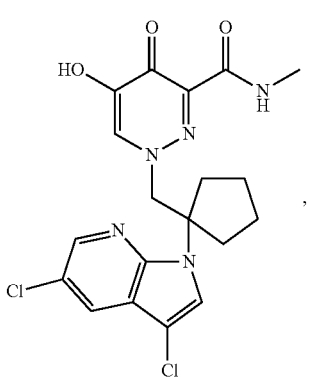
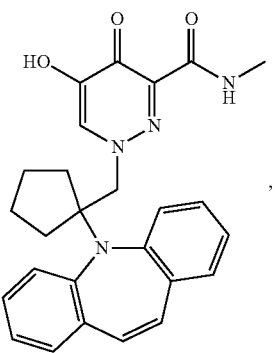
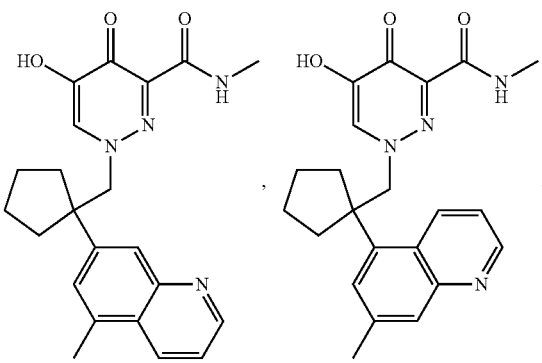

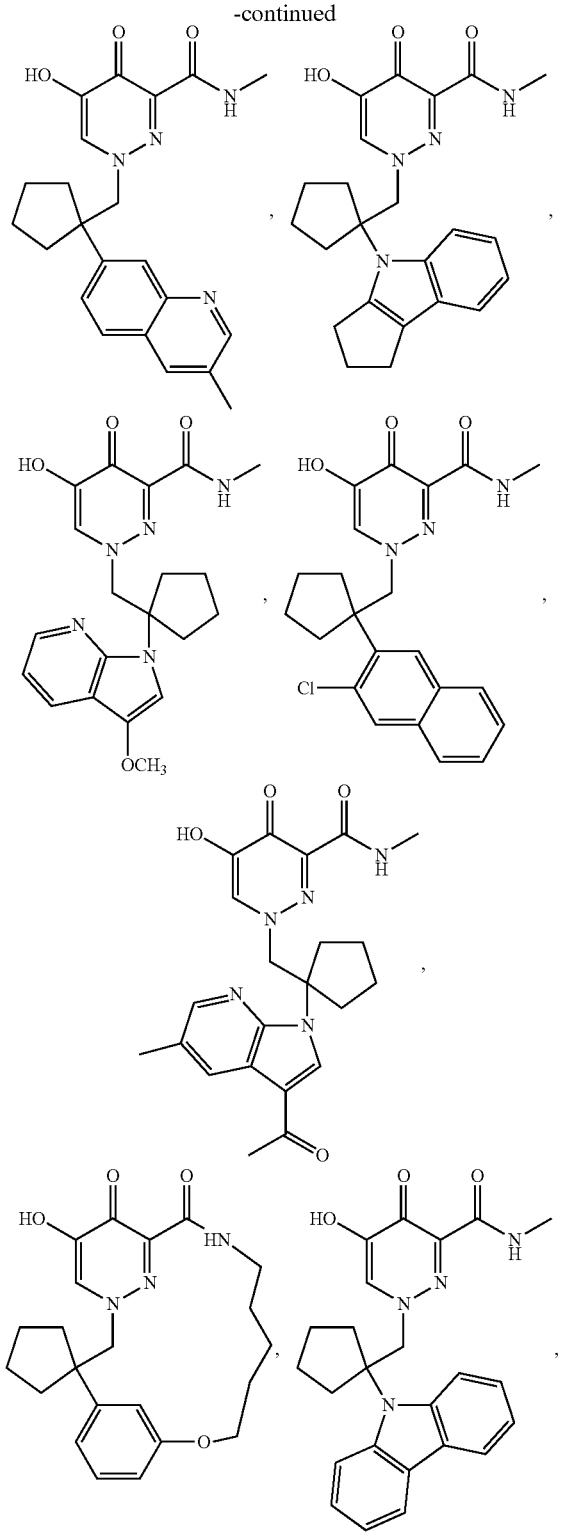
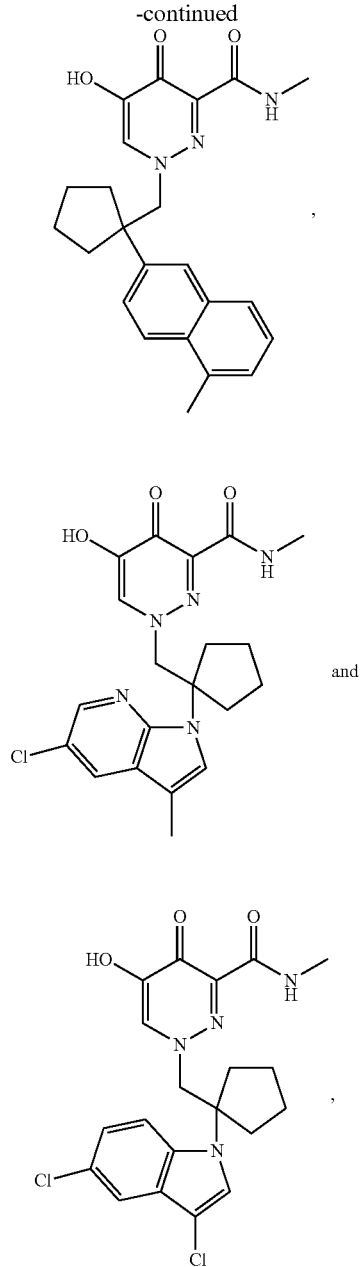
or a pharmaceutically acceptable salt of any of the foregoing.
36. A pharmaceutical composition comprising an effective amount of a compound of claim 1, or a pharmaceutically acceptable salt thereof, and a pharmaceutically acceptable carrier, diluent, excipient, or combination thereof.
* * * * *

UNITED STATES PATENT AND TRADEMARK OFFICE
CERTIFICATE OF CORRECTION

PATENT NO. : 10,364,226 B2
APPLICATION NO. : 15/021073
DATED : July 30, 2019
INVENTOR(S) : Leonid Beigelman et al.

It is certified that error appears in the above-identified patent and that said Letters Patent is hereby corrected as shown below:

In the Claims

In Column 230, Line 43, in Claim 1, delete "is" and insert -- is an --, therefor.

In Column 230, Line 43, in Claim 1, before "optionally" insert -- an --.

In Column 230, Line 51, in Claim 1, delete "heteroalkenylene," and insert -- heteroalkenylene; --, therefor.

In Column 230, Line 52, in Claim 1, delete "alkylene," and insert -- alkylene; --, therefor.

In Column 230, Line 57, in Claim 1, delete "C1.6" and insert -- $C_{1-6}$ --, therefor.

In Column 230, Line 58, in Claim 1, delete "heteroalkylene," and insert -- heteroalkylene; --, therefor.

In Column 231, Line 23, in Claim 2, delete "amino;" and insert -- amino group; --, therefor.

In Column 232, Line 37, in Claim 7, delete "(CH$_2$)$_2$—S" and insert -- (CH$_2$)$_2$—S—, --, therefor.

In Column 232, Line 42, in Claim 8, delete "therof," and insert -- thereof, --, therefor.

In Column 232, Line 49, in Claim 10, delete "pharmaceutcially" and insert -- pharmaceutically --, therefor.

In Column 232, Line 59, in Claim 13, delete "accceptable" and insert -- acceptable --, therefor.

In Column 233, Line 16, in Claim 19, delete "accetpable" and insert -- acceptable --, therefor.

Signed and Sealed this
First Day of March, 2022

Drew Hirshfeld
*Performing the Functions and Duties of the
Under Secretary of Commerce for Intellectual Property and
Director of the United States Patent and Trademark Office*